United States Patent
Ban et al.

(10) Patent No.: US 11,795,195 B2
(45) Date of Patent: Oct. 24, 2023

(54) ANTIBODY-DRUG CONJUGATES INCLUDING HEMIASTERLIN DERIVATIVE

(71) Applicant: Sumitomo Pharma Co., Ltd., Osaka (JP)

(72) Inventors: Hitoshi Ban, Osaka (JP); Atsushi Suwa, Osaka (JP); Yosuke Takanashi, Osaka (JP)

(73) Assignee: Sumitomo Pharma Co., Ltd., Osaka (JP)

( * ) Notice: Subject to any disclaimer, the term of this patent is extended or adjusted under 35 U.S.C. 154(b) by 299 days.

(21) Appl. No.: 16/637,099

(22) PCT Filed: Aug. 10, 2018

(86) PCT No.: PCT/JP2018/030143
§ 371 (c)(1),
(2) Date: Feb. 6, 2020

(87) PCT Pub. No.: WO2019/031614
PCT Pub. Date: Feb. 14, 2019

(65) Prior Publication Data
US 2020/0247847 A1  Aug. 6, 2020

(30) Foreign Application Priority Data
Aug. 10, 2017  (JP) .................. 2017-155990

(51) Int. Cl.
*C07K 5/02* (2006.01)
*A61K 47/65* (2017.01)
*A61K 47/68* (2017.01)

(52) U.S. Cl.
CPC ............ *C07K 5/0222* (2013.01); *A61K 47/65* (2017.08); *A61K 47/68* (2017.08)

(58) Field of Classification Search
None
See application file for complete search history.

(56) References Cited

U.S. PATENT DOCUMENTS

| | | | |
|---|---|---|---|
| 6,154,590 A | 11/2000 | Jin et al. | |
| 7,579,323 B1 | 8/2009 | Andersen et al. | |
| 2005/0171014 A1 | 8/2005 | Tarasova et al. | |
| 2008/0293951 A1* | 11/2008 | Iwama .................. | C07D 233/61 548/337.1 |
| 2009/0136526 A1 | 5/2009 | McDonagh et al. | |
| 2011/0171125 A1 | 7/2011 | Elkins et al. | |
| 2017/0007714 A1 | 1/2017 | Kontermann et al. | |

FOREIGN PATENT DOCUMENTS

| | | | |
|---|---|---|---|
| JP | 11-505211 | * | 5/1999 |
| JP | H11-505211 A | | 5/1999 |
| JP | 2011-500725 A | | 1/2011 |
| JP | 2012-522513 A | | 9/2012 |
| JP | 2016-516063 A | * | 6/2016 |
| JP | 2017-506234 A | | 3/2017 |
| WO | 96/033211 A1 | | 10/1996 |
| WO | 03/082268 A2 | | 10/2003 |
| WO | 2004/026293 A2 | | 4/2004 |
| WO | 2006/063135 A2 | | 6/2006 |
| WO | 2014/057436 A2 | | 4/2014 |
| WO | 2014/144871 A1 | | 9/2014 |
| WO | 2015/095952 A1 | | 7/2015 |
| WO | 2015/095953 A1 | | 7/2015 |
| WO | 2015/151079 A2 | | 10/2015 |
| WO | 2016/123582 A1 | | 8/2016 |

OTHER PUBLICATIONS

Talpir et al., "Hemiasterlin and geodiamolide TA: Two New Cytotoxic Peptides from the Marine Sponge *Hemiasterella minor* (Kirkpatrick)," Tetrahedron Letters, 35 (25): 4453-4456 (1994).

Zask et al., "D-pience modifications of the hemiasterlin analog HTI-286 produce potent tubulin inhibitors," Bioorganic & Medicinal Chemistry Letters, 14: 4353-4358 (2004).

Zask et al., "Synthesis and Biological Activity of Analogues of the Antimicrotubule Agent N,beta,beta-Trimethyl-L-phenylalanyl-N1-[(1S,2E)-3-carboxy-1-isopropylbut-2-enyl]-N1,3-dimethyl-L-valinamide (HTI-286)," Journal of Medicinal Chemistry, 47: 4774-4786 (2004).

Yamashita et al., "Synthesis and activity of novel analogs of hemiasterlin as inhibitors of tubulin polymerization: modification of the A segment," Bioorganic & Medicinal Chemistry Letters, 14: 5317-5322 (2004).

Nieman et al., "Synthesis and Antimitotic/Cytotoxic Activity of Hemiasterlin Analogues," Journal of Natural Products, 66: 183-199 (2003).

Rocha-Lima et al., "A phase 1 trial of E7974 administered on day 1 of a 21-day cycle in patients with advanced solid tumors," Cancer, 4262-4270 (2012).

Alley et al., "Contribution of Linker Stability to the Activities of Anticancer Immunoconjugates," Bioconjugate Chemistry, 19: 759-765 (2008).

Baldwin et al., "Tunable Degradation of Maleimide-Thiol Adducts in Reducing Environments," Bioconjugate Chemistry, 22: 1946-1953 (2011).

(Continued)

*Primary Examiner* — Maury A Audet
(74) *Attorney, Agent, or Firm* — Morgan, Lewis & Bockius LLP

(57) ABSTRACT

A compound represented by formula (1-1):

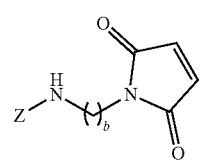

(1-1)

wherein b represents an integer of 1 to 5; and Z is a group represented by formula (Z-1), formula (Z-2), formula (Z-3), formula (Za-1), formula (Za-2), formula (Za-3), formula (Za-4) or formula (Za-5),
or a salt thereof.

24 Claims, No Drawings

(56) References Cited

OTHER PUBLICATIONS

International Search Report issued in corresponding International Patent Application No. PCT/JP2018/030143 dated Nov. 13, 2018.
International Preliminary Report on Patentability issued in corresponding International Patent Application No. PCT/JP2018/030143 dated Feb. 20, 2020.
Extended European Search Report issued in counterpart European Patent Application No. 18843388.2 dated Apr. 9, 2021.
Office Action issued in related U.S. Appl. No. 16/637,097 dated Aug. 11, 2022.

* cited by examiner

ANTIBODY-DRUG CONJUGATES INCLUDING HEMIASTERLIN DERIVATIVE

TECHNICAL FIELD

The present invention relates to hemiasterlin derivatives and antibody-drug conjugates thereof.

BACKGROUND ART

Hemiasterlin is a naturally occurring compound having a tripeptide structure, isolated from marine sponges, and is involved in microtubule depolymerization and mitotic arrest in cells (Non Patent Literature 1).

Several groups have so far conducted structural modification of hemiasterlin derivatives, and have found hemiasterlin derivatives exhibiting strong cytotoxicity and antimitotic effects for treatment for diseases such as cancer (Patent Literatures 1 to 5 and Non Patent Literatures 2 to 5). However, it has been reported that these hemiasterlin derivatives are delivered systemically due to the lack of target directing property, exhibiting cytotoxicity even to normal cells and showing side effects (Non Patent Literature 6).

An antibody-drug conjugate is a conjugate formed by conjugating an antibody to a drug directly or via an appropriate linker. The antibody-drug conjugate has characteristics of reducing systemic exposure of the drug to enhance the drug efficacy to the target cells, by delivering the drug to target cells via the antibody that binds to an antigen expressed on the target cells.

In addition, several groups have so far reported conjugates in which thiosuccinimide is formed between a hemiasterlin derivative having a maleimide group and a cysteine residue of an antibody or the like (Patent Literatures 4 and 6 to 8). It has been reported that reversible reaction between dissociation and binding occurs at such thiosuccinimide site in an organism (Non Patent Literatures 7 and 8).

CITATION LIST

Patent Literature

Patent Literature 1: International Publication No. WO 2004/026293
Patent Literature 2: International Publication No. WO 96/33211
Patent Literature 3: U.S. Pat. No. 7,579,323
Patent Literature 4: International Publication No. WO 2014/144871
Patent Literature 5: International Publication No. WO 2003/082268
Patent Literature 6: International Publication No. WO 2015/095952
Patent Literature 7: International Publication No. WO 2015/095953
Patent Literature 8: International Publication No. WO 2014/057436

Non Patent Literature

Non Patent Literature 1: Talpir, R. et al., Tetrahedron Lett., 1994, 35, 4453-4456.
Non Patent Literature 2: Zask, A. et. al., Bioorg. Med. Chem. Lett., 2004, 14, 4353-4358.
Non Patent Literature 3: Zask, A. et. al., J. Med. Chem., 2004, 47, 4774-4786.
Non Patent Literature 4: Yamashita, A. et. al., Bioorg. Med. Chem. Lett., 2004, 14, 5317-5322.
Non Patent Literature 5: Nieman, J. A. et. al., J, Nat. Prod., 2003, 66, 183-199.
Non Patent Literature 6: Rocha-Lima, C. M. et. al., Cancer, 2012, 118, 4262-4270.
Non Patent Literature 7: Alley, S. C. et. al., Bioconjugate Chem., 2008, 19, 759-765.
Non Patent Literature 8: Baldwin, A. D. et. al., Bioconjugate Chem., 2011, 22, 1946-1953.

SUMMARY OF INVENTION

Technical Problem

An object of the present invention is to provide a hemiasterlin derivative that, when conjugated with an antibody to form an antibody-drug conjugate, provide cell damage specifically to target cells while suppressing cytotoxicity to normal cells, and an antibody-drug conjugate.

Solution to Problem

As a result of diligent studies, the present inventors have found that an antibody-drug conjugate represented by formula (2-1) or (2-2) has strong antitumor activity while suppressing cytotoxicity to normal cells, thereby completing the present invention.

That is, the present invention is as follows:
[Item 1]
A compound represented by formula (1-1):

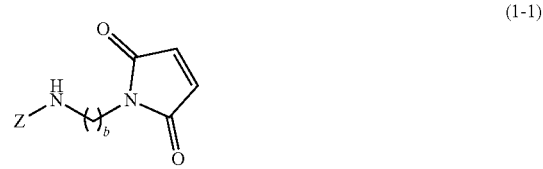

wherein
b represents an integer of 1 to 5; and
Z is a group represented by formula (Z-1), formula (Z-2), formula (Z-3), formula (Za-1), formula (Za-2), formula (Za-3), formula (Za-4) or formula (Za-5):

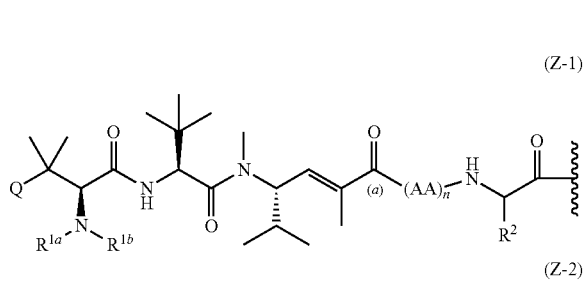

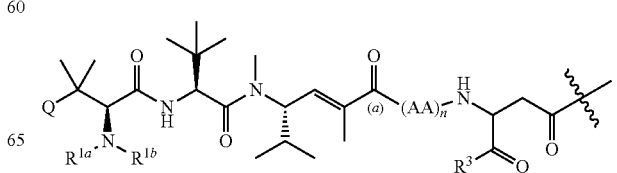

-continued

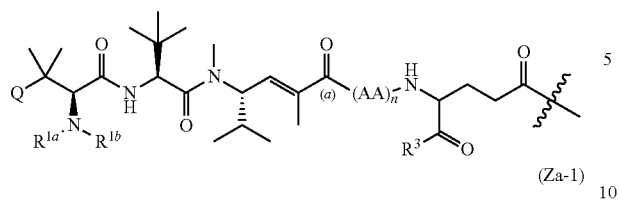
(Z-3)

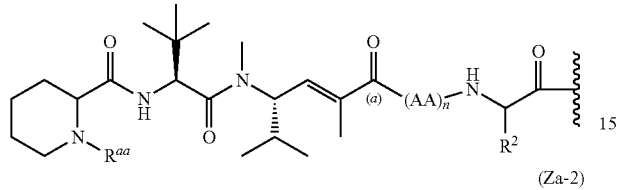
(Za-1)

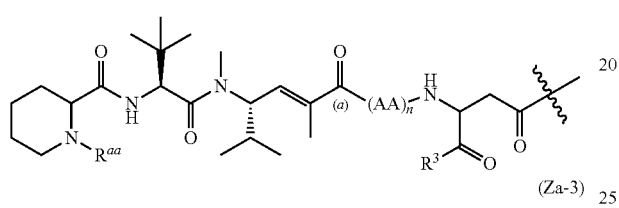
(Za-2)

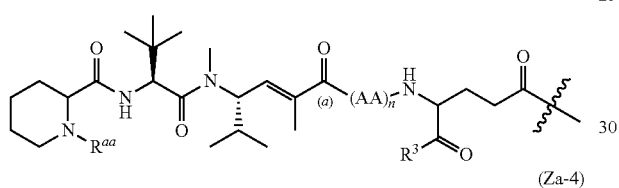
(Za-3)

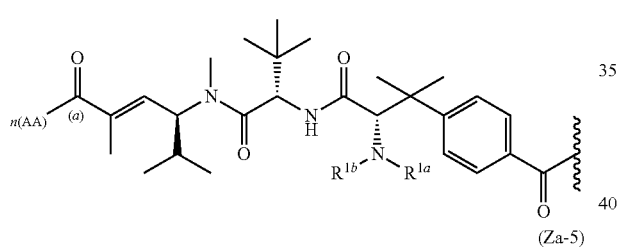
(Za-4)

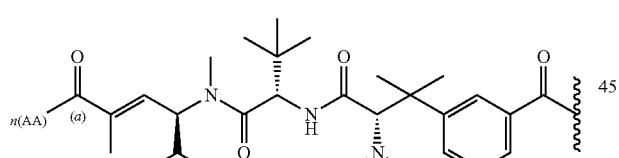
(Za-5)

where n represents an integer of 0 to 4, where n is an integer of 1 to 4 when Z is a group represented by formula (Za-4) or formula (Za-5);

AA represents a glutamic acid residue (Glu), an aspartic acid residue (Asp) or a lysine residue (Lys), and when there is a plurality of AAs, each AA may be the same as or different from each other and AAs are bonded to each other via an amide bond;

an N-terminal nitrogen atom of $(AA)_n$ forms an amide bond together with carbonyl group (a);

$R^{aa}$ represents a $C_{1-6}$ alkyl group;

Q represents a group represented by formula (Qa-1), formula (Qa-2), formula (Qa-3), formula (Qa-4), formula (Qa-5), formula (Qa-6) or formula (Qa-7):

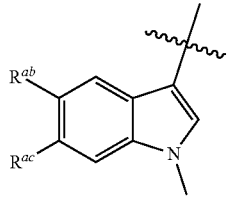
(Qa-1)

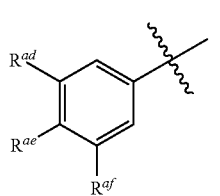
(Qa-2)

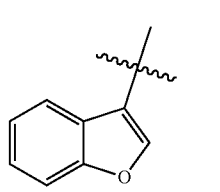
(Qa-3)

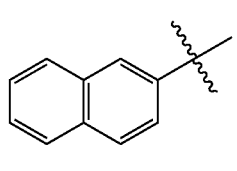
(Qa-4)

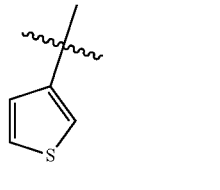
(Qa-5)

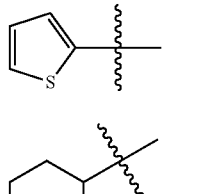
(Qa-6)

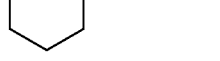
(Qa-7)

where $R^{ab}$ and $R^{ac}$ each independently represent a hydrogen atom, a halogen atom, a $C_{1-6}$ alkyl group or a $C_{1-6}$ alkoxy group; and $R^{ad}$, $R^{ae}$ and $R^{af}$ each independently represent a hydrogen atom, a halogen atom, a hydroxy group, a cyano group, an amino group, a carboxyl group, a phenyl group, or a $C_{1-6}$ alkyl group, $C_{1-6}$ alkoxy group or $C_{1-6}$ alkyl ester group optionally substituted with 1 to 3 fluorine atoms;

$R^{1a}$ and $R^{1b}$ each independently represent a hydrogen atom or a methyl group;

$R^2$ represents $—(CH_2)_u—COR^4$;

u represents 1 or 2;

$R^3$ and $R^4$ each independently represent —OH or $-(AB)_p$;

AB represents Glu, Asp or Lys, and when there is a plurality of ABs, each AB may be the same as or different from each other and ABs are bonded to each other via an amide bond; and p represents an integer of 1 to 4;
with a proviso that when $R^3$ or $R^4$ is -(AB)$_p$, a sum of n and p is an integer of 1 to 5,
or a salt thereof.

[Item 2]

The compound according to item 1, represented by formula (1-1):

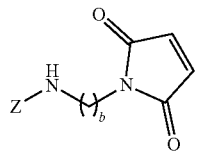

(1-1)

wherein
b represents an integer of 1 to 5; and
Z is a group represented by formula (Z-1), formula (Z-2) or formula (Z-3):

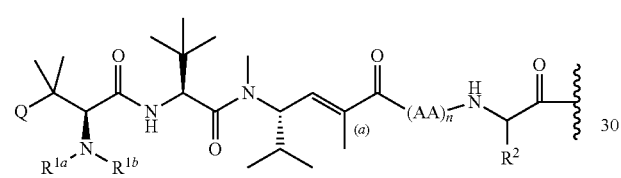

(Z-1)

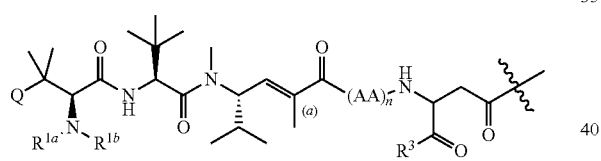

(Z-2)

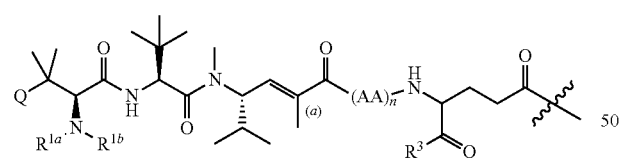

(Z-3)

where
n represents an integer of 0 to 4;
AA represents a glutamic acid residue (Glu), an aspartic acid residue (Asp) or a lysine residue (Lys), and when there is a plurality of AAs, each AA may be the same as or different from each other and AAs are bonded to each other via an amide bond;
an N-terminal nitrogen atom of (AA)$_n$ forms an amide bond together with carbonyl group (a);
Q represents an unsubstituted phenyl group or a group represented by formula (Q-1):

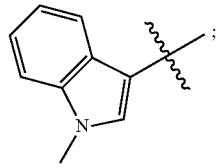

(Q-1)

$R^{1a}$ and $R^{1b}$ each independently represent a hydrogen atom or a methyl group;
$R^2$ represents —(CH$_2$)$_u$—COR$^4$;
u represents 1 or 2;
$R^3$ and $R^4$ each independently represent —OH or -(AB)$_p$;
AB represents Glu, Asp or Lys, and when there is a plurality of ABs, each AB may be the same as or different from each other and ABs are bonded to each other via an amide bond; and
p represents an integer of 1 to 4;
with a proviso that when $R^3$ or $R^4$ is -(AB)$_p$, a sum of n and p is an integer of 1 to 5,
or a salt thereof.

[Item 3]

The compound according to item 1 or 2, wherein b is 2, or a salt thereof.

[Item 4]

A compound represented by formula (1-2):

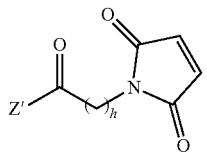

(1-2)

wherein
h represents an integer of 1 to 5; and
Z' is a group represented by formula (Z-4), formula (Z-5), formula (Za-6), formula (Za-7), formula (Za-8), formula (Za-9), formula (Za-10) or formula (Za-11):

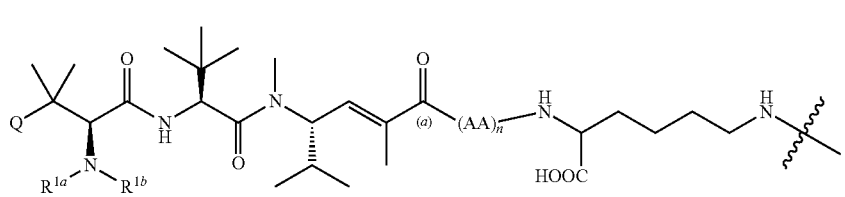

(Z-4)

(Z-5)
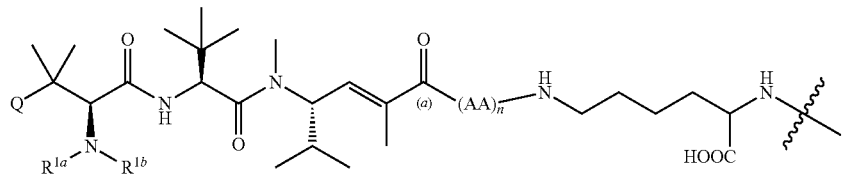

(Za-6)
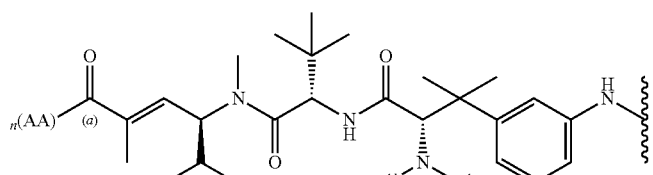

(Za-7)
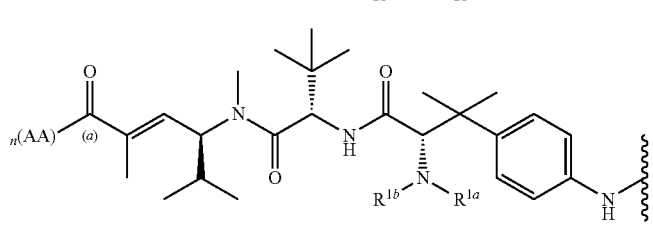

(Za-8)
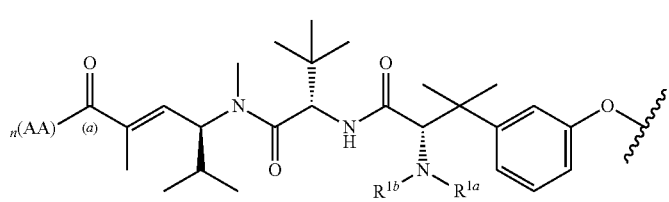

(Za-9)
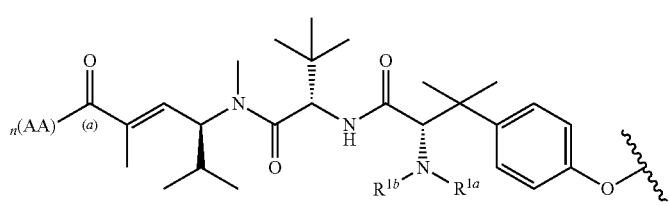

(Za-10)
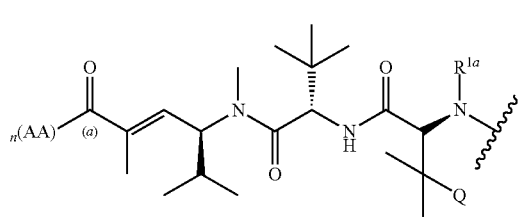

(Za-11)

where n represents an integer of 0 to 4, where n is an integer of 1 to 4 when Z is a group represented by formula (Za-6), formula (Za-7), formula (Za-8), formula (Za-9), formula (Za-10) or formula (Za-11);

AA represents a glutamic acid residue (Glu), an aspartic acid residue (Asp) or a lysine residue (Lys), and when there is a plurality of AAs, each AA may be the same as or different from each other and AAs are bonded to each other via an amide bond;

an N-terminal nitrogen atom of $(AA)_n$ forms an amide bond together with carbonyl group (a);

Q represents a group represented by formula (Qa-1), formula (Qa-2), formula (Qa-3), formula (Qa-4), formula (Qa-5), formula (Qa-6) or formula (Qa-7):

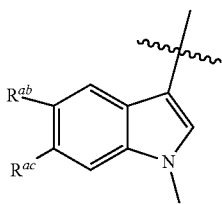
(Qa-1)

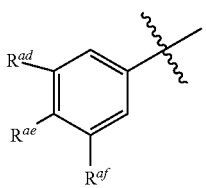
(Qa-2)

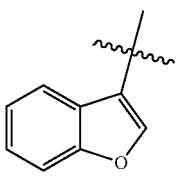
(Qa-3)

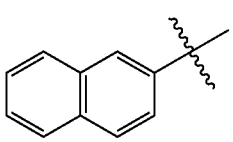
(Qa-4)

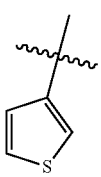
(Qa-5)

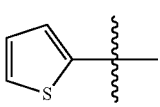
(Qa-6)

-continued

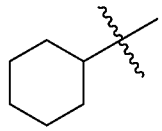
(Qa-7)

where $R^{ab}$ and $R^{ac}$ each independently represent a hydrogen atom, a halogen atom, a $C_{1-6}$ alkyl group or a $C_{1-6}$ alkoxy group; and $R^{ad}$, $R^{ae}$ and $R^{af}$ each independently represent a hydrogen atom, a halogen atom, a hydroxy group, a cyano group, an amino group, a carboxyl group, a phenyl group, or a $C_{1-6}$ alkyl group, $C_{1-6}$ alkoxy group or $C_{1-6}$ alkyl ester group optionally substituted with 1 to 3 fluorine atoms; and $R^{1a}$ and $R^{1b}$ each independently represent a hydrogen atom or a methyl group, or a salt thereof.

[Item 5]

The compound according to item 4, represented by formula (1-2):

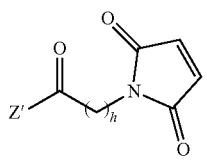
(1-2)

wherein h represents an integer of 1 to 5; and

Z' is a group represented by formula (Z-4) or formula (Z-5):

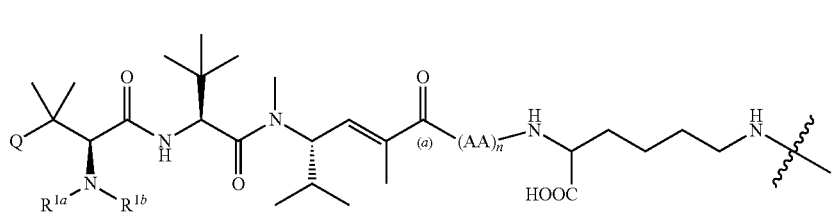
(Z-4)

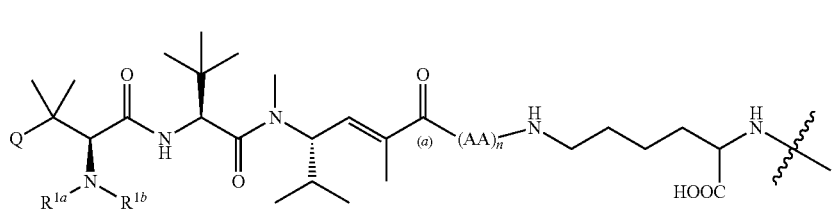
(Z-5)

where n represents an integer of 0 to 4;

AA represents a glutamic acid residue (Glu), an aspartic acid residue (Asp) or a lysine residue (Lys), and when there is a plurality of AAs, each AA may be the same as or different from each other and AAs are bonded to each other via an amide bond;

an N-terminal nitrogen atom of $(AA)_n$ forms an amide bond together with carbonyl group (a);

Q represents an unsubstituted phenyl group or a group represented by formula (Q-1):

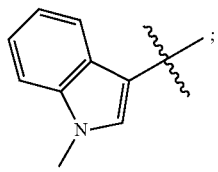

(Q-1)

and $R^{1a}$ and $R^{1b}$ each independently represent a hydrogen atom or a methyl group, or a salt thereof.

[Item 6]
The compound according to item 4 or 5, wherein h is 5, or a salt thereof.

[Item 7]
The compound according to item 1 or 4, wherein
Q is a group represented by formula (Qa-1) or formula (Qa-2);
$R^{ab}$ and $R^{ac}$ are each independently a hydrogen atom, a fluorine atom, a chlorine atom, a bromine atom, a $C_{1-6}$ alkyl group or a $C_{1-6}$ alkoxy group; and
$R^{ad}$, $R^{ae}$ and $R^{af}$ are each independently a hydrogen atom, a fluorine atom, a chlorine atom, a bromine atom, or a $C_{1-6}$ alkyl group or $C_{1-6}$ alkoxy group optionally substituted with 1 to 3 fluorine atoms, or a salt thereof.

[Item 8]
The compound according to any one of items 1 to 7, wherein n is an integer of 0 to 2, or a salt thereof.

[Item 9]
The compound according to any one of items 1 to 3, wherein $R^3$ or $R^4$ is -$(AB)_p$ and a sum of n and p is 1 or 2, or a salt thereof.

[Item 10]
The compound according to item 2 or 5, wherein $(AA)_n$ is a group represented by formula (A-1):

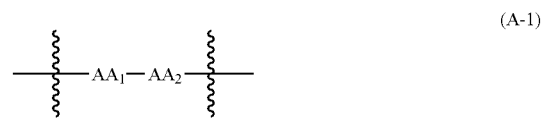

(A-1)

where $AA_1$ and $AA_2$ are each independently represented by Glu, Asp or Lys,
or a salt thereof.

[Item 11]
The compound according to item 2 or 5, wherein $(AA)_n$ is a group represented by formula (A-2):

(A-2)

where $AA_1$ and $AA_2$ are each independently represented by Glu, Asp or Lys,
or a salt thereof.

[Item 12]
The compound according to any one of items 1 to 3, wherein
$R^3$ and $R^4$ are —OH; and
n is an integer of 0 to 2,
or a salt thereof.

[Item 13]
The compound according to any one of items 1 to 3, wherein
$R^3$ and $R^4$ are -$(AB)_p$; and
n is 0 and p is 2, or n and p are each 1,
or a salt thereof.

[Item 14]
The compound according to any one of items 1 to 3, selected from the following compounds:

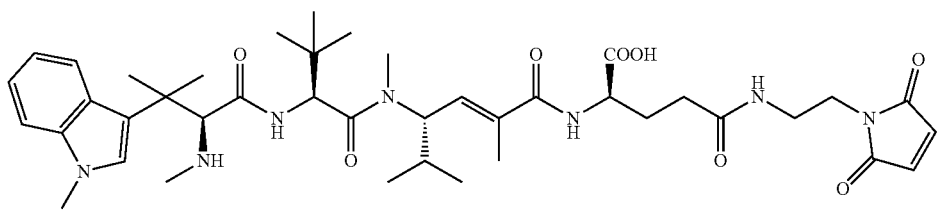

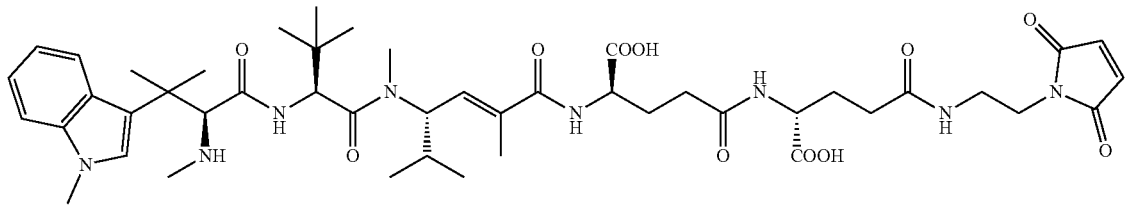

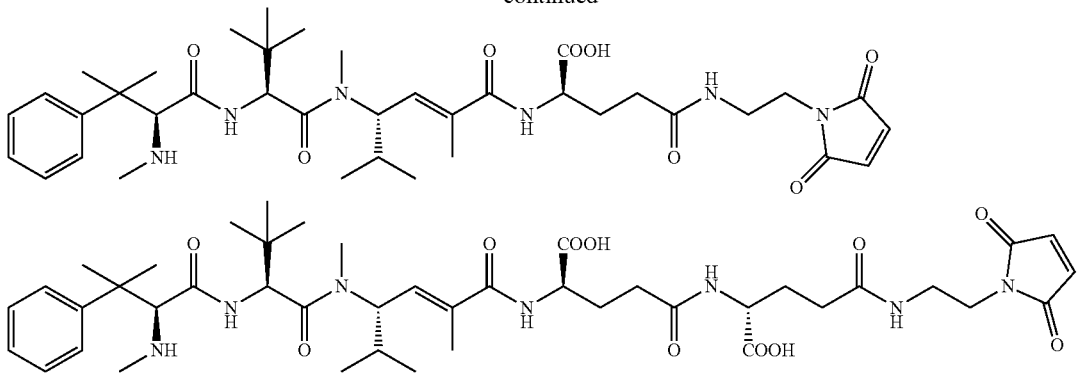

or a salt thereof.

[Item 15]

The compound according to any one of items 4 to 6, wherein the compound is the following compound,

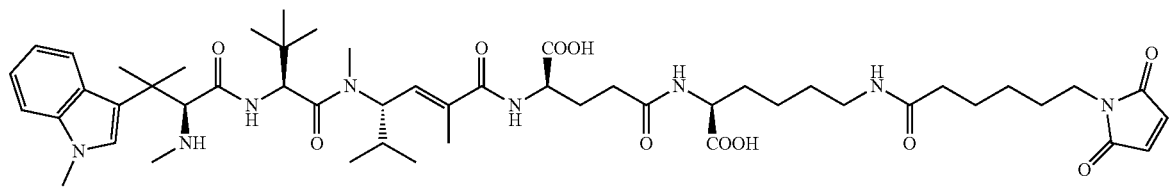 [SMILES: CN[C@H](C(=O)N[C@H](C(=O)N(C)[C@H](/C=C(\C)C(=O)N[C@H](CCC(=O)N[C@@H](CCCCNC(=O)CCCCCN1C(=O)C=CC1=O)C(=O)O)C(=O)O)C(C)C)C(C)(C)C)C(C)(C)c1cn(C)c2ccccc12]

or a salt thereof

[Item 16]

An antibody-drug conjugate represented by formula (2-1):

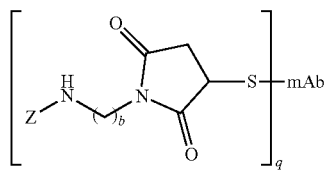

(2-1)

wherein mAb represents an antibody;

q represents an integer of 1 to 8;

b represents an integer of 1 to 5; and

Z is a group represented by formula (Z-1), formula (Z-2), formula (Z-3), formula (Za-1), formula (Za-2), formula (Za-3), formula (Za-4) or formula (Za-5):

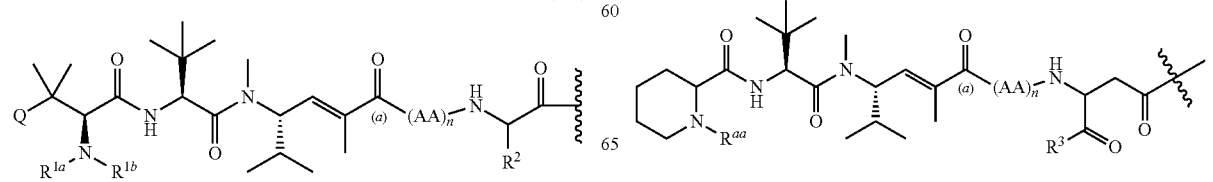

(Z-1)

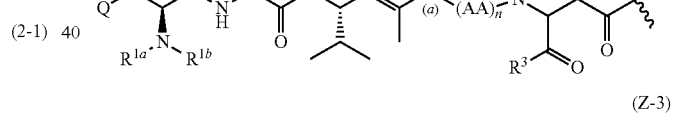

(Z-2)

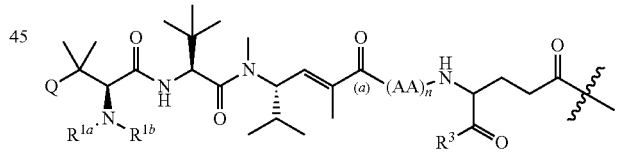

(Z-3)

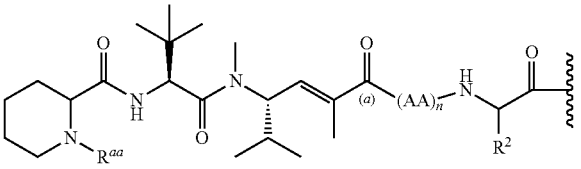

(Za-1)

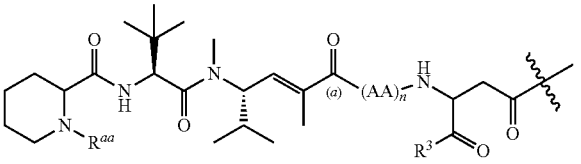

(Za-2)

-continued

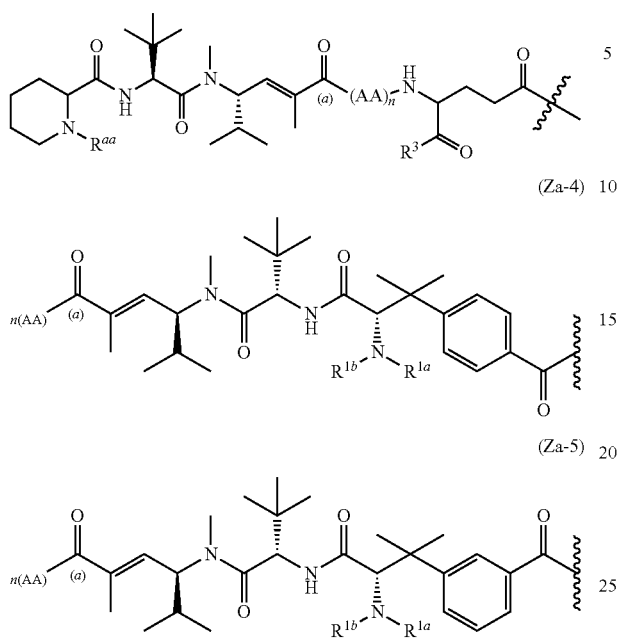

where n represents an integer of 0 to 4, where n is an integer of 1 to 4 when Z is a group represented by formula (Za-4) or formula (Za-5);

AA represents a glutamic acid residue (Glu), an aspartic acid residue (Asp) or a lysine residue (Lys), and when there is a plurality of AAs, each AA may be the same as or different from each other and AAs are bonded to each other via an amide bond;

an N-terminal nitrogen atom of $(AA)_n$ forms an amide bond together with carbonyl group (a);

$R^{aa}$ represents a $C_{1-6}$ alkyl group;

Q represents a group represented by formula (Qa-1), formula (Qa-2), formula (Qa-3), formula (Qa-4), formula (Qa-5), formula (Qa-6) or formula (Qa-7):

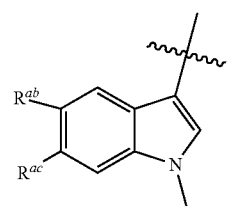

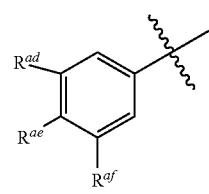

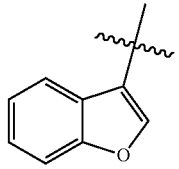

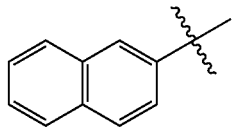

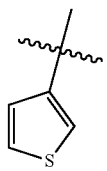

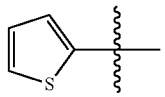

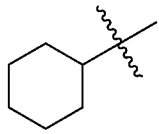

where $R^{ab}$ and $R^{ac}$ each independently represent a hydrogen atom, a halogen atom, a $C_{1-6}$ alkyl group or a $C_{1-6}$ alkoxy group; and $R^{ad}$, $R^{ae}$ and $R^{af}$ each independently represent a hydrogen atom, a halogen atom, a hydroxy group, a cyano group, an amino group, a carboxyl group, a phenyl group, or a $C_{1-6}$ alkyl group, $C_{1-6}$ alkoxy group or $C_{1-6}$ alkyl ester group optionally substituted with 1 to 3 fluorine atoms;

$R^{1a}$ and $R^{1b}$ each independently represent a hydrogen atom or a methyl group;

$R^2$ represents —$(CH_2)_u$—$COR^4$;

u represents 1 or 2;

$R^3$ and $R^4$ each independently represent —OH or -$(AB)_p$;

AB represents Glu, Asp or Lys, and when there is a plurality of ABs, each AB may be the same as or different from each other and ABs are bonded to each other via an amide bond; and p represents an integer of 1 to 4;

with a proviso that when $R^3$ or $R^4$ is -$(AB)_p$, a sum of n and p is an integer of 1 to 5, or a pharmaceutically acceptable salt thereof.

[Item 17]
The antibody-drug conjugate according to item 16, represented by formula (2-1):

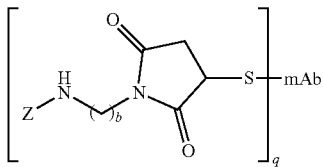

(2-1)

wherein
mAb represents an antibody;
q represents an integer of 1 to 8;
b represents an integer of 1 to 5; and
Z is a group represented by formula (Z-1), formula (Z-2) or formula (Z-3):

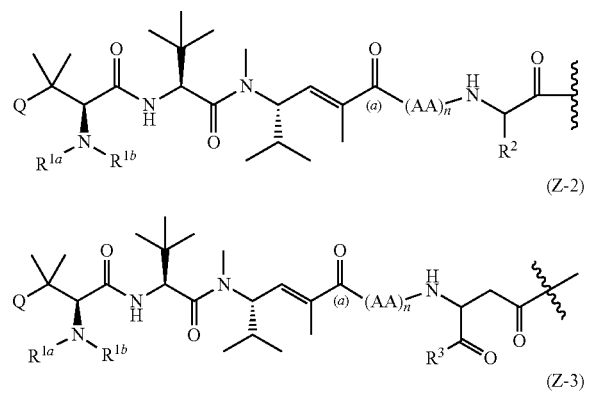

(Z-1)

(Z-2)

(Z-3)

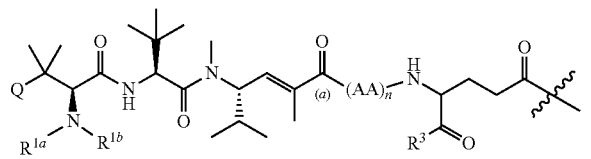

where
n represents an integer of 0 to 4;
AA represents a glutamic acid residue (Glu), an aspartic acid residue (Asp) or a lysine residue (Lys), and when there is a plurality of AAs, each AA may be the same as or different from each other and AAs are bonded to each other via an amide bond;
an N-terminal nitrogen atom of $(AA)_n$ forms an amide bond together with carbonyl group (a);
Q represents an unsubstituted phenyl group or a group represented by formula (Q-1):

(Q-1)

$R^{1a}$ and $R^{1b}$ each independently represent a hydrogen atom or a methyl group;
$R^2$ represents —$(CH_2)_u$—$COR^4$;
u represents 1 or 2;
$R^3$ and $R^4$ each independently represent —OH or -$(AB)_p$;
AB represents Glu, Asp or Lys, and when there is a plurality of ABs, each AB may be the same as or different from each other and ABs are bonded to each other via an amide bond; and
p represents an integer of 1 to 4;
with a proviso that when $R^3$ or $R^4$ is -$(AB)_p$, a sum of n and p is an integer of 1 to 5,
or a pharmaceutically acceptable salt thereof.

[Item 18]
The antibody-drug conjugate according to item 16 or 17, wherein b is 2,
or a pharmaceutically acceptable salt thereof.

[Item 19]
An antibody-drug conjugate represented by formula (2-2):

(2-2)

wherein
mAb represents an antibody;
q represents an integer of 1 to 8;
h represents an integer of 1 to 5; and
Z' is a group represented by formula (Z-4), formula (Z-5), formula (Za-6), formula (Za-7), formula (Za-8), formula (Za-9), formula (Za-10) or formula (Za-11):

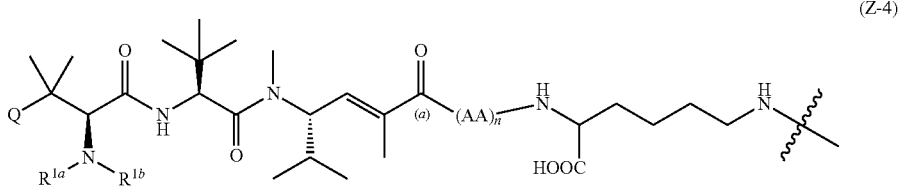

(Z-4)

(Z-5)

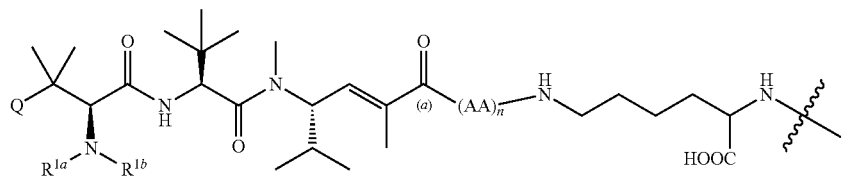

(Za-6)

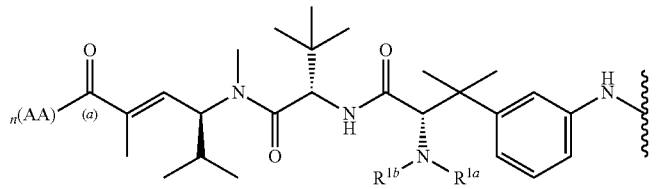

(Za-7)

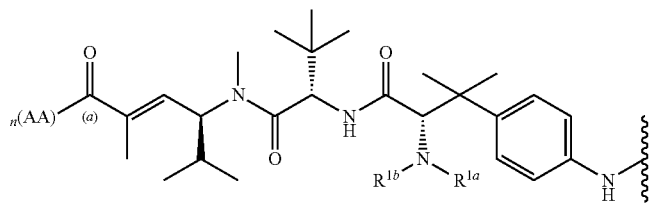

(Za-8)

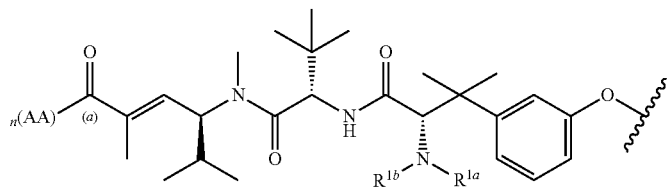

(Za-9)

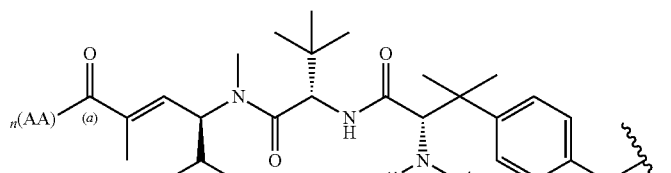

(Za-10)

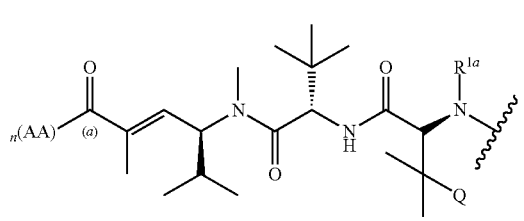

(Za-11)

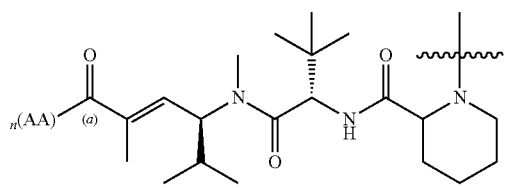

where n represents an integer of 0 to 4, where n is an integer of 1 to 4 when Z is a group represented by formula (Za-6), formula (Za-7), formula (Za-8), formula (Za-9), formula (Za-10) or formula (Za-11);

AA represents a glutamic acid residue (Glu), an aspartic acid residue (Asp) or a lysine residue (Lys), and when there is a plurality of AAs, each AA may be the same as or different from each other and AAs are bonded to each other via an amide bond;

an N-terminal nitrogen atom of $(AA)_n$ forms an amide bond together with carbonyl group (a);

Q represents a group represented by formula (Qa-1), formula (Qa-2), formula (Qa-3), formula (Qa-4), formula (Qa-5), formula (Qa-6) or formula (Qa-7):

(Qa-1)

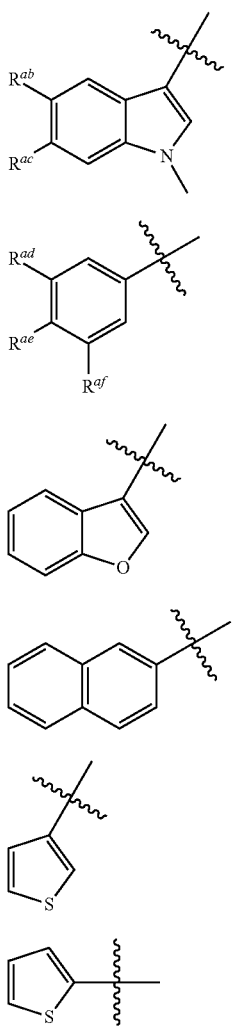

(Qa-2)

(Qa-3)

(Qa-4)

(Qa-5)

(Qa-6)

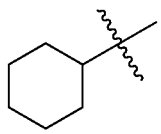

(Qa-7)

where $R^{ab}$ and $R^{ac}$ each independently represent a hydrogen atom, a halogen atom, a $C_{1-6}$ alkyl group or a $C_{1-6}$ alkoxy group; and $R^{ad}$, $R^{ae}$ and $R^{af}$ each independently represent a hydrogen atom, a halogen atom, a hydroxy group, a cyano group, an amino group, a carboxyl group, a phenyl group, or a $C_{1-6}$ alkyl group, $C_{1-6}$ alkoxy group or $C_{1-6}$ alkyl ester group optionally substituted with 1 to 3 fluorine atoms; and $R^{1a}$ and $R^{1b}$ each independently represent a hydrogen atom or a methyl group, or a pharmaceutically acceptable salt thereof.

[Item 20]

The antibody-drug conjugate according to item 19, represented by formula (2-2):

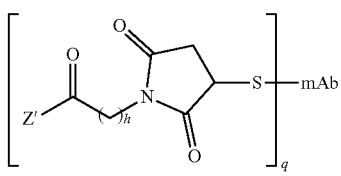

(2-2)

wherein mAb represents an antibody;

q represents an integer of 1 to 8;

h represents an integer of 1 to 5; and

Z' is a group represented by formula (Z-4) or formula (Z-5):

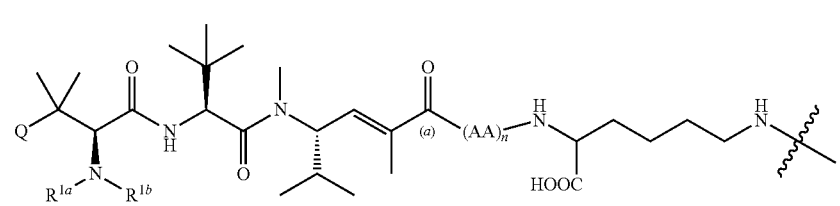

(Z-4)

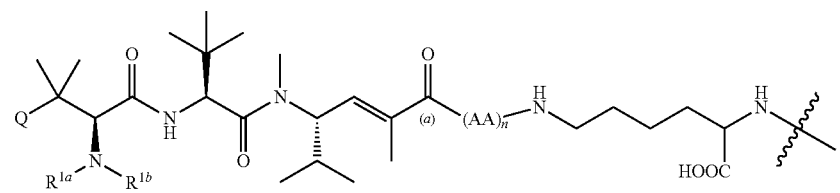

(Z-5)

where
n represents an integer of 0 to 4;
AA represents a glutamic acid residue (Glu), an aspartic acid residue (Asp) or a lysine residue (Lys), and when there is a plurality of AAs, each AA may be the same as or different from each other and AAs are bonded to each other via an amide bond;
an N-terminal nitrogen atom of $(AA)_n$ forms an amide bond together with carbonyl group (a);
Q represents an unsubstituted phenyl group or a group represented by formula (Q-1):

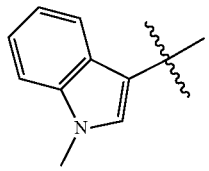

(Q-1)

and
$R^{1a}$ and $R^{1b}$ each independently represent a hydrogen atom or a methyl group,
or a pharmaceutically acceptable salt thereof.

[Item 21]
The antibody-drug conjugate according to item 19 or 20, wherein h is 5,
or a pharmaceutically acceptable salt thereof.

[Item 22]
The antibody-drug conjugate according to item 16 or 19, wherein
Q is a group represented by formula (Qa-1) or formula (Qa-2);
$R^{ab}$ and $R^{ac}$ are each independently a hydrogen atom, a fluorine atom, a chlorine atom, a bromine atom, a $C_{1-6}$ alkyl group or a $C_{1-6}$ alkoxy group; and
$R^{ad}$, $R^{ae}$ and $R^{af}$ are each independently a hydrogen atom, a fluorine atom, a chlorine atom, a bromine atom, or a $C_{1-6}$ alkyl group or $C_{1-6}$ alkoxy group optionally substituted with 1 to 3 fluorine atoms, or a pharmaceutically acceptable salt thereof.

[Item 23]
The antibody-drug conjugate according to any one of items 16 to 22, wherein n is an integer of 0 to 2,
or a pharmaceutically acceptable salt thereof.

[Item 24]
The antibody-drug conjugate according to any one of items 16 to 18, wherein $R^3$ or $R^4$ is $-(AB)_p$ and a sum of n and p is 1 or 2,
or a pharmaceutically acceptable salt thereof.

[Item 25]
The antibody-drug conjugate according to item 17 or 20, wherein $(AA)_n$ is a group represented by formula (A-1):

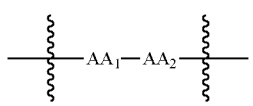

(A-1)

where $AA_1$ and $AA_2$ are each independently represented by Glu, Asp or Lys,
or a pharmaceutically acceptable salt thereof.

[Item 26]
The antibody-drug conjugate according to item 17 or 20, wherein $(AA)_n$ is a group represented by formula (A-2):

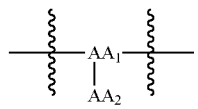

(A-2)

where $AA_1$ and $AA_2$ are each independently represented by Glu, Asp or Lys,
or a pharmaceutically acceptable salt thereof.

[Item 27]
The antibody-drug conjugate according to any one of items 16 to 18, wherein
$R^3$ and $R^4$ are —OH; and
n is an integer of 0 to 2,
or a pharmaceutically acceptable salt thereof.

[Item 28]
The antibody-drug conjugate according to any one of items 16 to 18, wherein
$R^3$ and $R^4$ are $-(AB)_p$; and
n is 0 and p is 2, or n and p are each 1,
or a pharmaceutically acceptable salt thereof.

[Item 29]
The antibody-drug conjugate according to any one of items 16 to 28, wherein mAb is brentuximab, trastuzumab, inotuzumab, gemtuzumab, glembatumumab, labetuzumab, sacituzumab, lifastuzumab, indusatumab, polatuzumab, pinatuzumab, coltuximab, indatuximab, milatuzumab, rovalpituzumab, anetumab, tisotumab, mirvetuximab, lorvotuzumab, rituximab, depatuxizumab, denintuzumab, enfortumab, telisotuzumab, vandortuzumab, sofituzumab, vorsetuzumab, mirvetuximab, naratuximab, cantuzumab, laprituximab, bivatuzumab, vadastuximab, lupartumab, aprutumab, abagovomab, abciximab, abituzumab, abrilumab, actoxumab, adalimumab, adecatumumab, aducanumab, afasevikumab, afelimomab, alacizumab, alemtuzumab, alirocumab, altumomab, amatuximab, anatumomab, anifrolumab, anrukinzumab, apolizumab, arcitumomab, ascrinvacumab, aselizumab, atezolizumab, atinumab, atorolimumab, avelumab, azintuxizumab, bapineuzumab, basiliximab, bavituximab, bectumomab, begelomab, belimumab, benralizumab, bertilimumab, besilesomab, bevacizumab, bezlotoxumab, biciromab, bimagrumab, bimekizumab, bleselumab, blinatumomab, blontuvetmab, blosozumab, bococizumab, brazikumab, briakinumab, brodalumab, brolucizumab, brontictuzumab, burosumab, cabiralizumab, camrelizumab, caplacizumab, capromab, carlumab, carotuximab, catumaxomab, cedelizumab, certolizumab, cetuximab, citatuzumab, cixutumumab, clenoliximab, clivatuzumab, codrituzumab, conatumumab, concizumab, cosfroviximab, crenezumab, crizanlizumab, crotedumab, dacetuzumab, daclizumab, dalotuzumab, dapirolizumab, daratumumab, dectrekumab, demcizumab, denosumab, detumomab, dezamizumab, dinutuximab, diridavumab, domagrozumab, dorlimomab, drozitumab, duligotuzumab, dupilumab, durvalumab, dusigitumab, duvortuxizumab, ecromeximab, eculizumab, edobacomab, edrecolomab, efalizumab, efungumab, eldelumab, elezanumab, elotuzumab, elsilimomab, emactuzumab, emapalumab, emibetuzumab, emicizumab, enavatuzumab, enlimomab, enoblituzumab, enokizumab, enoticumab, ensituximab, epitumomab, epratuzumab, eptinezumab, erenumab, erlizumab, ertumaxomab, etaracizumab, etrolizumab, evinacumab, evolocumab, exbivirumab, faralimomab, farletuzumab, fasinumab, felvizumab, fezakinumab, ficlatuzumab, figitumumab, firivumab, flanvotumab, fletikumab, fontolizumab, foralumab, foravirumab, fremanezumab, fresolimumab, frunevetmab, fulranumab, futuximab, galcanezumab, galiximab, ganitumab, gantenerumab, gatipotuzumab, gavilimomab, gedivumab, gevokizumab, gilvetmab, girentuximab, golimumab, guselkumab, ibalizumab, ibritumomab, icrucumab, idarucizumab, ifabotuzumab, igovomab, imalumab, imciromab, imgatuzumab, inclacumab, inebilizumab, infliximab, inolimomab, intetumumab, ipilimumab, iratumumab, isatuximab, itolizumab, ixekizumab, keliximab, lacnotuzumab, lampalizumab, lanadelumab, landogrozumab, larcaviximab, lebrikizumab, lemalesomab, lenzilumab, lerdelimumab, lesofavumab, letolizumab, lexatumumab, libivirumab, lifatuzumab, ligelizumab, lilotomab, lintuzumab, lirilumab, lodelcizumab, lokivetmab, lorvotuzumab, losatuximab, lucatumumab, lulizumab, lumretuzumab, lutikizumab, mapatumumab, margetuximab, maslimomab, matuzumab, mavrilimumab, mepolizumab, metelimumab, minretumomab, mitumomab, modotuximab, mogamulizumab, monalizumab, morolimumab, motavizumab, moxetumomab, muromonab, nacolomab, namilumab, naptumomab, narnatumab, natalizumab, navicixizumab, navivumab, nebacumab, necitumumab, nemolizumab, nerelimomab, nesvacumab, nimotuzumab, nivolumab, obiltoxaximab, obinutuzumab, ocaratuzumab, ocrelizumab, odulimomab, ofatumumab, olaratumab, oleclumab, olendalizumab, olokizumab, omalizumab, onartuzumab, ontuxizumab, opicinumab, oportuzumab, oregovomab, oreticumab, orticumab, otelixizumab, otlertuzumab, oxelumab, ozanezumab, ozoralizumab, pagibaximab, palivizumab, pamrevlumab, panitumumab, panobacumab, parsatuzumab, pascolizumab, pasotuxizumab, pateclizumab, patritumab, pembrolizumab, perakizumab, pertuzumab, pexelizumab, pidilizumab, placulumab, plozalizumab, ponezumab, porgaviximab, prezalumab, priliximab, pritoxaximab, pritumumab, quilizumab, racotumomab, radretumab, rafivirumab, ralpancizumab, ramucirumab, ranevetmab, ranibizumab, raxibacumab, refanezumab, regavirumab, remtolumab, reslizumab, rilotumumab, rinucumab, risankizumab, rivabazumab, robatumumab, roledumab, romosozumab, rontalizumab, rosmantuzumab, rovelizumab, rozanolixizumab, ruplizumab, samalizumab, sarilumab, satralizumab, satumomab, secukinumab, selicrelumab, seribantumab, setoxaximab, sevirumab, sibrotuzumab, sifalimumab, siltuximab, simtuzumab, siplizumab, sirukumab, solanezumab, solitomab, sontuzumab, stamulumab, sulesomab, suptavumab, suvizumab, suvratoxumab, tabalumab, tadocizumab, talizumab, tamtuvetmab, tanezumab, taplitumomab, tarextumab, tavolixizumab, fanolesomab, nofetumomab, pintumomab, tefibazumab, telimomab, telisotuzumab, tenatumomab, teneliximab, teplizumab, teprotumumab, tesidolumab, tezepelumab, tigatuzumab, tildrakizumab, timigutuzumab, timolumab, tocilizumab, tomuzotuximab, toralizumab, tosatoxumab, tositumomab, tovetumab, tralokinumab, tregalizumab, tremelimumab, trevogrumab, tucotuzumab, tuvirumab, ublituximab, ulocuplumab, urelumab, urtoxazumab, ustekinumab, utomilumab, vantictumab, vanucizumab, vapaliximab, varisakumab, varlilumab, vatelizumab, vedolizumab, veltuzumab, vepalimomab, vesencumab, visilizumab, vobarilizumab, volociximab, vonlerolizumab, votumumab, vunakizumab, tacatuzumab, zalutumumab, zanolimumab, ziralimumab, zolimomab, camidanlumab, cofetuzumab, ladiratuzumab, loncastuximab, telisotuzumab, enapotamab, an antibody of AMG 595 or anti-embigin antibody, or a pharmaceutically acceptable salt thereof.

[Item 30]

The antibody-drug conjugate according to item 29, wherein mAb is brentuximab, trastuzumab, inotuzumab, gemtuzumab, labetuzumab, polatuzumab, coltuximab, indatuximab, anetumab, rituximab, denintuzumab, laprituximab, vadastuximab, glembatumumab, cetuximab, alemtuzumab or depatuxizumab, or a pharmaceutically acceptable salt thereof.

[Item 31]

The antibody-drug conjugate according to item 30, wherein mAb is brentuximab or trastuzumab, or a pharmaceutically acceptable salt thereof.

[Item 32]

A pharmaceutical composition comprising the antibody-drug conjugate according to any one of items 16 to 31 or a pharmaceutically acceptable salt thereof.

[Item 33]

A pharmaceutical composition comprising:

the antibody-drug conjugate according to any one of items 16 to 31 or a pharmaceutically acceptable salt thereof; and one or more anticancer compounds selected from the group consisting of an anticancer alkylating agent, an anticancer antimetabolite, an anticancer antibiotic, an anticancer platinum coordination compound, an anticancer camptothecin derivative, an anticancer tyrosine kinase inhibitor, an anticancer serine-threonine kinase inhibitor, an anticancer phospholipid kinase inhibitor, an anticancer monoclonal antibody, an interferon, a biological response modifier, a hormonal agent, an immune checkpoint inhibitor, an epigenetics-related molecule inhibitor and a post-translational protein modification inhibitor, or pharmaceutically acceptable salts thereof.

[Item 34]

An anticancer agent comprising the antibody-drug conjugate according to any one of items 16 to 31 or a pharmaceutically acceptable salt thereof.

[Item 35]

The anticancer agent according to item 34, wherein cancer is breast cancer, gastric cancer, lung cancer, liver cancer, cervical cancer, large bowel cancer, rectal cancer, colon cancer, glioma, lymphoma, ovarian cancer, pancreatic cancer, prostate cancer, renal cancer, urothelial cancer, skin cancer, thyroid cancer, bladder cancer, head and neck cancer, endometrial cancer, mesothelioma, melanoma, multiple myeloma or leukemia.

[Item 36]

A method of treating cancer, comprising administering the antibody-drug conjugate according to any one of items 16 to 31 or a pharmaceutically acceptable salt thereof to a patient in need thereof.

[Item 37]

Use of the compound according to any one of items 1 to 15 or a salt thereof for producing an anticancer agent.

[Item 38]

Use of the antibody-drug conjugate according to any one of items 16 to 31 or a pharmaceutically acceptable salt thereof for producing an anticancer agent.

[Item 39]

The antibody-drug conjugate according to any one of items 16 to 31 or a pharmaceutically acceptable salt thereof for use in treatment of cancer.

[Item 40]

The antibody-drug conjugate according to any one of items 16 to 31 or a pharmaceutically acceptable salt thereof for use in combination with one or more anticancer compounds selected from the group consisting of an anticancer alkylating agent, an anticancer antimetabolite, an anticancer antibiotic, an anticancer platinum coordination compound, an anticancer camptothecin derivative, an anticancer tyrosine kinase inhibitor, an anticancer serine-threonine kinase inhibitor, an anticancer phospholipid kinase inhibitor, an anticancer monoclonal antibody, an interferon, a biological response modifier, a hormonal agent, an immune checkpoint inhibitor, an epigenetics-related molecule inhibitor and a post-translational protein modification inhibitor, or pharmaceutically acceptable salts thereof. to treat cancer.

Advantageous Effects of Invention

Antibody-drug conjugate formed of the hemiasterlin derivative according to the present invention and an antibody exhibits cytotoxic activity specifically to antigen-expressing cells and has low cytotoxicity in nomal cells other than the antigen-expressing cells, and therefore, can be anticancer agent excellent in safety.

DESCRIPTION OF EMBODIMENTS

In the present specification, the "$C_{1-6}$ alkyl group" means a linear or branched saturated hydrocarbon group having 1 to 6 carbon atoms. Examples of the "$C_{1-6}$ alkyl group" preferably include a "$C_{1-4}$ alkyl group", more preferably include a "$C_{1-3}$ alkyl group", further preferably include a methyl group, an ethyl group, a propyl group or an isopropyl group, and particularly preferably include a methyl group or an ethyl group.

Specific examples of the "$C_{1-3}$ alkyl group" include a methyl group, an ethyl group, a propyl group and an isopropyl group. Specific examples of the "$C_{1-4}$ alkyl group" include a butyl group, a 1,1-dimethylethyl group, a 1-methylpropyl group and a 2-methylpropyl group in addition to those mentioned as the specific examples of the "$C_{1-3}$ alkyl group". Specific examples of the "$C_{1-6}$ alkyl group" include a pentyl group, a 3-methylbutyl group, a 2-methylbutyl group, a 2,2-dimethylpropyl group, a 1-ethylpropyl group, a 1,1-dimethylpropyl group, a hexyl group, a 4-methylpentyl group, a 3-methylpentyl group, a 2-methylpentyl group, a 1-methylpentyl group, a 3,3-dimethylbutyl group, a 2,2-dimethylbutyl group, a 1,1-dimethylbutyl group and a 1,2-dimethylbutyl group in addition to those mentioned as the specific examples of the "$C_{1-4}$ alkyl group".

In the present specification, the "$C_{1-6}$ alkyl ester" means an ester (—COOR') in which R' is the "$C_{1-6}$ alkyl group" described above. Examples of the "$C_{1-6}$ alkyl ester" preferably include a "$C_{1-4}$ alkyl ester", more preferably include a "$C_{1-3}$ alkyl ester", further preferably include a methyl ester, an ethyl ester, an isopropyl ester or a tert-butyl ester, and particularly preferably include a methyl ester or an ethyl ester.

Specific examples of the "$C_{1-3}$ alkyl ester" include a methyl ester, an ethyl ester, a propyl ester and an isopropyl ester. Specific examples of the "$C_{1-4}$ alkyl ester" include a butyl ester and a tert-butyl ester in addition to those mentioned as the specific examples of the "$C_{1-3}$ alkyl ester". Specific examples of the "$C_{1-6}$ alkyl ester" include a pentyl ester, a 3-methylbutyl ester, a 2-methylbutyl ester, a 2,2-dimethylpropyl ester, a 1-ethylpropyl ester, a 1,1-dimethylpropyl ester, a hexyl ester, a 4-methylpentyl ester, a 3-methylpentyl ester, a 2-methylpentyl ester, a 1-methylpentyl ester, a 3,3-dimethylbutyl ester, a 2,2-dimethylbutyl ester, a 1,1-dimethylbutyl ester and a 1,2-dimethylbutyl ester in addition to those mentioned as the specific examples of the "$C_{1-4}$ alkyl ester".

In the present specification, the "$C_{1-6}$ alkoxy group" means an oxy group substituted with a "$C_{1-6}$ alkyl group". Examples of the "$C_{1-6}$ alkoxy group" preferably include a "$C_{1-4}$ alkoxy group", more preferably include a "$C_{1-3}$ alkoxy group", further preferably include a methoxy group, an ethoxy group, a propoxy group or a 1-methylethoxy group, and particularly preferably include a methoxy group or an ethoxy group.

Specific examples of the "$C_{1-3}$ alkoxy group" include a methoxy group, an ethoxy group, a propoxy group or a 1-methylethoxy group. Specific examples of the "$C_{1-4}$ alkoxy group" include a butoxy group, a 1,1-dimethylethoxy group, a 1-methylpropoxy group and a 2-methylpropoxy group in addition to those mentioned as the specific examples of the "$C_{1-3}$ alkoxy group". Specific examples of the "$C_{1-6}$ alkoxy group" include a pentyloxy group, a 3-methylbutoxy group, a 2-methylbutoxy group, a 2,2-dimethylpropoxy group, a 1-ethylpropoxy group, a 1,1-dimethylpropoxy group, a hexyloxy group, a 4-methylpentyloxy group, a 3-methylpentyloxy group, a 2-methylpentyloxy group, a 1-methylpentyloxy group, a 3,3-dimethylbutoxy group, a 2,2-dimethylbutoxy group, a 1,1-dimethylbutoxy group and a 1,2-dimethylbutoxy group in addition to those mentioned as the specific examples of the "$C_{1-4}$ alkoxy group".

In the present specification, examples of the "halogen atom" include a fluorine atom, a chlorine atom, a bromine atom or an iodine atom. Preferably, examples thereof include a fluorine atom or a chlorine atom, and more preferably, examples thereof include a fluorine atom.

<Hemiasterlin Derivative>

A compound represented by formula (1-1) or formula (1-2), and a salt thereof (hereinafter, may be referred to as the "hemiasterlin derivative according to the present invention") are as follows:

(1) Compound Represented by Formula (1-1) or Salt Thereof

At first, among hemiasterlin derivatives according to the present invention, a compound represented by the following formula (1-1) and a salt thereof will be explained:

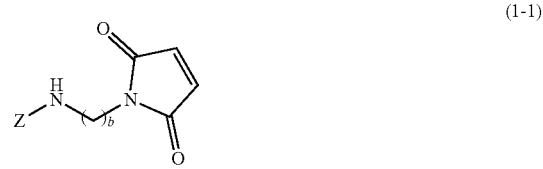

(1-1)

In the formula, b represents an integer of 1 to 5. That is, b is 1, 2, 3, 4 or 5. Examples of one aspect of b include an integer of 1 to 4; examples of another aspect thereof include an integer of 1 to 3; and examples of another aspect thereof include 2 or 3.

In the formula, Z represents a group represented by formula (Z-1), formula (Z-2), formula (Z-3), formula (Za-1), formula (Za-2), formula (Za-3), formula (Za-4) or formula (Za-5):

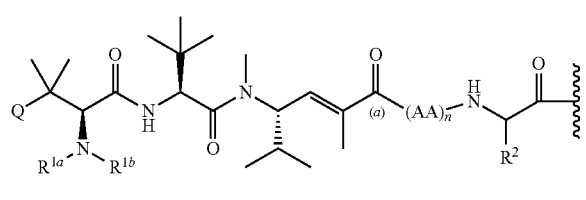

(Z-1)

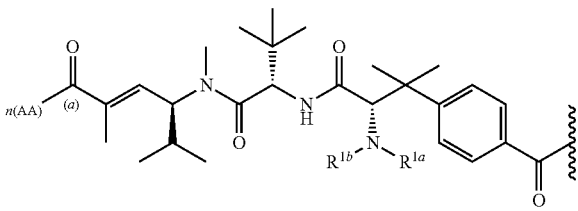

(Za-4)

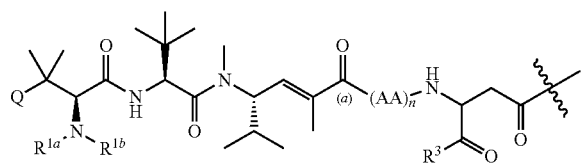

(Z-2)

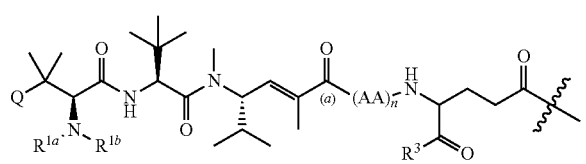

(Z-3)

(Za-5)

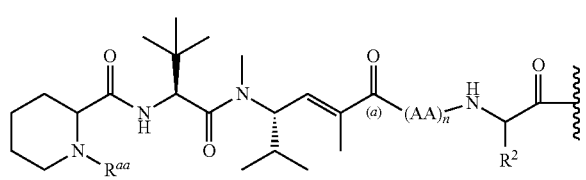

(Za-1)

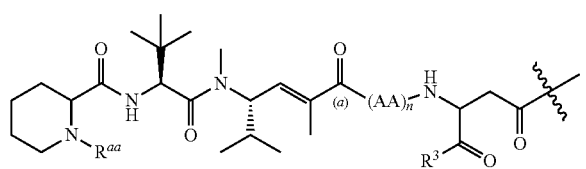

(Za-2)

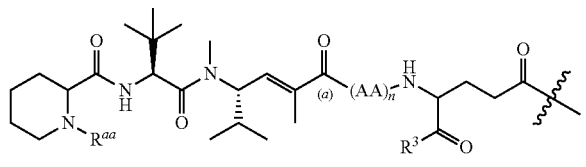

(Za-3)

In these formulas, AA represents a glutamic acid residue, an aspartic acid residue or a lysine residue, and preferable examples thereof include a glutamic acid residue or an aspartic acid residue. In the present specification, except when it is particularly necessary to make distinction, the three letter abbreviated notations shown below may be used for representing both α-amino acids and corresponding amino acid residues. In addition, the optical activity of the α-amino acids may include any of DL form, D form and L form unless otherwise specified. For example, "glutamic acid" or "Glu" represents DL-glutamic acid or a residue thereof, D-glutamic acid or a residue thereof, or L-glutamic acid or a residue thereof.

Asp: aspartic acid, Glu: glutamic acid, Lys: lysine.

In these formulas, n represents an integer of 0 to 4. That is, n is 0, 1, 2, 3 or 4. Examples of one aspect of n include an integer of 0 to 2; examples of another aspect thereof include 0 or 1; examples of another aspect thereof include 1 or 2; examples of another aspect thereof include an integer of 1 to 3; and examples of another aspect thereof include 0. Provided that n is an integer of 1 to 4 when Z is a group represented by formula (Za-4) or formula (Za-5).

When there is a plurality of AAs, each AA may be the same as or different from each other and AAs are bonded to each other via an amide bond. "AAs are bonded to each other via an amide bond" means that the carboxyl group of one amino acid and the amino group of another amino acid are condensed to form an amide bond. For example, when n is 2 and two AAs are both Glu, nitrogen atom (d) of one Glu and carbonyl group (c) of the other Glu may be linked by forming an amide bond, as represented by the following formula:

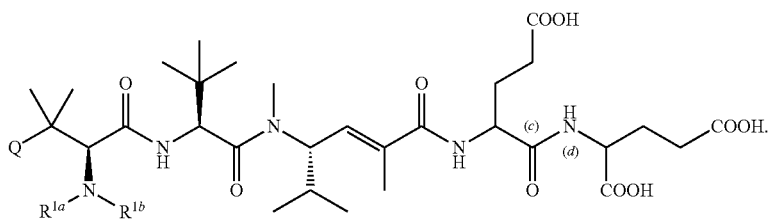

The N-terminal nitrogen atom of (AA)$_n$ forms an amide bond together with carbonyl group (a). "The N-terminal nitrogen atom of AA forms an amide bond together with carbonyl group (a)" means that, for example, when AA is Asp, nitrogen atom (b) of Asp and carbonyl group (a) are linked to form an amide bond, as represented by the following formula:

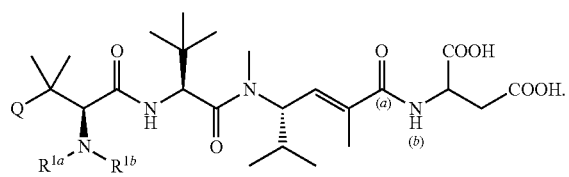

Examples of one aspect of (AA)$_n$ include a group represented by formula (A-1) or formula (A-2), wherein n is 2.

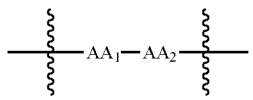
(A-1)

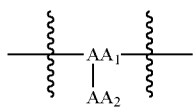
(A-2)

In these formulas, AA$_1$ and AA$_2$ are each independently represented by Glu, Asp or Lys.

In formula (Z-1), formula (Z-2), and formula (Z-3), Q represents a group represented by formula (Qa-1), formula (Qa-2), formula (Qa-3), formula (Qa-4), formula (Qa-5), formula (Qa-6) or formula (Qa-7):

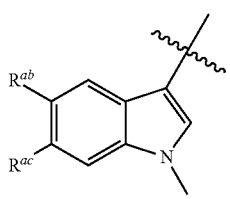
(Qa-1)

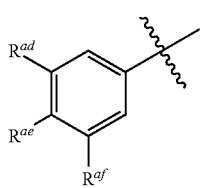
(Qa-2)

-continued

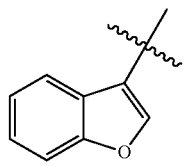
(Qa-3)

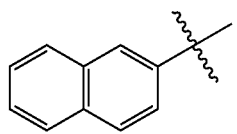
(Qa-4)

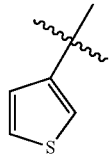
(Qa-5)

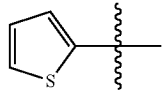
(Qa-6)

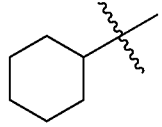
(Qa-7)

In formula (Qa-1), $R^{ab}$ and $R^{ac}$ each independently represent a hydrogen atom, a halogen atom, a C$_{1-6}$ alkyl group or a C$_{1-6}$ alkoxy group. In formula (Qa-2), $R^{ad}$, $R^{ae}$ and $R^{af}$ each independently represent a hydrogen atom, a halogen atom, a hydroxy group, a cyano group, an amino group, a carboxyl group, a phenyl group, or a C$_{1-6}$ alkyl group, C$_{1-6}$ alkoxy group or C$_{1-6}$ alkyl ester group optionally substituted with 1 to 3 fluorine atoms. The halogen atom may be, for example, a fluorine atom, a chlorine atom or a bromine atom.

Q may be a group represented by formula (Qa-2) or formula (Qa-1), or may be an unsubstituted phenyl group or a group represented by formula (Q-1):

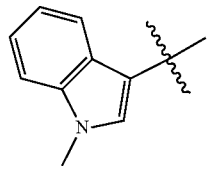
(Q-1)

In formula (Z-1), formula (Z-2), formula (Z-3), formula (Za-4) and formula (Za-5), $R^{1a}$ and $R^{1b}$ each independently represent a hydrogen atom or a methyl group. It is preferable that $R^{1a}$ be a methyl group and $R^{1b}$ be a hydrogen atom.

In the present specification, a hydrogen atom may be $^1H$ or $^2H(D)$. That is, for example, a deuterated product in which one or two or more $^1H$ of the compound represented by formula (1-1) are converted into $^2H(D)$ is also encompassed in the compound represented by formula (1-1).

In formula (Z-1) and formula (Za-1), $R^2$ represents —$(CH_2)_u$—$COR^4$. Here, u is 1 or 2 and $R^4$ represents —OH or -$(AB)_p$. AB represents Glu, Asp or Lys, and when there is a plurality of ABs, each AB may be the same as or different from each other and ABs are bonded to each other via an amide bond. Examples of AB preferably include Glu or Asp. p is an integer of 1 to 4, that is, 1, 2, 3 or 4. Examples of one aspect of p include 1 or 2; examples of another aspect thereof include 1; examples of another aspect thereof include 2; examples of another aspect thereof include an integer of 1 to 3; and examples of another aspect thereof include 3.

In formula (Z-2), formula (Z-3), formula (Za-2) and formula (Za-3), $R^3$ represents —OH or -$(AB)_p$. Here, -$(AB)_p$ is as defined in formula (Z-1) and formula (Za-1).

In formula (Z-1), formula (Z-2), formula (Z-3), formula (Za-1), formula (Za-2) and formula (Za-3), when $R^3$ or $R^4$ is -$(AB)_p$, the sum of n and p is an integer of 1 to 5, that is, 1, 2, 3, 4 or 5. Examples of one aspect of the sum of n and p include an integer of 1 to 4; examples of another aspect thereof include an integer of 1 to 3; and examples of another aspect thereof include 1 or 2.

In formula (Za-1), formula (Za-2) and formula (Za-3), $R^{aa}$ is a $C_{1-6}$ alkyl group. $R^{aa}$ may be, for example, a methyl group, an ethyl group, a propyl group, an isopropyl group or the like.

In one aspect, Z may be a group represented by formula (Z-1), formula (Z-2) or formula (Z-3), and Q may be an unsubstituted phenyl group or a group represented by formula (Q-1).

Examples of one aspect of a combination of $R^3$, $R^4$ and n in formula (1-1) include a combination in which $R^3$ and $R^4$ represent —OH and n is an integer of 0 to 2. Alternatively, examples of one aspect of a combination of $R^3$, $R^4$, n and p include a combination in which $R^3$ and $R^4$ are -$(AB)_p$, and n is 0 and p is 2, or n and p are 1.

Examples of one aspect of the hemiasterlin derivative according to the present invention include the following (1-1-A).

(1-1-A)

A compound, wherein, in formula (1-1), b is 2, 3, 4 or 5;

n is an integer of 0 or 1;

Z is a group represented by formula (Z-1), formula (Z-2) or formula (Z-3);

Q is an unsubstituted phenyl group or a group represented by formula (Q-1);

$R^{1a}$ is a methyl group;

$R^{1b}$ is a hydrogen atom;

AA is Glu or Asp;

$R^2$ is —$(CH_2)_u$—$COR^4$;

u is an integer of 1 or 2;

$R^3$ is —OH or -$(AB)_p$;

$R^4$ is —OH or -$(AB)_p$;

p is an integer of 1 or 2;

AB represents Glu or Asp, and when there is a plurality of ABs, each AB may be the same as or different from each other and ABs are bonded to each other via an amide bond; and when $R^3$ or $R^4$ is -$(AB)_p$, the sum of n and p is 1 or 2, or a salt thereof.

Examples of one aspect of the hemiasterlin derivative according to the present invention include any of the following compounds or salts thereof:

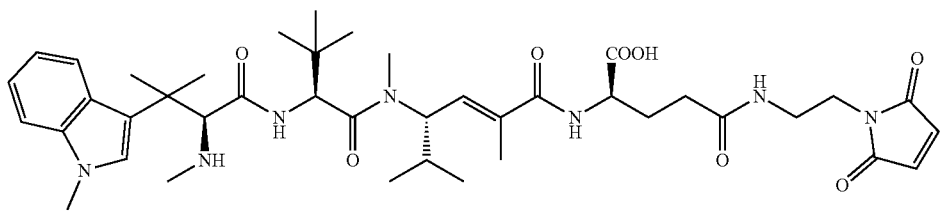

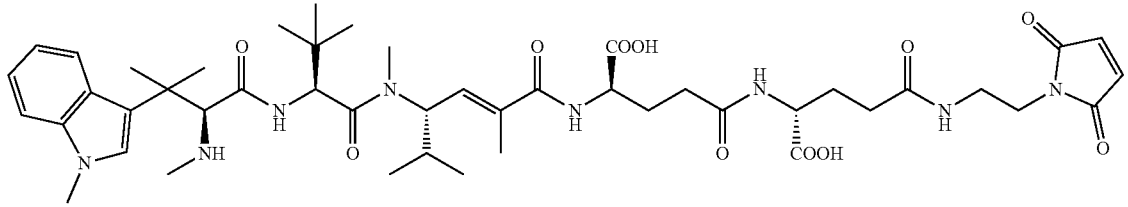

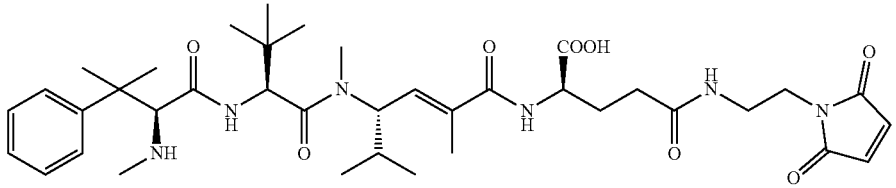

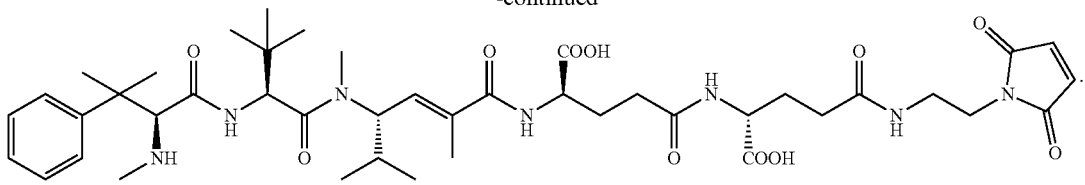

(2) Compound Represented by Formula (1-2) or Salt Thereof

Next, among hemiasterlin derivatives according to the present invention, a compound represented by the following formula (1-2) and a salt thereof will be explained:

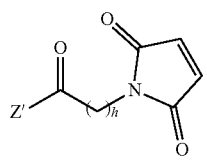
(1-2)

In the formula, h represents an integer of 1 to 5. That is, h is 1, 2, 3, 4 or 5. Examples of one aspect of h include an integer of 2 to 5; examples of another aspect thereof include an integer of 3 to 5; and examples of another aspect thereof include 4 or 5.

In the formula, Z' represents a group represented by formula (Z-4), formula (Z-5), formula (Za-6), formula (Za-7), formula (Za-8), formula (Za-9), formula (Za-10) or formula (Za-11):

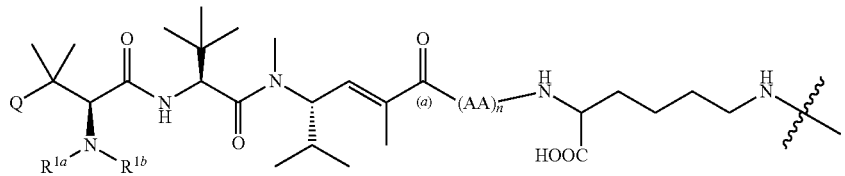
(Z-4)

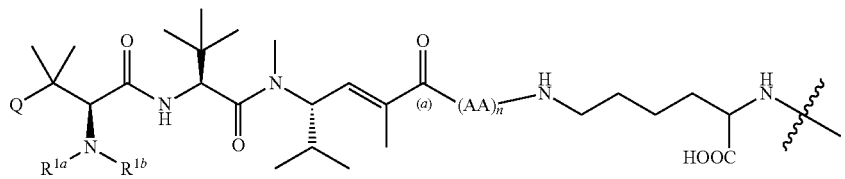
(Z-5)

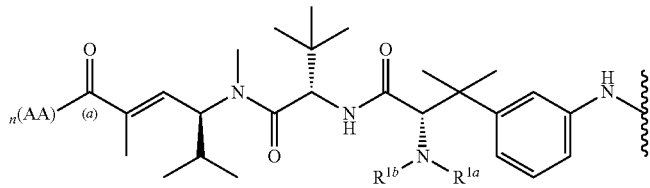
(Za-6)

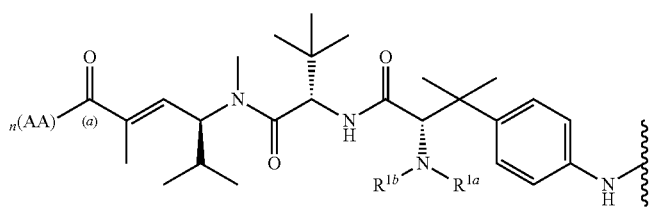
(Za-7)

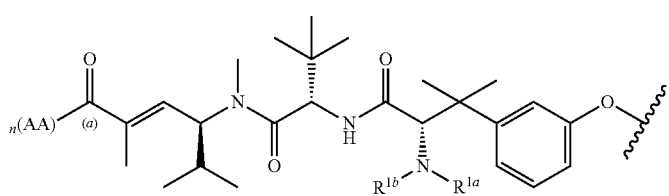
(Za-8)

(Za-9)

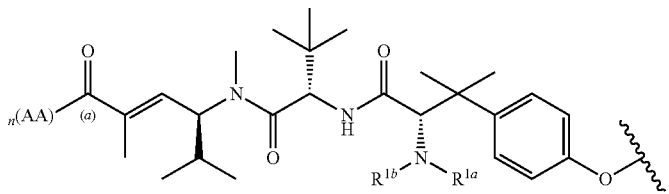

(Za-10)

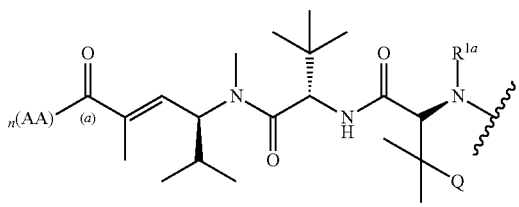

(Za-11)

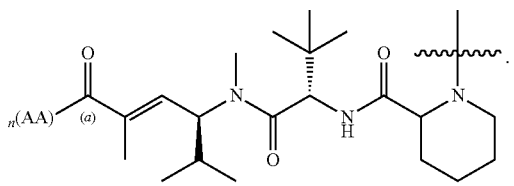

Here, n, AA, Q, $R^{1a}$ and $R^{1b}$ are as defined in formula (1-1). Provided that when Z' is a group represented by formula (Za-6), formula (Za-7), formula (Za-8), formula (Za-9), formula (Za-10) or formula (Za-11), n is an integer of 1 to 4.

In one aspect, Z' may be a group represented by formula (Z-4) or formula (Z-5), and Q may be an unsubstituted phenyl group or a group represented by formula (Q-1).

Examples of one aspect of the hemiasterlin derivative according to the present invention include the following (1-2-A).

(1-2-A)

A compound, wherein, in formula (1-2),
h is 2, 3, 4 or 5;
Z' is a group represented by formula (Z-4) or formula (Z-5);
Q is an unsubstituted phenyl group or a group represented by formula (Q-1);
$R^{1a}$ is a methyl group;
$R^{1b}$ is a hydrogen atom;
AA is Glu or Asp; and
n is 0, 1 or 2,
or a salt thereof.

Examples of one aspect of the hemiasterlin derivative according to the present invention include the following compound or a salt thereof:

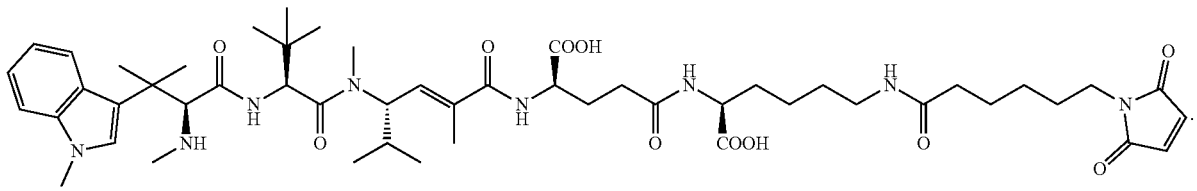 [SMILES: CN[C@H](C(=O)N[C@H](C(=O)N(C)[C@H](/C=C(\C)C(=O)N[C@H](CCC(=O)N[C@@H](CCCCNC(=O)CCCCCN1C(=O)C=CC1=O)C(=O)O)C(=O)O)C(C)C)C(C)(C)C)C(C)(C)c1cn(C)c2ccccc12]

<Antibody-Drug Conjugate>

An antibody-drug conjugate represented by formula (2-1) or formula (2-2), or a pharmaceutically acceptable salt thereof (hereinafter, may be referred to as the "antibody-drug conjugate according to the present invention") is, as shown below, a conjugate in which the antibody moiety derived from an antibody molecule and a drug moiety derived from a drug molecule are covalently bonded directly. In the present specification, the "antibody-drug conjugate" may be referred to as "ADC".

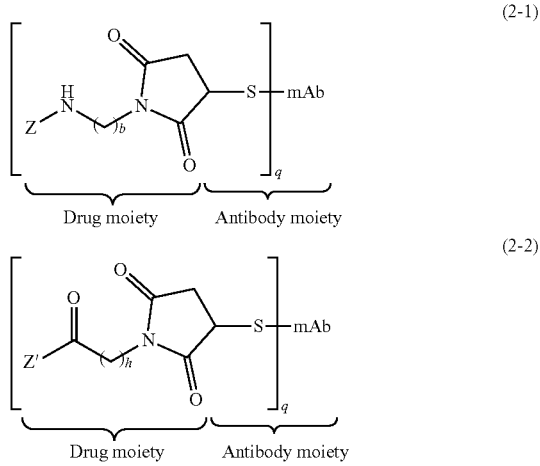

Z, Z', b and h in formula (2-1) and formula (2-2) are as defined for these symbols in formula (1-1) and formula (1-2).

q indicates the drug antibody ratio (alternatively, referred to as DAR) in the antibody-drug conjugate represented by formula (2-1) and formula (2-2). Drug antibody ratio q means the number of drug molecules per antibody molecule in one molecule of the antibody-drug conjugate, that is, per antibody-drug conjugate molecule. Note that antibody-drug conjugates obtained through chemical synthesis are often a mixture of a plurality of antibody-drug conjugate molecules that may have different drug antibody ratio q. In the present specification, the overall drug antibody ratio in such a mixture of antibody-drug conjugates (that is, the average value of drug antibody ratio q of each antibody-drug conjugate) is referred to as the "average drug antibody ratio" or "average DAR".

q is 1, 2, 3, 4, 5, 6, 7 or 8. Examples of one aspect of q include an integer of 2 to 8; examples of another aspect thereof include an integer of 2 to 6; examples of another aspect thereof include an integer of 4 to 8; examples of another aspect thereof include an integer of 6 to 8; examples of another aspect thereof include 2 or 4; examples of another aspect thereof include 6 or 8; and examples of another aspect thereof include 8.

Examples of one aspect of the average DAR include 2 to 8; examples of another aspect thereof include 3.5 to 4.5; and examples of another aspect thereof include 1 to 2, 2 to 3, 3 to 4, 4 to 5, 5 to 6, 6 to 7 or 7 to 8. It is possible to determine the average DAR by methods conventionally used to determine the average DAR, such as SDS-PAGE, mass spectrometry, ELISA (enzyme-linked immunosorbent assay) and HPLC (high performance liquid chromatography). It is possible to separate, purify and characterize an antibody-drug conjugate of a particular DAR from a mixture of a plurality of antibody-drug conjugates having different DARs by methods such as hydrophobic interaction column (HIC) HPLC, reversed phase HPLC and electrophoresis.

In formula (2-1) and formula (2-2), the antibody mAb is not particularly limited as long as it is an antibody that can recognize antigens present on the surface of target cells. It is sufficient that the target cell be a cell in need of treatment with a hemiasterlin derivative, and it is preferable that the target cell be a cancer cell. It is preferable that the antigen present on the surface of target cells be an antigen specific for the target cells, not expressed or expressed in a small amount in normal cells. Examples of one aspect of mAb include the known antibodies recited above; examples of another aspect thereof include brentuximab, trastuzumab, inotuzumab, gemtuzumab, glembatumumab, labetuzumab, sacituzumab, lifastuzumab, indusatumab, polatuzumab, pinatuzumab, coltuximab, indatuximab, milatuzumab, rovalpituzumab, anetumab, tisotumab, mirvetuximab, lorvotuzumab, rituximab, depatuxizumab, denintuzumab, enfortumab, telisotuzumab, vandortuzumab, sofituzumab, vorsetuzumab, mirvetuximab, naratuximab, cantuzumab, lapritiximab, bivatuzumab, vadastuximab, lupartumab, aprutumab, abagovomab, abciximab, abituzumab, abrilumab, actoxumab, adalimumab, adecatumumab, aducanumab, afasevikumab, afelimomab, alacizumab, alemtuzumab, alirocumab, altumomab, amatuximab, anatumomab, anifrolumab, anrukinzumab, apolizumab, arcitumomab, ascrinvacumab, aselizumab, atezolizumab, atinumab, atorolimumab, avelumab, azintuxizumab, bapineuzumab, basiliximab, bavituximab, bectumomab, begelomab, belimumab, benralizumab, bertilimumab, besilesomab, bevacizumab, bezlotoxumab, biciromab, bimagrumab, bimekizumab, bleselumab, blinatumomab, blontuvetmab, blosozumab, bococizumab, brazikumab, briakinumab, brodalumab, brolucizumab, brontictuzumab, burosumab, cabiralizumab, camrelizumab, caplacizumab, capromab, carlumab, carotuximab, catumaxomab, cedelizumab, certolizumab, cetuximab, citatuzumab, cixutumumab, clenoliximab, clivatuzumab, codrituzumab, conatumumab, concizumab, cosfroviximab, crenezumab, crizanlizumab, crotedumab, dacetuzumab, daclizumab, dalotuzumab, dapirolizumab, daratumumab, dectrekumab, demcizumab, denosumab, detumomab, dezamizumab, dinutuximab, diridavumab, domagrozumab, dorlimomab, drozitumab, duligotuzumab, dupilumab, durvalumab, dusigitumab, duvortuxizumab, ecromeximab, eculizumab, edobacomab, edrecolomab, efalizumab, efungumab, eldelumab, elezanumab, elotuzumab, elsilimomab, emactuzumab, emapalumab, emibetuzumab, emicizumab, enavatuzumab, enlimomab, enoblituzumab, enokizumab, enoticumab, ensituximab, epitumomab, epratuzumab, eptinezumab, erenumab, erlizumab, ertumaxomab, etaracizumab, etrolizumab, evinacumab, evolocumab, exbivirumab, faralimomab, farletuzumab, fasinumab, felvizumab, fezakinumab, ficlatuzumab, figitumumab, firivumab, flanvotumab, fletikumab, fontolizumab, foralumab, foravirumab, fremanezumab, fresolimumab, frunevetmab, fulranumab, futuximab, galcanezumab, galiximab, ganitumab, gantenerumab, gatipotuzumab, gavilimomab, gedivumab, gevokizumab, gilvetmab, girentuximab, golimumab, guselkumab, ibalizumab, ibritumomab, icrucumab, idarucizumab, ifabotuzumab, igovomab, imalumab, imciromab, imgatuzumab, inclacumab, inebilizumab, infliximab, inolimomab, intetumumab, ipilimumab, iratumumab, isatuximab, itolizumab, ixekizumab, keliximab, lacnotuzumab, lampalizumab, lanadelumab, landogrozumab, larcaviximab, lebrikizumab, lemalesomab, lenzilumab, lerdelimumab, lesofavumab, letolizumab, lexatumumab, libivirumab, lifatuzumab, ligelizumab, lilotomab, lintuzumab, lirilumab, lodelcizumab, lokivetmab, lorvotuzumab, losatuximab, lucatumumab, lulizumab, lumretuzumab, lutikizumab, mapatumumab, margetuximab, maslimomab, matuzumab, mavrilimumab, mepolizumab, metelimumab, minretumomab, mitumomab, modotuximab, mogamulizumab, monalizumab, morolimumab, motavizumab, moxetumomab, muromonab, nacolomab, namilumab, naptumomab, narnatumab, natalizumab, navicixizumab, navivumab, nebacumab, necitumumab, nemolizumab, nerelimomab, nesvacumab, nimotuzumab, nivolumab, obiltoxaximab, obinutuzumab, ocaratuzumab, ocrelizumab, odulimomab, ofatumumab, olaratumab, oleclumab, olendalizumab, olokizumab, omalizumab, onartuzumab, ontuxizumab, opicinumab, oportuzumab, oregovomab, oreticumab, orticumab, otelixizumab, otlertuzumab, oxelumab, ozanezumab, ozoralizumab, pagibaximab, palivizumab, pamrevlumab, panitumumab, panobacumab, parsatuzumab, pascolizumab, pasotuxizumab, pateclizumab, patritumab, pembrolizumab, perakizumab, pertuzumab, pexelizumab, pidilizumab, placulumab, plozalizumab, ponezumab, porgaviximab, prezalumab, priliximab, pritoxaximab, pritumumab, quilizumab, racotumomab, radretumab, rafivirumab, ralpancizumab, ramucirumab, ranevetmab, ranibizumab, raxibacumab, refanezumab, regavirumab, remtolumab, reslizumab, rilotumumab, rinucumab, risankizumab, rivabazumab, robatumumab, roledumab, romosozumab, rontalizumab, rosmantuzumab, rovelizumab, rozanolixizumab, ruplizumab, samalizumab, sarilumab, satralizumab, satumomab, secukinumab, selicrelumab, seribantumab, setoxaximab, sevirumab, sibrotuzumab, sifalimumab, siltuximab, simtuzumab, siplizumab, sirukumab, solanezumab, solitomab, sontuzumab, stamulumab, sulesomab, suptavumab, suvizumab, suvratoxumab, tabalumab, tadocizumab, talizumab, tamtuvetmab, tanezumab, taplitumomab, tarextumab, tavolixizumab, fanolesomab, nofetumomab, pintumomab, tefibazumab, telimomab, telisotuzumab, tenatumomab, teneliximab, teplizumab, teprotumumab, tesidolumab, tezepelumab, tigatuzumab, tildrakizumab, timigutuzumab, timolumab, tocilizumab, tomuzotuximab, toralizumab, tosatoxumab, tositumomab, tovetumab, tralokinumab, tregalizumab, tremelimumab, trevogrumab, tucotuzumab, tuvirumab, ublituximab, ulocuplumab, urelumab, urtoxazumab, ustekinumab, utomilumab, vanticutamab, vanucizumab, vapaliximab, varisakumab, varlilumab, vatelizumab, vedolizumab, veltuzumab, vepalimomab, vesencumab, visilizumab, vobarilizumab, volociximab, vonlerolizumab, votumumab, vunakizumab, tacatuzumab, zalutumumab, zanolimumab, ziralimumab, zolimomab or anti-embigin antibody; examples of another aspect thereof include brentuximab, trastuzumab, inotuzumab, gemtuzumab, labetuzumab, polatuzumab, coltuximab, indatuximab, anetumab, rituximab, denintuzumab, lapriruximab, vadastuximab, glembatumumab, cetuximab, alemtuzumab or depatuxizumab; examples of another aspect thereof include brentuximab, trastuzumab, rituximab or anti-embigin antibody; and examples of another aspect thereof include brentuximab or trastuzumab, and preferably, examples of another aspect include brentuximab.

Examples of another aspect of mAb include anti-19A antibody, anti-AXL antibody, anti-BCMA antibody, anti-C4.4a antibody, anti-CA6 antibody, anti-CA9 antibody, anti-CA-125 antibody, anti-cadherin-6 antibody, anti-CD166 antibody, anti-CD19 antibody, anti-CD20 antibody, anti-CD22 antibody, anti-CD25 antibody, anti-CD27 antibody, anti-CD30 antibody, anti-CD33 antibody, anti-CD37 antibody, anti-CD40 antibody, anti-CD41 antibody, anti-CD44v6 antibody, anti-CD51 antibody, anti-CD52 antibody, anti-CD56 antibody, anti-CD70 antibody, anti-CD74 antibody, anti-CD79 antibody, anti-CD79b antibody, anti-CEACAM5 antibody, anti-c-Met antibody, anti-DLL3 antibody, anti-DPEP3 antibody, anti-EGFR antibody, anti-EGFRvIII antibody, anti-ENPP3 antibody, anti-EpCAM antibody, anti-EphA4 antibody, anti-FGFR2 antibody, anti-FGFR3 antibody, anti-FTL3 antibody, anti-folate receptor a antibody, anti-gripican 3 antibody, anti-gpNMB antibody, anti-HER2 antibody, anti-HER3 antibody, anti-IL-3RA antibody, anti-LAMP1 antibody, anti-LIV-1 antibody, anti-LRRC15 antibody, anti-Ly6E antibody, anti-mesothelin antibody, anti-MUC-16 antibody, anti-*NaPi*2b antibody, anti-nectin-4 antibody, anti-CD352 antibody, anti-P-cadherin antibody, anti-PMSA antibody, anti-protein tyrosine kinase 7 antibody, anti-SLITRK antibody, anti-STEAP1 antibody, anti-CD138 antibody, anti-tissue factor antibody, anti-CD71 antibody, anti-TIM-1 antibody, anti-Trop2 antibody, anti-5T4 antibody, anti-B7-H3 antibody, anti-CD163 macrophage receptor antibody, anti-CD38 antibody, anti-CD48 antibody, anti-cKit antibody, anti-guanylate cyclase C antibody, anti-gastrin releasing peptide antibody, anti-solute carrier antibody, anti-tumor-associated MUC-1 antibody, anti-GD2 antibody, anti-α4β7 integrin antibody or anti-embigin antibody. Examples of another aspect of mAb include anti-CD19 antibody, anti-CD20 antibody, anti-CD22 antibody, anti-CD30 antibody, anti-CD33 antibody, anti-CD52 antibody, anti-CD70 antibody, anti-CD79b antibody, anti-CEACAM5 antibody, anti-EGFR antibody, anti-EGFRvIII antibody, anti-gpNMB antibody, anti-HER2 antibody, anti-mesothelin antibody, anti-CD138 antibody, anti-CD38 antibody or anti-GD2 antibody. Examples of another aspect of mAb include anti-CD19 antibody, anti-CD20 antibody, anti-CD22 antibody, anti-CD30 antibody, anti-CD33 antibody, anti-CD52 antibody, anti-CD79b antibody, anti-CEACAM5 antibody, anti-EGFR antibody, anti-EGFRvIII antibody, anti-gpNMB antibody, anti-HER2 antibody, anti-mesothelin antibody or anti-CD138 antibody.

Here, it is sufficient that the "antibody" be an antibody including at least a heavy chain variable domain and a light chain variable domain, and it may be a complete antibody or a fragment of a complete antibody that is an antigen-binding fragment having an antigen-recognition site. The complete antibody has two full length light chains and two full length heavy chains, and respective light chains and heavy chains are linked by disulfide bonds. The complete antibody includes IgA, IgD, IgE, IgM and IgG, and IgG includes $IgG_1$, $IgG_2$, $IgG_3$ and $IgG_4$ as subtypes. In addition, it is preferable that the antibody be a monoclonal antibody. The antibody moiety and the drug moiety are linked via a sulfhydryl group obtained by reducing a disulfide bond in the antibody.

The "antibody of AMG 595" means anti-EGFRvIII antibody that can be obtained by the method described in Mol. Cancer Ther., 2015, 14, 1614-1624.

In one aspect, Z may be a group represented by formula (Z-1), formula (Z-2) or formula (Z-3), and Q may be an unsubstituted phenyl group or a group represented by formula (Q-1).

In one aspect, Z' may be a group represented by formula (Z-4) or formula (Z-5), and Q may be an unsubstituted phenyl group or a group represented by formula (Q-1).

Examples of one aspect of the antibody-drug conjugate according to the present invention include the following (2-1-A).

(2-1-A)
An antibody-drug conjugate, wherein, in formula (2-1),
mAb is brentuximab;
q is an integer of 1 to 8;
b is 2, 3, 4 or 5;
Z is a group represented by formula (Z-1), formula (Z-2) or formula (Z-3);
n is an integer of 0 or 1;
Q is an unsubstituted phenyl group or a group represented by formula (Q-1);
$R^{1a}$ is a methyl group;
$R^{1b}$ is a hydrogen atom;
$R^2$ is —$(CH_2)_u$—$COR^4$;
u is an integer of 1 or 2;
AA is Glu or Asp;
$R^3$ is —OH or -$(AB)_p$;
$R^4$ is —OH or -$(AB)_p$;
p is an integer of 1 or 2;
AB represents Glu or Asp, and when there is a plurality of ABs, each AB may be the same as or different from each other and ABs are bonded to each other via an amide bond; and
when $R^3$ or $R^4$ is -$(AB)_p$, the sum of n and p is 1 or 2, or a pharmaceutically acceptable salt thereof.

Examples of one aspect of the antibody-drug conjugate according to the present invention include the following (2-1-B).

(2-1-B)
An antibody-drug conjugate, wherein, in formula (2-1),
mAb is trastuzumab;
q is an integer of 1 to 8;
b is 2, 3, 4 or 5;
Z is a group represented by formula (Z-1), formula (Z-2) or formula (Z-3);
n is an integer of 0 or 1;
Q is an unsubstituted phenyl group or a group represented by formula (Q-1);
$R^{1a}$ is a methyl group;
$R^{1b}$ is a hydrogen atom;
$R^2$ is —$(CH_2)_u$—$COR^4$;
u is an integer of 1 or 2;
AA is Glu or Asp;
$R^3$ is —OH or -$(AB)_p$;
$R^4$ is —OH or -$(AB)_p$;
p is an integer of 1 or 2;
AB represents Glu or Asp, and when there is a plurality of ABs, each AB may be the same as or different from each other and ABs are bonded to each other via an amide bond; and
when $R^3$ or $R^4$ is -$(AB)_p$, the sum of n and p is 1 or 2, or a pharmaceutically acceptable salt thereof.

Examples of one aspect of the antibody-drug conjugate according to the present invention include the following (2-1-C).

(2-1-C)
An antibody-drug conjugate, wherein, in formula (2-1),
mAb is gemtuzumab;
q is an integer of 1 to 8;
b is 2, 3, 4 or 5;
Z is a group represented by formula (Z-1), formula (Z-2) or formula (Z-3);
n is an integer of 0 or 1;
Q is an unsubstituted phenyl group or a group represented by formula (Q-1);
$R^{1a}$ is a methyl group;
$R^{1b}$ is a hydrogen atom;
$R^2$ is —$(CH_2)_u$—$COR^4$;
u is an integer of 1 or 2;
AA is Glu or Asp;
$R^3$ is —OH or -$(AB)_p$;
$R^4$ is —OH or -$(AB)_p$;
p is an integer of 1 or 2;
AB represents Glu or Asp, and when there is a plurality of ABs, each AB may be the same as or different from each other and ABs are bonded to each other via an amide bond; and
when $R^3$ or $R^4$ is -$(AB)_p$, the sum of n and p is 1 or 2, or a pharmaceutically acceptable salt thereof.

Examples of one aspect of the antibody-drug conjugate according to the present invention include the following (2-1-D).

(2-1-D)
An antibody-drug conjugate, wherein, in formula (2-1),
mAb is inotuzumab;
q is an integer of 1 to 8;
b is 2, 3, 4 or 5;
Z is a group represented by formula (Z-1), formula (Z-2) or formula (Z-3);
n is an integer of 0 or 1;
Q is an unsubstituted phenyl group or a group represented by formula (Q-1);
$R^{1a}$ is a methyl group;
$R^{1b}$ is a hydrogen atom;
$R^2$ is —$(CH_2)_u$—$COR^4$;
u is an integer of 1 or 2;
AA is Glu or Asp;
$R^3$ is —OH or -$(AB)_p$;
$R^4$ is —OH or -$(AB)_p$;
p is an integer of 1 or 2;
AB represents Glu or Asp, and when there is a plurality of ABs, each AB may be the same as or different from each other and ABs are bonded to each other via an amide bond; and
when $R^3$ or $R^4$ is -$(AB)_p$, the sum of n and p is 1 or 2, or a pharmaceutically acceptable salt thereof.

Examples of one aspect of the antibody-drug conjugate according to the present invention include the following (2-1-E).

(2-1-E)
An antibody-drug conjugate, wherein, in formula (2-1),
mAb is rituximab;
q is an integer of 1 to 8;
b is 2, 3, 4 or 5;
Z is a group represented by formula (Z-1), formula (Z-2) or formula (Z-3);
n is an integer of 0 or 1;
Q is an unsubstituted phenyl group or a group represented by formula (Q-1);
$R^{1a}$ is a methyl group;
$R^{1b}$ is a hydrogen atom;
$R^2$ is —$(CH_2)_u$—$COR^4$;
u is an integer of 1 or 2;
AA is Glu or Asp;
$R^3$ is —OH or -$(AB)_p$;
$R^4$ is —OH or -$(AB)_p$;
p is an integer of 1 or 2;
AB represents Glu or Asp, and when there is a plurality of ABs, each AB may be the same as or different from each other and ABs are bonded to each other via an amide bond; and
when $R^3$ or $R^4$ is -$(AB)_p$, the sum of n and p is 1 or 2, or a pharmaceutically acceptable salt thereof.

Examples of one aspect of the antibody-drug conjugate according to the present invention include the following (2-1-F).

(2-1-F)

An antibody-drug conjugate, wherein, in formula (2-1), mAb is cetuximab;

q is an integer of 1 to 8;

b is 2, 3, 4 or 5;

Z is a group represented by formula (Z-1), formula (Z-2) or formula (Z-3);

n is an integer of 0 or 1;

Q is an unsubstituted phenyl group or a group represented by formula (Q-1);

$R^{1a}$ is a methyl group;

$R^{1b}$ is a hydrogen atom;

$R^2$ is —$(CH_2)_u$—$COR^4$;

u is an integer of 1 or 2;

AA is Glu or Asp;

$R^3$ is —OH or -$(AB)_p$;

$R^4$ is —OH or -$(AB)_p$;

p is an integer of 1 or 2;

AB represents Glu or Asp, and when there is a plurality of ABs, each AB may be the same as or different from each other and ABs are bonded to each other via an amide bond; and when $R^3$ or $R^4$ is -$(AB)_p$, the sum of n and p is 1 or 2, or a pharmaceutically acceptable salt thereof.

Examples of one aspect of the antibody-drug conjugate according to the present invention include the following (2-1-G).

(2-1-G)

An antibody-drug conjugate, wherein, in formula (2-1), mAb is coltuximab;

q is an integer of 1 to 8;

b is 2, 3, 4 or 5;

Z is a group represented by formula (Z-1), formula (Z-2) or formula (Z-3);

n is an integer of 0 or 1;

Q is an unsubstituted phenyl group or a group represented by formula (Q-1);

$R^{1a}$ is a methyl group;

$R^{1b}$ is a hydrogen atom;

$R^2$ is —$(CH_2)_u$—$COR^4$;

u is an integer of 1 or 2;

AA is Glu or Asp;

$R^3$ is —OH or -$(AB)_p$;

$R^4$ is —OH or -$(AB)_p$;

p is an integer of 1 or 2;

AB represents Glu or Asp, and when there is a plurality of ABs, each AB may be the same as or different from each other and ABs are bonded to each other via an amide bond; and when $R^3$ or $R^4$ is -$(AB)_p$, the sum of n and p is 1 or 2, or a pharmaceutically acceptable salt thereof.

Examples of one aspect of the antibody-drug conjugate according to the present invention include the following (2-1-H).

(2-1-H)

An antibody-drug conjugate, wherein, in formula (2-1), mAb is denintuzumab;

q is an integer of 1 to 8;

b is 2, 3, 4 or 5;

Z is a group represented by formula (Z-1), formula (Z-2) or formula (Z-3);

n is an integer of 0 or 1;

Q is an unsubstituted phenyl group or a group represented by formula (Q-1);

$R^{1a}$ is a methyl group;

$R^{1b}$ is a hydrogen atom;

$R^2$ is —$(CH_2)_u$—$COR^4$;

u is an integer of 1 or 2;

AA is Glu or Asp;

$R^3$ is —OH or -$(AB)_p$;

$R^4$ is —OH or -$(AB)_p$;

p is an integer of 1 or 2;

AB represents Glu or Asp, and when there is a plurality of ABs, each AB may be the same as or different from each other and ABs are bonded to each other via an amide bond; and when $R^3$ or $R^4$ is -$(AB)_p$, the sum of n and p is 1 or 2, or a pharmaceutically acceptable salt thereof.

Examples of one aspect of the antibody-drug conjugate according to the present invention include the following (2-1-I).

(2-1-I)

An antibody-drug conjugate, wherein, in formula (2-1), mAb is alemtuzumab;

q is an integer of 1 to 8;

b is 2, 3, 4 or 5;

Z is a group represented by formula (Z-1), formula (Z-2) or formula (Z-3);

n is an integer of 0 or 1;

Q is an unsubstituted phenyl group or a group represented by formula (Q-1);

$R^{1a}$ is a methyl group;

$R^{1b}$ is a hydrogen atom;

$R^2$ is —$(CH_2)_u$—$COR^4$;

u is an integer of 1 or 2;

AA is Glu or Asp;

$R^3$ is —OH or -$(AB)_p$;

$R^4$ is —OH or -$(AB)_p$;

p is an integer of 1 or 2;

AB represents Glu or Asp, and when there is a plurality of ABs, each AB may be the same as or different from each other and ABs are bonded to each other via an amide bond; and when $R^3$ or $R^4$ is -$(AB)_p$, the sum of n and p is 1 or 2, or a pharmaceutically acceptable salt thereof.

Examples of one aspect of the antibody-drug conjugate according to the present invention include the following (2-1-J).

(2-1-J)

An antibody-drug conjugate, wherein, in formula (2-1), mAb is anetumab;

q is an integer of 1 to 8;

b is 2, 3, 4 or 5;

Z is a group represented by formula (Z-1), formula (Z-2) or formula (Z-3);

n is an integer of 0 or 1;

Q is an unsubstituted phenyl group or a group represented by formula (Q-1); $R^{1a}$ is a methyl group;

$R^{1b}$ is a hydrogen atom;

$R^2$ is —$(CH_2)_u$—$COR^4$;

u is an integer of 1 or 2;

AA is Glu or Asp;

$R^3$ is —OH or -$(AB)_p$;

$R^4$ is —OH or -$(AB)_p$;

p is an integer of 1 or 2;

AB represents Glu or Asp, and when there is a plurality of ABs, each AB may be the same as or different from each other and ABs are bonded to each other via an amide bond; and when $R^3$ or $R^4$ is -$(AB)_p$, the sum of n and p is 1 or 2, or a pharmaceutically acceptable salt thereof.

Examples of one aspect of the antibody-drug conjugate according to the present invention include the following (2-1-K).

(2-1-K)

An antibody-drug conjugate, wherein, in formula (2-1),
mAb is polatuzumab;
q is an integer of 1 to 8;
b is 2, 3, 4 or 5;
Z is a group represented by formula (Z-1), formula (Z-2) or formula (Z-3);
n is an integer of 0 or 1;
Q is an unsubstituted phenyl group or a group represented by formula (Q-1);
$R^{1a}$ is a methyl group;
$R^{1b}$ is a hydrogen atom;
$R^2$ is —$(CH_2)_u$—$COR^4$;
u is an integer of 1 or 2;
AA is Glu or Asp;
$R^3$ is —OH or -$(AB)_p$;
$R^4$ is —OH or -$(AB)_p$;
p is an integer of 1 or 2;
AB represents Glu or Asp, and when there is a plurality of ABs, each AB may be the same as or different from each other and ABs are bonded to each other via an amide bond; and
when $R^3$ or $R^4$ is -$(AB)_p$, the sum of n and p is 1 or 2,
or a pharmaceutically acceptable salt thereof.

Examples of one aspect of the antibody-drug conjugate according to the present invention include the following (2-1-L).

(2-1-L)

A compound, wherein, in formula (2-1),
mAb is vadastuximab;
q is an integer of 1 to 8;
b is 2, 3, 4 or 5;
Z is a group represented by formula (Z-1), formula (Z-2) or formula (Z-3);
n is an integer of 0 or 1;
Q is an unsubstituted phenyl group or a group represented by formula (Q-1);
$R^{1a}$ is a methyl group;
$R^{1b}$ is a hydrogen atom;
$R^2$ is —$(CH_2)_u$—$COR^4$;
u is an integer of 1 or 2;
AA is Glu or Asp;
$R^3$ is —OH or -$(AB)_p$;
$R^4$ is —OH or -$(AB)_p$;
p is an integer of 1 or 2;
AB represents Glu or Asp, and when there is a plurality of ABs, each AB may be the same as or different from each other and ABs are bonded to each other via an amide bond; and
when $R^3$ or $R^4$ is -$(AB)_p$, the sum of n and p is 1 or 2,
or a pharmaceutically acceptable salt thereof.

Examples of one aspect of the antibody-drug conjugate according to the present invention include the following (2-1-M).

(2-1-M)

A compound, wherein, in formula (2-1),
mAb is glembatumumab;
q is an integer of 1 to 8;
b is 2, 3, 4 or 5;
Z is a group represented by formula (Z-1), formula (Z-2) or formula (Z-3);
n is an integer of 0 or 1;
Q is an unsubstituted phenyl group or a group represented by formula (Q-1);
$R^{1a}$ is a methyl group;
$R^{1b}$ is a hydrogen atom;
$R^2$ is —$(CH_2)_u$—$COR^4$;
u is an integer of 1 or 2;
AA is Glu or Asp;
$R^3$ is —OH or -$(AB)_p$;
$R^4$ is —OH or -$(AB)_p$;
p is an integer of 1 or 2;
AB represents Glu or Asp, and when there is a plurality of ABs, each AB may be the same as or different from each other and ABs are bonded to each other via an amide bond; and
when $R^3$ or $R^4$ is -$(AB)_p$, the sum of n and p is 1 or 2,
or a pharmaceutically acceptable salt thereof.

Examples of one aspect of the antibody-drug conjugate according to the present invention include the following (2-1-N).

(2-1-N)

An antibody-drug conjugate, wherein, in formula (2-1),
mAb is indatuximab;
q is an integer of 1 to 8;
b is 2, 3, 4 or 5;
Z is a group represented by formula (Z-1), formula (Z-2) or formula (Z-3);
n is an integer of 0 or 1;
Q is an unsubstituted phenyl group or a group represented by formula (Q-1);
$R^{1a}$ is a methyl group;
$R^{1b}$ is a hydrogen atom;
$R^2$ is —$(CH_2)_u$—$COR^4$;
u is an integer of 1 or 2;
AA is Glu or Asp;
$R^3$ is —OH or -$(AB)_p$;
$R^4$ is —OH or -$(AB)_p$;
p is an integer of 1 or 2;
AB represents Glu or Asp, and when there is a plurality of ABs, each AB may be the same as or different from each other and ABs are bonded to each other via an amide bond; and
when $R^3$ or $R^4$ is -$(AB)_p$, the sum of n and p is 1 or 2,
or a pharmaceutically acceptable salt thereof.

Examples of one aspect of the antibody-drug conjugate according to the present invention include the following (2-1-O).

(2-1-O)

An antibody-drug conjugate, wherein, in formula (2-1),
mAb is depatuxizumab;
q is an integer of 1 to 8;
b is 2, 3, 4 or 5;
Z is a group represented by formula (Z-1), formula (Z-2) or formula (Z-3);
n is an integer of 0 or 1;
Q is an unsubstituted phenyl group or a group represented by formula (Q-1);
$R^{1a}$ is a methyl group;
$R^{1b}$ is a hydrogen atom;
$R^2$ is —$(CH_2)_u$—$COR^4$;
u is an integer of 1 or 2;
AA is Glu or Asp;
$R^3$ is —OH or -$(AB)_p$;
$R^4$ is —OH or -$(AB)_p$;
p is an integer of 1 or 2;

AB represents Glu or Asp, and when there is a plurality of ABs, each AB may be the same as or different from each other and ABs are bonded to each other via an amide bond; and when $R^3$ or $R^4$ is $-(AB)_p$, the sum of n and p is 1 or 2, or a pharmaceutically acceptable salt thereof.

Examples of one aspect of the antibody-drug conjugate according to the present invention include the following (2-1-P).

(2-1-P)

An antibody-drug conjugate, wherein, in formula (2-1),
mAb is laprituximab;
q is an integer of 1 to 8;
b is 2, 3, 4 or 5;
Z is a group represented by formula (Z-1), formula (Z-2) or formula (Z-3);
n is an integer of 0 or 1;
Q is an unsubstituted phenyl group or a group represented by formula (Q-1);
$R^{1a}$ is a methyl group;
$R^{1b}$ is a hydrogen atom;
$R^2$ is $-(CH_2)_u-COR^4$;
u is an integer of 1 or 2;
AA is Glu or Asp;
$R^3$ is $-OH$ or $-(AB)_p$;
$R^4$ is $-OH$ or $-(AB)_p$;
p is an integer of 1 or 2;
AB represents Glu or Asp, and when there is a plurality of ABs, each AB may be the same as or different from each other and ABs are bonded to each other via an amide bond; and when $R^3$ or $R^4$ is $-(AB)_p$, the sum of n and p is 1 or 2, or a pharmaceutically acceptable salt thereof.

Examples of one aspect of the antibody-drug conjugate according to the present invention include the following (2-1-P).

(2-1-O)

An antibody-drug conjugate, wherein, in formula (2-1),
mAb is labetuzumab;
q is an integer of 1 to 8;
b is 2, 3, 4 or 5;
Z is a group represented by formula (Z-1), formula (Z-2) or formula (Z-3);
n is an integer of 0 or 1;
Q is an unsubstituted phenyl group or a group represented by formula (Q-1);
$R^{1a}$ is a methyl group;
$R^{1b}$ is a hydrogen atom;
$R^2$ is $-(CH_2)_u-COR^4$;
u is an integer of 1 or 2;
AA is Glu or Asp;
$R^3$ is $-OH$ or $-(AB)_p$;
$R^4$ is $-OH$ or $-(AB)_p$;
p is an integer of 1 or 2;
AB represents Glu or Asp, and when there is a plurality of ABs, each AB may be the same as or different from each other and ABs are bonded to each other via an amide bond; and when $R^3$ or $R^4$ is $-(AB)_p$, the sum of n and p is 1 or 2, or a pharmaceutically acceptable salt thereof.

Examples of one aspect of the antibody-drug conjugate according to the present invention include the following (2-2-A).

(2-2-A)

An antibody-drug conjugate, wherein, in formula (2-2),
mAb is brentuximab;
q is an integer of 1 to 8;
his 2, 3, 4 or 5;
Z' is a group represented by formula (Z-4) or formula (Z-5);
Q is an unsubstituted phenyl group or a group represented by formula (Q-1);
$R^{1a}$ is a methyl group;
$R^{1b}$ is a hydrogen atom;
AA is Glu or Asp; and
n is 0, 1 or 2, or a pharmaceutically acceptable salt thereof.

In general, it is possible to carry out production and analysis of the antibody-drug conjugate by an arbitrary technology known to a person having ordinary skill in the art. Examples of such a method include the method described in Antibody-Drug Conjugates (edited by Laurent Ducry, published by Humana Press, 2013).

The antibody-drug conjugate according to the present invention may be formed by, for example, reducing a disulfide bond in the antibody into a sulfhydryl group and allowing this sulfhydryl group to react with a hemiasterlin derivative.

With regard to the antibody-drug conjugate according to the present invention, the antibody may be metabolized in target cells (antigen-expressing cells), and the drug moiety or a structure including a part of the antibody (antibody fragment) and the drug moiety may be released. For example, in Doronina, S. O., et al., 2006, Bioconjugate Chem. 17: 114-124, it is described that, due to metabolism of the antibody, the Cys-drug moiety of the antibody-drug conjugate is released in cells.

The antibody-drug conjugate according to the present invention has a structure that is unlikely to be cleaved by blood peptidase, and therefore, a state in which the drug moiety is bonded to the antibody moiety can be maintained in the blood and release of the free drug into the blood can be suppressed. Therefore, according to the antibody-drug conjugate according to the present invention, release of the drug into the blood before reaching target cells is reduced.

In addition, the drug moiety of the antibody-drug conjugate according to the present invention has low cell membrane permeability, and therefore, the drug moiety that has once been released in target cells is unlikely to be transferred to the outside of the cells. As a result, the drug efficacy is exerted only in the target cells, and cytotoxicity due to the drug can be provided specifically to antigen-expressing cells.

Furthermore, even if dissociation of the thiosuccinimide site in an organism, which is reported in Non Patent Literatures 7 and 8, occurs to the antibody-drug conjugate according to the present invention and the drug moiety is released in the blood before the antibody-drug conjugate reaches target cells, the drug is unlikely to be passively diffused into normal cells, and is quickly metabolized and excreted, because the drug moiety of the antibody-drug conjugate according to the present invention has low cell membrane permeability.

From the above, according to the antibody-drug conjugate according to the present invention, cytotoxicity due to the drug (hemiasterlin derivative) can be provided specifically to antigen-expressing cells, and it can be expected that side effects due to systemic exposure is small.

The "salt" is a suitable salt of the hemiasterlin derivative according to the present invention and is acceptable as a pharmaceutical raw material, and is preferably a common non-toxic salt. For the "salt", for example, in addition to acid addition salts such as organic acid salts (for example, acetate, trifluoroacetate, maleate, fumarate, citrate, tartrate, methanesulfonate, benzenesulfonate, formate, p-toluenesulfonate or the like) and inorganic acid salts (for example, hydrochloride, hydrobromide, hydroiodide, sulfate, nitrate, phosphateor the like); salts with amino acids (for example, arginine, aspartic acid, glutamic acid or the like); metal salts such as alkali metal salts (for example, sodium salt, potassium salt or the like) and alkaline earth metal salts (for example, calcium salt, magnesium salt or the like); ammonium salts; or organic base salts (for example, trimethylamine salt, triethylamine salt, pyridine salt, picoline salt, dicyclohexylamine salt, N,N'-dibenzylethylenediamine salt or the like), a person having ordinary skill in the art may select appropriate salts as appropriate.

Examples of the "pharmaceutically acceptable salt" include acid addition salts and base addition salts. Examples of the acid addition salt include inorganic acid salts such as hydrochloride, hydrobromide, sulfate, hydroiodide, nitrate and phosphate, or organic acid salts such as citrate, oxalate, phthalate, fumarate, maleate, succinate, malate, acetate, formate, propionate, benzoate, trifluoroacetate, methanesulfonate, benzenesulfonate, p-toluenesulfonate and camphorsulfonate. In addition, examples of the base addition salt include inorganic base salts such as sodium salt, potassium salt, calcium salt, magnesium salt, barium salt and aluminum salt, or organic base salts such as trimethylamine, triethylamine, pyridine, picoline, 2,6-lutidine, ethanolamine, diethanolamine, triethanolamine, tromethamine[tris(hydroxymethyl)methylamine], tert-butylamine, cyclohexylamine, dicyclohexylamine and N,N-dibenzylethylamine. Furthermore, examples of the "pharmaceutically acceptable salt" include salts (amino acid salts) with basic amino acids or acidic amino acids such as arginine, lysine, ornithine, aspartic acid and glutamic acid.

When it is desired to acquire a salt of the hemiasterlin derivative or antibody-drug conjugate according to the present invention, if the target compound is obtained in the form of salt, that compound may be purified as is, and if the target compound is obtained in the free form, that compound may be dissolved or suspended in an appropriate organic solvent, to which an acid or base is added to form a salt by a conventional method.

The hemiasterlin derivative and antibody-drug conjugate according to the present invention may be present in the form of hydrates and/or solvates (ethanolate and the like) with various solvents, and these hydrates and/or solvates are also included in the hemiasterlin derivative and antibody-drug conjugate according to the present invention. Furthermore, all modes of crystal forms of the hemiasterlin derivative and antibody-drug conjugate according to the present invention are also included in the present invention.

Among the hemiasterlin derivative and antibody-drug conjugate according to the present invention, some may have optical isomers based on the optically active center, atropisomers based on axial or planar chirality caused by restraint of intramolecular rotation, and all of the other stereoisomers, tautomers and geometrical isomers, and all possible isomers including the above are encompassed within the scope of the present invention.

In particular, optical isomers and atropisomers may be obtained as racemate, and when optically active starting materials or intermediates are used, optically active substances may be obtained. If necessary, at an appropriate stage in the following production methods, corresponding raw material, intermediate or racemate, the final product, may be optically resolved into optical enantiomers physically or chemically through known separation methods such as a method using an optically active column and fractional crystallization method. Specifically, for example, in diastereomer method, two diastereomers are formed from racemate through a reaction using an optically active resolving agent. In general, these different diastereomers have different physical properties, and thus, can be optically resolved by known methods such as fractional crystallization.

Production methods for the hemiasterlin derivative according to the present invention will be mentioned below. The hemiasterlin derivative according to the present invention represented by formula (1-1) or (1-2) may be produced by, for example, the following production method A to I, L to P, T, U or W.

Production Method A

When Z is a group represented by formula (Z-1); Q is a group represented by formula (Q-1); $R^{1a}$ is a methyl group; $R^{1b}$ is a hydrogen atom or a methyl group; and $R^2$ is —$(CH_2)_u$—COOH, the compound represented by formula (1-1) may be produced by, for example, the following production method:

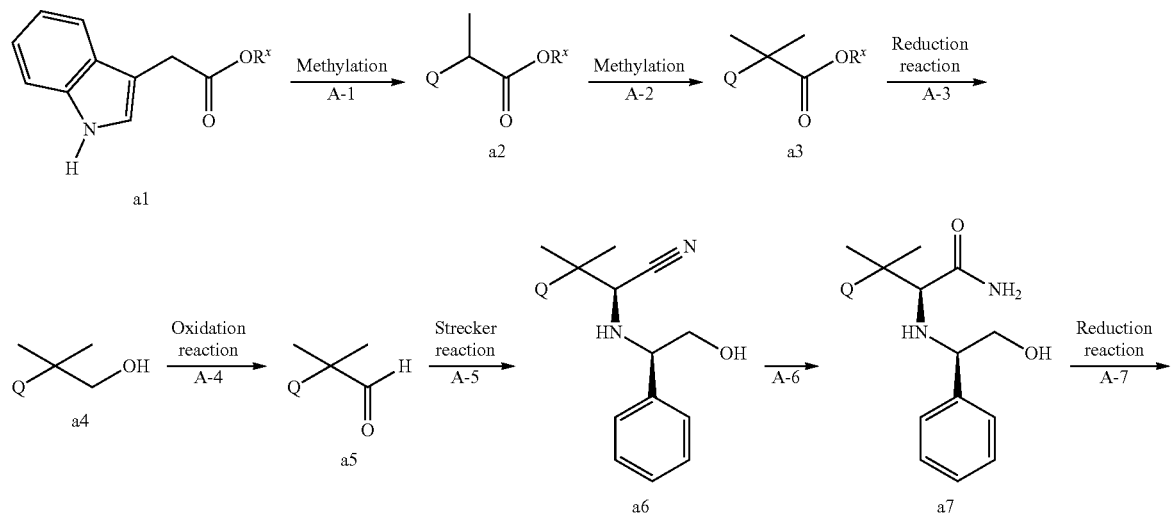

-continued
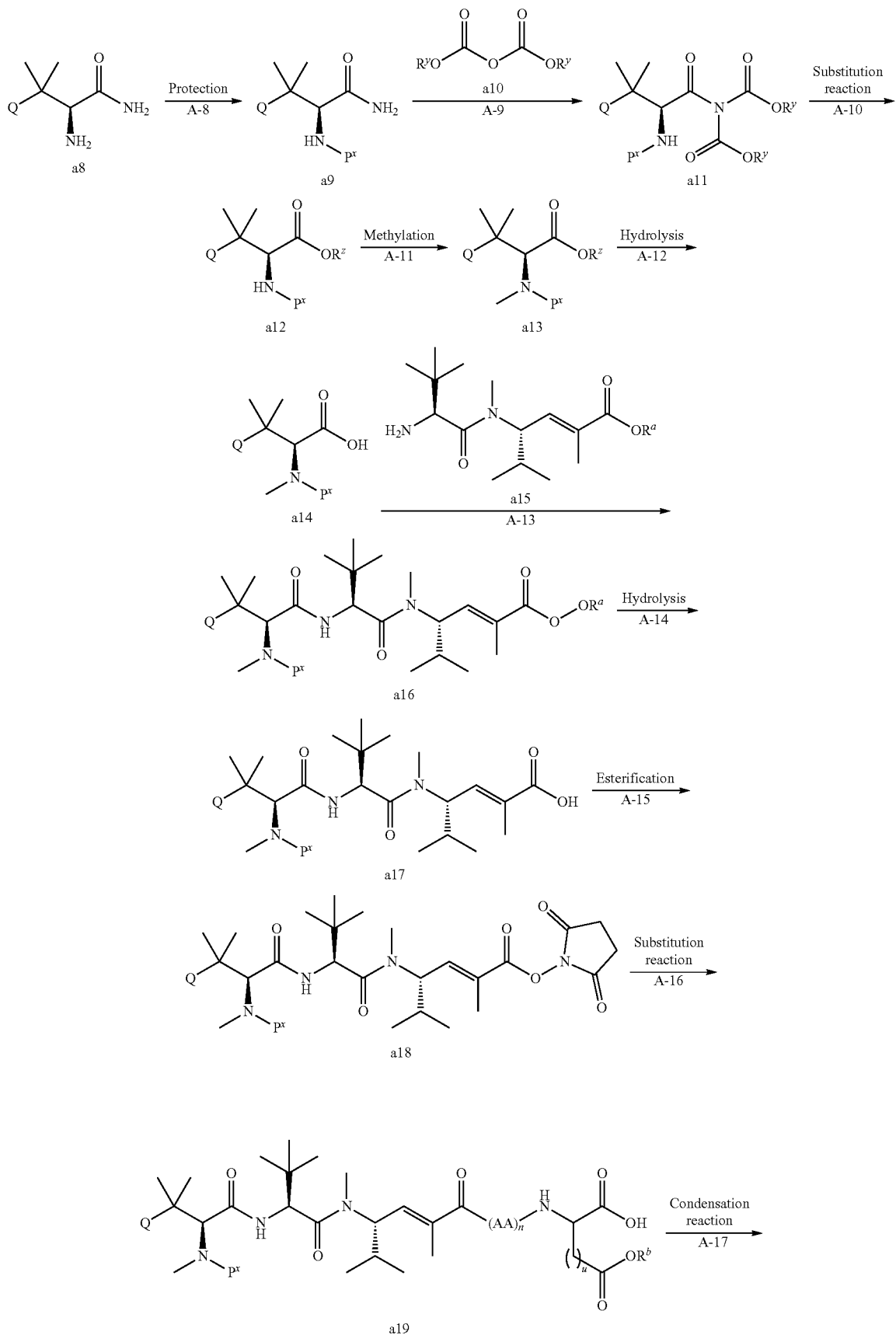

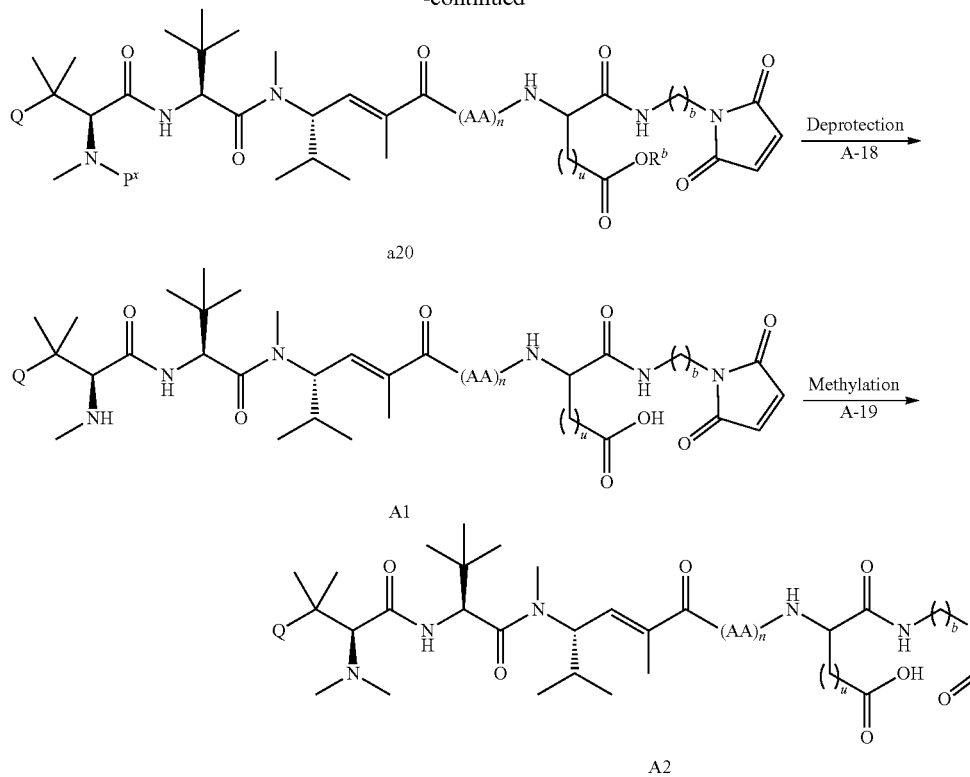

wherein, AA, u, b and n are as defined in item 2; $R^a$, $R^b$, $R^x$, $R^y$ and $R^z$ each independently represent a $C_{1-6}$ alkyl group or a benzyl group; and $P^x$ represents a protecting group for the amino group.

As the above protecting group for the amino group, represented by $P^x$, the protecting groups described in Protective Groups in Organic Synthesis (authored by Theodora W. Greene, Peter G. M. Wuts, issued by John Wiley & Sons, Inc., 1999) and the like may be used.

Compound a1 may be produced by the method described in, for example, J. Med. Chem., 2007, 50, 4329-4339 and the like, or may be purchased as a commercial product. Compound a15 may be produced by the method described in, for example, Tetrahedron Lett., 1997, 38, 317-320 and the like, or may be purchased as a commercial product.

[A-1 Step]

Compound a2 may be produced by allowing compound a1 to react with various methylating reagents in an appropriate solvent in the presence of an appropriate base. Examples of the methylating reagent include methyl halide, and preferably include methyl iodide, methyl bromide and methyl chloride. Examples of the base preferably include potassium hexamethyldisilazide. Examples of the solvent preferably include tetrahydrofuran. The reaction time is normally 5 minutes to 48 hours, and is preferably 10 minutes to 2 hours. The reaction temperature is normally −78° C. to 100° C., and is preferably −78° C. to 10° C. This step may be carried out in accordance with the method described in J. Nat. Prod. 2003, 66, 183-199 and the like.

[A-2 Step]

Compound a3 may be produced from compound a2 in accordance with the method described in the above A-1 step.

[A-3 Step]

Compound a4 may be produced by allowing compound a3 to react with an appropriate reducing agent in an appropriate solvent. The reducing agent is selected from reducing agents used in usual organic synthesis reactions as appropriate, and examples thereof preferably include diisobutylaluminum hydride. Examples of the solvent preferably include diethyl ether. The reaction time is normally 5 minutes to 48 hours, and is preferably 10 minutes to 24 hours. The reaction temperature is normally −78° C. to 100° C., and is preferably −78° C. to 50° C. This step may be carried out in accordance with the method described in J. Nat. Prod. 2003, 66, 183-199 and the like.

[A-4 Step]

Compound a5 may be produced by oxidizing compound a4 using an appropriate oxidizing agent in an appropriate solvent. The oxidizing agent may be selected from oxidizing agents used in usual organic synthesis reactions as appropriate, and examples thereof preferably include tetrapropylammonium perruthenate. Examples of the solvent preferably include dichloromethane. The reaction time is normally 5 minutes to 72 hours, and is preferably 30 minutes to 24 hours. The reaction temperature is normally −78° C. to 100° C., and is preferably −78° C. to 50° C. This step may be carried out in accordance with the method described in J. Nat. Prod. 2003, 66, 183-199 and the like.

[A-5 Step]

Compound a6 may be produced by α-aminocyanating the aldehyde of the compound a5 in an appropriate solvent. Examples of the solvent preferably include toluene and dichloromethane. The reaction time is normally 5 minutes to 96 hours, and is preferably 24 hours to 72 hours. The reaction temperature is normally 0° C. to 200° C., and is preferably 0° C. to 100° C. This step may be carried out in accordance with the method described in Org. Lett. 2002, 4, 695-697 and the like.

[A-6 Step]

Compound a7 may be produced from compound a6 by using an appropriate oxidizing agent in an appropriate solvent in the presence of or in the absence of an appropriate base. The oxidizing agent may be selected from oxidizing agents used in usual organic synthesis reactions as appropriate, and examples thereof preferably include hydrogen peroxide. Examples of the base preferably include potassium carbonate. Examples of the solvent preferably include methanol. The reaction time is normally 5 minutes to 72 hours, and is preferably 30 minutes to 24 hours. The reaction temperature is normally 0° C. to 200° C., and is preferably 0° C. to 60° C. This step may be carried out in accordance with the method described in J. Org. Chem. 2001, 66, 7355-7364 and the like.

[A-7 Step]

Compound a8 may be produced by reducing compound a7 using a reducing agent in an appropriate solvent in the presence of an appropriate catalyst. The reducing agent may be selected from reducing agents used in usual organic synthesis reactions as appropriate, and examples thereof preferably include hydrogen, formate such as ammonium formate, or hydrazine. Examples of the catalyst include transition metals such as palladium, nickel, rhodium, cobalt and platinum, salts thereof or complexes thereof, or supports such as polymer having the above transition metals supported thereon. Examples of the solvent preferably include ethanol or methanol. The reaction time is normally 5 minutes to 72 hours, and is preferably 30 minutes to 24 hours. The reaction temperature is normally 0° C. to 200° C., and is preferably 0° C. to 100° C. This step may be carried out in accordance with the method described in J. Org. Chem. 2001, 66, 7355-7364 and the like.

[A-8 Step]

Compound a9 may be produced by protecting the amino group of compound a8 with protecting group, $P^x$. This step may be carried out in accordance with the method described in Protective Groups in Organic Synthesis (authored by Theodora W. Greene, Peter G. M. Wuts, issued by John Wiley & Sons, Inc., 1999) and the like.

[A-9 Step]

Compound a11 may be produced by allowing compound a9 to react with various acylating reagents (for example, compound a10) in an appropriate solvent in the presence of or in the absence of an appropriate base. Examples of the acylating reagent include carboxylic halide and carboxylic anhydride, and preferably include di-tert-butyl dicarbonate. Examples of the base preferably include diisopropylethylamine. Examples of the solvent preferably include chloroform. The reaction time is normally 5 minutes to 72 hours, and is preferably 30 minutes to 24 hours. The reaction temperature is normally 0° C. to 200° C., and is preferably 0° C. to 50° C.

[A-10 Step]

Compound a12 may be produced by allowing compound a11 to react with an appropriate alkali metal alkoxide in an appropriate solvent. The alkali metal alkoxide may be selected from alkali metal alkoxides used in usual organic synthesis reactions as appropriate, and examples thereof preferably include lithium methoxide or lithium ethoxide. Examples of the solvent preferably include methanol or ethanol. The reaction time is normally 5 minutes to 72 hours, and is preferably 30 minutes to 6 hours. The reaction temperature is normally −78° C. to 200° C., and is preferably −78° C. to 50° C.

[A-11 Step]

Compound a13 may be produced by allowing compound a12 to react with various methylating reagents in an appropriate solvent in the presence of an appropriate base. Examples of the methylating reagent include methyl halide, and preferably include methyl iodide, methyl bromide and methyl chloride. Examples of the base preferably include sodium hydride. Examples of the solvent preferably include tetrahydrofuran. The reaction time is normally 5 minutes to 48 hours, and is preferably 10 minutes to 2 hours. The reaction temperature is normally −78° C. to 100° C., and is preferably −78° C. to 10° C.

[A-12 Step]

Compound a14 may be produced by hydrolyzing the ester of compound a13, in an appropriate solvent in the presence of an appropriate base. Examples of the base preferably include lithium hydroxide. Examples of the solvent preferably include water or methanol. The reaction time is normally 5 minutes to 72 hours, and is preferably 30 minutes to 24 hours. The reaction temperature is normally 0° C. to 200° C., and is preferably 0° C. to 100° C.

[A-13 Step]

Compound a16 may be produced by condensing compound a14 and compound a15 using various condensing agents in an appropriate solvent in the presence of an appropriate base. As the condensing agent, various condensing agents used in usual organic synthesis reactions may be used, and examples thereof preferably include (1-ethyl-3-(3-dimethylaminopropyl)carbodiimide or bromotripyrrolidinophosphonium hexafluorophosphate. In addition a carbonyl activating reagent such as 1-hydroxybenzotriazole may be used together as necessary, in order to improve efficiency of the condensation reaction. Examples of the base preferably include diisopropylethylamine. Examples of the solvent preferably include N,N-dimethylformamide. The reaction time is normally 5 minutes to 72 hours, and is preferably 30 minutes to 24 hours. The reaction temperature is normally −78° C. to 200° C., and is preferably 0° C. to 100° C. This step may be carried out in accordance with the method described in Tetrahedron Lett., 1997, 38, 317-320 and the like.

[A-14 Step]

Compound a17 may be produced by hydrolyzing the ester of compound a16, in accordance with the method described in the above A-12 step. This step may be carried out in accordance with the method described in Tetrahedron Lett., 1997, 38, 317-320 and the like.

[A-15 Step]

Compound a18 may be produced by allowing compound a17 to react with N-hydroxysuccinimide using various condensing agents in an appropriate solvent in the presence of an appropriate base. As the condensing agent, various condensing agents used in usual organic synthesis reactions may be used, and examples thereof preferably include (1-ethyl-3-(3-dimethylaminopropyl)carbodiimide or bromotripyrrolidinophosphonium hexafluorophosphate. In addition, a carbonyl activating reagent such as 1-hydroxybenzotriazole may be used together as necessary, in order to improve efficiency of the reaction. Examples of the base preferably include diisopropylethylamine. Examples of the solvent preferably include N,N-dimethylformamide. The reaction time is normally 5 minutes to 72 hours, and is preferably 30 minutes to 24 hours. The reaction temperature is normally −78° C. to 200° C., and is preferably 0° C. to 100° C.

[A-16 Step]

Compound a19 may be produced by allowing compound a18 to react with an ester of an amino acid or a peptide in an appropriate solvent in the presence of an appropriate base. Examples of the base preferably include diisopropylethylamine. Examples of the solvent preferably include N,N-dimethylformamide. The reaction time is normally 5 minutes to 72 hours, and is preferably 30 minutes to 24 hours. The reaction temperature is normally 0° C. to 200° C., and is preferably 0° C. to 100° C.

[A-17 Step]

Compound a20 may be produced by condensing compound a19 and an aminoalkylmaleimide compound in accordance with the method described in the above A-13 step.

[A-18 Step]

Compound A1 may be produced by deprotecting the protecting group, $P^X$, for the amino group of compound a20. This step may be carried out in accordance with the method described in Protective Groups in Organic Synthesis (authored by Theodora W. Greene, Peter G. M. Wuts, issued by John Wiley & Sons, Inc., 1999) and the like.

In addition, when $(AA)_n$ has an ester or a protected amino group, hydrolysis of the ester and deprotection of the protecting group for the amino group may also be carried out in the present deprotecting step, as necessary.

[A-19 Step]

Compound A2 may be produced by allowing compound A1 and a formaldehyde to react together with an appropriate reducing agent in an appropriate solvent. Examples of the solvent preferably include acetonitrile. As the reducing agent, various reducing agents used in usual organic synthesis reactions may be used, and examples thereof preferably include sodium triacetoxyborohydride. The reaction time is normally 5 minutes to 72 hours, and is preferably 30 minutes to 24 hours. The reaction temperature is normally 0° C. to about 200° C., and is preferably 0° C. to 100° C.

Production Method B

When Z is a group represented by formula (Z-1); Q is an unsubstituted phenyl group; $R^{1a}$ is a methyl group; $R^{1b}$ is a hydrogen atom or a methyl group; and $R^2$ is —$(CH_2)_u$—COOH, the compound represented by formula (1-1) may be produced by, for example, the following production method:

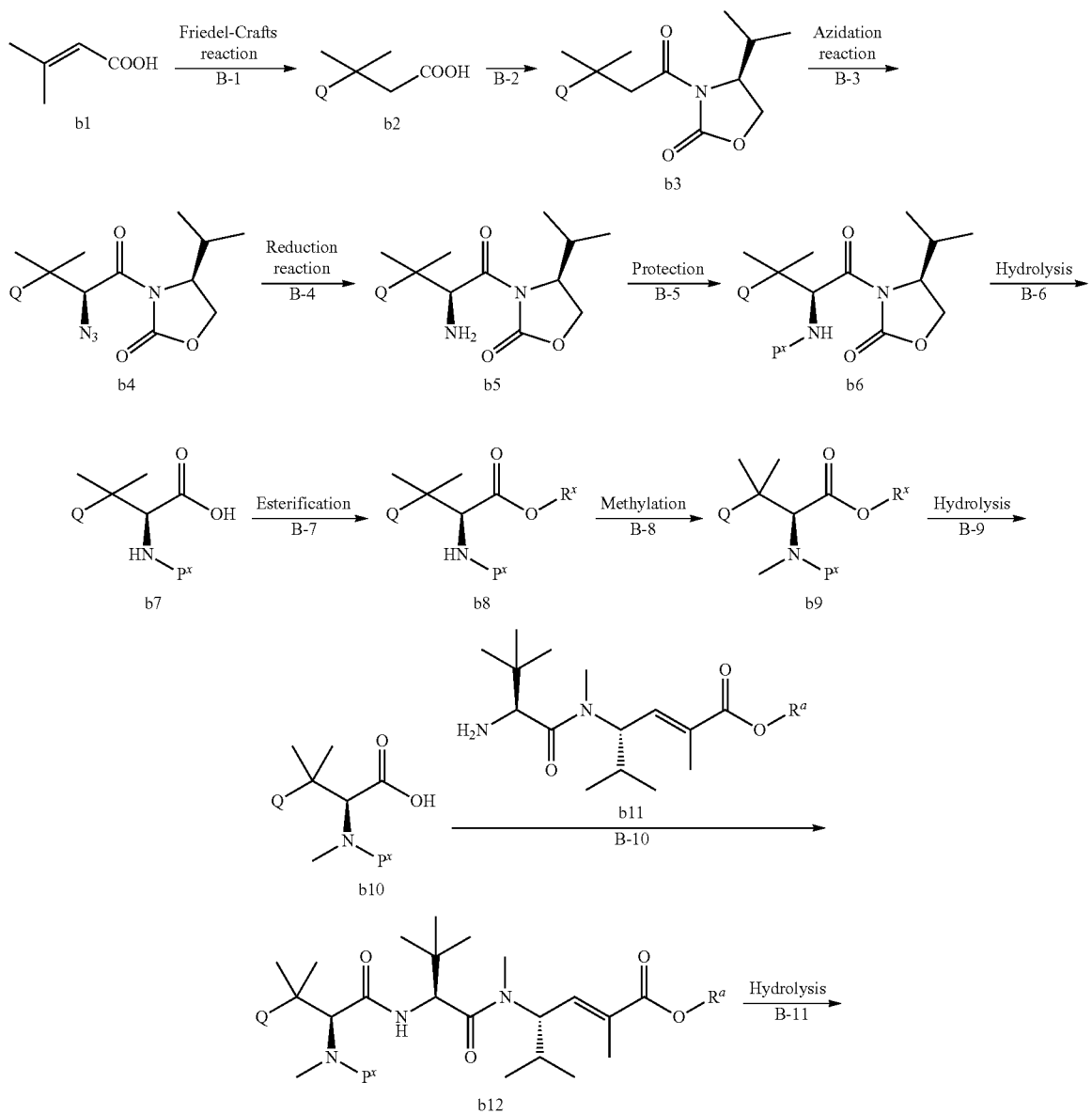

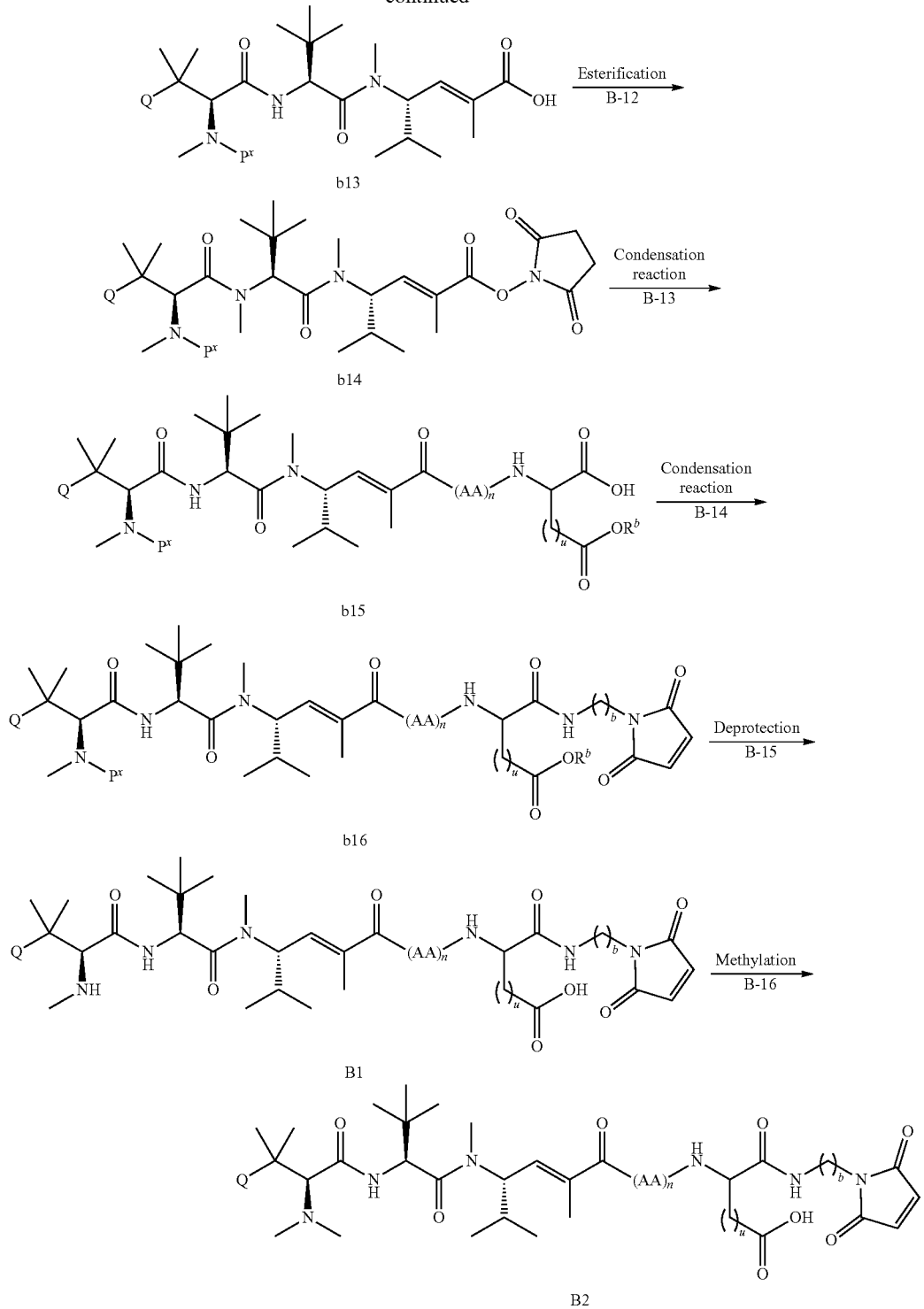

wherein, AA, u, b and n are as defined in item 2; $R^a$, $R^b$ and $R^x$ represent a $C_{1-6}$ alkyl group or a benzyl group; and $P^x$ represents a protecting group for the amino group.

Compound b1 may be, for example, purchased as a commercial product. Compound b11 may be produced by the method described in, for example, Tetrahedron Lett., 1997, 38, 317-320 and the like, or may be purchased as a commercial product.

[B-1 Step]

Compound b2 may be produced by allowing compound b to react with benzene in the presence of various Lewis acids. Examples of the Lewis acid include boron halide, aluminum halide, gallium halide, iron halide and titanium halide, and preferably include aluminum chloride and iron chloride. The reaction time is normally 5 minutes to 48 hours, and is preferably 30 minutes to 4 hours. The reaction temperature is normally −78° C. to 200° C., and is preferably 50° C. to 150° C. This step may be carried out in accordance with the method described in J. Nat. Prod. 2003, 66, 183-199 and the like.

[B-2 Step]

Compound b3 may be produced by allowing compound b2 to react with various carboxylic halides and then to react with an alkali metallized 4-alkyl-2-oxazolidinone in an appropriate solvent in the presence of an appropriate base. Examples of the base preferably include triethylamine or diisopropylethylamine. Examples of the solvent preferably include tetrahydrofuran. Examples of the carboxylic halide include carboxylic chloride, and preferably include pivaloyl chloride. Examples of the alkali metallized 4-alkyl-2-oxazolidinone include 4-alkyl-2-oxazolidinone lithium and 4-alkyl-2-oxazolidinone sodium, and preferably include 4-isopropyl-2-oxazolidinone lithium. The reaction time is normally 5 minutes to 48 hours, and is preferably 10 minutes to 24 hours. The reaction temperature is normally −78° C. to 100° C., and is preferably −78° C. to 50° C. This step may be carried out in accordance with the method described in J. Nat. Prod. 2003, 66, 183-199 and the like.

[B-3 Step]

Compound b4 may be produced by allowing compound b3 to react with various azidating reagents in an appropriate solvent in the presence of an appropriate base. Examples of the azidating reagent include sodium azide, trimethylsilyl azide and diphenylphosphoryl azide, and preferably include trimethylsilyl azide. Examples of the base preferably include potassium hexamethyldisilazide. Examples of the solvent preferably include tetrahydrofuran. The reaction time is normally 5 minutes to 72 hours, and is preferably 30 minutes to 24 hours. The reaction temperature is normally −78° C. to 200° C., and is preferably −78° C. to 75° C. This step may be carried out in accordance with the method described in J. Nat. Prod. 2003, 66, 183-199 and the like.

[B-4 Step]

Compound b5 may be produced from compound b4 in accordance with the method described in the above A-7 step.

[B-5 Step]

Compound b6 may be produced from compound b5 in accordance with the method described in the above A-8 step.

[B-6 Step]

Compound b7 may be produced from compound b6 by using an appropriate oxidizing agent in an appropriate solvent in the presence of an appropriate base. Examples of the base preferably include lithium hydroxide. Examples of the solvent preferably include methanol, tetrahydrofuran or water. The oxidizing agent may be selected from oxidizing agents used in usual organic synthesis reactions as approproate, and examples thereof preferably include hydrogen peroxide. The reaction time is normally 5 minutes to 72 hours, and is preferably 30 minutes to 24 hours. The reaction temperature is normally 0° C. to 200° C., and is preferably 0° C. to 60° C. This step may be carried out in accordance with the method described in J. Nat. Prod. 2003, 66, 183-199 and the like.

[B-7 Step]

Compound b8 may be produced by allowing compound b7 to react with various alkylating reagents in an appropriate solvent in the presence of an appropriate base. Examples of the alkylating reagent include alkyl halide, and preferably include alkyl iodide, alkyl bromide and alkyl chloride. Examples of the base preferably include sodium carbonate and potassium carbonate. Examples of the solvent preferably include N,N-dimethylformamide. The reaction time is normally 5 minutes to 48 hours, and is preferably 10 minutes to 2 hours. The reaction temperature is normally −78° C. to 100° C., and is preferably −10° C. to 25° C. This step may be carried out in accordance with the method described in Protective Groups in Organic Synthesis (authored by Theodora W. Greene, Peter G. M. Wuts, issued by John Wiley & Sons, Inc., 1999) and the like.

[B-8 Step]

Compound b9 may be produced from compound b8 in accordance with the method described in the above A-11 step.

[B-9 Step]

Compound b10 may be produced from compound b9 in accordance with the method described in the above A-12 step.

[B-10 Step]

Compound b12 may be produced from compound b10 and compound b11 in accordance with the method described in the above A-13 step.

[B-11 Step]

Compound b13 may be produced by hydrolyzing the ester of compound b12, in accordance with the method described in the above A-12 step.

[B-12 Step]

Compound b14 may be produced from compound b13 in accordance with the method described in the above A-15 step.

[B-13 Step]

Compound b15 may be produced from compound b14 in accordance with the method described in the above A-16 step.

[B-14 Step]

Compound b16 may be produced from compound b15 in accordance with the method described in the above A-17 step.

[B-15 Step]

Compound B1 may be produced from compound b16 in accordance with the method described in the above A-18 step.

[B-16 Step]

Compound B2 may be produced from compound B1 in accordance with the method described in the above A-19 step.

Production Method C

When Z is a group represented by formula (Z-1); $R^{1a}$ is a methyl group; $R^{1b}$ is a hydrogen atom or a methyl group; and $R^2$ is —$(CH_2)_u$—COOH, the compound represented by formula (1-1) may be produced by, for example, the following production method:

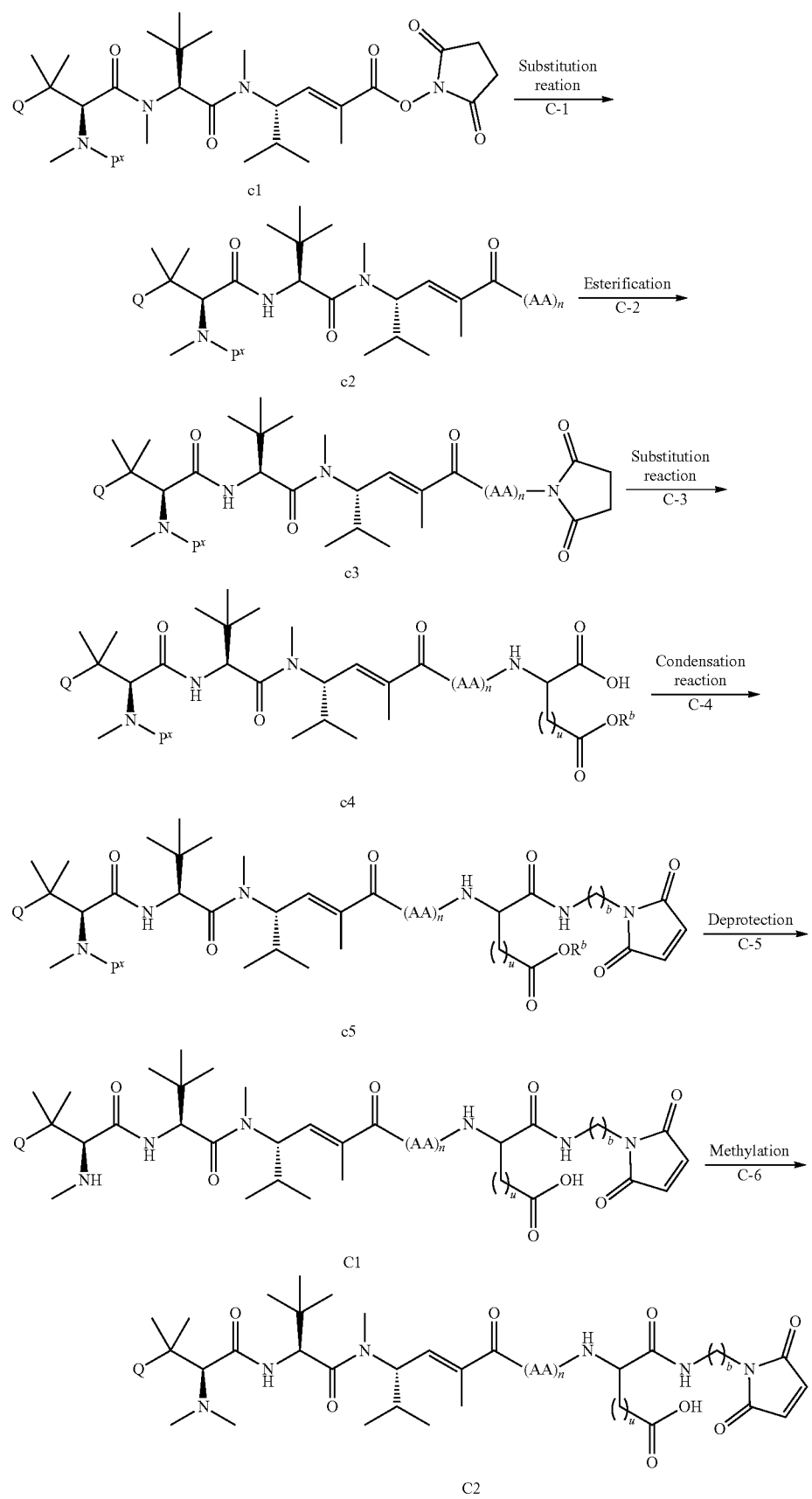

wherein, Q, AA, u, b and n are as defined in item 2; and $R^b$ and $P^x$ are as defined above.

Compound c1 represents compound a18 in Production Method A or compound b14 in Production Method B.

[C-1 Step]

Compound c2 may be produced from compound c1 in accordance with the method described in the above A-16 step.

[C-2 Step]

Compound c3 may be produced from compound c2 in accordance with the method described in the above A-15 step.

[C-3 Step]

Compound c4 may be produced from compound c3 in accordance with the method described in the above A-16 step.

[$C_{1-4}$ Step]

Compound c5 may be produced from compound c4 in accordance with the method described in the above A-17 step.

[C-5 Step]

Compound C1 may be produced from compound c5 in accordance with the method described in the above A-18 step.

[C-6 Step]

Compound C2 may be produced from compound C1 in accordance with the method described in the above A-19 step.

Production Method D

When Z is a group represented by formula (Z-1); $R^{1a}$ is a methyl group; $R^{1b}$ is a hydrogen atom or a methyl group; $R^2$ is —$(CH_2)_u$—$COR^4$; $R^4$ is -$(AB)_p$; and n is 1, 2, 3 or 4, the compound represented by formula (1-1) may be produced by, for example, the following production method:

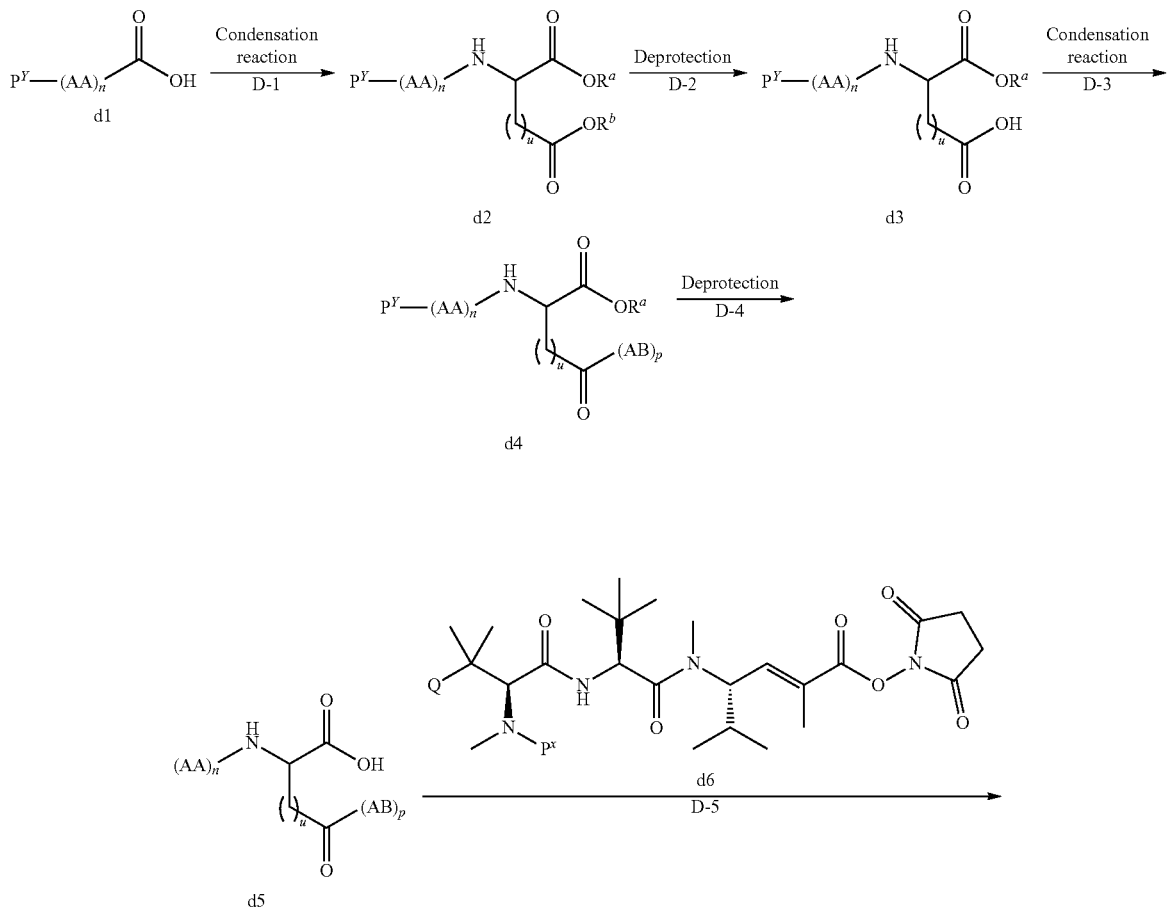

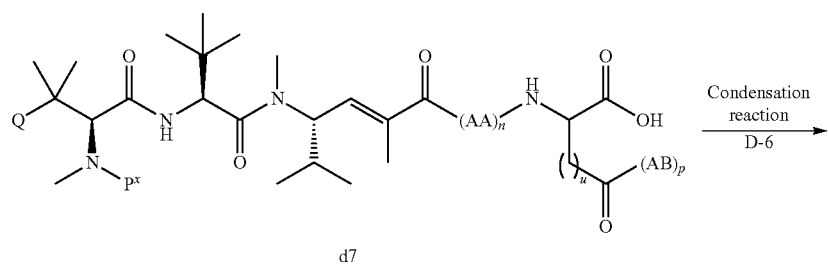

-continued

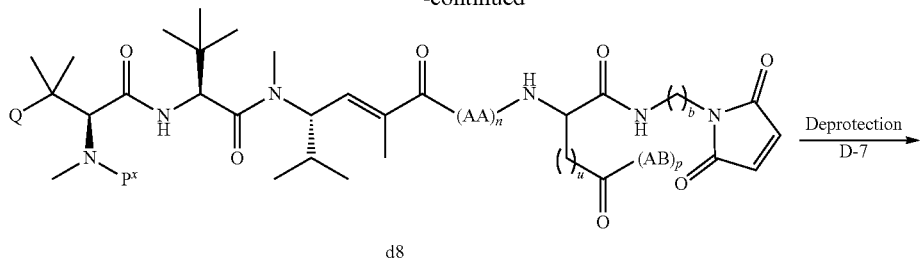

d8

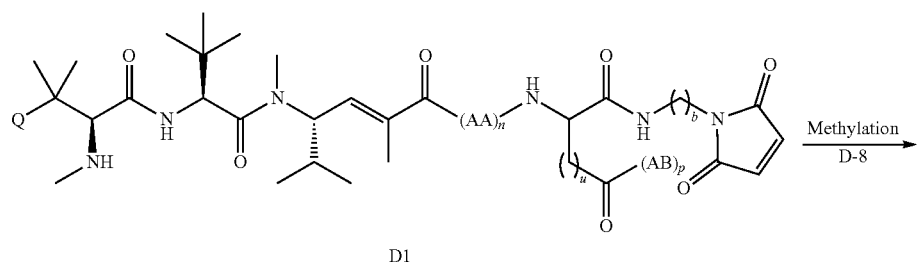

D1

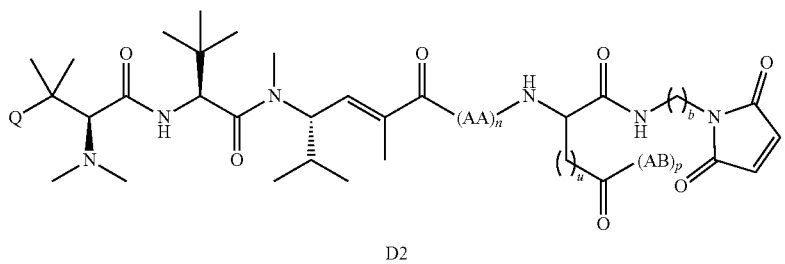

D2 wherein, Q, AA, AB, u, b and p are as defined in item 2; $P^Y$ represents a protecting group for the amino group; and $R^a$, $R^b$ and $P^X$ are as defined above.

As the above protecting group for the amino group, represented by $P^Y$, the protecting groups described in Protective Groups in Organic Synthesis (authored by Theodora W. Greene, Peter G. M. Wuts, issued by John Wiley & Sons, Inc., 1999) and the like may be used.

Compound d1 may be, for example, purchased as a commercial product. Compound d6 represents compound a18 in Production Method A or compound b14 in Production Method B.

[D-1 Step]
Compound d2 may be produced by condensing compound d1 and an aspartic acid diester or glutamic acid diester in accordance with the method described in the above A-13 step.

[D-2 Step]
Compound d3 may be produced by hydrolyzing the ester of compound d2, in accordance with the method described in the above A-12 step.

[D-3 Step]
Compound d4 may be produced by condensing compound d3 and (AB)$_p$ in accordance with the method described in the above A-13 step.

[D-4 Step]
Compound d5 may be produced by carrying out hydrolysis of the ester of compound d4, and deprotection of the protecting group for the amino group in accordance with the method described in the above A-18 step. In addition, when (AB)$_p$ has an ester or a protected amino group, hydrolysis of the ester and deprotection of the protecting group for the amino may also be carried out in the present deprotecting step, as necessary.

[D-5 Step]
Compound d7 may be produced from compound d5 and compound d6 in accordance with the method described in the above A-16 step.

[D-6 Step]
Compound d8 may be produced from compound d7 in accordance with the method described in the above A-17 step.

[D-7 Step]
Compound D1 may be produced from compound d8 in accordance with the method described in the above A-18 step.

[D-8 Step]
Compound D2 may be produced from compound D1 in accordance with the method described in the above A-19 step.

Production Method E
When Z is a group represented by formula (Z-2) or formula (Z-3); $R^{1a}$ is a methyl group; $R^{1b}$ is a hydrogen atom or a methyl group; and $R^3$ is —OH, the compound represented by formula (1-1) may be produced by, for example, the following production method:

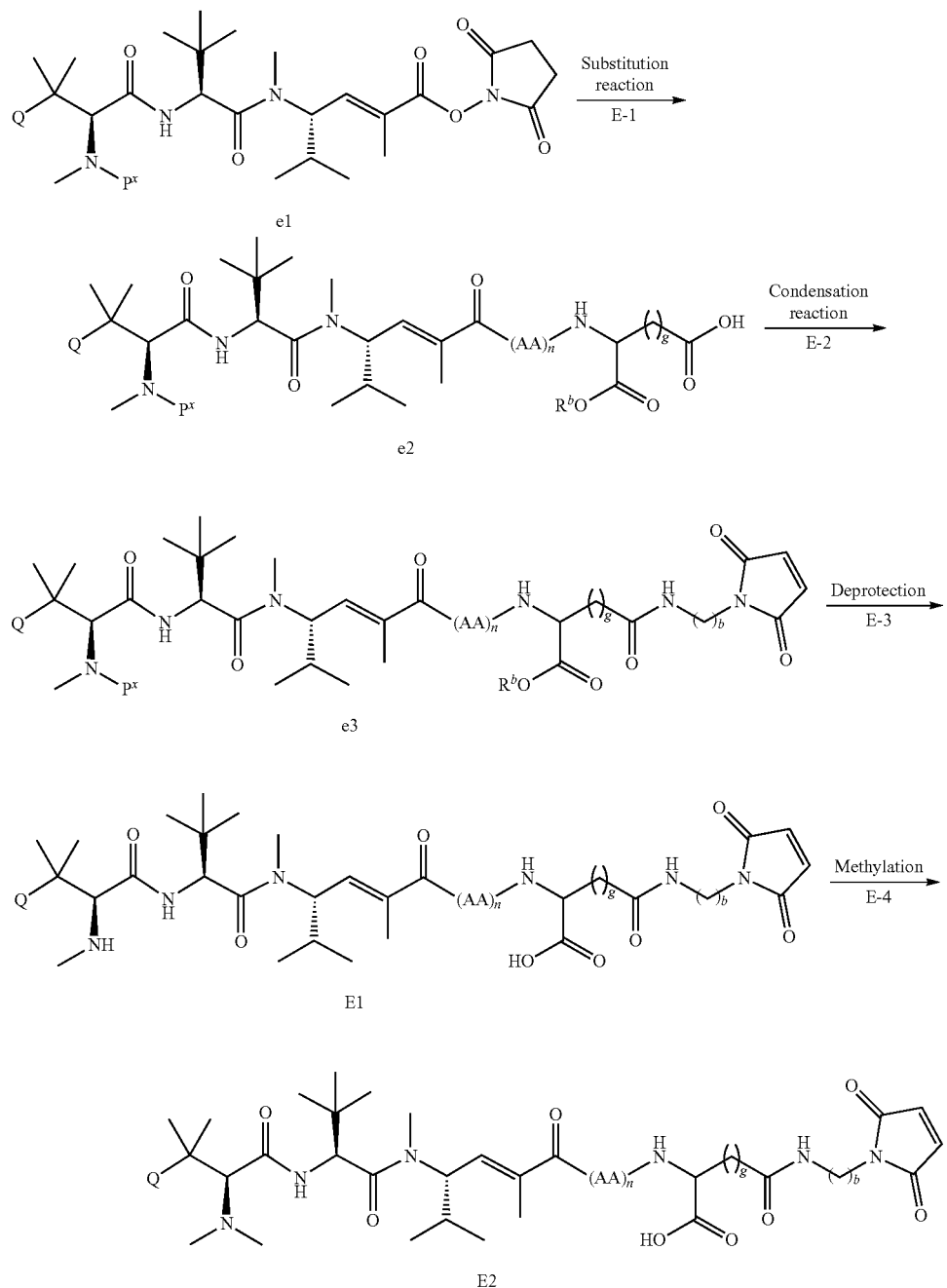

wherein, Q, AA, b and n are as defined in item 2; g represents 1 or 2; and $R^b$ and $P^x$ are as defined above.

Compound e1 represents compound a18 in Production Method A or compound b14 in Production Method B.

[E-1 Step]

Compound e2 may be produced from compound e1 in accordance with the method described in the above A-16 step.

[E-2 Step]

Compound e3 may be produced from compound e2 in accordance with the method described in the above A-17 step.

[E-3 Step]

Compound E1 may be produced from compound e3 in accordance with the method described in the above A-18 step.

[E-4 Step]

Compound E2 may be produced from compound E1 in accordance with the method described in the above A-19 step.

Production Method F

When Z is a group represented by formula (Z-2) or formula (Z-3); $R^{1a}$ is a methyl group; $R^{1b}$ is a hydrogen atom or a methyl group; and $R^3$ is —OH, the compound represented by formula (1-1) may be produced by, for example, the following production method:

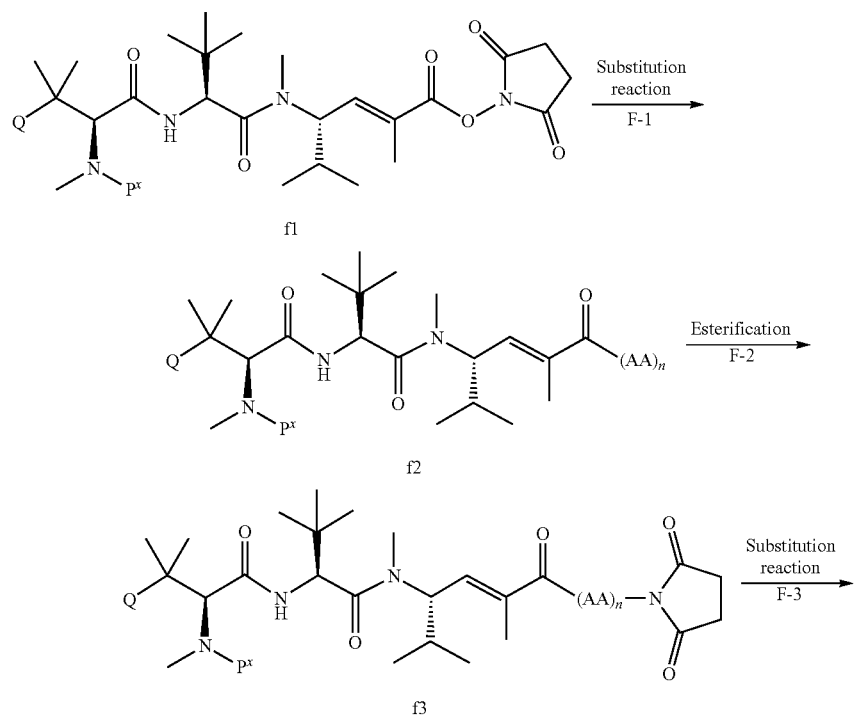
f1 → Substitution reaction F-1
f2 → Esterification F-2
f3 → Substitution reaction F-3
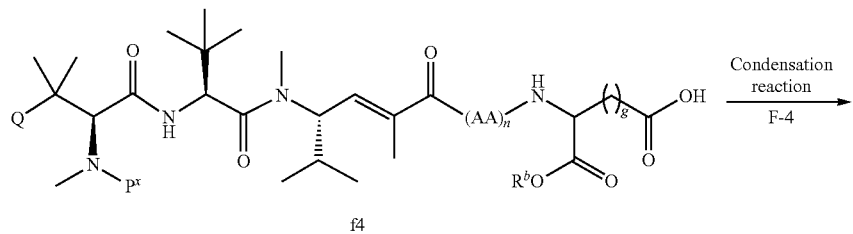
f4 → Condensation reaction F-4
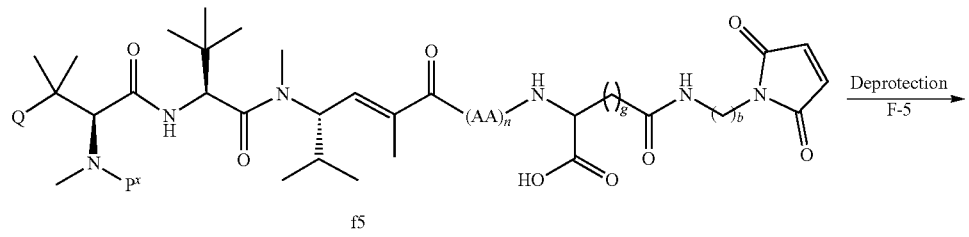
f5 → Deprotection F-5
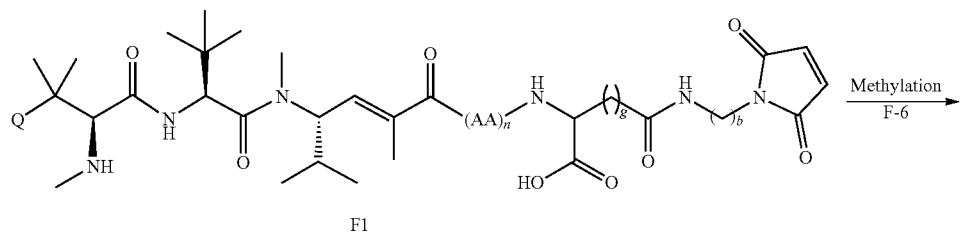
F1 → Methylation F-6

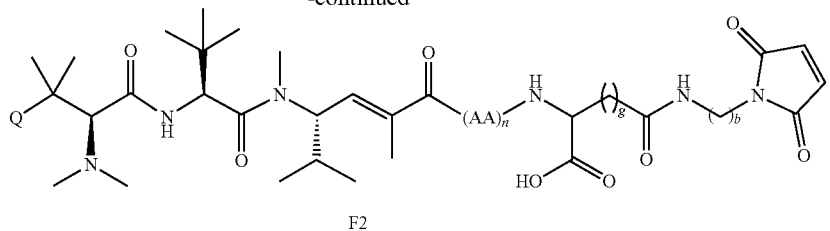

F2 wherein, Q, AA, b and n are as defined in item 2; and g, $R^b$ and $P^x$ are as defined above.

Compound f1 represents compound a18 in Production Method A or compound b14 in Production Method B.

[F-1 Step]
Compound f2 may be produced from compound f1 in accordance with the method described in the above A-16 step.

[F-2 Step]
Compound f3 may be produced from compound f2 in accordance with the method described in the above A-15 step.

[F-3 Step]
Compound f4 may be produced from compound f3 in accordance with the method described in the above A-16 step.

[F-4 Step]
Compound f5 may be produced from compound f4 in accordance with the method described in the above A-17 step.

[F-5 Step]
Compound F1 may be produced from compound f5 in accordance with the method described in the above A-18 step.

[F-6 Step]
Compound F2 may be produced from compound F1 in accordance with the method described in the above A-19 step.

Production Method G

When Z is a group represented by formula (Z-2) or formula (Z-3); $R^{1a}$ is a methyl group; $R^{1b}$ is a hydrogen atom or a methyl group; and $R^3$ is $-(AB)_p$, the compound represented by formula (1-1) may be produced by, for example, the following production method:

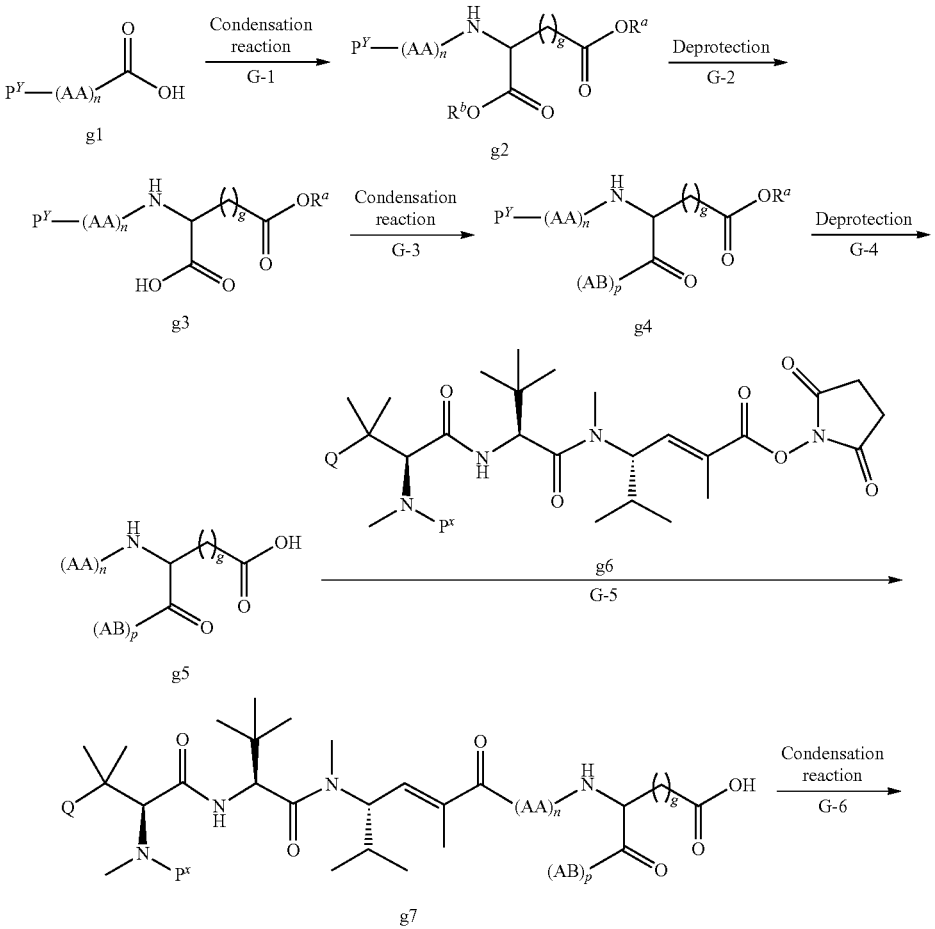

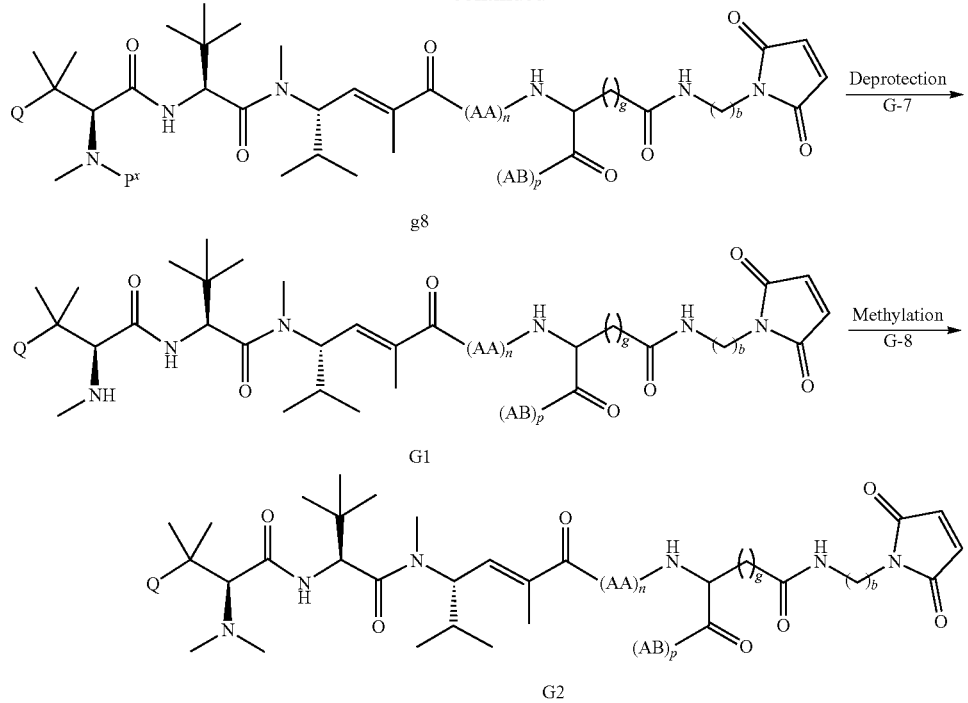

g8

G1

G2 wherein, Q, AA, AB, b, p and n are as defined in item 2; and g, $R^a$, $R^b$, $P^X$ and $P^Y$ are as defined above.

Compound g1 may be, for example, purchased as a commercial product. Compound g6 represents compound a18 in Production Method A or compound b14 in Production Method B.

[G-1 Step]
Compound g2 may be produced by condensing compound g1 and an aspartic acid diester or glutamic acid diester in accordance with the method described in the above A-13 step.

[G-2 Step]
Compound g3 may be produced by hydrolyzing the ester of compound g2, in accordance with the method described in the above A-12 step.

[G-3 Step]
Compound g4 may be produced from compound g3 and $(AB)_p$ in accordance with the method described in the above A-13 step.

[G-4 Step]
Compound g5 may be produced by carrying out hydrolysis of the ester of compound g4, and deprotection of the protecting group for the amino in accordance with the method described in the above A-18 step. In addition, when $(AB)_p$ has an ester or a protected amino group, hydrolysis of the ester and deprotection of the protecting group for the amino group may also be carried out in the present deprotecting step, as necessary.

[G-5 Step]
Compound g7 may be produced from compound g5 and compound g6 in accordance with the method described in the above A-16 step.

[G-6 Step]
Compound g8 may be produced from compound g7 in accordance with the method described in the above A-17 step.

[G-7 Step]
Compound G1 may be produced from compound g8 in accordance with the method described in the above A-18 step.

[G-8 Step]
Compound G2 may be produced from compound G1 in accordance with the method described in the above A-19 step.

Production Method H

When Z' is a group represented by formula (Z-4); $R^{1a}$ is a methyl group; and $R^{1b}$ is a hydrogen atom or a methyl group, the compound represented by formula (1-2) may be produced by, for example, the following production method:

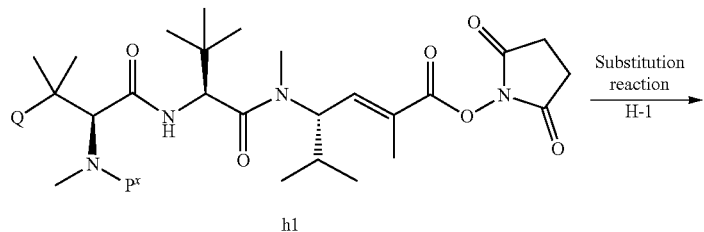

h1

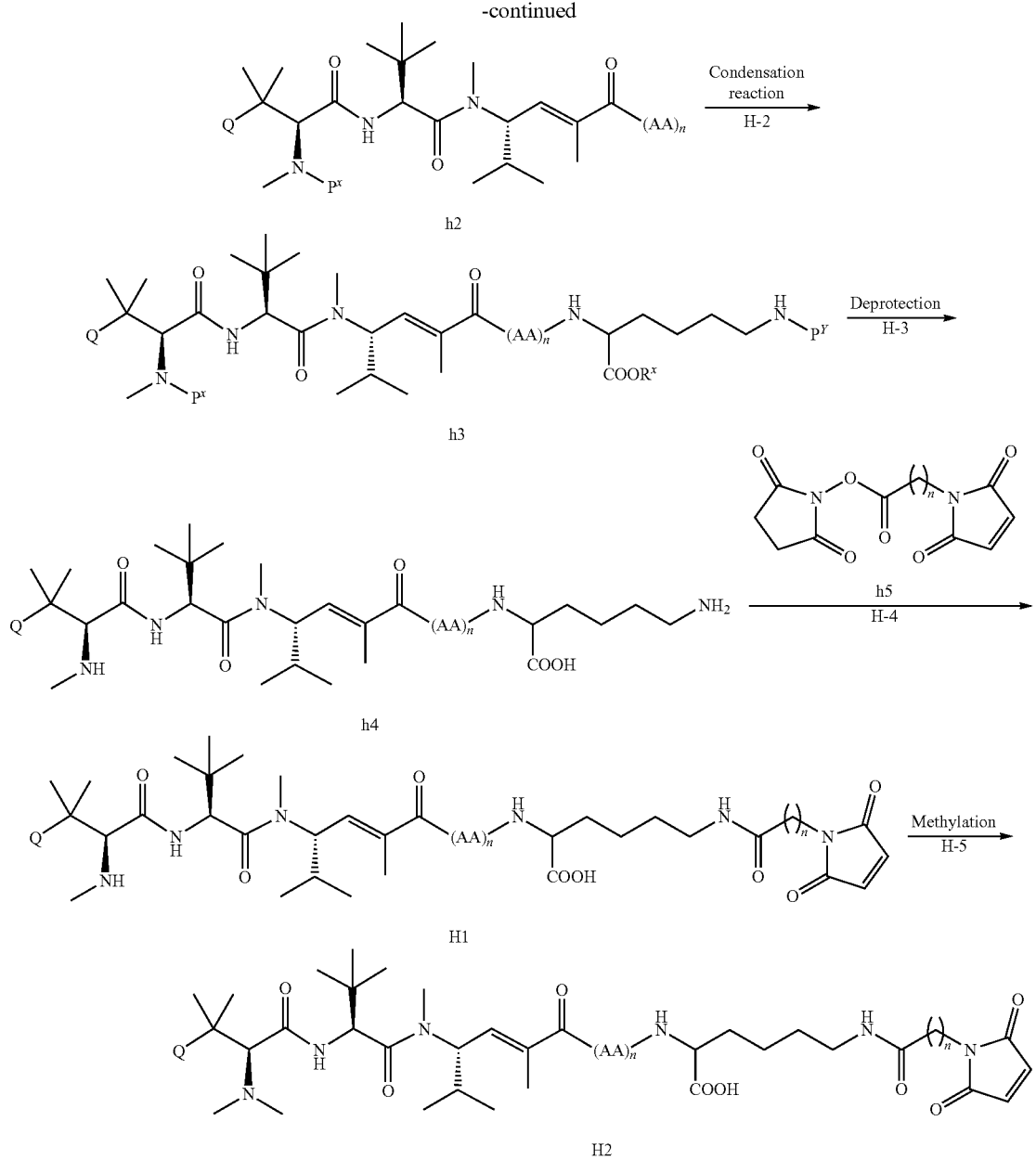

wherein, Q, AA, h and n are as defined in item 5; and $R^x$, $P^X$ and $P^Y$ are as defined above.

Compound h1 represents compound a18 in Production Method A or compound b14 in Production Method B. Compound h5 may be, for example, purchased as a commercial product.

[H-1 Step]
Compound h2 may be produced from compound h1 in accordance with the method described in the above A-16 step.

[H-2 Step]
Compound h3 may be produced by condensing compound h2 and a lysine derivative in accordance with the method described in the above A-13 step.

[H-3 Step]
Compound h4 may be produced from compound h3 in accordance with the method described in the above A-18 step.

[H-4 Step]
Compound H1 may be produced from compound h4 and compound h5 in accordance with the method described in the above A-16 step.

[H-5 Step]
Compound H2 may be produced from compound H1 in accordance with the method described in the above A-19 step.

Production Method I
When Z' is a group represented by formula (Z-5); $R^{1a}$ is a methyl group; and $R^{1b}$ is a hydrogen atom or methyl, the compound represented by formula (1-2) may be produced by, for example, the following production method:

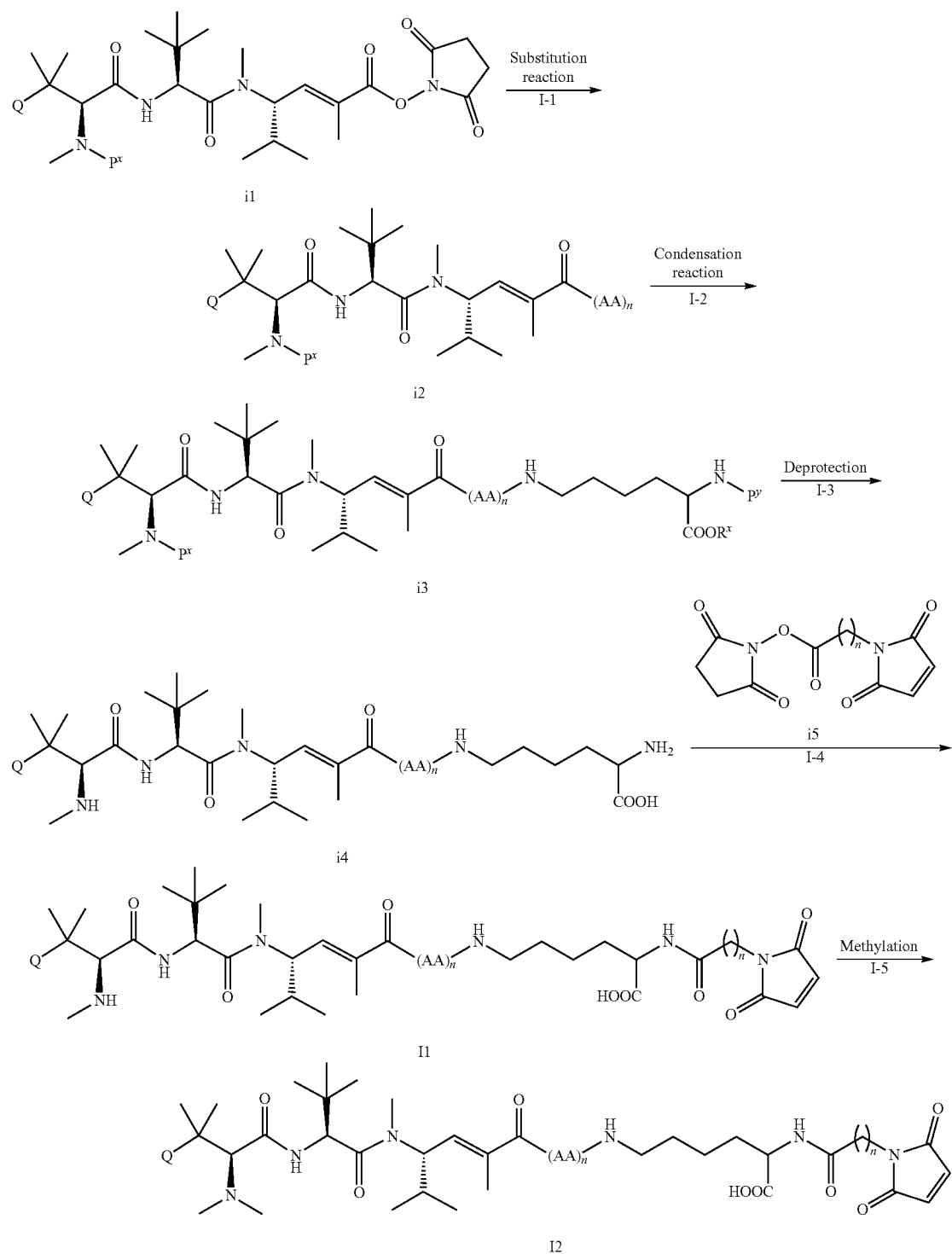

wherein, Q, AA, h and n are as defined in item 5; and $R^x$, $P^X$ and $P^Y$ are as defined above.

Compound i1 represents compound a18 in Production Method A or compound b14 in Production Method B. Compound i5 may be, for example, purchased as a commercial product.

[I-1 Step]

Compound i2 may be produced from compound i1 in accordance with the method described in the above A-16 step.

[I-2 Step]

Compound i3 may be produced by condensing compound i2 and a lysine derivative in accordance with the method described in the above A-13 step.

[I-3 Step]

Compound i4 may be produced from compound i3 in accordance with the method described in the above A-18 step.

[I-4 Step]

Compound I1 may be produced from compound i4 and compound i5 in accordance with the method described in the above A-16 step.

[I-5 Step]

Compound I2 may be produced from compound I1 in accordance with the method described in the above A-19 step.

Production Method L

Compound I6 is a production intermediate of compound L1 represented by formula (1-1), wherein Z is a group represented by formula (Z-1), formula (Z-2) or formula (Z-3); and Q is a group represented by formula (Qa-1), formula (Qa-2), formula (Qa-3), formula (Qa-4), formula (Qa-5) or formula (Qa-6). Compound I6 may be produced by, for example, the following production method. In addition, compound L may be produced from compound I6 in accordance with the production method described in A-16 step to A-19 step of Production Method A:

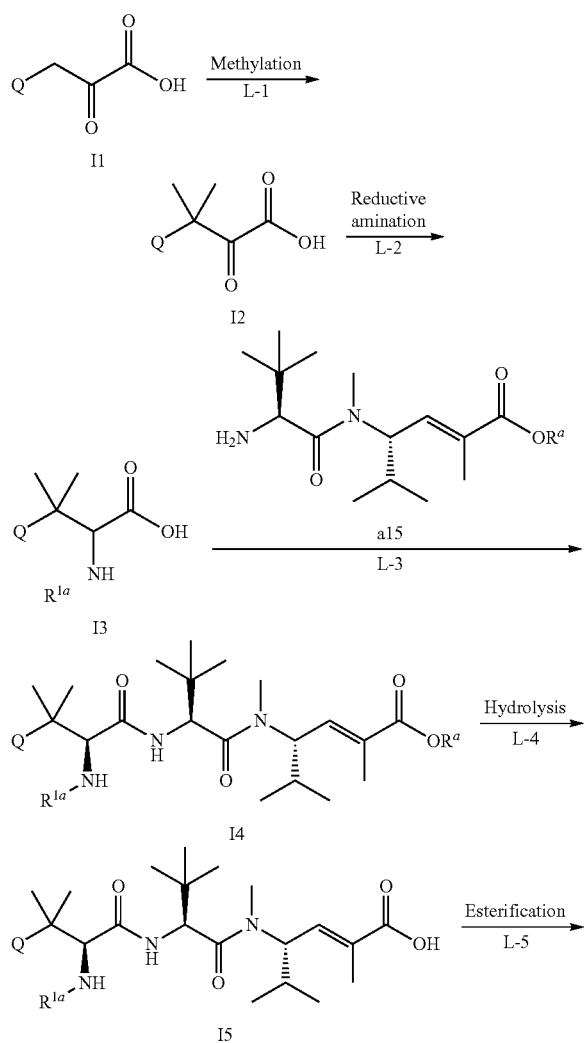

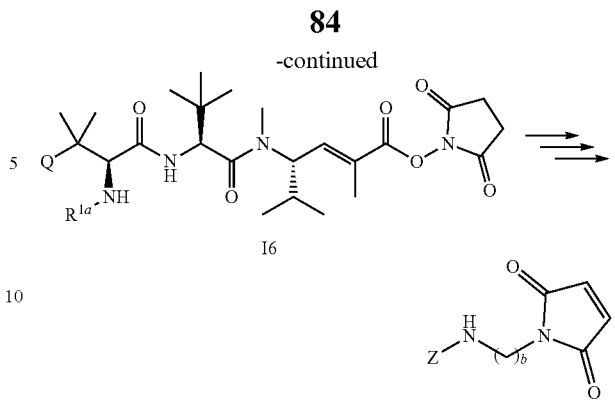

wherein, $R^{1a}$ and b are as defined in item 1; and $R^a$ represents a $C_{1-6}$ alkyl group.

Compound I1 may be, for example, purchased as a commercial product. Compound a15 may be produced by, for example, the method described in Production Method A.

[L-1 Step]

Compound 12 may be produced in accordance with the method described in, for example, Bioorg. Med. Chem. Lett. 14 (2004) 5317-5322 and the like.

[L-2 Step]

Compound 13 may be produced in accordance with the method described in, for example, Bioorg. Med. Chem. Lett. 14 (2004) 5317-5322 and the like.

[L-3 Step]

Compound 14 may be produced in accordance with the method described in, for example, Bioorg. Med. Chem. Lett. 14 (2004) 5317-5322 and the like.

[L-4 Step]

Compound 15 may be produced from compound 14 in accordance with A-14 step of Production Method A.

[L-5 Step]

Compound 16 may be produced from compound 15 in accordance with A-15 step of Production Method A.

Production Method M

Compound m7 is a production intermediate of compound Ma1 represented by formula (1-1), wherein Z is a group represented by formula (Z-1), formula (Z-2) or formula (Z-3) and Q is a group represented by formula (Qa-7). Compound m7 may be produced by, for example, the following production method. In addition, compound Ma1 may be produced from compound m7 in accordance with the production method described in A-16 step to A-19 step of Production Method A:

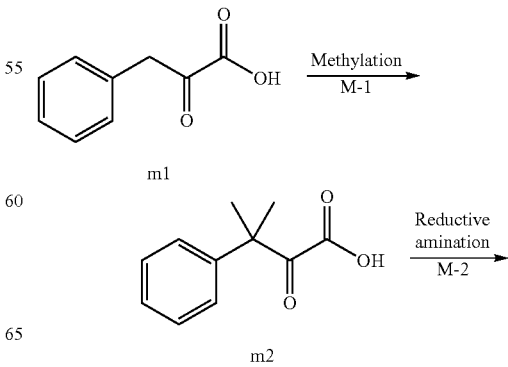

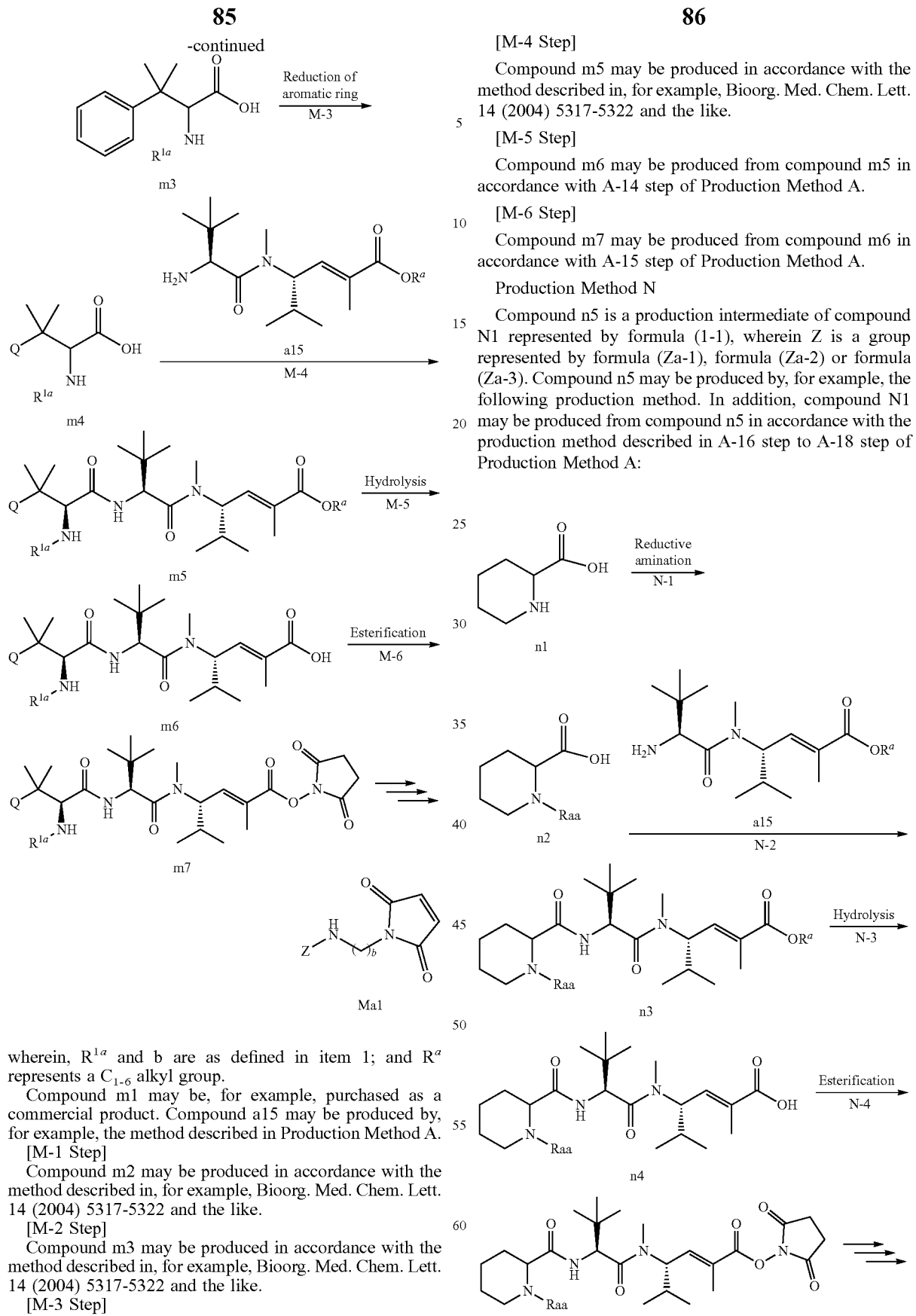

[M-4 Step]

Compound m5 may be produced in accordance with the method described in, for example, Bioorg. Med. Chem. Lett. 14 (2004) 5317-5322 and the like.

[M-5 Step]

Compound m6 may be produced from compound m5 in accordance with A-14 step of Production Method A.

[M-6 Step]

Compound m7 may be produced from compound m6 in accordance with A-15 step of Production Method A.

Production Method N

Compound n5 is a production intermediate of compound N1 represented by formula (1-1), wherein Z is a group represented by formula (Za-1), formula (Za-2) or formula (Za-3). Compound n5 may be produced by, for example, the following production method. In addition, compound N1 may be produced from compound n5 in accordance with the production method described in A-16 step to A-18 step of Production Method A:

wherein, $R^{1a}$ and b are as defined in item 1; and $R^a$ represents a $C_{1-6}$ alkyl group.

Compound m1 may be, for example, purchased as a commercial product. Compound a15 may be produced by, for example, the method described in Production Method A.

[M-1 Step]

Compound m2 may be produced in accordance with the method described in, for example, Bioorg. Med. Chem. Lett. 14 (2004) 5317-5322 and the like.

[M-2 Step]

Compound m3 may be produced in accordance with the method described in, for example, Bioorg. Med. Chem. Lett. 14 (2004) 5317-5322 and the like.

[M-3 Step]

Compound m4 may be produced in accordance with the method described in, for example, J. Med. Chem. 2004, 47, 4774-4786 and the like.

-continued

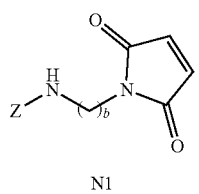

n1 wherein, $R^{aa}$ and b are as defined in item 1; and $R^a$ represents a $C_{1-6}$ alkyl group.

Compound n1 may be, for example, purchased as a commercial product. Compound a15 may be produced by, for example, the method described in Production Method A.

[N-1 Step]

Compound n2 may be produced in accordance with the method described in, for example, International Publication No. WO 2003/082268 and the like.

[N-2 Step]

Compound n3 may be produced from compound n2 in accordance with the method described in A-13 step.

[N-3 Step]

Compound n4 may be produced from compound n3 in accordance with the method described in A-14 step.

[N-4 Step]

Compound n5 may be produced from compound n4 in accordance with A-15 step of Production Method A.

Production Method O

Compound O1 and compound O2 are compounds represented by formula (1-1), wherein Z is a group represented by formula (Za-4) or formula (Za-5). Compound O1 and compound O2 may be produced by, for example, the following production method:

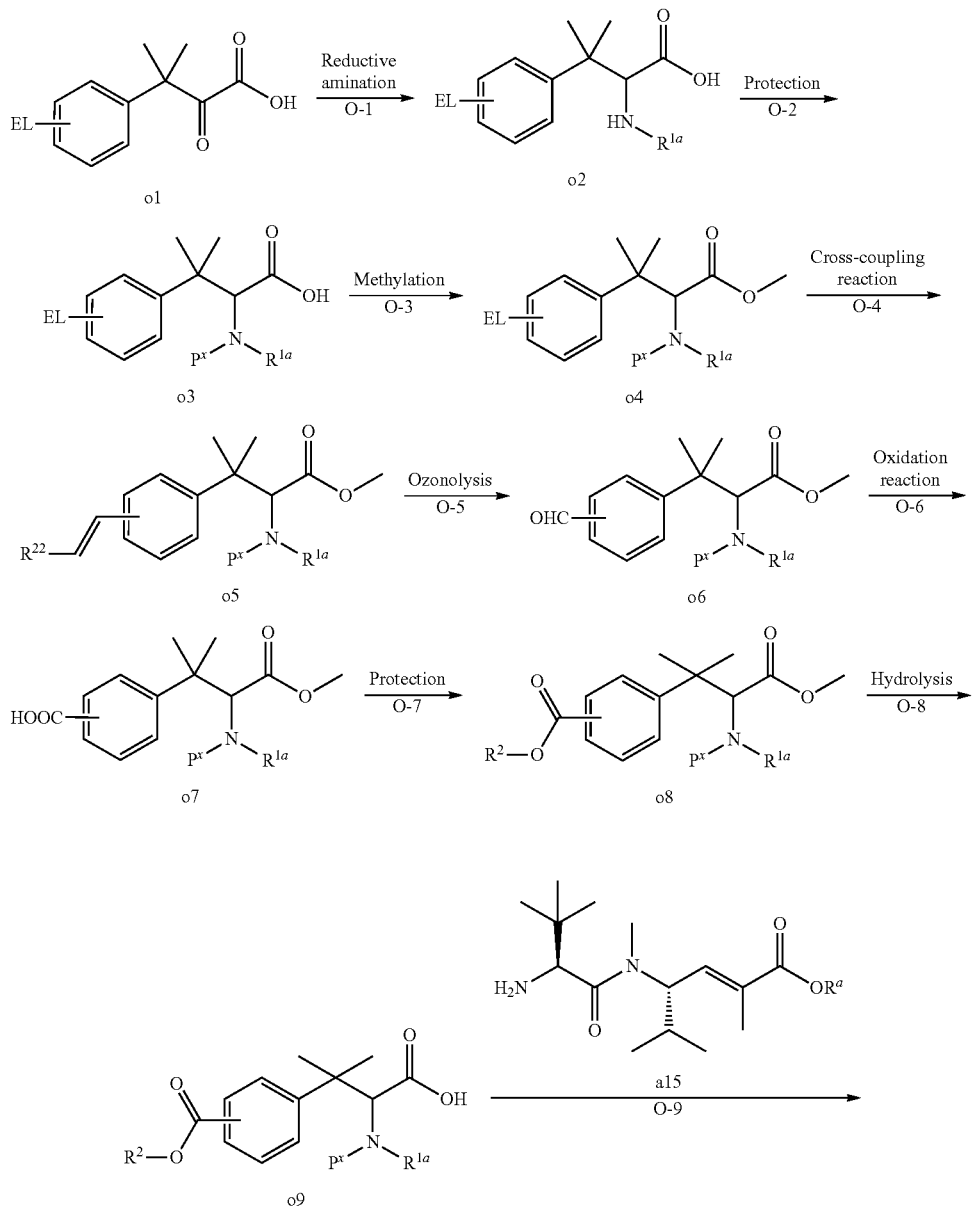

-continued
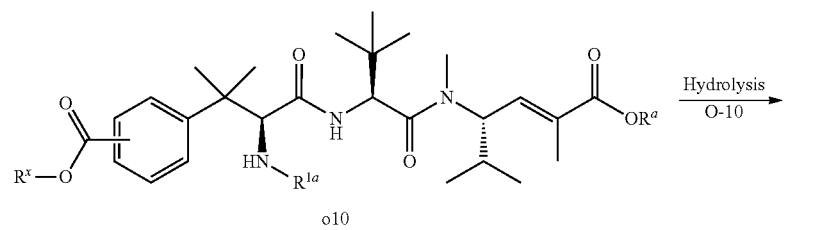
o10 → Hydrolysis O-10
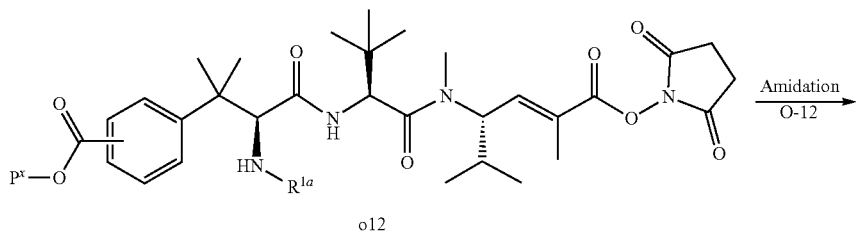
o11 → Esterification O-11
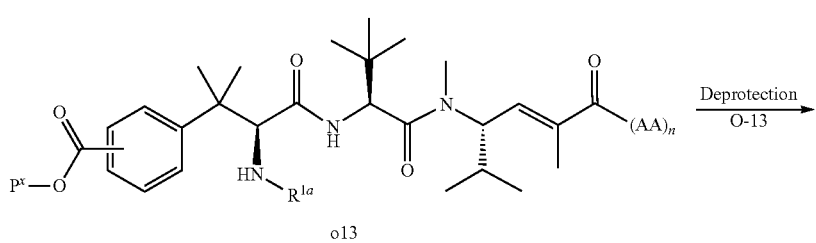
o12 → Amidation O-12
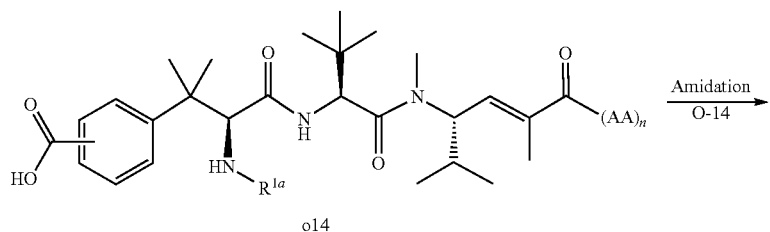
o13 → Deprotection O-13
o14 → Amidation O-14
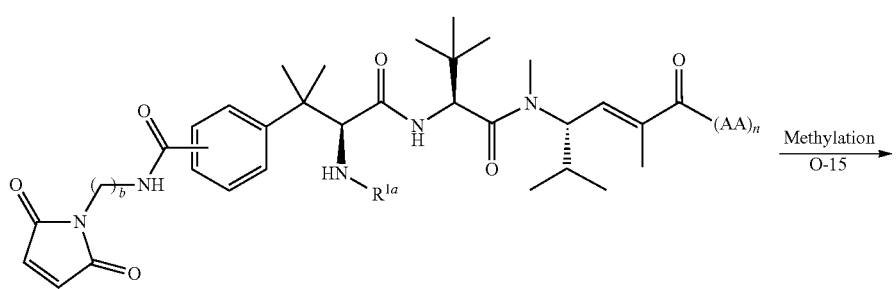
→ Methylation O-15 wherein, AA, $R^{1a}$, b and n are as defined in item 1; EL represents a chlorine atom, a bromine atom, an iodine atom, a trifluoromethylsulfonyl group or a tosyl group; $R^{zz}$ represents a hydrogen atom or —$COOR^a$; $P^x$ represents a protecting group for the amino group; $P^z$ represents a protecting group for the carboxyl group; and $R^a$ represents a $C_{1-6}$ alkyl group.

Compound o1 may be produced by the methods described in, for example, International Publication No. WO 2004/026293, International Publication No. WO 2016/123582 and the like, or may be purchased as a commercial product. Compound a15 may be produced by, for example, the method described in Production Method A.

[O-1 Step]

Compound o2 may be produced from compound o1 in accordance with the methods described in, for example, International Publication No. WO 2004/026293; Bioorg. Med. Chem. Lett. 14 (2004) 5317-5322; and the like.

[O-2 Step]

Compound o3 may be produced from compound o2 in accordance with the method described in the above A-8 step.

[O-3 Step]

Compound o4 may be produced from compound o3 in accordance with the method described in the above A-11 step.

[O-4 Step]

Compound o5 may be produced from compound o4 by the method described in, for example, International Publication No. WO 2004/026293 and the like.

[O-5 Step]

Compound o6 may be produced from compound o5 by the method described in, for example, International Publication No. WO 2004/026293 and the like.

[O-6 Step]

Compound o7 may be produced from compound o6 by the method described in, for example, International Publication No. WO 2004/026293 and the like.

[O-7 Step]

Compound o8 may be produced by protecting the carboxyl group of compound o7 with protecting group, $P^z$. This step may be carried out in accordance with the method described in Protective Groups in Organic Synthesis (authored by Theodora W. Greene, Peter G. M. Wuts, issued by John Wiley & Sons, Inc., 1999) and the like.

[O-8 Step]

Compound o9 may be produced from compound o8 in accordance with the method described in the above A-12 step.

[O-9 Step]

Compound o10 may be produced from compound o9 in accordance with the method described in the above A-13 step.

[O-10 Step]

Compound o11 may be produced from compound o10 in accordance with the method described in the above A-14 step.

[O-11 Step]

Compound o12 may be produced from compound o11 in accordance with the method described in the above A-15 step.

[O-12 Step]

Compound o13 may be produced from compound o12 in accordance with the method described in the above A-16 step.

[O-13 Step]

Compound o14 may be produced from compound o13 by deprotecting the protecting group, $P^z$. This step may be carried out in accordance with the method described in Protective Groups in Organic Synthesis (authored by Theodora W. Greene, Peter G. M. Wuts, issued by John Wiley & Sons, Inc., 1999) and the like.

[O-14 Step]

Compound 01 may be produced from compound o14 in accordance with the method described in the above A-17 step.

[O-15 Step]

Compound 02 may be produced from compound 01 in accordance with the methods described in the above A-19 step.

Production Method P

Compound P1 and compound P2 are the compounds represented by formula (1-2), wherein Z is a group represented by formula (Za-8) or formula (Za-9). Compound P1 and compound P2 may be produced by, for example, the following production method:

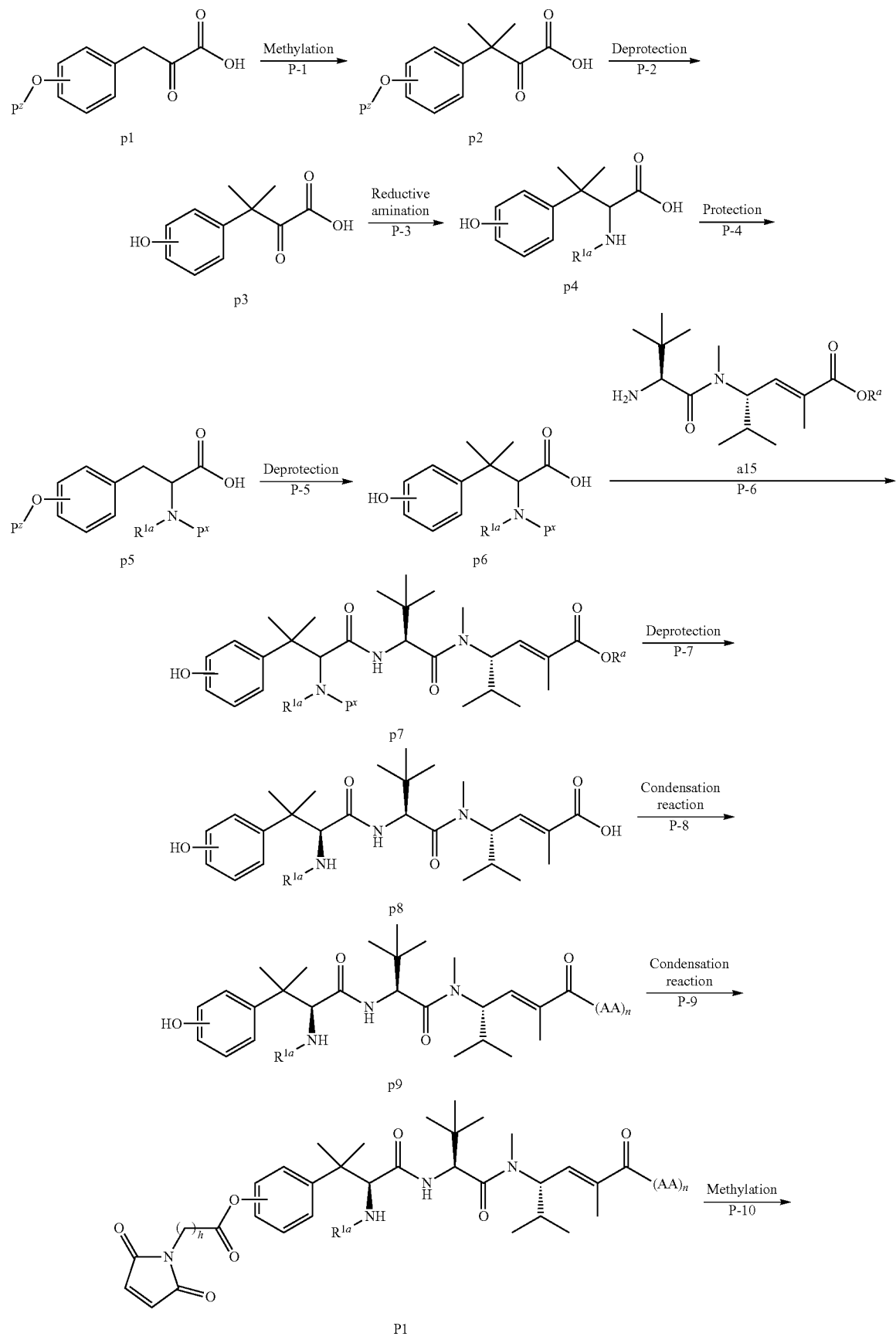

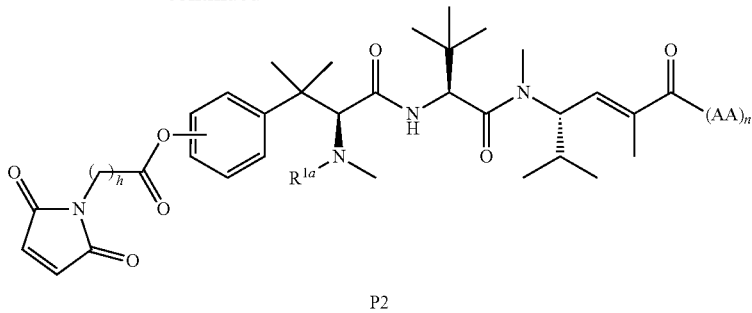

P2 wherein, AA, n, h and $R_{1a}$ are as defined in item 4; $P^x$ represents a protecting group for the amino group; $P^z$ represents a protecting group for the hydroxy group; and $R^a$ represents a $C_{1-6}$ alkyl group.

Compound p1 may be, for example, purchased as a commercial product. Compound a15 may be produced by, for example, the method described in Production Method A.

[P-1 Step]

Compound p2 may be produced from compound p in accordance with the method described in, for example, International Publication No. WO 2004/026293 and the like.

[P-2 Step]

Compound p3 may be produced from compound p2 by deprotecting the protecting group, $P^z$. This step may be carried out in accordance with the method described in Protective Groups in Organic Synthesis (authored by Theodora W. Greene, Peter G. M. Wuts, issued by John Wiley & Sons, Inc., 1999) and the like.

[P-3 Step]

Compound p4 may be produced from compound p3 in accordance with the method described in, for example, International Publication No. WO 2004/026293 and the like.

[P-4 Step]

Compound p5 may be produced by protecting the amino group and the hydroxy group of compound p4 with protecting group $P^x$ and protecting group $P^z$, respectively. This step may be carried out in accordance with the method described in Protective Groups in Organic Synthesis (authored by Theodora W. Greene, Peter G. M. Wuts, issued by John Wiley & Sons, Inc., 1999) and the like.

[P-5 Step]

Compound p6 may be produced from compound p5 by deprotecting the protecting group, $P^z$. This step may be carried out in accordance with the method described in Protective Groups in Organic Synthesis (authored by Theodora W. Greene, Peter G. M. Wuts, issued by John Wiley & Sons, Inc., 1999), or Tetrahedron Lett. 45 (2004) 495-499 and the like.

[P-6 Step]

Compound p7 may be produced from compound p6 in accordance with the method described in A-13 step.

[P-7 Step]

Compound p8 may be produced from compound p7 in accordance with the method described in the above A-18 step.

[P-8 Step]

Compound p9 may be produced from compound p8 by carrying out condensation in accordance with the method described in the above A-13 step. In addition, when $(AA)_n$ has an ester or a protected amino group, hydrolysis of the ester and deprotection of the protecting group for the amino group may also be carried out as necessary after the condensation reaction, in accordance with the method described in Protective Groups in Organic Synthesis (authored by Theodora W. Greene, Peter G. M. Wuts, issued by John Wiley & Sons, Inc., 1999) and the like.

[P-9 Step]

Compound P1 may be produced by condensing compound p9 and a succinimide derivative in accordance with the method described in the above A-16 step.

[P-10 Step]

Compound P2 may be produced from compound P1 in accordance with the method described in the above A-19 step.

Production Method T

Compound T1 and compound T2 are the compounds represented by formula (1-2), wherein Z is a group represented by formula (Za-6) or formula (Za-7). Compound T1 and compound T2 may be produced by, for example, the following production method:

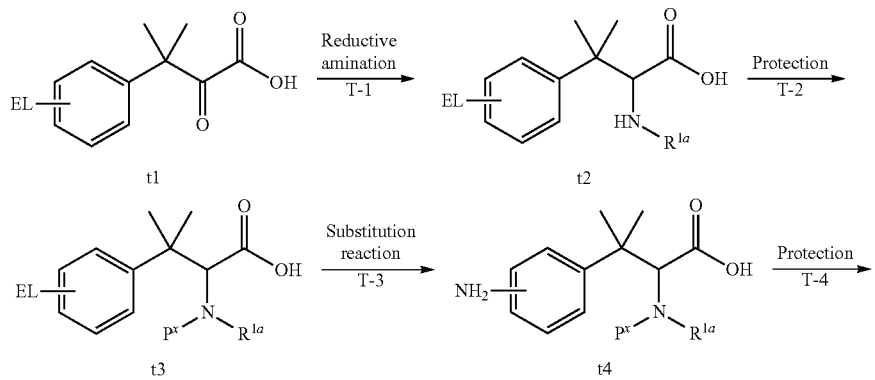

-continued
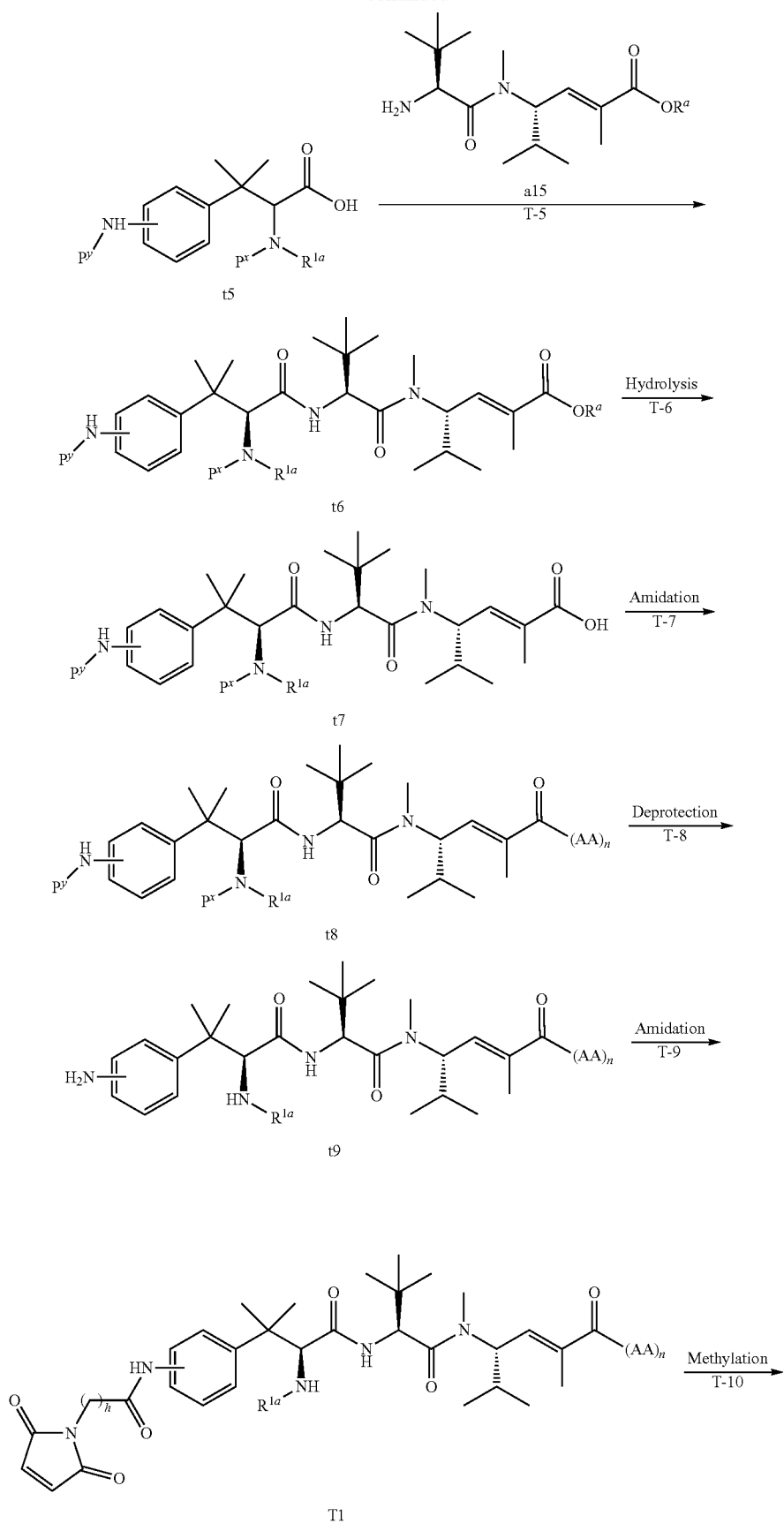

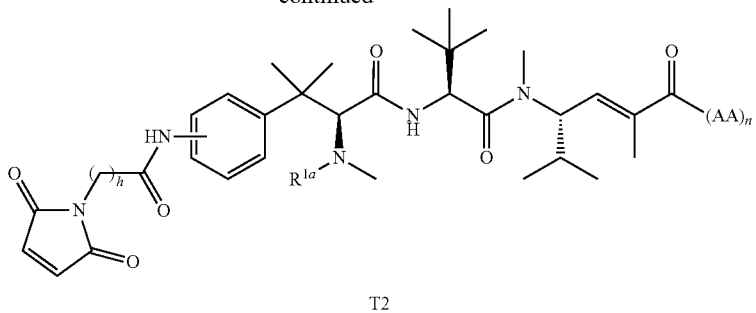

T2 wherein, AA, n, h and $R^{1a}$ are as defined in item 4; EL represents a chlorine atom, a bromine atom, an iodine atom, a trifluoromethylsulfonyl group or a tosyl group; $P^x$ and $P^y$ represent a protecting group for the amino group; and $R^a$ represents a $C_{1-6}$ alkyl group.

Compound t1 may be produced by the methods described in, for example, International Publication No. WO 2004/026293, International Publication No. WO 2016/123582 and the like, or may be purchased as a commercial product. Compound a15 may be produced by, for example, the method described in Production Method A.

[T-1 Step]

Compound t2 may be produced from compound t1 in accordance with the methods described in, for example, International Publication No. WO 2004/026293; Bioorg. Med. Chem. Lett. 14 (2004) 5317-5322; and the like.

[T-2 Step]

Compound t3 may be produced from compound t2 in accordance with the method described in the above A-8 step.

[T-3 Step]

Compound t4 may be produced from compound t3 by the method described in, for example, International Publication No. WO 2016/123582 and the like.

[T-4 Step]

Compound t5 may be produced by protecting the amino group of compound t4 with protecting group, $P^Y$. This step may be carried out in accordance with the method described in Protective Groups in Organic Synthesis (authored by Theodora W. Greene, Peter G. M. Wuts, issued by John Wiley & Sons, Inc., 1999) and the like.

[T-5 Step]

Compound t6 may be produced from compound t5 in accordance with the method described in the above A-13 step.

[T-6 Step]

Compound t7 may be produced from compound t6 in accordance with the method described in the above A-14 step.

[T-7 Step]

Compound t8 may be produced from compound t7 in accordance with the method described in the above A-13 step.

[T-8 Step]

Compound t9 may be produced by deprotecting the protecting groups $P^x$ and $P^y$ of compound t8. This step may be carried out in accordance with the methods described in Protective Groups in Organic Synthesis (authored by Theodora W. Greene, Peter G. M. Wuts, issued by John Wiley & Sons, Inc., 1999), Tetrahedron Lett. 45 (2004) 495-499 and the like. In addition, when $(AA)_n$ has an ester or a protected amino group, hydrolysis of the ester and deprotection of the protecting group for the amino group may also be carried out in the present deprotecting step, as necessary.

[T-9 Step]

Compound T1 may be produced from compound t9 in accordance with the method described in the above A-13 or A-16 step.

[T-10 Step]

Compound T2 may be produced from compound T2 in accordance with the method described in the above A-19 step.

Production Method U

Compound U1 and compound U2 are compounds represented by formula (1-2), wherein Z is a group represented by formula (Za-10). Compound U1 and compound U2 may be produced by, for example, the following production method:

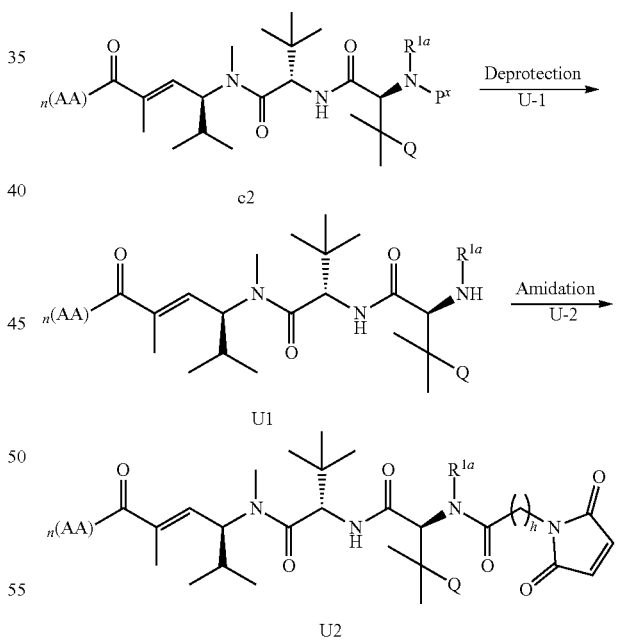

wherein, AA, h, Q, n and $R^{1a}$ are as defined in item 4; and $P^x$ represents a protecting group for the amino group.

[U-1 Step]

Compound U1 may be produced from compound c2 in accordance with the method described in the above A-18.

[U-2 Step]

Compound U2 may be produced from compound U1 in accordance with the method described in the above A-13 or A-16.

Production Method W

Compound W1 is a compound represented by formula (1-2), wherein Z is a group represented by formula (Za-11). Compound W1 may be produced by, for example, the following production method:

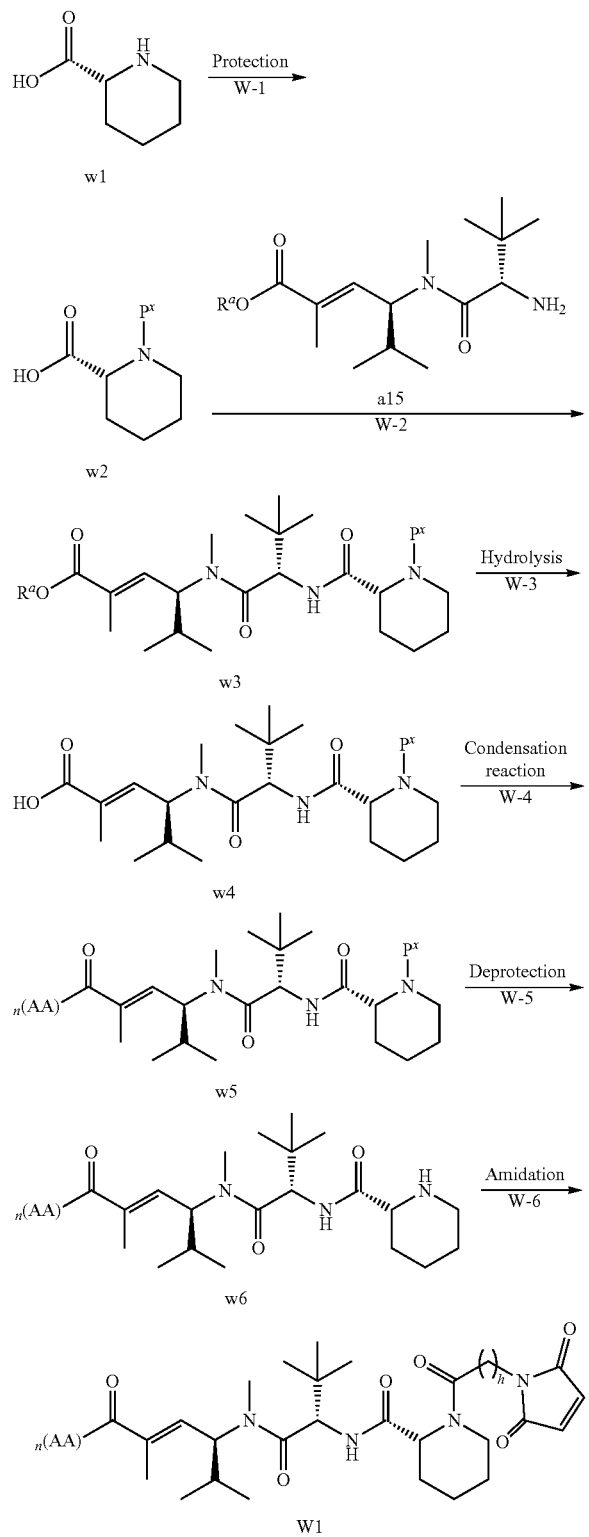

wherein, AA, h and n are as defined in item 4; $P^x$ represents a protecting group for the amino group; and $R^a$ represents a $C_{1-6}$ alkyl group.

Compound w1 may be, for example, purchased as a commercial product. Compound a15 may be produced by, for example, the method described in Production Method A.

[W-1 Step]

Compound w2 may be produced by protecting the amino group of compound w1 with protecting group, $P^x$. This step may be carried out in accordance with the method described in Protective Groups in Organic Synthesis (authored by Theodora W. Greene, Peter G. M. Wuts, issued by John Wiley & Sons, Inc., 1999) and the like.

[W-2 Step]

Compound w3 may be produced from compound w2 in accordance with the method described in the above A-13 step.

[W-3 Step]

Compound w4 may be produced from compound w3 in accordance with the method described in the above A-14 step.

[W-4 Step]

Compound w5 may be produced from compound w4 in accordance with the method described in the above A-13 step.

[W-5 Step]

Compound w6 may be produced by deprotecting the protecting groups $P^x$ of compound w5. This step may be carried out in accordance with the methods described in Protective Groups in Organic Synthesis (authored by Theodora W. Greene, Peter G. M. Wuts, issued by John Wiley & Sons, Inc., 1999), Tetrahedron Lett. 45 (2004) 495-499 and the like. In addition, when $(AA)_n$ has an ester or a protected amino group, hydrolysis of the ester and deprotection of the protecting group for the amino group may also be carried out in the present deprotecting step, as necessary.

[W-6 Step]

Compound W1 may be produced from compound w6 in accordance with the method described in the above A-13 or the above A-16 step.

Production methods for the antibody-drug conjugate according to the present invention will be mentioned below. The antibody-drug conjugate according to the present invention represented by formula (2-1) or (2-2) may be produced by, for example, the following production method J or production method K.

Production Method J

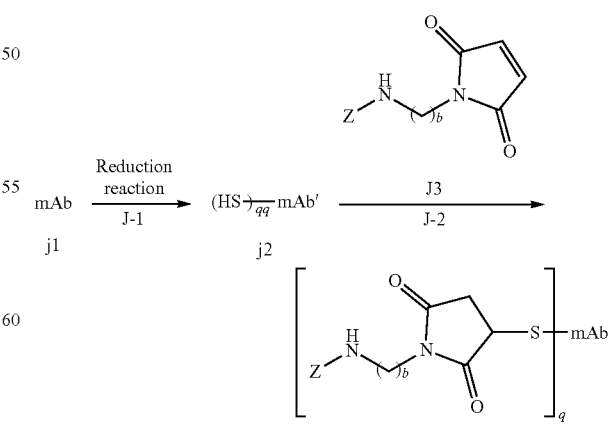

wherein, mAb, q, b and Z are as defined in item 16; mAb' represents mAb in which a disulfide bond is reduced; and qq represents an integer of 1 to 8.

[J-1 Step]

Compound j2 may be produced by allowing compound j1 to react with an appropriate disulfide reducing agent in an appropriate buffer solution. Examples of the disulfide reducing agent include dithiothreitol, mercaptoethanol and tris(2-carboxyethyl)phosphine; and preferably include tris(2-carboxyethyl)phosphine. Examples of the buffer solution include Tris-HCl, PBS, HEPES, acetate, borate, phosphate and carbonate buffers, and preferably include Tris-HCl and PBS. The pH upon the reaction is normally 2 to 12, and is preferably 4 to 9. The reaction time is normally 5 minutes to 24 hours, and is preferably 5 minutes to 5 hours. The reaction temperature is normally −10° C. to 50° C., and is preferably 0° C. to 40° C.

[J-2 Step]

Compound J1 may be produced by allowing compound j2 and compound j3 to react in an appropriate buffer solution. Examples of the buffer solution include Tris-HCl, PBS, HEPES, acetate, borate, phosphate and carbonate buffers, and preferably include Tris-HCl and PBS. The pH upon the reaction is normally 2 to 12, and is preferably 4 to 9. The reaction time is normally 5 minutes to 72 hours, and is preferably 30 minutes to 24 hours. The reaction temperature is normally −78° C. to 200° C., and is preferably 0° C. to 25° C.

Production Method K

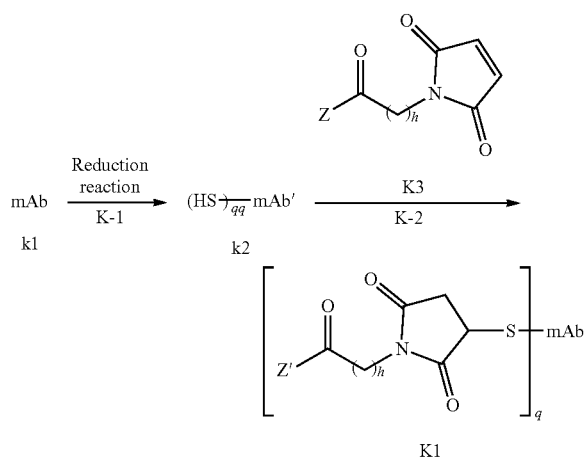

wherein, mAb, q, h and Z' are as defined in item 19; mAb' represents mAb in which a disulfide bond is reduced; and qq represents an integer of 1 to 8.

[K-1 Step]

Compound k2 may be produced from compound k1 in accordance with the method described in the above J-1 step.

[K-2 Step]

Compound K1 may be produced from compound k2 and compound k3 in accordance with the method described in the above J-2 step.

In the above, production methods of the hemiasterlin derivative and antibody-drug conjugate according to the present invention are shown. However, the hemiasterlin derivative and antibody-drug conjugate according to the present invention may also be produced by methods other than the above, for example, by combining methods known to a person having ordinary skill in the art as appropriate.

Appropriate bases used in each step of the above production methods should be selected as appropriate depending on reactions, types of raw material compounds and the like, and examples thereof include alkali bicarbonates such as sodium bicarbonate and potassium bicarbonate; alkali carbonates such as sodium carbonate and potassium carbonate; metal hydrides such as sodium hydride and potassium hydride; alkali metal hydroxides such as sodium hydroxide and potassium hydroxide; alkali metal alkoxides such as sodium methoxide and sodium t-butoxide; organometallic bases such as butyllithium and lithium diisopropylamide; and organic bases such as triethylamine, diisopropylethylamine, pyridine, 4-dimethylaminopyridine (DMAP) and 1,8-diazabicyclo[5.4.0]-7-undecene (DBU).

Appropriate solvents used in each step of the above production methods should be selected as appropriate depending on reactions, types of raw material compounds and the like, and examples thereof include alcohols such as methanol, ethanol and isopropanol; ketones such as acetone and methyl ketone; halogenated hydrocarbons such as methylene chloride and chloroform; ethers such as tetrahydrofuran (THF) and dioxane; aromatic hydrocarbons such as toluene and benzene; aliphatic hydrocarbons such as hexane and heptane; esters such as ethyl acetate and propyl acetate; amides such as N,N-dimethylformamide (DMF) and N-methyl-2-pyrrolidone; sulfoxides such as dimethylsulfoxide (DMSO); nitriles such as acetonitrile; distilled water; and the like, and one of these solvents may be used singly, or two or more of them may be mixed for use. In addition, depending on the type of reactions, organic bases such as triethylamine, diisopropylethylamine and pyridine may be used as the solvent.

The hemiasterlin derivative and antibody-drug conjugate according to the present invention may be separated and purified by methods known to a person having ordinary skill in the art. Examples thereof include extraction, partitioning, reprecipitation, column chromatography (for example, silica gel column chromatography, ion exchange column chromatography or preparative liquid chromatography) or recrystallization.

As the recrystallization solvent, for example, alcohol solvents such as methanol, ethanol and 2-propanol; ether solvents such as diethyl ether; ester solvents such as ethyl acetate; aromatic hydrocarbon solvents such as benzene and toluene; ketone solvents such as acetone; halogenated solvents such as dichloromethane and chloroform; hydrocarbon solvents such as hexane; aprotic solvents such as dimethylformamide acetonitrile; water; or mixed solvents thereof may be used.

As other purification method, the method described in The Experimental Chemistry (edited by The Chemical Society of Japan, Maruzen), vol. 1 and the like may be used. In addition, determination of the molecular structure of the hemiasterlin derivative and antibody-drug conjugate according to the present invention may be readily carried out by spectroscopic approaches such as nuclear magnetic resonance, infrared absorption technique and circular dichroism spectroscopy, or mass spectrometry, with reference to the structure deriverd from their respective raw material compounds.

In addition, intermediates or final products in the above production methods may also be derivatized into other compounds included in the present invention by converting their functional groups as appropriate, in particular, by extending various side chains using an amino group, hydroxy group, carbonyl group, halogen atom or the like as the basis, and upon this, by carrying out protection and deprotection of the above functional groups as necessary. The conversion of functional groups and extension of side chains may be carried out by general methods that are conventionally performed (for example, see Comprehensive Organic Transformations, R. C. Larock, John Wiley & Sons Inc. (1999) and the like).

The hemiasterlin derivative and antibody-drug conjugate according to the present invention may have asymmetry or may have a substituent having an asymmetric carbon, and optical isomers are present in such compounds. Optical isomers may be produced in accordance with conventional methods. Examples of the production method include a method of using a raw material having an asymmetric point or a method of introducing asymmetry in the midway stage. For example, in the case of optical isomers, optical isomers may be obtained by using optically active raw materials or by carrying out optical resolution or the like at an appropriate stage during the production process. When the hemiasterlin derivative and antibody-drug conjugate according to the present invention has a basic functional group, examples of the optical resolution method include a diastereomer method, in which a salt is formed using an optically active acid (for example, monocarboxylic acids such as mandelic acid, N-benzyloxyalanine and lactic acid; dicarboxylic acids such as tartaric acid, o-diisopropylidene tartaric acid and malic acid; sulfonic acids such as camphorsulfonic acid and bromocamphorsulfonic acid) in an inert solvent (for example, an alcohol solvent such as methanol, ethanol and 2-propanol; an ether solvent such as diethyl ether; an ester solvent such as ethyl acetate; a hydrocarbon solvent such as toluene; an aprotic solvent such as acetonitrile; or a mixed solvent of two or more selected from the above solvents). When the hemiasterlin derivative according to the present invention or a synthetic intermediate thereof has an acidic functional group such as carboxyl, optical resolution may also be carried out by using an optically active amine (for example, an organic amine such as 1-phenylethylamine, quinine, quinidine, cinchonidine, cinchonine and strychnine) to form a salt.

Examples of the temperature at which the salt is formed include the range from −50° C. to the boiling point of the solvent, preferably include the range from 0° C. to the boiling point, and more preferably include the range from room temperature to the boiling point of the solvent. In order to improve optical purity, it is desirable that the temperature be once raised to the vicinity of the boiling point of the solvent. Upon separating the precipitated salt by filtration, the yield may be improved by cooling as necessary. Examples of the amount of the optically active acid or amine to be used include the range of about 0.5 to about 2.0 equivalent to the substrate, and preferably include the range around 1 equivalent. As necessary, an optically active salt with high purity can be obtained by recrystallizing a crystal in an inert solvent (for example, an alcohol solvent such as methanol, ethanol and 2-propanol; an ether solvent such as diethyl ether; an ester solvent such as ethyl acetate; a hydrocarbon solvent such as toluene; an aprotic solvent such as acetonitrile; or a mixed solvent of two or more selected from the above solvents). In addition, a free form may be obtained by treating a salt that has been optically resolved with an acid or base through a conventional method, as necessary.

Among the raw materials or intermediates in the production methods described above, those, for which the production method was not described, are either commercially available compounds or may be synthesized from commercially available compounds by methods known to a person having ordinary skill in the art or methods equivalent thereto.

The antibody-drug conjugate according to the present invention and a pharmaceutical composition containing the same are useful as an anticancer agent (for example, a therapeutic drug for breast cancer, gastric cancer, lung cancer, liver cancer, cervical cancer, large bowel cancer, rectal cancer, colon cancer, glioma, lymphoma, ovarian cancer, pancreatic cancer, prostate cancer, renal cancer, urothelial cancer, skin cancer, thyroid cancer, bladder cancer, head and neck cancer, endometrial cancer, mesothelioma, melanoma, multiple myeloma, leukemia and the like).

The antibody-drug conjugate according to the present invention may be administered through oral administration or parenteral administration, directly or as a formulation using an appropriate dosage form. Examples of the dosage form include, but are not limited to, liquid, suspension and injection. These formulations are produced by known methods, using a pharmaceutically acceptable additive.

For the additive, excipients, disintegrating agents, binders, glidants, lubricants, coating agents, solubilizing agents, solubilization aids, thickening agents, dispersing agents, stabilizers, sweetening agents, perfumes and the like may be used depending on purposes. Specifically, examples thereof include lactose, mannitol, crystalline cellulose, low substituted hydroxypropyl cellulose, corn starch, partially pregelatinized starch, carmellose calcium, croscarmellose sodium, hydroxypropyl cellulose, hydroxypropyl methylcellulose, polyvinyl alcohol, magnesium stearate, sodium stearyl fumarate, polyethylene glycol, propylene glycol, titanium oxide and talc.

Examples of an "anticancer compound" that may be used in combination with or combined with the antibody-drug conjugate according to the present invention include at least one or more antitumor agents selected from the group consisting of anticancer alkylating agents, anticancer antimetabolites, anticancer antibiotics, anticancer platinum coordination compounds, anticancer camptothecin derivatives, anticancer tyrosine kinase inhibitors, anticancer serine-threonine kinase inhibitors, anticancer phospholipid kinase inhibitors, anticancer monoclonal antibodies, interferons, biological response modifiers, hormonal agents, immune checkpoint inhibitors, epigenetics-related molecule inhibitors, post-translational protein modification inhibitors and other antitumor agents. Specific examples of the "anticancer compound" that may be used in combination with or combined with the antibody-drug conjugate according to the present invention include azacitidine, vorinostat, decitabine, romidepsin, idarubicin, daunorubicin, doxorubicin, enocitabine, cytarabine, mitoxantrone, thioguanine, etoposide, ifosfamide, cyclophosphamide, dacarbazine, temozolomide, nimustine, busulfan, procarbazine, melphalan, ranimustine, all-trans-retinoic acid, tamibarotene, cisplatin, carboplatin, oxaliplatin, irinotecan, bleomycin, mitomycin C, methotrexate, paclitaxel, docetaxel, gemcitabine, tamoxifen, thiotepa, tegafur, fluorouracil, everolimus, temsirolimus, gefitinib, erlotinib, imatinib, crizotinib, osimertinib, afatinib, dasatinib, bosutinib, vandetanib, sunitinib, axitinib, pazopanib, lenvatinib, lapatinib, nilotinib, ibrutinib, ceritinib, alectinib, tofacitinib, baricitinib, ruxolitinib, olaparib, sorafenib, vemurafenib, dabrafenib, trametinib, palbociclib, bortezomib, carfilzomib, rituximab, cetuximab, trastuzumab, bevacizumab, panitumumab, nivolumab, atezolizumab, mogamulizumab, alemtuzumab, ofatumumab, ipilimumab, ramucirumab, brentuximab vedotin, trastuzumab emtansine, gemtuzumab ozogamicin and inotuzumab ozogamicin.

From the above, the antibody-drug conjugate according to the present invention and a pharmaceutical composition containing the same may be used for treatment of cancer. That is, it can also be said that one aspect of the present invention is a method of treating cancer, comprising administering the antibody-drug conjugate or a pharmaceutical composition comprising the same to a subject suffering from cancer. The subject suffering from cancer may be a human patient or animals other than human.

EXAMPLES

Hereinafter, the present invention will be explained further specifically with reference to Reference Examples, Examples and Test Examples, but the present invention is not limited to them, of course. Note that the names of compounds shown in the following Reference Examples and Examples do not necessarily follow the IUPAC nomenclature of chemistry.

Compounds of Reference Examples and Examples may be obtained as an acid addition salt such as a TFA salt, depending on a method of treatment after the reaction and the like.

In order to simplify description of the specification, abbreviations as shown below may be used in Examples and the tables in Examples. As abbreviations used for substituents, Me represents a methyl group, Et represents an ethyl group, Boc represents a tert-butoxycarbonyl group, Fmoc represents a 9-fluorenylmethyloxycarbonyl group, trt represents a trityl group, Ph represents a phenyl group, and Bn represents a benzyl group. TFA represents trifluoroacetic acid, THF represents tetrahydrofuran, TCEP represents tris (2-carboxyethyl)phosphine, Tris-HCl represents trishydroxymethylaminomethane hydrochloride, PBS represents phosphate buffered saline, HEPES represents 2-[4-(2-hydroxyethyl)piperazin-1-yl]ethanesulfonic acid, and PIPES represents piperazine-1,4-bis(2-ethanesulfonic acid). For symbols used for NMR, s means a singlet, d means a doublet, dd means a doublet of doublets, t means a triplet, q means a quartet, m means a multiplet, br means broad, brs means a broad singlet, brd means a broad doublet, brm means a broad multiplet, and J means the binding constant.

High Performance Liquid Chromatography-Mass Spectrometer; measurement conditions for LCMS are as follows, and the observed value of mass spectrometry [MS (m/z)] is shown as $[M+nH]^{n+}/n$, $[M+Na]^+$ or $[M-nH]^{n-}/n$, and the retention time is shown as Rt (min). Note that, for each found value, the measurement conditions used for the measurement are denoted by A to D or F to H.

Measurement Condition A
Detection Equipment: Shimadzu LCMS-IT-TOF
Column: Phenomenex Kinetex (1.7 μm C18, 50 mm×2.10 mm)
Solvents: solution A: 0.1% HCOOH/CH$_3$CN, solution B: 0.1% HCOOH/H$_2$O
Gradient Condition:
 0.0 min; A/B=1:99
 0.0 to 1.4 min; Linear gradient from 1% to 95% A
 1.4 to 1.6 min; A/B=95:5
 1.6 to 2.0 min; A/B=1:99
Flow Rate: 1.2 mL/min
UV: 220/254 nm
Column Temperature: 40° C.
 Measurement Condition B
Detection Equipment: Shimadzu LCMS-IT-TOF
Column: Phenomenex Kinetex (1.7 μm C18, 50 mm×2.10 mm)
Solvents: solution A: 0.1% HCOOH/CH$_3$CN, solution B: 0.1% HCOOH/H$_2$O
Gradient Condition:
 0.0 min; A/B=10:90
 0.0 to 1.4 min; Linear gradient from 10% to 90% A
 1.4 to 1.6 min; A/B=90:10
 1.6 to 2.0 min; A/B=10:90
Flow Rate: 1.2 mL/min
UV: 220/254 nm
Column Temperature: 40° C.
 Measurement Condition C
Detection Equipment: Shimadzu LCMS-IT-TOF
Column: Phenomenex Kinetex (1.7 μm C8, 50 mm×2.10 mm)
Solvents: solution A: 0.1% HCOOH/CH$_3$CN, solution B: 0.1% HCOOH/H$_2$O
Gradient Condition:
 0.0 min; A/B=1:99
 0.0 to 1.4 min; Linear gradient from 1% to 95% A
 1.4 to 1.6 min; A/B=95:5
 1.6 to 2.0 min; A/B=1:99
Flow Rate: 1.2 mL/min
UV: 220/254 nm
Column Temperature: 40° C.
 Measurement Condition D
Detection Equipment: Shimadzu LCMS-IT-TOF
Column: Phenomenex Kinetex (1.7 μm C8, 50 mm×2.10 mm)
Solvents: solution A: 0.1% HCOOH/CH$_3$CN, solution B: 0.1% HCOOH/H$_2$O
Gradient Condition:
 0.0 min; A/B=10:90
 0.0 to 1.4 min; Linear gradient from 10% to 90% A
 1.4 to 1.6 min; A/B=90:10
 1.6 to 2.0 min; A/B=10:90
Flow Rate: 1.2 mL/min
UV: 220/254 nm
Column Temperature: 40° C.
 Measurement Condition F
Detection Equipment: ACQUITY (registered Trademark) SQdetecter (Waters Corporation)
HPLC: CQUITY (registered Trademark) system
Column: Waters ACQUITY UPLC (registered Trademark) BEH C18 (1.7 μm, 2.1 mm×30 mm)
Solvents: solution A: 0.06% formic acid/CH$_3$CN, solution B: 0.06% formic acid/H$_2$O
Gradient Condition: 0.0 to 1.3 min Linear gradient from 2% to 96% A
Flow Rate: 0.8 mL/min
UV: 220/254 nm
Column Temperature: 25° C.
 Measurement Condition G
Detection Equipment: Shimadzu LCMS-IT-TOF
Column: Phenomenex Kinetex (1.7 μm C8, 50 mm×2.10 mm)
Solvents: solution A: 0.1% HCOOH/CH$_3$CN, solution B: 0.1% HCOOH/H$_2$O
Gradient Condition:
 0.0 min; A/B=10:90
 0.0 to 1.4 min; Linear gradient from 10% to 95% A 1.4 to 1.6 min; A/B=95:5
1.6 to 2.0 min; A/B=10:90
Flow Rate: 1.2 mL/min
UV: 220/254 nm
Column Temperature: 40° C.
Measurement Condition H
Detection Equipment: Shimadzu LCMS-IT-TOF
Column: Phenomenex Kinetex (1.7 μm C8, 50 mm×2.10 mm)
Solvents: solution A: 0.1% HCOOH/CH$_3$CN, solution B: 0.1% HCOOH/H$_2$O
Gradient Condition:
0.0 min; A/B=40:60
0.0 to 1.4 min; Linear gradient from 40% to 95% A
1.4 to 1.6 min; A/B=95:5
1.6 to 2.0 min; A/B=5:95
Flow Rate: 1.2 mL/min
UV: 220/254 nm
Column Temperature: 40° C.

High Performance Liquid Chromatography; measurement conditions for determining the average drug antibody ratio (average DAR) are as follows, and the retention time is shown as Rt (min). Note that, for each found value, the measurement conditions used for the measurement are denoted by E or I.

Measurement Condition E
HPLC: Shimadzu LC-10A series
Column: nonporous TSKgel Butyl-NPR column (Tosoh Bioscience, 2.5 μm, 35 mm×4.6 mm)
Solvents: solution A: 1.5 mol/L ammonium sulfate, 25 mmol/L aqueous sodium phosphate solution (pH 6.95), solution B: 25% isopropanol/25 mmol/L aqueous sodium phosphate solution (pH 6.95)
Gradient Condition:
0.0 min; A/B=100:0
0.0 to 12.0 min; Linear gradient from 0% to 100% B
12.1 to 18.0 min; A/B=100:0
Flow Rate: 0.8 mL/min
UV: 230 nm
Column Temperature: 25° C.

Measurement Condition I
HPLC: Shimadzu LC-10A series
Column: nonporous TSKgel Butyl-NPR column (Tosoh Bioscience, 2.5 μm, 35 mm×4.6 mm)
Solvents: solution A: 1.5 mol/L ammonium sulfate, 25 mmol/L aqueous sodium phosphate solution (pH 6.95), solution B: 25% isopropanol/25 mmol/L aqueous sodium phosphate solution (pH 6.95)
Gradient Condition:
0.0 min; A/B=100:0
0.0 to 24.0 min; Linear gradient from 0% to 100% B
24.1 to 60.0 min; A/B=100:0
Flow Rate: 0.8 mL/min
UV: 230 nm
Column Temperature: 25° C.

Reference Example 1 tert-butyl (6S,9S,12S,13E,17R)-9-tert-butyl-17-{3-[(2,5-dioxo-2,5-dihydro-1H-pyrrol-1-yl)ethyl]amino}-3-oxopropyl)-2,2,5,11,14-pentamethyl-6-[2-(1-methyl-1H-indol-3-yl)propan-2-yl]-4,7,10,15-tetraoxo-12-(propan-2-yl)-3-oxo-5,8,11,16-tetraazaoctadec-13-en-18-oate

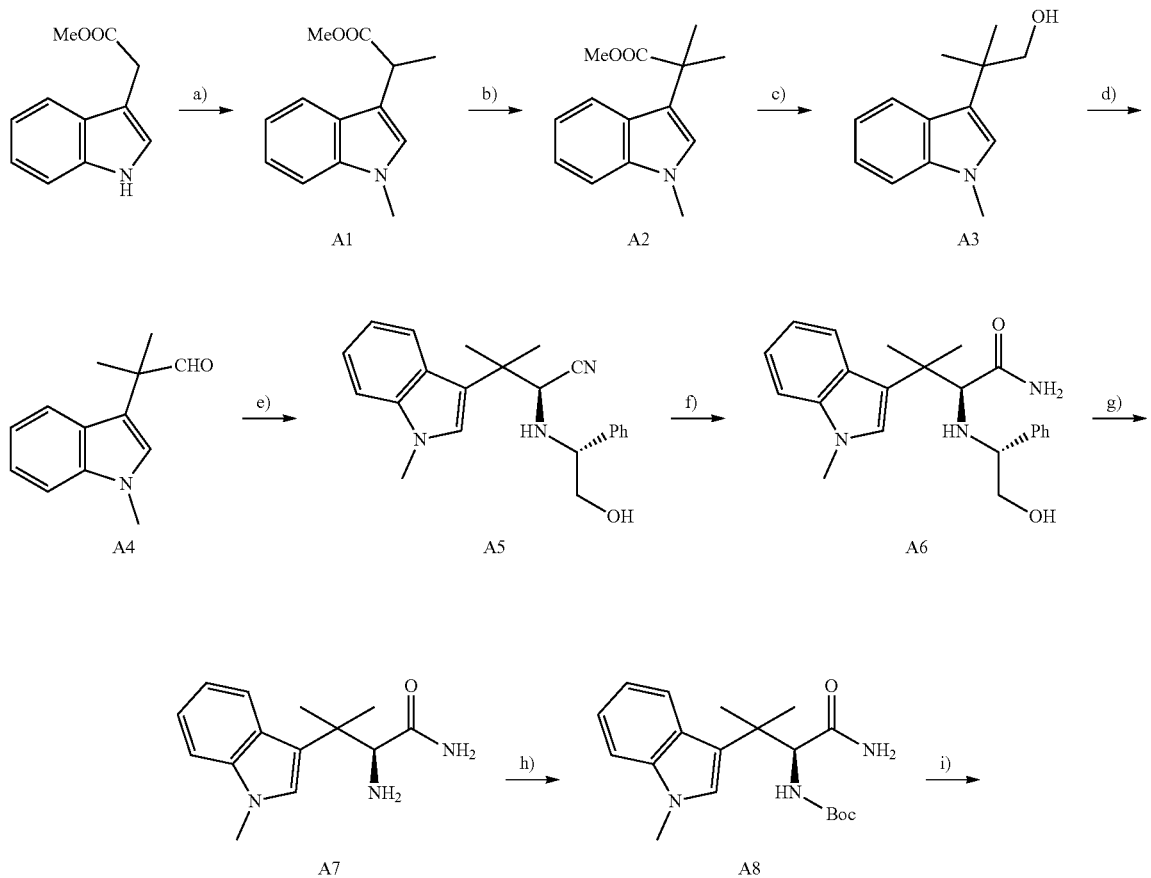

-continued
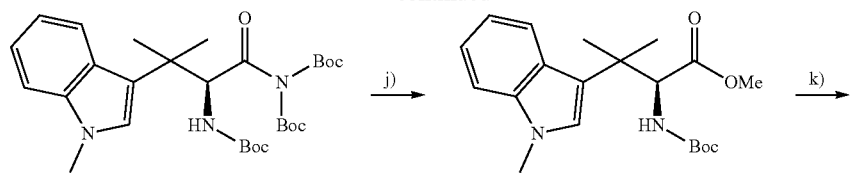
A9 → A10
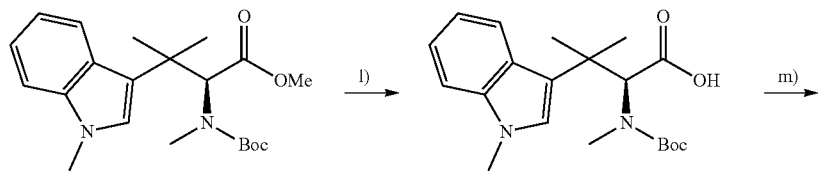
A11 → A12
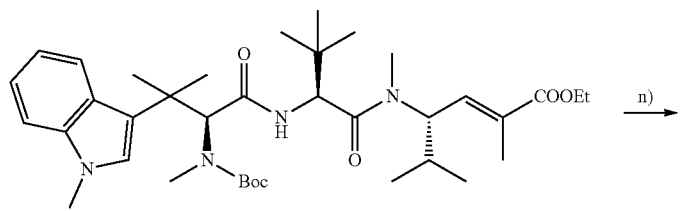
A13
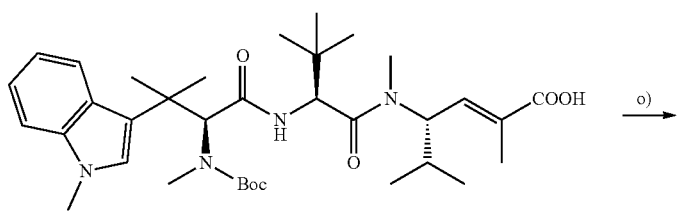
A14
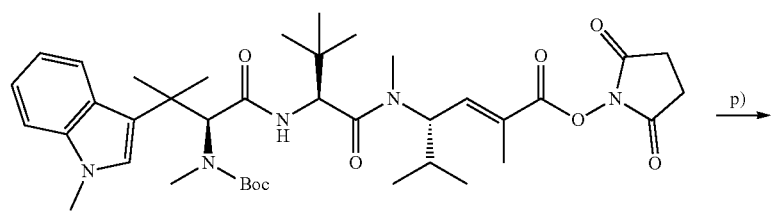
A15
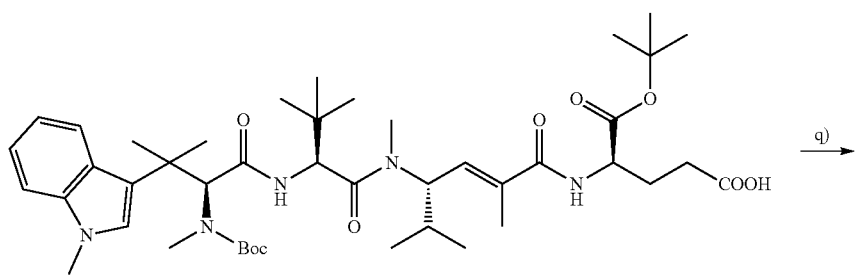
A16

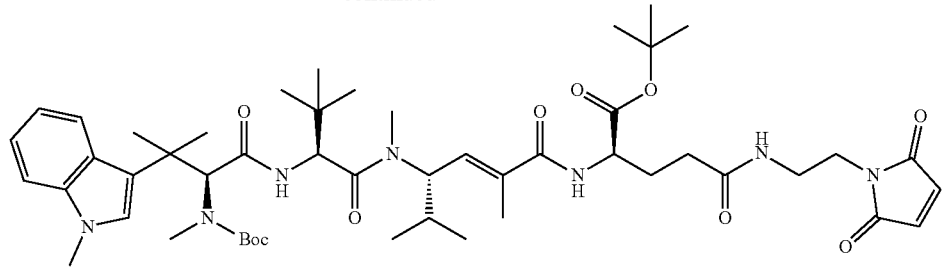

Reference Example 1 a) Production of methyl 2-(1-methyl-1H-indol-3-yl)propanoate (Compound A1)

Under nitrogen atmosphere, to a solution of indole-3-acetic acid methyl ester (3.8 g) in tetrahydrofuran (87 mL) at −78° C., potassium hexamethyldisilazide (1 mol/L tetrahydrofuran solution, 65.5 mL) was added dropwise, and the resultant mixture was then stirred at 0° C. for 2 hours. After cooling the reaction solution to −78° C., methyl iodide (23 g) was added dropwise thereto, and the reaction solution was then stirred at 0° C. for 3 hours. After the reaction ended, water was added and the resultant mixture was extracted with diethyl ether. The organic layer was washed with saturated brine, followed by drying over anhydrous magnesium sulfate, and the solvent was distilled off under reduced pressure. The residue was purified by silica gel column chromatography (eluting solvent; hexane:ethyl acetate) to give compound A1 (3.95 g).

$^1$H-NMR (400 MHz, CDCl$_3$): 1.60 (3H, d, J=7.1 Hz), 3.67 (3H, s), 3.76 (3H, s), 4.02 (1H, q, J=7.1 Hz), 7.00 (1H, s), 7.12 (1H, t, J=7.8 Hz), 7.23 (1H, t, J=7.8 Hz), 7.29 (1H, d, J=7.8 Hz), 7.66 (1H, d, J=7.8 Hz).

b) Production of methyl 2-methyl-2-(1-methyl-1H-indol-3-yl)propanoate (Compound A2)

Under nitrogen atmosphere, to a solution of compound A1 (3.94 g) in tetrahydrofuran (200 mL) at −78° C., potassium hexamethyldisilazide (1 mol/L tetrahydrofuran solution, 27.7 mL) was added dropwise, and the resultant mixture was then stirred at 0° C. for 2 hours. After cooling the reaction solution to −78° C., methyl iodide (15.4 g) was added dropwise thereto, and the reaction solution was then stirred at 0° C. for 3 hours. After the reaction ended, water was added and the resultant mixture was extracted with diethyl ether. The organic layer was washed with saturated brine, followed by drying over anhydrous magnesium sulfate, and the solvent was distilled off under reduced pressure. The residue was purified by silica gel column chromatography (eluting solvent; hexane:ethyl acetate) to give compound A2 (3.59 g).

$^1$H-NMR (400 MHz, CDCl$_3$): 1.66 (6H, s), 3.61 (3H, s), 3.73 (3H, s), 6.91 (1H, s), 7.06 (1H, t, J=8.0 Hz), 7.19 (1H, t, J=8.0 Hz), 7.27 (1H, d, J=8.0 Hz), 7.61 (1H, d, J=7.9 Hz).

c) Production of 2-methyl-2-(1-methyl-1H-indol-3-yl)propan-1-ol (Compound A3)

Under nitrogen atmosphere, to a solution of compound A2 (3.59 g) in diethyl ether (169 mL) and dichloromethane (47 mL) at −78° C., diisobutylaluminum hydride (1 mol/L n-hexane solution, 38.8 mL) was added dropwise, and the resultant mixture was then stirred at 0° C. for 1 hour. After the reaction ended, water was added, and then, to the reaction mixture at 25° C., a saturated aqueous solution of potassium sodium tartrate was added, and the resultant mixture was then extracted with diethyl ether. The organic layer was washed with saturated brine, followed by drying over anhydrous magnesium sulfate, and the solvent was distilled off under reduced pressure. The residue was purified by silica gel column chromatography (eluting solvent; hexane:ethyl acetate) to give compound A3 (3.14 g).

$^1$H-NMR (400 MHz, CDCl$_3$): 1.42 (6H, s), 3.74 (3H, s), 3.77 (2H, s), 6.87 (1H, s), 7.07 (1H, t, J=7.9 Hz), 7.20 (1H, t, J=7.9 Hz), 7.29 (1H, d, J=8.0 Hz), 7.75 (1H, d, J=8.0 Hz).

d) Production of 2-methyl-2-(1-methyl-1H-indol-3-yl)propanal (Compound A4)

Under nitrogen atmosphere, a mixed solution of compound A3 (3.14 g), tetrapropylammonium perruthenate (271 mg), N-methylmorpholine-N-oxide (3.26 g) and molecular sieve 4A (7.7 g) in dichloromethane (110 mL) was stirred at 25° C. for 1 hour. After the reaction ended, the reaction solution was filtered through celite and the solvent was then distilled off, and the residue was purified by silica gel column chromatography (eluting solvent; hexane:ethyl acetate) to give compound A4 (2.4 g).

$^1$H-NMR (400 MHz, CDCl$_3$): 1.53 (6H, s), 3.77 (3H, s), 6.94 (1H, s), 7.07 (1H, t, J=8.0 Hz), 7.22 (1H, t, J=8.0 Hz), 7.30 (1H, d, J=8.0 Hz), 7.53 (1H, d, J=8.0 Hz), 9.47 (1H, s).

e) Production of (2 S)-2-{[(1R)-2-hydroxy-1-phenylethyl]amino}-3-methyl-3-(1-methyl-1H-indol-3-yl)butanenitrile (Compound A5)

Under nitrogen atmosphere, a solution of compound A4 (2.4 g) and (R)-(−)-2-phenylglycinol (1.63 g) in toluene (47 mL) was subjected to heating reflux for 1.5 hours, and after distilling off water with a Dean-Stark apparatus, the solvent was distilled off. Under nitrogen atmosphere, dichloromethane (69 mL) at 0° C. was added to the residue and trimethylsilyl cyanide (2.36 g) was then added, and the resultant mixture was stirred at 25° C. for 96 hours. To the reaction solution, tetra-n-butylammonium fluoride (1 mol/L tetrahydrofuran solution, 1 mL) was added, and after stirring the solution for further 30 minutes, water was added and the resultant mixture was extracted with chloroform. The organic layer was dried over anhydrous sodium sulfate, and the solvent was distilled off under reduced pressure. The residue was purified by silica gel column chromatography (eluting solvent; hexane:ethyl acetate) to give compound A5 (2.74 g).

¹H-NMR (400 MHz, CDCl₃): 1.64 (3H, s), 1.65 (3H, s), 3.49-3.55 (1H, m), 3.73 (1H, dd, J=10.9, 4.2 Hz), 3.79 (1H, s), 3.80 (3H, s), 4.05 (1H, dd, J=7.9, 3.6 Hz), 6.96-7.00 (2H, m), 7.11 (2H, d, J=8.0 Hz), 7.21-7.40 (6H, m).

f) Production of Nα-[(1R)-2-hydroxy-1-phenyl-ethyl]-β,β,1-trimethyl-L-tryptophanamide (Compound A6)

To a suspension of compound A5 (2.74 g), dimethyl sulfoxide (6.16 g) and potassium carbonate (10.9 g) in methanol (50 mL) and water (2.1 mL), a 30% aqueous hydrogen peroxide solution (8.94 mL) was added at 0° C., and the resultant mixture was stirred at 45° C. for 1.5 hours. After the reaction ended, a saturated aqueous sodium thiosulfate solution was added, and the resultant mixture was extracted with ethyl acetate. The organic layer was washed with water and then dried over anhydrous sodium sulfate, and the solvent was distilled off under reduced pressure. The residue was purified by silica gel column chromatography (eluting solvent; chloroform:methanol) to give compound A6 (2.32 g).

¹H-NMR (400 MHz, CDCl₃): 1.49 (3H, s), 1.51 (3H, s), 2.06-2.14 (1H, br), 2.37 (1H, dd, J=6.0, 6.0 Hz), 3.44-3.50 (1H, m), 3.50-3.54 (1H, m), 3.56-3.63 (m, 2H), 3.75 (3H, s), 5.52 (1H, brs), 6.14 (1H, brs), 6.71-6.73 (2H, m), 6.81-6.85 (2H, m), 6.97-7.00 (2H, m), 7.10-7.18 (2H, m), 7.24-7.28 (2H, m).

g) Production of β,β,1-trimethyl-L-tryptophanamide (Compound A7)

To a solution of compound A6 (2.32 g) in methanol (65 mL), palladium hydroxide/carbon (2.8 g) was added, and the resultant mixture was stirred at room temperature for 3 hours under hydrogen atmosphere. The reaction solution was filtered through celite and the solvent was then distilled off, and the residue was purified by silica gel column chromatography (eluting solvent; chloroform:methanol) to give compound A7 (1.27 g).

¹H-NMR (400 MHz, DMSO-d₆): 1.24 (2H, brs), 1.28 (3H, s), 1.42 (3H, s), 3.68 (1H, s), 3.71 (3H, s), 6.93-7.00 (2H, m), 7.06 (1H, s), 7.11 (1H, t, J=7.7 Hz), 7.29 (1H, brs), 7.36 (1H, d, J=8.3 Hz), 7.88 (1H, d, J=8.2 Hz).

h) Production of Nα-(tert-butoxycarbonyl)-3, (3,1-trimethyl-L-tryptophanamide (Compound A8)

A mixed solution of compound A7 (1.27 g), sodium bicarbonate (522 mg), di-tert-butyl dicarbonate (1.35 g), tetrahydrofuran (13 mL), chloroform (13 mL) and water (6.5 mL) was stirred at 25° C. for 16 hours. After the reaction ended, water was added and the resultant mixture was extracted with chloroform. The organic layer was dried over anhydrous sodium sulfate, and the solvent was distilled off under reduced pressure. The residue was purified by silica gel column chromatography (eluting solvent; chloroform:methanol) to give compound A8 (1.80 g).

¹H-NMR (400 MHz, CDCl₃): 1.33 (3H, s), 1.47 (9H, s), 1.50 (3H, s), 3.73 (3H, d, J=1.3 Hz), 4.51 (1H, brs), 4.86 (1H, brs), 5.02 (1H, brd, J=8.2 Hz), 5.59 (1H, brd, J=6.4 Hz), 6.83 (1H, d, J=1.8 Hz), 7.15 (1H, t, J=7.3 Hz), 7.21-7.25 (1H, m), 7.30 (1H, d, J=8.2 Hz), 8.05 (1H, brd, J=7.3 Hz).

LC-MS: 346(M+H)⁺ (1.211 min, Measurement Condition A)

i) Production of N,N,Nα-tris(tert-butoxycarbonyl)-3, (3,1-trimethyl-L-tryptophanamide (Compound A9)

A mixed solution of compound A8 (1.79 g), di-tert-butyl dicarbonate (2.8 g), N,N-diisopropylethylamine (2.68 g), 4-dimethylaminopyridine (0.19 g) and chloroform (20 mL) was stirred at 25° C. for 2.5 hours. After the reaction ended, water was added and the resultant mixture was extracted with chloroform. The organic layer was washed with saturated brine and then dried over anhydrous sodium sulfate, and the solvent was distilled off under reduced pressure. The residue was purified by silica gel column chromatography (eluting solvent; hexane:ethyl acetate) to give compound A9 (1.99 g).

¹H-NMR (400 MHz, CDCl₃): 1.08-1.58 (33H, m), 3.70 (3H, s), 4.67-4.90 (0.2H, m), 5.25-5.45 (0.8H, m), 6.00-6.03 (1H, m), 6.81-6.87 (1H, m), 7.04-7.09 (1H, m), 7.13-7.18 (1H. m), 7.21-7.27 (1H, m), 7.91-7.94 (1H, m).

LC-MS: 546(M+H)⁺ (1.630 min, Measurement Condition A)

j) Production of methyl N-(tert-butoxycarbonyl)-β,β,1-trimethyl-L-tryptophanate (Compound A10)

Under nitrogen atmosphere, to a solution of compound A9 (2.29 g) in methanol (21 mL), lithium methoxide (176 mg) was added at 0° C., and the resultant mixture was then stirred at 25° C. for 2 hours. After the reaction ended, a saturated aqueous ammonium chloride solution was added, and the reaction mixture was extracted with ethyl acetate. The organic layer was washed with saturated brine and then dried over anhydrous sodium sulfate, and the solvent was distilled off under reduced pressure. The residue was purified by silica gel column chromatography (eluting solvent; hexane: ethyl acetate) to give compound A10 (927 mg).

¹H-NMR (400 MHz, CDCl₃): 1.17-1.59 (15H, m), 3.45 and 3.58 (3H, 2brs), 3.71 (3H, s), 4.56-4.73 (1.2H, m), 5.06 (0.8H, brd, J=7.3 Hz), 6.81-6.82 (1H, m), 7.05-7.10 (1H, m), 7.16-7.21 (1H, m), 7.24-7.29 (1H, m), 7.73-7.80 (1H, m).

LC-MS: 361(M+H)⁺ (1.379 min, Measurement Condition A).

k) Production of methyl N-(tert-butoxycarbonyl)-N,β,β,1-tetramethyl-L-tryptophanate (Compound A11)

Under nitrogen atmosphere, to a solution of compound A10 (927 mg) in N,N-dimethylformamide (13 mL), sodium hydride 60% dispersion (168 mg) was added at 0° C., and the resultant mixture was then stirred at 25° C. for 15 minutes. After cooling the reaction suspension to 0° C., methyl iodide (1.1 g) was added thereto, and the reaction solution was then stirred at 25° C. for 1 hour. After the reaction ended, water was added and the resultant mixture was extracted with ethyl acetate. The organic layer was dried over anhydrous sodium sulfate, and the solvent was distilled off under reduced pressure. The residue was purified by silica gel column chromatography (eluting solvent; hexane: ethyl acetate) to give compound A11 (915 mg).

¹H-NMR (400 MHz, CDCl₃): 1.42 (9H, s), 1.52 and 1.64 (6H, 2s), 2.80 and 2.86 (3H, 2s), 3.46 (3H, s), 3.71 (3H, s), 5.27 and 5.52 (1H, 2s), 6.85 (1H, s), 7.07-7.27 (3H, m), 7.78 and 7.92 (1H, 2d, J=7.88 Hz). LC-MS: 397 (M+Na)⁺ (1.406 min, Measurement Condition B)

l) Production of N-(tert-butoxycarbonyl)-N,β,β,1-tetramethyl-L-tryptophan (Compound A12)

To a solution of compound A11 (639 mg) in water (11 mL)-methanol (44 mL), 1 mol/L lithium hydroxide (13.5 mL) was added, and the resultant mixture was stirred at 60° C. for 24 hours. After the reaction ended, a 1 mol/L aqueous oxalic acid solution was added to change the pH of the reaction solution to 4, and water was then added and the resultant mixture was extracted with chloroform. The organic layer was washed with saturated brine and then dried over anhydrous sodium sulfate, and the solvent was distilled off under reduced pressure. The residue was purified by silica gel column chromatography (eluting solvent; chloroform:methanol) to give compound A12 (610 mg).

$^1$H-NMR (400 MHz, CDCl$_3$): 1.43 (9H, s), 1.53 (3H, s), 1.63 (3H, s), 2.76 and 2.89 (3H, 2s), 3.71 (3H, s), 5.36 and 5.44 (1H, 2s), 6.85 and 6.87 (1H, 2s), 7.02-7.11 (1H, m), 7.18 (1H, t, J=7.3 Hz), 7.24-7.27 (1H, m), 7.81 and 7.96 (1H, 2d, J=7.9 Hz).

LC-MS: 361(M+H)$^+$, 359 (M−H)$^-$ (1.300 min, Measurement Condition A).

m) Production of N-(tert-butoxycarbonyl)-N,β,β,1-tetramethyl-L-tryptophyl-N-[(3S,4E)-6-ethoxy-2,5-dimethyl-6-oxohex-4-en-3-yl]-N,3-dimethyl-L-valinamide (Compound A13)

A mixed solution of compound A12 (500 mg), ethyl (2E,4S)-2,5-dimethyl-4-[methyl(3-methyl-L-valyl)amino]hex-2-enoate (520 mg), 1-ethyl-3-(3-dimethylaminopropyl)carbodiimide hydrochloride (399 mg), 1-hydroxy-1H-benzotriazole monohydrate (425 mg) and N,N-dimethylformamide (5 mL) was stirred at 25° C. for 16 hours. After the reaction ended, water was added and the resultant mixture was extracted with chloroform. The organic layer was washed with saturated brine and then dried over anhydrous sodium sulfate, and the solvent was distilled off under reduced pressure. The residue was purified by silica gel column chromatography (eluting solvent; hexane:ethyl acetate) to give compound A13 (759 mg).

LC-MS: 655(M+H)$^+$ (1.714 min, Measurement Condition A)

n) Production of N-(tert-butoxycarbonyl)-N,β,β,1-tetramethyl-L-tryptophyl-N-[(3S,4E)-5-carboxy-2-methylhex-4-en-3-yl]-N,3-dimethyl-L-valinamide (Compound A14)

To a solution of compound A13 (127 mg) in water (1.55 mL)-methanol (4.65 mL), 1 mol/L lithium hydroxide (1.65 mL) was added, and the resultant mixture was stirred at 25° C. for 24 hours. After the reaction ended, a 1 mol/L aqueous oxalic acid solution was added to change the pH of the reaction solution to 4, and water was then added and the resultant mixture was extracted with chloroform. The organic layer was washed with saturated brine and then dried over anhydrous sodium sulfate, and the solvent was distilled off under reduced pressure. The residue was purified by silica gel column chromatography (eluting solvent; chloroform: methanol) to give compound A14 (93 mg).

LC-MS: 627(M+H)$^+$ (1.508 min, Measurement Condition A)

o) Production of N-(tert-butoxycarbonyl)-N,β,β,1-tetramethyl-L-tryptophyl-N-{(3S,4E)-6-[(2,5-dioxopyrrolidin-1-yl)oxy]-2,5-dimethyl-6-oxohex-4-en-3-yl}-N, 3-dimethyl-L-valinamide (Compound A15)

A mixed solution of compound A14 (185 mg), N-hydroxysuccinimide (97 mg), bromotripyrrolidinophosphonium hexafluorophosphate (391 mg), 4-dimethylaminopyridine (102 mg), N,N-diisopropylethylamine (108 mg) and N,N-dimethylformamide (2.8 mL) was stirred at 25° C. for 4 hours. After the reaction ended, water was added and the resultant mixture was extracted with ethyl acetate. The organic layer was washed with water and then dried over anhydrous sodium sulfate, and the solvent was distilled off under reduced pressure. The residue was purified by silica gel column chromatography (eluting solvent; chloroform:methanol) to give compound A15 (166 mg).

$^1$H-NMR (400 MHz, CDCl$_3$): 8.27 and 7.96 (1H, 2d, J=7.9 Hz), 7.16-7.04 (4H, m), 6.88 (1H, d, J=9.1 Hz), 6.17 and 6.09 (1H, 2d, J=8.5 Hz), 5.96 and 5.66 (1H, 2s), 5.07 (1H, t, J=9.3 Hz), 4.45 and 3.87 (1H, 2d, J=8.6 Hz), 3.74 and 3.73 (3H, 2s), 2.99 (3H, s), 2.95 (3H, s), 2.83 (4H, brs), 1.97 (3H, s), 1.92-1.86 (1H, m), 1.57-1.42 (14H, m), 0.89 (3H, d, J=6.1 Hz), 0.83-0.80 (3H, m), 0.48 and 0.41 (9H, 2s).

LC-MS: 724(M+H)$^+$ (1.573 min, Measurement Condition A)

p) Production of (6S,9S,12S,13E,17R)-17-(tert-butoxycarbonyl)-9-tert-butyl-2,2,5,11,14-pentamethyl-6-[2-(1-methyl-1H-indol-3-yl)propan-2-yl]-4,7,10,15-tetraoxo-12-(propan-2-yl)-3-oxa-5,8,11,16-tetraazaicos-13-en-20-oic Acid (Compound A16)

A mixed solution of compound 15 (30 mg), α-tert-butyl D-glutamate hydrochloride (10.7 mg), N,N-diisopropylethylamine (49.7 mg) and N,N-dimethylformamide (1.0 mL) was stirred at 25° C. for 3 hours. After the reaction ended, water was added and the resultant mixture was extracted with chloroform. The organic layer was washed with water and then dried over anhydrous sodium sulfate, and the solvent was distilled off under reduced pressure. The residue was purified by silica gel column chromatography (eluting solvent; chloroform:methanol) to give compound A16 (14.2 mg).

LC-MS 834 (M+Na)$^+$ (1.574 min, Measurement Condition D)

q) Production of tert-butyl (6S,9S,12S,13E,17R)-9-tert-butyl-17-(3-{[2-(2,5-dioxo-2,5-dihydro-1H-pyrrol-1-yl)ethyl]amino}-3-oxopropyl)-2,2,5,11,14-pentamethyl-6-[2-(1-methyl-1H-indol-3-yl)propan-2-yl]-4,7,10,15-tetraoxo-12-(propan-2-yl)-3-oxa-5,8,11,16-tetraazaoctadec-13-en-18-oate (Reference Example 1)

A mixed solution of compound A16 (14 mg), N-(2-aminoethyl)maleimide hydrochloride (3.0 mg), 1-ethyl-3-(3-dimethylaminopropyl)carbodiimide hydrochloride (6.6 mg), 1-hydroxy-1H-benzotriazole monohydrate (5.2 mg) and N,N-diisopropylethylamine (4.4 mg) and N,N-dimethylformamide (0.5 mL) was stirred at 25° C. for 2 hours. After the reaction ended, water was added and the resultant mixture was extracted with ethyl acetate. The organic layer was washed with water and then dried over anhydrous sodium sulfate, and the solvent was distilled off under reduced pressure. The residue was purified by silica gel column chromatography (eluting solvent; chloroform: methanol) to give compound A15 (166 mg).

LC-MS: 934(M+H)$^+$ (1.597 min, Measurement Condition D)

Reference Example 2

N-(tert-butoxycarbonyl)-N,β,β-trimethyl-L-phenyl-alanyl-N-{(3S,4E)-6-[(2,5-dioxopyrrolidin-1-yl)oxy]-2,5-dimethyl-6-oxohex-4-en-3-yl}-N,3-dimethyl-L-valinamide

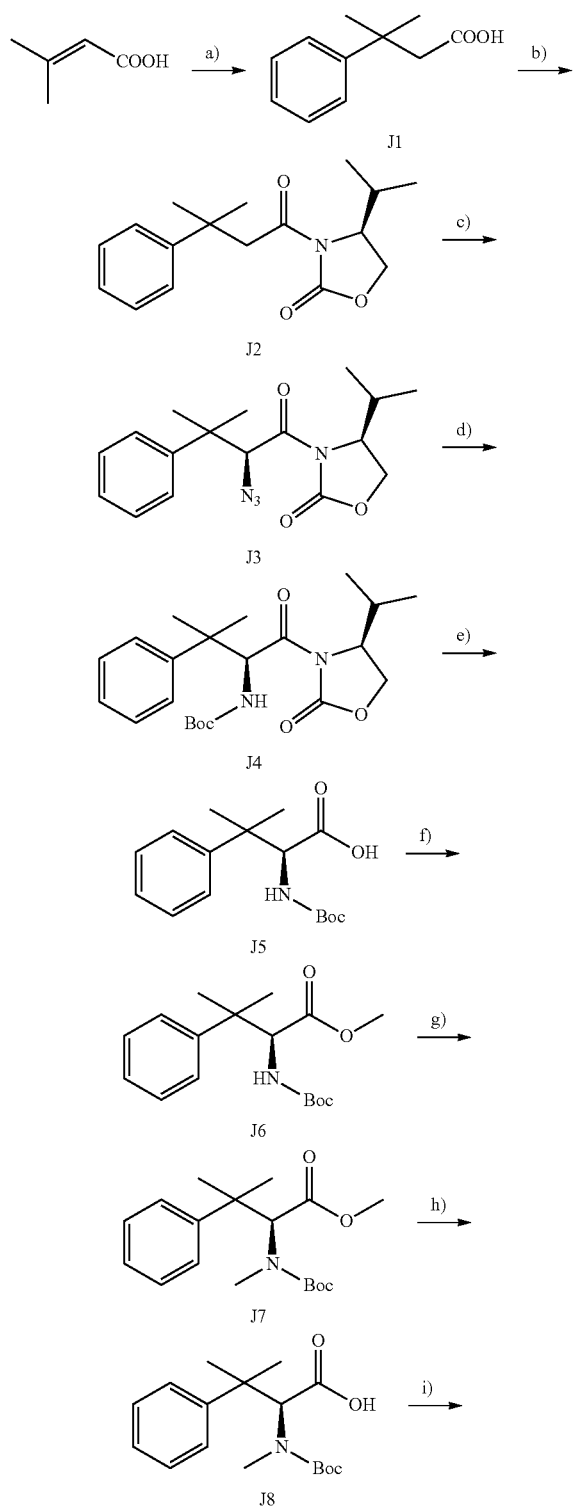

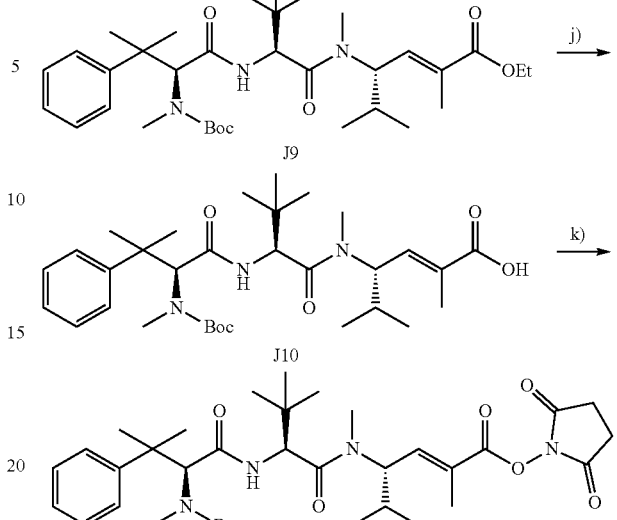

Reference Example 2 a) Production of 3-methyl-3-phenylbutanoic Acid (Compound J1)

To a solution of 3-methyl-2-butenoic acid (15 g) in benzene (100 mL), aluminum chloride (24.1 g) was added at 10° C., and the resultant mixture was stirred for 30 minutes and then stirred at 40° C. for 1 hour. After cooling the reaction solution to 0° C., ice water was added, and the resultant mixture was extracted with tert-butyl methyl ether, concentrated to some extent, and the organic layer was extracted with a saturated aqueous sodium bicarbonate solution. The pH of the aqueous layer was changed to 2 with concentrated hydrochloric acid, and the resultant mixture was extracted with tert-butyl methyl ether. The organic layer was dried over anhydrous magnesium sulfate, and the solvent was distilled off under reduced pressure to give compound J1 (26.3 g).

$^1$H-NMR (400 MHz, CDCl$_3$): 1.46 (6H, s), 2.65 (2H, s), 7.20 (1H, t, J=7.2 Hz), 7.31 (1H, t, J=7.2 Hz), 7.37 (2H, d, J=7.2 Hz).

b) Production of (4S)-3-(3-methyl-3-phenylbutanoyl)-4-(propan-2-yl)-1,3-oxazolidin-2-one (Compound J2)

To a solution of compound J1 (17.2 g) in THF (900 mL), triethylamine (23.7 mL) and pivaloyl chloride (15.3 mL) was added at −78° C. After raising the temperature to 0° C., the resultant mixture was stirred for 1 hour. Separately, to a solution of (S)-isopropyloxazolidinone (19.5 g) in THF (760 mL), n-butyllithium (1.64 mol/L hexane solution, 89.8 mL) was added at −78° C., the resultant mixture was stirred for 30 minutes to prepare a lithium salt. The previous reaction solution was cooled to −78° C., the lithium salt was added dropwise, the resultant mixture was stirred for 1 hour, and the temperature was then raised to 0° C. After stirring the mixture for further 30 minutes, water was added, and the resultant mixture was extracted with tert-butyl methyl ether. The organic layer was washed with saturated brine and dried over anhydrous magnesium sulfate. The solvent was distilled off under reduced pressure, and the residue was purified by silica gel column chromatography (eluting solvent; hexane:tert-butyl methyl ether) to give compound J2 (27.0 g).

$^1$H-NMR (400 MHz, CDCl$_3$): 0.723 (3H, d, J=6.8 Hz), 0.80 (3H, d, J=6.8 Hz), 1.49 (s, 6H), 2.13-2.18 (m, 1H), 3.36 (s, 3H), 3.99-4.09 (m, 2H), 4.20-4.23 (m, 1H), 7.16-7.20 (m, 1H), 7.28-7.32 (m, 2H), 7.38-7.40 (m, 2H).

c) Production of (4S)-3-[(2S)-2-azido-3-methyl-3-phenylbutanoyl]-4-(propan-2-yl)-1,3-oxazolidin-2-one (Compound J3)

A suspension of compound J2 (27.0 g) in THF (560 mL) was cooled to −78° C., potassium hexamethyldisilazide (1.06 mol/L tetrahydrofuran solution, 99.5 mL) was added, and the resultant mixture was stirred for 1.5 hours. A solution of 2,4,6-triisopropylbenzenesulfonyl azide (40 g) in THF (330 mL) at −78° C. was added, and after 10 minutes, acetic acid (24.5 mL) was added, the temperature was raised to 40° C., and the resultant mixture was stirred for 1 hour. Saturated brine was added, and the resultant mixture was extracted with tert-butyl methyl ether. The organic layer was washed with a saturated aqueous sodium bicarbonate solution and saturated brine, and the organic layer was then dried over anhydrous magnesium sulfate. The solvent was distilled off under reduced pressure, and the residue was purified by silica gel column chromatography (eluting solvent; hexane:chloroform) to give compound J3 (16.4 g).

$^1$H-NMR (400 MHz, CDCl$_3$): 0.80 (3H, d, J=6.8 Hz), 0.84 (3H, d, J=7.2 Hz), 1.54 (3H, s), 1.56 (3H, s), 2.28-2.33 (1H, m), 3.54-3.59 (1H, m), 3.87-3.90 (1H, m), 3.95-3.98 (1H, m), 5.66 (1H, s), 7.23-7.420 (5H, m).

d) Production of tert-butyl {(2S)-3-methyl-1-oxo-1-[(4S)-2-oxo-4-(propan-2-yl)-1,3-oxazolidin-3-yl]-3-phenylbutan-2-yl}carbamate (Compound J4)

To a solution of compound J3 (16.4 g) in ethyl acetate (1200 mL), di-tert-butyl dicarbonate (24.0 g) and 10% Pd—C (11.6 g, 50% wet) were added, and the resultant mixture was stirred for 2 hours under hydrogen atmosphere. The reaction solution was filtered through celite, and was washed with ethyl acetate. The solvent was distilled off under reduced pressure, and the residue was purified by silica gel column chromatography (eluting solvent; hexane:tert-butyl methyl ether) to give compound J4 (16.1 g).

$^1$H-NMR (400 MHz, CDCl$_3$): 0.77 (3H, d, J=6.8 Hz), 0.82 (3H, d, J=6.8 Hz), 1.42 (3H, s), 1.43 (9H, s), 1.48 (3H, s), 2.20-2.29 (1H, m), 3.45 (1H, t, J=8.8 Hz), 3.80-3.83 (1H, m), 3.89-3.92 (1H, dd, J=2.0 Hz, J=8.4 Hz), 5.16 (1H, brs), 6.13 (1H, d, J=9.6 Hz), 7.21-7.26 (1H, m), 7.29-7.33 (2H, m). 7.42 (2H, d, J=7.2 Hz).

e) Production of N-(tert-butoxycarbonyl)-β,β-dimethyl-L-phenylalanine (Compound J5)

To a solution of compound J4 (16.1 g) in THF (468 mL) and water (117 mL), a 30% aqueous hydrogen peroxide solution (32.5 mL) and an aqueous lithium hydroxide solution (1 mol/L, 119 mL) were added at 0° C., the temperature was raised to 25° C., and the resultant mixture was stirred for 3 hours. An aqueous sodium bisulfate solution (1.5 mol/L, 470 mL) was added at 0° C., the temperature was raised to 25° C., and the resultant mixture was stirred for 1 hour. The pH was changed to 3 with an aqueous citric acid solution (1 mol/L), and the resultant mixture was extracted with tert-butyl methyl ether. The organic layer was washed with saturated brine, and the organic layer was dried over anhydrous magnesium sulfate. The solvent was distilled off under reduced pressure to give compound J5 (14.2 g).

$^1$H-NMR (400 MHz, CDCl$_3$): 1.38 (9H, s), 1.44 (3H, s), 1.46 (3H, s), 4.56 (1H, brd, J=11.6 Hz), 4.94 (1H, brd, J=14.4 Hz), 7.21-7.38 (5H, m).

f) Production of methyl N-(tert-butoxycarbonyl)-β,β-dimethyl-L-phenylalaninate (Compound J6)

To a solution of compound J5 (14.2 g) in N,N-dimethylformamide (84 ml), sodium carbonate (8.44 g) and methyl iodide (9.91 mL) were added, and the resultant mixture was stirred at 25° C. for 15 hours. After cooling the mixture to 0° C., chilled water was added and the resultant mixture was extracted with tert-butyl methyl ether, and the organic layer thus obtained was washed with saturated brine and then dried over anhydrous magnesium sulfate. The solvent was distilled off under reduced pressure, and the residue was purified by silica gel column chromatography (eluting solvent; hexane:tert-butyl methyl ether) to give compound J6 (11.1 g).

$^1$H-NMR (400 MHz, CDCl$_3$): 1.36 (9H, s), 1.37 (3H, s), 1.41 (3H, s), 3.48 (3H, brs), 4.49 (1H, brd, J=9.8 Hz), 4.98 (1H, brd, J=9.1 Hz), 7.18-7.22 (1H, m), 7.27-7.33 (4H, m).

g) Production of methyl N-(tert-butoxycarbonyl)-N,β,β-trimethyl-L-phenylalaninate (Compound J7)

By the same approach as Reference Example 1-k), from compound J6 (307 mg), compound J7 (245 mg) was obtained.

LC-MS: 344 (M+Na)$^+$ (1.589 min, Measurement Condition C)

h) Production of N-(tert-butoxycarbonyl)-N,β,β-trimethyl-L-phenylalanine (Compound J8)

By the same approach as Reference Example 1-l), from compound J7 (235 mg), compound J8 (195 mg) was obtained.

LC-MS: 330 (M+Na)$^+$ (1.420 min, Measurement Condition C)

i) Production of N-(tert-butoxycarbonyl)-N,β,β-trimethyl-L-phenylalanyl-N-[(3S,4E)-6-ethoxy-2,5-dimethyl-6-oxohex-4-en-3-yl]-N,3-dimethyl-L-valinamide (Compound J9)

By the same approach as Reference Example 1-m), from compound J8 (195 mg), compound J9 (307 mg) was obtained.

LC-MS: 624 (M+Na)$^+$ (1.797 min, Measurement Condition C)

j) Production of N-(tert-butoxycarbonyl)-N,β,β-trimethyl-L-phenylalanyl-N-[(3S,4E)-5-carboxy-2-methylhex-4-en-3-yl]-N,3-dimethyl-L-valinamide (Compound J10)

By the same approach as Reference Example 1-n), from compound J9 (307 mg), compound J10 (286 mg) was obtained.

LC-MS: 596 (M+Na)$^+$, 572 (M−H)$^−$ (1.596 min, Measurement Condition C)

k) Production of N-(tert-butoxycarbonyl)-N,β,β-trimethyl-L-phenylalanyl-N-{(3S,4E)-6-[(2,5-dioxopyrrolidin-1-yl)oxy]-2,5-dimethyl-6-oxohex-4-en-3-yl}-N,3-dimethyl-L-valinamide (Reference Example 2)

By the same approach as Reference Example 1-o), from compound J10 (286 mg), Reference Example 2 (227 mg) was obtained.

LC-MS: 693 (M+Na)⁺ (1.658 min, Measurement Condition C)

Reference Example 3

Di-tert-butyl (6S,9S,12S,13E,17R,22R)-9-tert-butyl-28-(2,5-dioxo-2,5-dihydro-1H-pyrrol-1-yl)-2,2,5,11,14-pentamethyl-6-[2-(1-methyl-1H-indol-3-yl)propan-2-yl]-4,7,10,15,20,25-hexaoxo-12-(propan-2-yl]-3-oxa-5,8,11,16,21,26-hexaazaoctacos-13-en-17,22-dicarboxylate

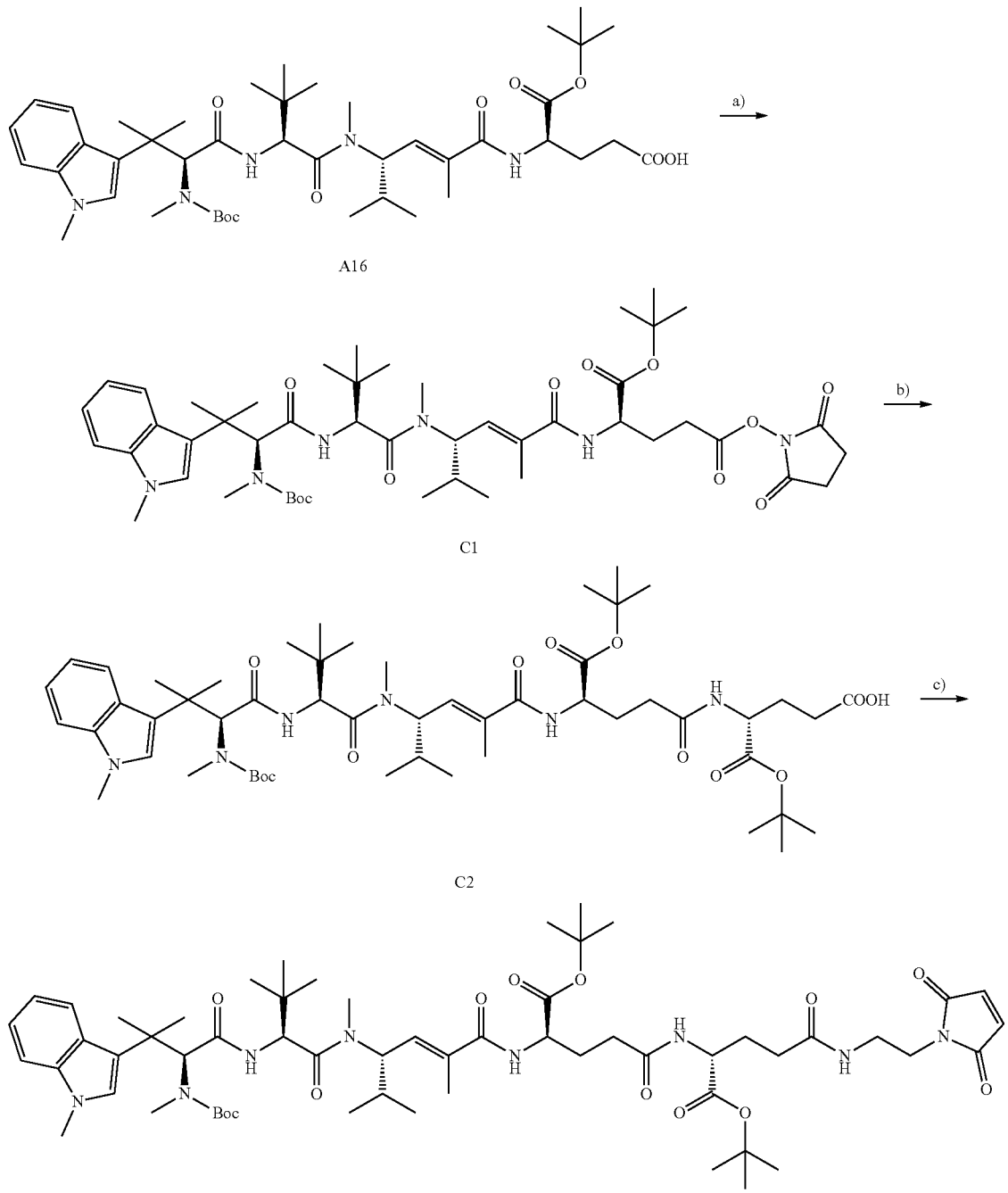

Reference Example 3 a) Production of tert-butyl (6S,9S,12S,13E,17R)-9-tert-butyl-17-{3-[(2,5-dioxopyrrolidin-1-yl)oxy]-3-oxopropyl}-2,2,5,11,14-pentamethyl-6-[2-(1-methyl-1H-indol-3-yl) propan-2-yl]-4,7,10,15-tetraoxo-12-(propan-2-yl)-3-oxa-5,8,11,16-tetraazaoctadec-13-en-18-oate (Compound C1)

Production was carried out by the same approach as Reference Example 1-o), and from compound A16 (90.2 mg), compound C1 (51.8 mg) was obtained.
LC-MS: 931 (M+Na)$^+$ (1.662 min, Measurement Condition D)

b) Production of (6S,9S,12S,13E,17R,22R)-17,22-bis(tert-butoxycarbonyl)-9-tert-butyl-2,2,5,11,14-pentamethyl-6-[2-(1-methyl-1H-indol-3-yl)propan-2-yl]-4,7,10,15,20-pentaoxo-12-(propan-2-yl)-3-oxa-5,8,11,16,21-pentaazapentacos-13-en-25-oic Acid (Compound C2)

Production was carried out by the same approach as Reference Example 1-p), and from compound C1 (51.8 mg), compound C2 (40 mg) was obtained.
LC-MS: 1019 (M+Na)$^+$ (1.422 min, Measurement Condition D)

c) Production of di-tert-butyl (6S,9S,12S,13E,17R,22R)-9-tert-butyl-28-(2,5-dioxo-2,5-dihydro-1H-pyrrol-1-yl)-2,2,5,11,14-pentamethyl-6-[2-(1-methyl-1H-indol-3-yl)propan-2-yl]-4,7,10,15,20,25-hexaoxo-12-(propan-2-yl)-3-oxa-5,8,11,16,21,26-hexaazaoctacos-13-en-17,22-dicarboxylate (Reference Example 3)

Production was carried out by the same approach as Reference Example 1-q), and from compound C2 (40 mg), Reference Example 3 (14 mg) was obtained.

LC-MS: 1141 (M+Na)$^+$ (1.618 min, Measurement Condition D)

Reference Example 4

N-{(2E,4S)-2,5-Dimethyl-4-[methyl(N,β,β,1-tetramethyl-L-tryptophyl-3-methyl-L-valyl)amino]hexa-2-enoyl}-D-γ-glutamyl-L-lysine

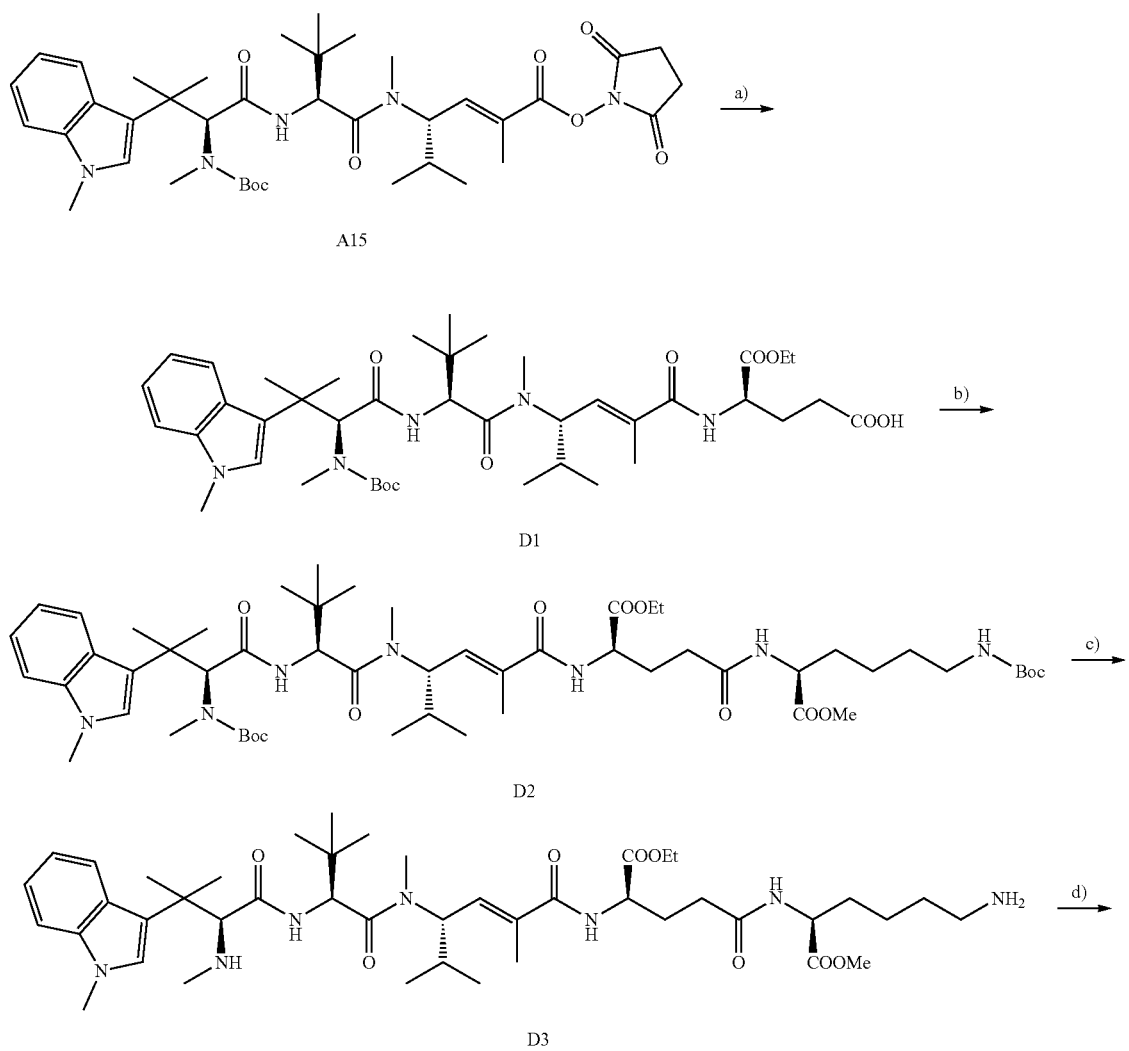

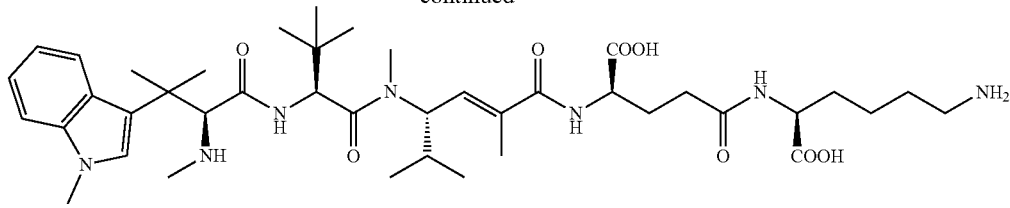

Reference Example 4 a) Production of (6S,9S,12S,13E,17R)-9-tert-butyl-17-(ethoxycarbonyl)-2,2,5,11,14-pentamethyl-6-[2-(1-methyl-1H-indol-3-yl)propan-2-yl]-4,7,10,15-tetraoxo-12-(propan-2-yl)-3-oxa-5,8,11,16-tetraazaicos-13-en-20-oic Acid (Compound D1)

A mixed solution of compound A15 (160 mg), D-glutamic acid α-ethyl ester-trifluoroacetate (122 mg), N,N-diisopropylethylamine (100 mg) and N,N-dimethylformamide (2.2 mL) was stirred at 25° C. for 6 hours. After the reaction ended, a 1 mol/L aqueous oxalic acid solution was added to change the pH to 4, and the resultant mixture was extracted with chloroform. The organic layer was washed with water and saturated brine and then dried over anhydrous sodium sulfate, and the solvent was distilled off under reduced pressure. The residue was purified by silica gel column chromatography (eluting solvent; chloroform:methanol) to give compound D1 (155 mg).

$^1$H-NMR (400 MHz, CDCl$_3$): 8.26 and 7.97 (1H, 2d, J=7.9 Hz), 7.32-7.05 (4H, m), 6.71 (1H, t, J=6.7 Hz), 6.45 (1H, d, J=8.6 Hz), 6.31-6.26 (1H, m), 5.95 and 5.63 (1H, 2s), 4.94-4.82 (1H, m), 4.64-4.59 (1H, m), 4.51 and 4.41 (1H, 2d, J=9.1 Hz), 4.21 (2H, q, J=7.3 Hz), 3.75 and 3.74 (3H, 2s), 3.00 (3H, s), 2.97 and 2.95 (3H, 2s), 2.52-2.38 (2H, m), 2.29-2.20 (1H, m), 2.10-2.00 (1H, m), 1.98-1.90 (1H, m), 1.90 (3H, s), 1.57-1.45 (14H, m), 1.28 (3H, t, J=7.3 Hz), 0.88 (3H, d, J=6.1 Hz), 0.82 (3H, d, J=6.7 Hz), 0.53 and 0.46 (9H, 2s).

LC-MS 784(M+H)$^+$, 782 (M−H)$^-$ (1.472 min, Measurement Condition A)

b) Production of 17-ethyl 22-methyl (6S,9S,12S,13E,17R,22S)-9-tert-butyl-2,2,5,11,14,30,30-heptamethyl-6-[2-(1-methyl-1H-indol-3-yl)propan-2-yl]-4,7,10,15,20,28-hexaoxo-12-(propan-2-yl)-3,29-dioxa-5,8,11,16,21,27-hexaazahentriacont-13-ene-17,22-dicarboxylate (Compound D2)

By the same approach as Reference Example 1-m), from compound D1 (20 mg), compound D2 (13 mg) was obtained.

LC-MS: 1026(M+H)$^+$ (1.597 min, Measurement Condition D)

c) Production of 14-ethyl 19-methyl (3S,6S,9S,10E,14R,19S)-23-amino-6-tert-butyl-8,11-dimethyl-3-[2-(1-methyl-1H-indol-3-yl)propan-2-yl]-4,7,12,17-tetraoxo-9-(propan-2-yl)-2,5,8,13,18-pentaazatricos-10-ene-14,19-dicarboxylate (Compound D3)

To a solution of compound D2 (13 mg) in chloroform (1.0 mL), trifluoroacetic acid (0.2 mL) was added, and the resultant mixture was stirred at 25° C. for 1 hour. After the reaction ended, the reaction solution was purified by silica gel column chromatography (eluting solvent; methanol:chloroform) to give compound D3 (10 mg).

LC-MS: 826(M+H)$^+$, 824 (M−H)$^-$ (0.978 min, Measurement Condition D)

d) Production of N-{(2E,4S)-2,5-dimethyl-4-[methyl(N,β,β,1-tetramethyl-L-tryptophyl-3-methyl-L-valyl)amino]hex-2-enoyl}-D-γ-glutamyl-L-lysine (Reference Example 4)

By carrying out production by the same approach as Reference Example 1-n), and through purification by reversed phase column chromatography (eluting solvent; acetonitrile with 0.1% TFA:water), from compound D3 (10 mg), Reference Example 4 (7.2 mg) was obtained.

LC-MS: 784(M+H)$^+$, 782 (M−H)$^-$ (0.889 min, Measurement Condition D)

Reference Example 5 tert-Butyl N5-(2-(2,5-dioxo-2,5-dihydro-1H-pyrrol-1-yl)ethyl)-D-glutaminate

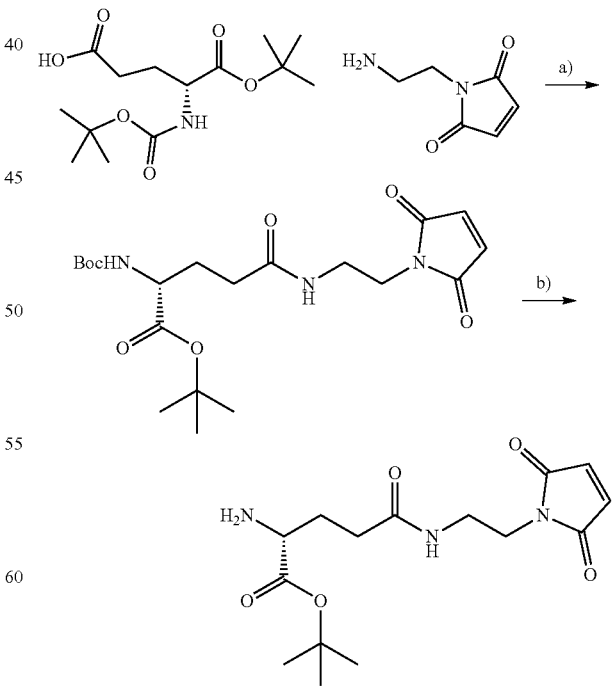

Reference Example 5 a) Production of tert-butyl N2-(tert-butoxycarbonyl)-N5-(2-(2,5-dioxy-2,5-dihydro-1H-pyrrol-1-yl) ethyl)-D-glutaminate A mixed solution of α-tert-butyl BOC-D-glutamate (2.061 g), 1-(2-amino-ethyl)-pyrrole-2,5-dione hydrochloride (1.20 g), 2-(1H-benzo[d][1,2,3]triazol-1-yl)-1,1,3,3-tetramethylisouronium hexafluorophosphate(V) (3.87 g), N,N-diisopropylethylamine (3.47 mL) and N,N-dimethylformamide (10 mL) was stirred at room temperature for 1 hour. After the reaction ended, ethyl acetate was added, and the organic layer was washed with a saturated sodium bicarbonate solution and saturated brine, and then dried over anhydrous sodium sulfate, and the solvent was distilled off under reduced pressure. The residue was purified by silica gel chromatography (eluting solvent; hexane:ethyl acetate) to give tert-butyl N2-(tert-butoxycarbonyl)-N5-(2-(2,5-dioxy-2,5-dihydro-1H-pyrrol-1-yl) ethyl)-D-glutaminate (2.8 g).

LC-MS: 426(M+H)+ (1.030 min, Measurement Condition F)

b) Production of tert-butyl N5-(2-(2,5-dioxo-2,5-dihydro-1H-pyrrol-1-yl)ethyl)-D-glutaminate Reference Example 5

A mixed solution of tert-butyl N2-(tert-butoxycarbonyl)-N5-(2-(2,5-dioxy-2,5-dihydro-1H-pyrrol-1-yl) ethyl)-D-glutaminate (51.8 mg) and TFA (1 mL) was stirred at room temperature for 1 hour and 20 minutes. The reaction solution was ice-cooled and then concentrated under reduced pressure to give Reference Example 5. The compound was used for the next reaction without purification.

LC-MS: 326(M+H)+ (0.496 min, Measurement Condition F)

Reference Example 6

N5-(2-(2,5-Dioxo-2,5-dihydro-1H-pyrrol-1-yl) ethyl)-D-glutamine

Reference Example 6

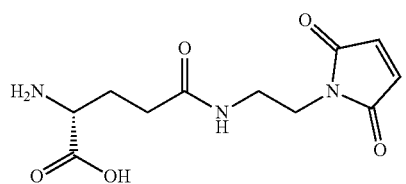

A mixed solution of tert-butyl N2-(tert-butoxycarbonyl)-N5-(2-(2,5-dioxy-2,5-dihydro-1H-pyrrol-1-yl) ethyl)-D-glutaminate (64.8 mg) and TFA (1 mL) was stirred at room temperature for 17 hours. After the reaction ended, the mixed solution was concentrated under reduced pressure to give Reference Example 6. The compound was used for the next reaction without purification.

LC-MS: 270(M+H)+ (0.254 min, Measurement Condition F)

Reference Example 7

N-[2-(2,5-Dioxo-2,5-dihydro-1H-pyrrol-1-yl)ethyl]-D-glutaminyl-D-glutamic Acid

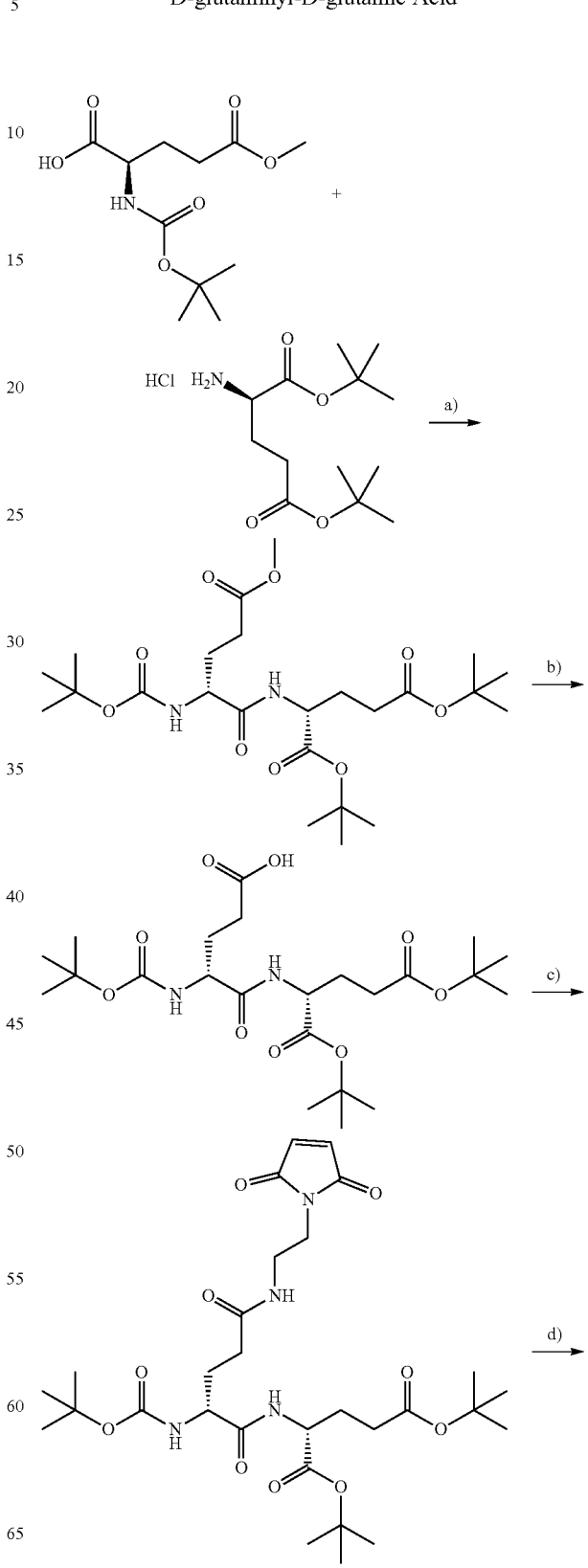

131
-continued

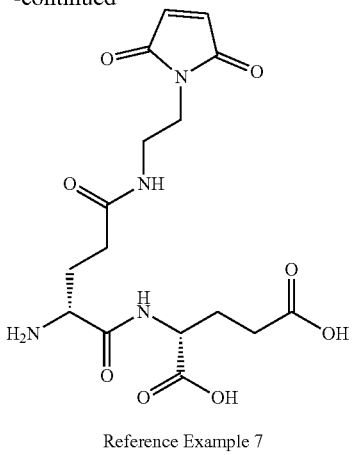

Reference Example 7 a) Production of di-tert-butyl ((R)-2-((tert-butoxy-carbonyl)amino)-5-methoxy-5-oxopentanoyl)-D-glutamate A mixed solution of γ-methyl N-α-(T-butoxycarbonyl)-D-glutamate (261 mg), di-tert-butyl D-glutamate hydrochloride (295 mg), 2-(1H-benzo[d][1,2,3]triazol-1-yl)-1,1,3,3-tetramethylisouronium hexafluorophosphate(V) (456 mg), N,N-diisopropylethylamine (0.446 mL) and N,N-dimethylformamide (4 mL) was stirred at room temperature for 2 hours. After the reaction ended, water was added and the resultant mixture was extracted with ethyl acetate. The organic layer was washed with water and a saturated aqueous sodium bicarbonate solution and then dried over anhydrous sodium sulfate, and the solvent was distilled off under reduced pressure. The residue was purified by silica gel chromatography (eluting solvent; hexane:ethyl acetate) to give di-tert-butyl ((R)-2-((tert-butoxycarbonyl)amino)-5-methoxy-5-oxopentanoyl)-D-glutamate (502 mg).

$^1$H-NMR (400 MHz, CDCl$_3$): 1.42 (18H, s), 1.44 (9H, s), 1.84-1.94 (2H, m), 2.12 (2H, dtt, J=22.5, 8.4, 3.0 Hz), 2.26 (2H, dtd, J=25.2, 10.0, 4.5 Hz), 2.43 (2H, tdd, J=24.8, 14.2, 7.5 Hz), 3.67 (3H, s), 4.14 (1H, t, J=6.1 Hz), 4.43 (1H, td, J=7.9, 4.9 Hz), 5.23 (1H, d, J=7.3 Hz), 6.81 (1H, d, J=7.3 Hz).

132 b) Production of (R)-4-((tert-butoxycarbonyl)amino)-5-(((R)-1,5-di-tert-butoxy-1,5-dioxopentan-2-yl)amino)-5-oxopentanoic Acid A mixture of di-tert-butyl ((R)-2-((tert-butoxycarbonyl)amino)-5-methoxy-5-oxopentanoyl)-D-glutamate (502 mg), a 1 mol/L aqueous lithium hydroxide solution (0.999 mL) and methanol (5 mL) was stirred at room temperature for 16 hours. After the reaction ended, a 1 mol/L aqueous citric acid solution was added to make the mixture into an acidic solution (pH 4), and after distilling off methanol under reduced pressure, the solution was extracted with chloroform. The organic layer was dried over anhydrous sodium sulfate, and the solvent was distilled off under reduced pressure. The residue was purified by silica gel chromatography (eluting solvent; chloroform:methanol) to give (R)-4-((tert-butoxycarbonyl)amino)-5-(((R)-1,5-di-tert-butoxy-1,5-dioxopentan-2-yl)amino)-5-oxopentanoic acid (393 mg).

LC-MS: 489(M+H)$^+$ (1.417 min, Measurement Condition G)

c) Production of di-tert-butyl N2-(tert-butoxycarbonyl)-N5-(2-(2,5-dioxo-2,5-dihydro-H-pyrrol-1-yl)ethyl)-D-glutaminyl-D-glutamate A mixed solution of (R)-4-((tert-butoxycarbonyl)amino)-5-(((R)-1,5-di-tert-butoxy-1,5-dioxopentan-2-yl)amino)-5-oxopentanoic acid (205 mg), 1-(2-amino-ethyl)-pyrrole-2,5-dione hydrochloride (89 mg), 2-(1H-benzo[d][1,2,3]triazol-1-yl)-1,1,3,3-tetramethylisouronium hexafluorophosphate (V) (191 mg), N,N-diisopropylethylamine (0.187 mL) and N,N-dimethylformamide (3 mL) was stirred at room temperature for 16 hours. After the reaction ended, water was added and the resultant mixture was extracted with chloroform. The organic layer was dried over anhydrous sodium sulfate, and the solvent was distilled off under reduced pressure. The residue was purified by silica gel chromatography (eluting solvent; chloroform:methanol) to give di-tert-butyl N2-(tert-butoxycarbonyl)-N5-(2-(2,5-dioxo-2,5-dihydro-H-pyrrol-1-yl) ethyl)-D-glutaminyl-D-glutamate (13 mg).

LC-MS: 611(M+H)$^+$ (1.638 min, Measurement Condition G)

d) Production of N-[2-(2,5-dioxo-2,5-dihydro-1H-pyrrol-1-yl)ethyl]-D-glutaminyl-D-glutamic Acid (Reference Example 7)

Through the same reaction and treatment as Example M1, Reference Example 7 was synthesized from di-tert-butyl N2-(tert-butoxycarbonyl)-N5-(2-(2,5-dioxo-2,5-dihydro-1H-pyrrol-1-yl) ethyl)-D-glutaminyl-D-glutamate (13 mg). The synthesized Reference Example 7 was used for the next reaction as is without purification.

Reference Examples 8 to 18

In accordance with the methods described in the literatures (Bioorg Med Chem Lett. 2004 Nov. 1; 14(21): 5317-22, J Med Chem. 2004 Sep. 9; 47(19): 4774-86., International Publication No. WO 2003/082268 and International Publication No. WO 2016/123582), the compounds shown in the following Table 1 were obtained.

TABLE 1

| Reference Example | Structural Formula | LC-MS/ Rt (min) | LC-MS Measurement Condition |
|---|---|---|---|
| 8 | | 438(M + H)+/ 0.886 | F |
| 9 | | 552(M + H)+/ 0.76 | H |
| 10 | | 552(M + H)+/ 0.76 | H |
| 11 | | 542(M + H)+/ 1.46 | G |
| 12 | | 492(M + H)+/ 1.26 | G |
| 13 | | 480(M + H)+/ 1.25 | G |
| 14 | | 480(M + H)+/ 1.30 | G |
| 15 | | 502(M − H)−/ 1.18 | G |

| Reference Example | Structural Formula | LC-MS/ Rt (min) | LC-MS Measurement Condition |
|---|---|---|---|
| 16 | | 502(M + H)+/ 1.11 | G |
| 17 | | 480(M + H)+/ 1.13 | G |
| 18 | | 524(M + H)+/ 1.304 | G |

Reference Example 19

N,3,3-Trimethyl-2-((S)-3-methyl-2-(methylamino)-3-(m-tolyl)butanamido)butanamido)hex-2-enoic Acid

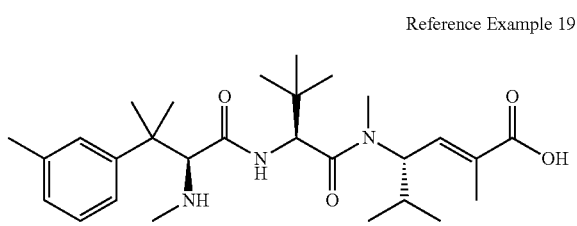 [SMILES: CN[C@H](C(=O)N[C@H](C(=O)N(C)[C@H](/C=C(\C)C(=O)O)C(C)C)C(C)(C)C)C(C)(C)c1cccc(C)c1]

Reference Example 19

A mixed solution of (S,E)-4-((S)-2-((S)-3-(3-bromophenyl)-3-methyl-2-(methylamino)butan amido)-N,3,3-trimethylbutanamido)-2,5-dimethylhex-2-enoic acid (62.5 mg), tetrakis(triphenylphosphine)palladium(0) (13.07 mg), dimethylzinc (0.113 mL) and tetrahydrofuran (5 mL) was stirred at 60° C. for 2.5 hours. After the reaction ended, the solvent was distilled off under reduced pressure. The residue was purified by silica gel chromatography (eluting solvent; chloroform:methanol) to give Reference Example 19 (29.7 mg).

LC-MS: 488(M+H)+ (0.68 min, Measurement Condition F)

Reference Example 20

(S,E)-4-((S)-2-((S)-3-(3-Cyanophenyl)-3-methyl-2-(methylamino)butan amido)-N,3,3-trimethylbutanamido)-2,5-dimethylhex-2-enoic Acid Reference Example 20

A mixed solution of (S,E)-4-((S)-2-((S)-3-(3-bromophenyl)-3-methyl-2-(methylamino)butan amido)-N,3,3-trimethylbutanamido)-2,5-dimethylhex-2-enoic acid (76.1 mg), tetrakis(triphenylphosphine)palladium(0) (15.92 mg), zinc (18.01 mg), zinc cyanide (32.3 mg) and N,N-dimethylformamide (1 mL) was stirred at 120° C. for 1 hour under microwave irradiation. After the reaction ended, the solvent was distilled off under reduced pressure. After partially purifying the residue by silica gel chromatography (eluting solvent; chloroform:methanol), through reversed phase HPLC (the mobile phase was water with 0.1% TFA/acetonitrile with 0.035% TFA solvent), Reference Example 20 (53.5 mg) was obtained.

LC-MS: 499(M+H)+ (0.99 min, Measurement Condition F)

Reference Example 21

(S,E)-4-((S)-2-((S)-3-([1,1'-Biphenyl]-3-yl)-3-methyl-2-(methylamino)butanamido)-N,3,3-trimethylbutanamido)-2,5-dimethylhex-2-enoic Acid

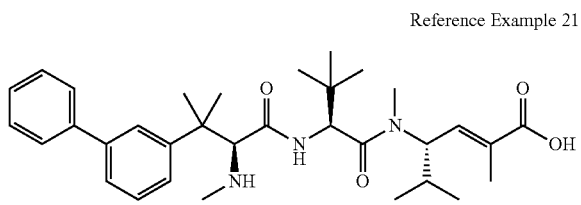 [SMILES: CN[C@H](C(=O)N[C@H](C(=O)N(C)[C@H](/C=C(\C)C(=O)O)C(C)C)C(C)(C)C)C(C)(C)c1cccc(-c2ccccc2)c1]

Reference Example 21

A mixed solution of (S,E)-4-((S)-2-((S)-3-(3-bromophenyl)-3-methyl-2-(methylamino)butanamido)-N,3,3-trimethylbutanamido)-2,5-dimethylhex-2-enoic acid (64.3 mg), tetrakis(triphenylphosphine)palladium(0) (13.45 mg), phenylboranic acid (28.4 mg), sodium carbonate (24.67 mg) and tetrahydrofuran (5 mL) was stirred at 80° C. for 3.5 hours. The solvent was distilled off under reduced pressure. Through reversed phase HPLC (the mobile phase was water with 0.1% TFA/acetonitrile with 0.035% TFA solvent), Reference Example 21 (10.7 mg) was obtained.

LC-MS: 550(M+H)$^+$ (0.88 min, Measurement Condition F)

Reference Example 22

4-(4-(((S)-1-((((S,E)-5-Carboxy-2-methylhex-4-en-3-yl)(methyl)amino)-3,3-dimethyl-1-oxabutan-2-yl)amino)-2-methyl-3-(methylamino)-4-oxo butan-2-yl)benzoic Acid

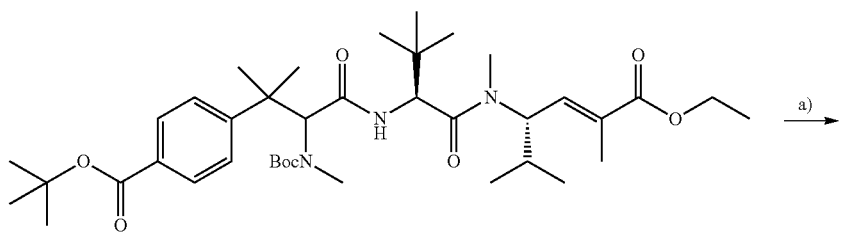

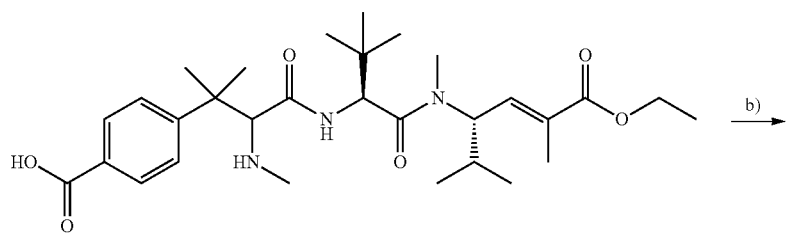

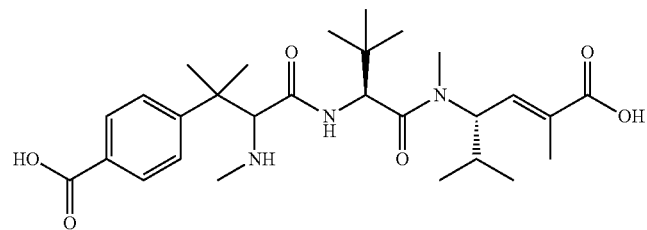

Reference Example 22 a) Production of 4-(4-(((S)-1-(((S,E)-6-ethoxy-2,5-dimethyl-6-oxohex-4-en-3-yl)(methyl)amino)-3,3-dimethyl-1-oxabutan-2-yl)amino)-2-methyl-3-(methylamino)-4-oxabutan-2-yl)benzoic Acid A mixed solution of ethyl (9S,12S,E)-6-(2-(4-(tert-butoxycarbonyl)phenyl)propan-2-yl)-9-(tert-butyl)-12-isopropyl-2,2,5,11,14-pentamethyl-4,7,10-trioxo-3-oxa-5,8,11-triazapentadec-13-en-15-oate (400 mg), TFA (2 mL) and chloroform (8 mL) was stirred at room temperature for 4 hours. The solvent was distilled off under reduced pressure, and 4-(4-(((S)-1-(((S,E)-6-ethoxy-2,5-dimethyl-6-oxohex-4-en-3-yl)(methyl)amino)-3,3-dimethyl-1-oxabutan-2-yl)amino)-2-methyl-3-(methylamino)-4-oxabutan-2-yl)benzoic acid (376 mg) was obtained. The compound thus obtained was used for the next step without purification.

LC-MS: 546(M+H)$^+$ (1.15 min, Measurement Condition F)

b) Production of 4-(4-(((S)-1-(((S,E)-5-carboxy-2-methylhex-4-en-3-yl)(methyl)amino)-3,3-dimethyl-1-oxabutan-2-yl)amino)-2-methyl-3-(methylamino)-4-oxo butan-2-yl)benzoic Acid (Reference Example 22)

While stirring a mixed solution of 4-(4-(((S)-1-(((S,E)-6-ethoxy-2,5-dimethyl-6-oxohex-4-en-3-yl)(methyl)amino)-3,3-dimethyl-1-oxabutan-2-yl)amino)-2-methyl-3-(methylamino)-4-oxobutan-2-yl)benzoic acid (55.2 mg), methanol (3 mL) and water (1 mL) under ice cooling, lithium hydroxide (16.98 mg) was added. The resultant mixture was stirred at room temperature for 2 days. The solvent was distilled off under reduced pressure. By subjecting the residue to reversed phase HPLC (the mobile phase was water with 0.1% TFA/acetonitrile with 0.035% TFA solvent), Reference Example 22 (21.1 mg) was obtained.

LC-MS: 518(M+H)$^+$ (1.18 min, Measurement Condition F)

Reference Example 23

(4S,E)-4-((2S)-2-(3-(4-(tert-Butoxycarbonyl)phenyl)-3-methyl-2-(methylamino)butanamido)-N,3,3-trimethylbutanamido)-2,5-dimethylhex-2-enoic Acid

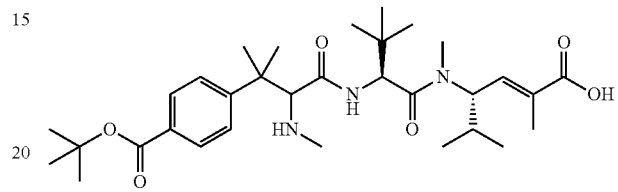

Reference Example 23

From tert-butyl 4-(4-(((S)-1-(((S,E)-6-ethoxy-2,5-dimethyl-6-oxohex-4-en-3-yl)(methyl)amino)-3,3-dimethyl-1-oxobutan-2-yl)amino)-2-methyl-3-(methylamino)-4-oxobutan-2-yl)benzoate, a compound shown in Reference Example 23 was obtained in the same manner as step n) of Reference Example 1.

LC-MS: 574(M+H)$^+$ (1.29 min, Measurement Condition G)

Reference Example 24

(S,E)-4-((S)-2-((S)-3-(4-(tert-Butoxycarbonyl)phenyl)-3-methyl-2-(methoxyamino)butanamido)-N,3,3-trimethylbutanamido)-2,5-dimethylhex-2-enoic Acid

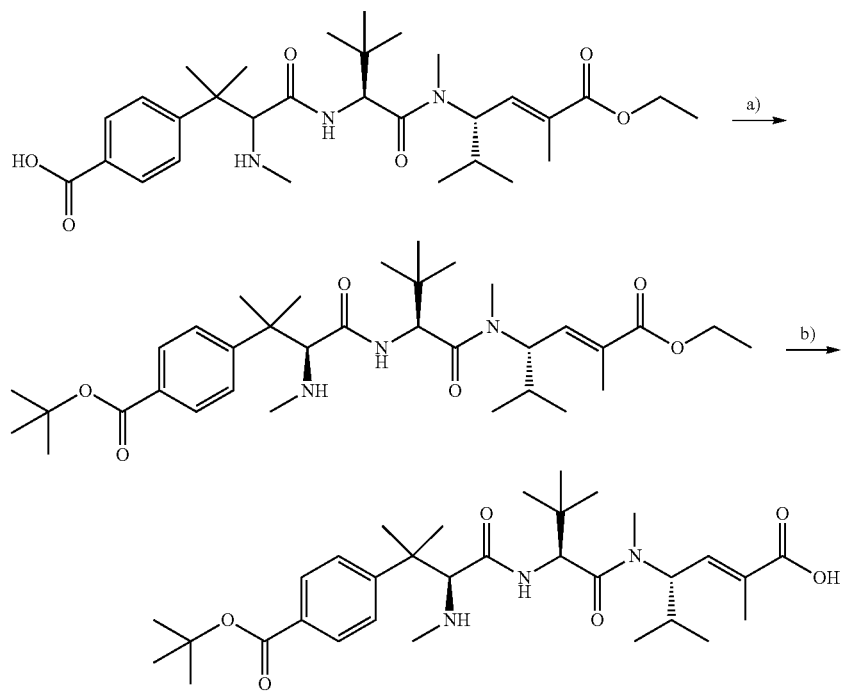

Reference Example 24 a) Production of tert-butyl 4-((S)-4-(((S)-1-(((S,E)-6-ethoxy-2,5-dimethyl-6-oxohex-4-en-3-yl)(methyl)amino)-3,3-dimethyl-1-oxobutan-2-yl)amino)-2-methyl-3-(methylamino)-4-oxobutan-2-yl)benzoate To a mixed solution of 4-(4-(((S)-1-(((S,E)-6-ethoxy-2,5-dimethyl-6-oxohex-4-en-3-yl)(methyl)amino)-3,3-dimethyl-1-oxobutan-2-yl)amino)-2-methyl-3-(methylamino)-4-oxobutan-2-yl)benzoic acid (104.0 mg) and toluene (1 mL), N,N-dimethylfluoroamido-di-tert-butyl acetate (0.456 mL) was added, and after subjecting the resultant mixture to heating reflux for 14 hours, the solvent was distilled off under reduced pressure. The residue was purified by silica gel chromatography to give tert-butyl 4-((S)-4-(((S)-1-(((S,E)-6-ethoxy-2,5-dimethyl-6-oxohex-4-en-3-yl)(methyl)amino)-3,3-dimethyl-1-oxobutan-2-yl)amino)-2-methyl-3-(methylamino)-4-oxobutan-2-yl)benzoate (21.0 mg).

LC-MS: 602(M+H)$^+$ (1.47 min, Measurement Condition F)

b) Production of (S,E)-4-((S)-2-((S)-3-(4-(tert-butoxycarbonyl)phenyl)-3-methyl-2-(methoxyamino)butanamido)-N,3,3-trimethylbutanamido)-2,5-dimethylhex-2-enoic Acid (Reference Example 24)

To a mixed solution of tert-butyl 4-((S)-4-(((S)-1-(((S,E)-6-ethoxy-2,5-dimethyl-6-oxohex-4-en-3-yl)(methyl)amino)-3,3-dimethyl-1-oxobutan-2-yl)amino)-2-methyl-3-(methylamino)-4-oxobutan-2-yl)benzoate (10.5 mg), methanol (3 mL) and water (1.000 mL), lithium hydroxide (4.39 mg) was added, and the resultant mixture was stirred at room temperature for 2 days. The solvent was distilled off under reduced pressure, and the residue was purified by reversed phase HPLC (the mobile phase was water with 0.1% TFA/acetonitrile with 0.035% TFA solvent) to give Reference Example 24 (7.0 mg).

LC-MS: 574(M+H)$^+$ (1.49 min, Measurement Condition F)

Reference Example 25

4-((S)-4-(((S)-1-(((S,E)-5-Carboxy-2-methylhex-4-en-3-yl)(methyl)amino)-3,3-dimethyl-1-oxobutan-2-yl)amino)-2-methyl-3-(methylamino)-4-oxobutan-2-yl)benzoic Acid

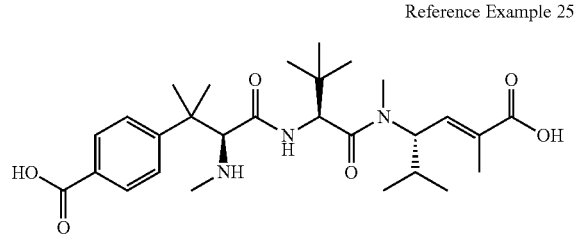 [SMILES: CN[C@H](C(=O)N[C@H](C(=O)N(C)[C@H](/C=C(\C)C(=O)O)C(C)C)C(C)(C)C)C(C)(C)c1ccc(C(=O)O)cc1]

Reference Example 25

To a mixed solution of tert-butyl 4-((S)-4-(((S)-1-(((S,E)-6-ethoxy-2,5-dimethyl-6-oxohex-4-en-3-yl)(methyl)amino)-3,3-dimethyl-1-oxobutan-2-yl)amino)-2-methyl-3-(methylamino)-4-oxobutan-2-yl)benzoate (10.5 mg), methanol (3 mL) and water (1 mL), lithium hydroxide (4.39 mg) was added, and after the resultant mixture was stirred at room temperature for 5 days, the solvent was distilled off under reduced pressure. The residue was dissolved in chloroform (4 mL), trifluoroacetic acid (1 mL) was added, and after the resultant mixture was stirred at room temperature for 17 hours, the solvent was distilled off under reduced pressure. The residue was purified by reversed phase HPLC (the mobile phase was water with 0.1% TFA/acetonitrile with 0.035% TFA solvent) to give Reference Example 25 (7.40 mg).

LC-MS: 518(M+H)$^+$ (1.08 min, Measurement Condition F)

Reference Example 26

(4S,E)-4-((2S)-2-(3-(4-Hydroxyphenyl)-3-methyl-2-(methylamino)butyl)-N,3,3-trimethylbutanamido)-2,5-dimethylhex-2-enoic Acid

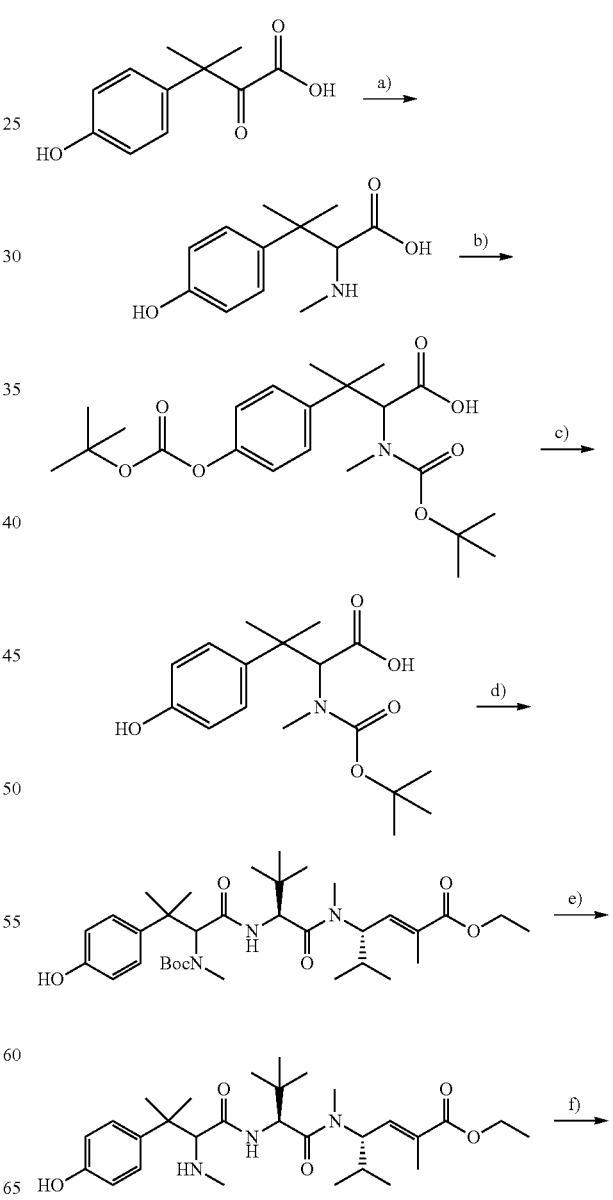

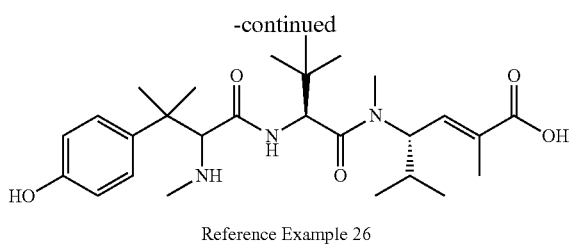

Reference Example 26 a) Production of 3-(4-hydroxyphenyl)-3-methyl-2-(methylamino)butanoic Acid

Under nitrogen atmosphere, a solution of 3-(4-hydroxyphenyl)-3-methyl-2-oxobutanoic acid (54.9 g) in anhydrous tetrahydrofuran (480 mL) was ice-cooled, and methylamine (280 mL) (2 mol/L tetrahydrofuran solution) was added dropwise. After stirring the mixture at room temperature for 1 hour, borane-pyridine complex (27.5 mL) was added dropwise, and the resultant mixture was stirred at 55° C. for 2.5 hours. Under ice cooling, methanol (240 mL) was added dropwise, and the mixture was stirred at room temperature for 2 hours. After distilling off the solvent under reduced pressure, tetrahydrofuran was added, and the suspension was subjected to suction filtration. The powder was washed with tetrahydrofuran to give 3-(4-hydroxyphenyl)-3-methyl-2-(methylamino)butanoic acid (40.7 g).

$^1$H-NMR (400 MHz, D$_2$O): 1.21 (3H, s), 1.24 (3H, s), 2.04 (3H, s), 3.06 (1H, s), 6.52 (2H, d, J=8.8 Hz), 7.11 (2H, d, J=8.8).

b) Production of 2-((tert-butoxycarbonyl)(methyl)amino)-3-(4-((tert-butoxycarbonyl)oxy)phenyl)-3-methylbutanoic Acid Under nitrogen atmosphere, to a suspension of compound i1 (10.2 g) in 1,4-dioxane/water (1:1) (160 mL), di-tert-butyl carbonate (39.9 g) and potassium carbonate (25.4 g) were added, and the resultant mixture was stirred at 40° C. overnight. Ethyl acetate and water were added to the reaction solution, and after changing the pH to 2 to 3 with a 1 mol/L aqueous potassium bisulfate solution, the mixture was extracted with ethyl acetate. The organic layer was washed with saturated brine, followed by drying over anhydrous magnesium sulfate, and the solvent was then distilled off under reduced pressure. The residue was purified by silica gel chromatography (eluting solvent; chloroform:methanol) to give 2-((tert-butoxycarbonyl)(methyl)amino)-3-(4-((tert-butoxycarbonyl)oxy)phenyl)-3-methylbutanoic acid.

$^1$H-NMR (400 MHz, DMSO-D$_6$): 1.38 (12H, s), 1.48 (12H, s), 2.64 (3H, s), 7.09 (2H, d, J=8.4 Hz), 7.40 (2H, d, J=8.8).

c) Production of (S)-2-((tert-butoxycarbonyl)(methyl)amino)-3-(4-hydroxyphenyl)-3-methylbutanoic Acid Under nitrogen atmosphere, compound i2 (15.7 g) was dissolved in dichloromethane (370 mL), a 28% sodium methoxide methanol solution (15.8 g) and methanol (14 mL) were added, and the resultant mixture was stirred at room temperature for 1.5 hours. Ethyl acetate and a 4% aqueous potassium bisulfate solution were added to the reaction solution, and the mixture was extracted. The organic layer was washed with saturated brine, followed by drying over anhydrous magnesium sulfate, and the solvent was distilled off under reduced pressure. The residue was purified by silica gel chromatography (eluting solvent; chloroform:methanol) to give (S)-2-((tert-butoxycarbonyl)(methyl)amino)-3-(4-hydroxyphenyl)-3-methylbutanoic acid (153.7 mg).

$^1$H-NMR (400 MHz, DMSO-D$_6$): 1.36 (12H, s), 1.42 (3H, s), 2.60 (3H, s), 6.66 (2H, d, J=8.0 Hz), 7.15 (2H, d, J=8.4).

d) Production of ethyl (9S,12S,E)-9-(tert-butyl)-6-(2-(4-hydroxyphenyl)propan-2-yl)-12-isopropyl-2,2,5,11,14-pentamethyl-4,7,10-trioxo-3-oxa-5,8,11-triazapentadec-13-en-15-oate A suspension of (S)-2-((tert-butoxycarbonyl)(methyl)amino)-3-(4-hydroxyphenyl)-3-methylbutanoic acid (153.7 mg), ethyl (S,E)-4-((S)-2-amino-N,3,3-trimethylbutanamido)-2,5-dimethylhex-2-enoate hydrochloride (117.6 mg), N-ethyl-N-isopropylpropan-2-amine (0.172 mL), 1-ethyl-3-(3-dimethylaminopropyl)carbodiimide hydrochloride (129 mg), 1-hydroxybenzotriazole (103 mg) and N,N-dimethylformamide (5 mL) was stirred at room temperature for 17 hours. After distilling off the solvent under reduced pressure, chloroform was added, the organic layer was washed with a saturated aqueous sodium bicarbonate solution and then dried over anhydrous sodium sulfate, and the solvent was distilled off under reduced pressure. The residue was purified by silica gel chromatography (eluting solvent; hexane:ethyl acetate) to give ethyl (9S,12S,E)-9-(tert-butyl)-6-(2-(4-hydroxyphenyl)propan-2-yl)-12-isopropyl-2,2,5,11,14-pentamethyl-4,7,10-trioxo-3-oxa-5,8,11-triazapentadec-13-en-15-oate (206.3 mg).

LC-MS: 618(M+H)$^+$ (1.69 min, Measurement Condition F)

e) Production of ethyl (4S,E)-4-((2S)-2-(3-(4-hydroxyphenyl)-3-methyl-2-(methylamino)butan amido)-N,3,3-trimethylbutanamido)-2,5-dimethylhex-2-enoate To a mixed solution of ethyl (9S,12S,E)-9-(tert-butyl)-6-(2-(4-hydroxyphenyl)propan-2-yl)-12-isopropyl-2,2,5,11,14-pentamethyl-4,7,10-trioxo-3-oxa-5,8,11-triazapentadec-13-en-15-oate (189.2 mg) and chloroform (4 mL), TFA (1 mL) was added, and after the resultant mixture was stirred at room temperature for 1 hour, the solvent was distilled off under reduced pressure. Chloroform was added to the residue, and the organic layer was washed with a saturated aqueous sodium bicarbonate solution and then dried over anhydrous sodium sulfate, and the solvent was distilled off under reduced pressure. The residue was purified by silica gel chromatography (eluting solvent; hexane:ethyl acetate) to give ethyl (4S,E)-4-((2S)-2-(3-(4-hydroxyphenyl)-3-methyl-2-(methylamino)butan amido)-N,3,3-trimethylbutanamido)-2,5-dimethylhex-2-enoate (110.1 mg).

LC-MS: 518(M+H)$^+$ (1.09 min, Measurement Condition F)

f) Production of (4S,E)-4-((2S)-2-(3-(4-hydroxyphenyl)-3-methyl-2-(methylamino)butyl)-N,3,3-trimethylbutanamido)-2,5-dimethylhex-2-enoic Acid (Reference Example 26)

To a mixed solution of ethyl (4S,E)-4-((2S)-2-(3-(4-hydroxyphenyl)-3-methyl-2-(methylamino)butan amido)-N,3,3-trimethylbutanamido)-2,5-dimethylhex-2-enoate (110.1 mg), methanol (3 mL) and water (1 mL), lithium hydroxide (35.7 mg) was added under ice cooling, and the resultant mixture was stirred at room temperature for 2 days. The solvent was distilled off under reduced pressure, and the residue was purified by reversed phase HPLC (the mobile phase was water with 0.1% TFA/acetonitrile with 0.035% TFA solvent) to give Reference Example 26 (113.2 mg).

LC-MS: 490(M+H)$^+$ (1.03 min, Measurement Condition F)

Reference Example 27

((4S,E)-4-((2 S)-2-(3-(4-Hydroxyphenyl)-3-methyl-2-(methylamino)butanamido)-N,3,3-trimethylbutanamido)-2,5-dimethylhex-2-enoyl)-D-glutamic Acid hydrochloride (13.59 mg), 1-hydroxybenzotriazole (9.58 mg) and N,N-dimethylformamide (1 mL) was stirred at room temperature for 15 hours. Ethyl acetate was added to the reaction solution, and after washing with saturated brine, the organic layer was dried over anhydrous sodium sulfate, and the solvent was distilled off under reduced pressure. The residue was purified by silica gel chromatography (eluting solvent; chloroform:methanol) to give dimethyl ((4S,E)-4-((2 S)-2-(3-(4-hydroxyphenyl)-3-methyl-2-(methylamino) butanamido)-N,3,3-trimethylbutanamido)-2,5-dimethylhex-2-enoyl)-D-glutamate (21.6 mg).

LC-MS: 647(M+H)$^+$ (1.21 min, Measurement Condition F)

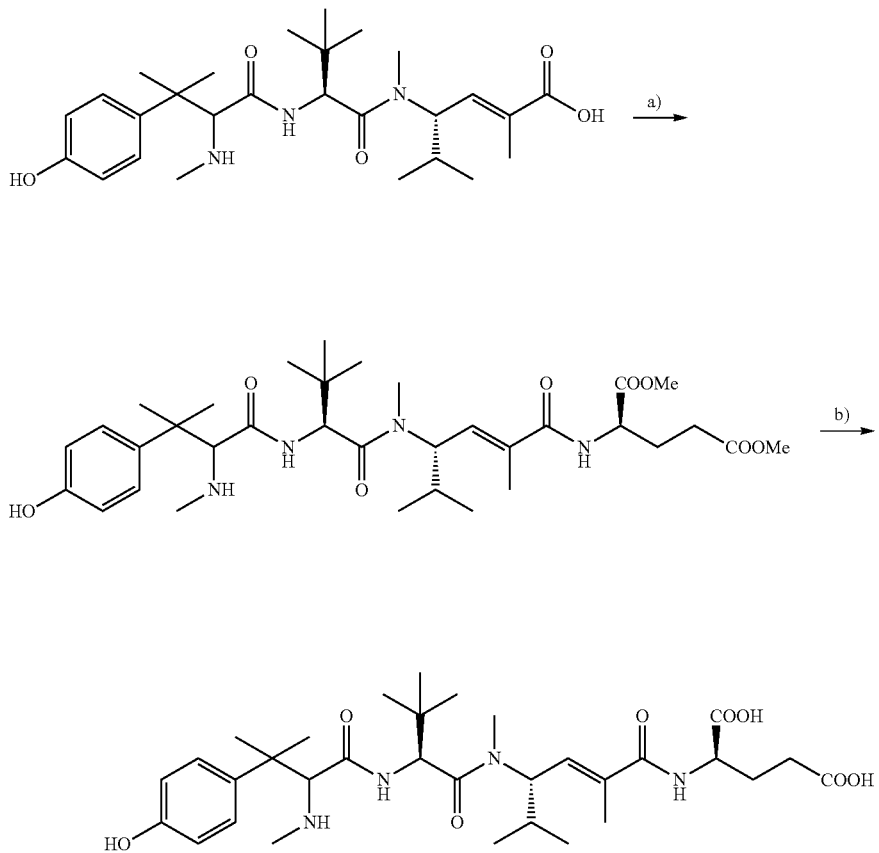

Reference Example 27 a) Production of dimethyl ((4S,E)-4-((2 S)-2-(3-(4-hydroxyphenyl)-3-methyl-2-(methylamino)butanamido)-N,3,3-trimethylbutanamido)-2,5-dimethylhex-2-enoyl)-D-glutamate A mixture of (4S,E)-4-((2S)-2-(3-(4-hydroxyphenyl)-3-methyl-2-(methylamino)butan amido)-N,3,3-trimethylbutanamido)-2,5-dimethylhex-2-enoic acid trifluoroacetate (21.4 mg), N-ethyl-N-isopropylpropan-2-amine (22.91 mg), dimethyl D-glutamate hydrochloride (15.01 mg), 3-(((ethylimino)methylene)amino)-N,N-dimethylpropan-1-amine b) Production of ((4S,E)-4-((2 S)-2-(3-(4-hydroxyphenyl)-3-methyl-2-(methylamino)butanamido)-N,3,3-trimethylbutanamido)-2,5-dimethylhex-2-enoyl)-D-glutamic Acid (Reference Example 27)

To a mixed solution of dimethyl ((4S,E)-4-((2 S)-2-(3-(4-hydroxyphenyl)-3-methyl-2-(methylamino)butanamido)-N,3,3-trimethylbutanamido)-2,5-dimethylhex-2-enoyl)-D-glutamate (21.6 mg), methanol (3 mL) and water (1 mL), lithium hydroxide (5.61 mg) was added at room temperature, and the resultant mixture was stirred. The solvent was distilled off under reduced pressure. The residue was purified by high performance liquid chromatography to give Reference Example 27 (15.8 mg).

LC-MS: 619(M+H)+ (1.04 min, Measurement Condition F)

Reference Example 28

N6-(tert-Butoxycarbonyl)-N2-((R)-4-((S,E)-4-((S)-2-((S)-2-((tert-butoxycarbonyl)(methyl)amino)-3-(5-fluoro-1-methyl-1H-indol-3-yl)-3-methylbutanamido)-N,3,3-trimethylbutanamido)-2,5-dimethylhex-2-enamido)-4-carboxybutanoyl)lysine 10,15-tetraoxo-3-oxa-5,8,11,16-tetraazaicos-13-en-20-oic acid (54.5 mg) and N,N-dimethylformamide (2 mL), 1-[bis(dimethylamino)methylene]-1H-1,2,3-triazole[4,5-b]pyridinium 3-oxide hexafluorophosphate (31.0 mg) was added under ice cooling, and the resultant mixture was stirred for 30 minutes. After adding N-(tert-butoxycarbonyl)-L-lysine methyl ester hydrochloride (24.20 mg) and N-ethyl-N-isopropylpropan-2-amine (0.028 mL) and stirring the resultant mixture at room temperature for 17 hours, the solvent was distilled off under reduced pressure. The residue was purified by silica gel chromatography (eluting solvent; chloroform:methanol) to give methyl N6-(tert-butoxycarbonyl)-N2-((R)-4-((S,E)-4-((S)-2-((S)-2-((tert-butoxy carbonyl)

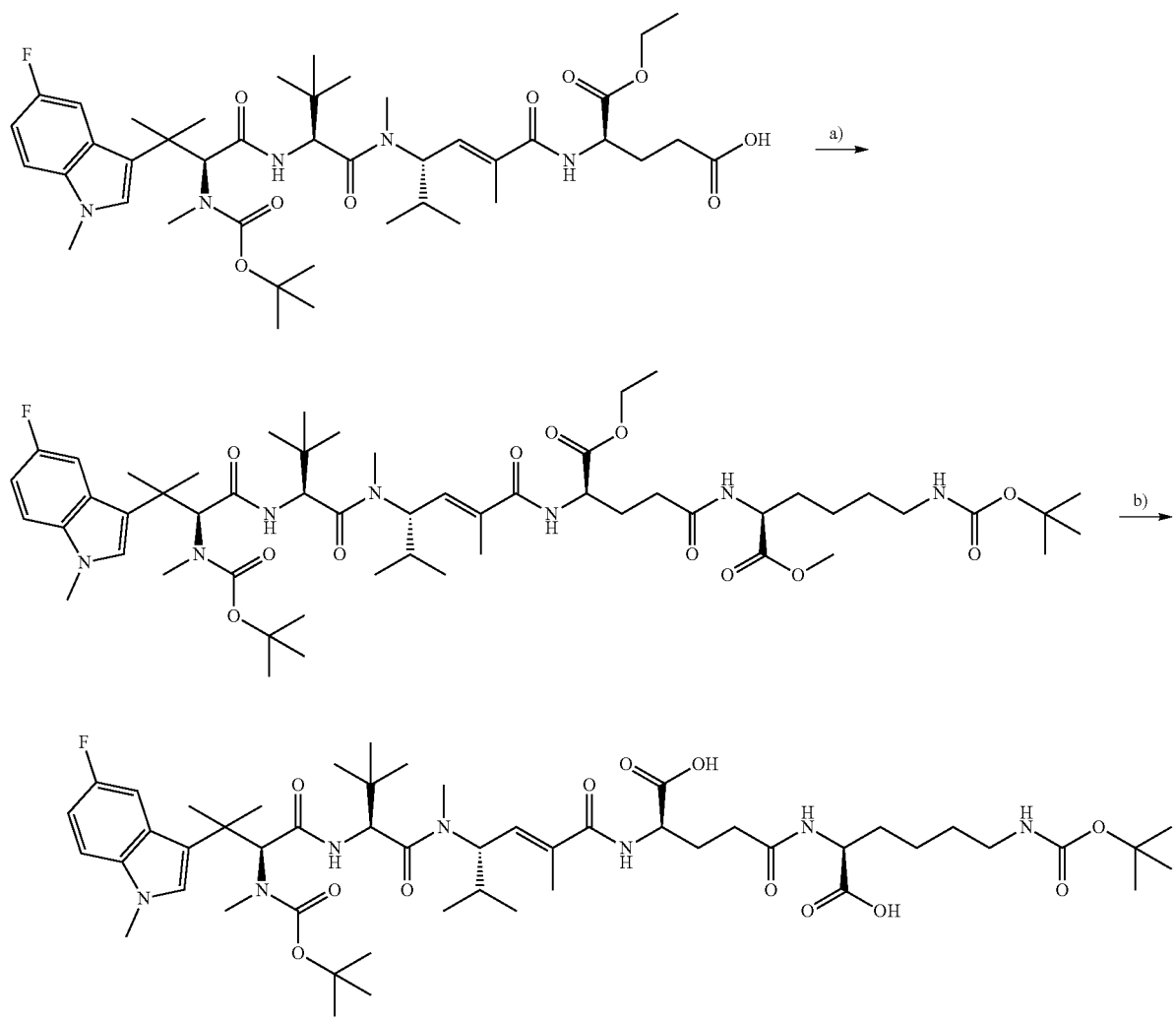

Reference Example 28 a) Production of methyl N6-(tert-butoxycarbonyl)-N2-((R)-4-((S,E)-4-((S)-2-((S)-2-((tert-butoxycarbonyl)(methyl)amino)-3-(5-fluoro-1-methyl-1H-indol-3-yl)-3-methyl butanamido)-N,3,3-trimethylbutanamido)-2,5-dimethylhex-2-enamido)-5-ethoxy-5-oxopentanoyl)lysinate To a mixed solution of (6S,9S,12S,17R,E)-9-(tert-butyl)-17-(ethoxycarbonyl)-6-(2-(5-fluoro-1-methyl-1H-indol-3-yl)propan-2-yl)-12-isopropyl-2,2,5,11,14-pentamethyl-4,7, (methyl)amino)-3-(5-fluoro-1-methyl-1H-indol-3-yl)-3-methyl butanamido)-N,3,3-trimethylbutanamido)-2,5-dimethylhex-2-enamido)-5-ethoxy-5-oxopentanoyl)lysinate (71 mg).

LC-MS: 1067 (M+Na)+ (1.557 min, Measurement Condition G)

149 b) Production of N6-(tert-butoxycarbonyl)-N2-((R)-4-((S,E)-4-((S)-2-((S)-2-((tert-butoxy carbonyl) (methyl)amino)-3-(5-fluoro-1-methyl-1H-indol-3-yl)-3-methyl butanamido)-N,3,3-trimethylbutanamido)-2,5-dimethylhex-2-enamido)-4-carboxybutanoyl)lysine (Reference Example 28)

A mixed solution of methyl N6-(tert-butoxycarbonyl)-N2-((R)-4-((S,E)-4-((S)-2-((S)-2-((tert-butoxy carbonyl) (methyl)amino)-3-(5-fluoro-1-methyl-1H-indol-3-yl)-3-methyl butanamido)-N,3,3-trimethylbutanamido)-2,5-dimethylhex-2-enamido)-5-ethoxy-5-oxopentanoyl)lysinate (71 mg), methanol (4 mL) and a 1 mol/L aqueous lithium hydroxide solution (4 mL) was stirred at 60° C. for 17 hours. To the reaction solution, a saturated aqueous citric acid solution was added to make the solution acidic, and the resultant solution was then extracted with ethyl acetate. The organic layer was dried over anhydrous magnesium sulfate, and the solvent was distilled off under reduced pressure. The residue was purified by ODS column chromatography (eluting solvent; water:acetonitrile) to give Reference Example 28 (49.0 mg).

LC-MS: 1024 (M+Na)$^+$ (1.416 min, Measurement Condition G)

Reference Example 29

Di-tert-butyl ((S,E)-4-((S)-2-((R)-1-(tert-butoxycarbonyl)piperidine-2-carboxamido)-N,3,3-trimethylbutanamido)-2,5-dimethylhex-2-enoyl)-D-glutamate

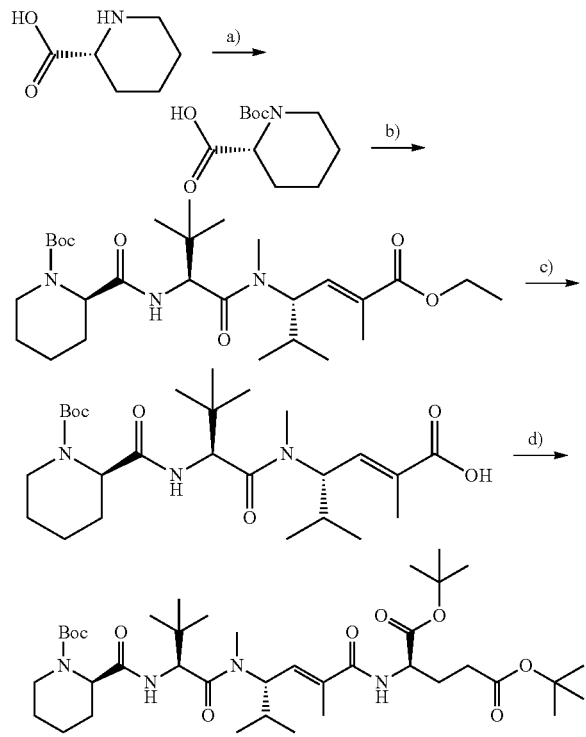

Reference Example 29

150 a) Production of (R)-1-(tert-butoxycarbonyl)piperidine-2-carboxylic Acid

A mixed solution of D-pipecolic acid, di-tert-butyl dicarbonate (8.36 mL), a 5 mol/L aqueous sodium hydroxide solution (19.20 mL), tetrahydrofuran (10 mL) and water (10 mL) was stirred at room temperature for 8 hours, and the solvent was then distilled off under reduced pressure. After washing the aqueous phase with diethyl ether, the aqueous phase was made neutral (pH 7) with a 0.1 mol/L hydrochloric acid water, and was extracted with diethyl ether. By drying over anhydrous sodium sulfate and distilling off the solvent under reduced pressure, (R)-1-(tert-butoxycarbonyl) piperidine-2-carboxylic acid (432.3 mg) was obtained.

LC-MS: 228 (M–H)$^-$ (1.51 min, Measurement Condition F)

b) Production of tert-butyl (R)-2-(((S)-1-(((S,E)-6-ethoxy-2,5-dimethyl-6-oxohex-4-en-3-yl)(methy l)amino)-3,3-dimethyl-1-oxobutan-2-yl)carbamoyl) piperidine-1-carboxylate A suspension of (R)-1-(tert-butoxycarbonyl)piperidine-2-carboxylic acid (432.3 mg), ethyl (S,E)-4-((S)-2-amino-N, 3,3-trimethylbutanamido)-2,5-dimethylhex-2-enoate (393 mg), o-(benzotriazol-1-yl)-N,N,N',N'-tetramethyluronium hexafluorophosphate (953 mg), N-ethyl-N-isopropylpropan-2-amine (0.659 mL) and N,N-dimethylformamide (3 mL) was stirred at room temperature for 15 hours, and then extracted with ethyl acetate. The organic layer was washed with a saturated aqueous sodium bicarbonate solution and saturated brine, and then dried over anhydrous sodium sulfate. The solvent was distilled off under reduced pressure. The residue was purified by silica gel chromatography (eluting solvent; hexane:ethyl acetate) to give tert-butyl (R)-2-(((S)-1-(((S,E)-6-ethoxy-2,5-dimethyl-6-oxohex-4-en-3-yl)(methyl)amino)-3,3-dimethyl-1-oxobutan-2-yl)carbamoyl)piperidine-1-carboxylate (658 mg).

LC-MS: 546 (M+Na)$^+$ (1.51 min, Measurement Condition F)

c) Production of (((S,E)-4-((S)-2-((R)-1-(tert-butoxycarbonyl)piperidine-2-carboxamido)-N,3,3-trimethylbutanamido)-2,5-dimethylhex-2-enoic Acid A mixed solution of tert-butyl (R)-2-(((S)-1-(((S,E)-6-ethoxy-2,5-dimethyl-6-oxohex-4-en-3-yl)(methy l)amino)-3,3-dimethyl-1-oxobutan-2-yl)carbamoyl)piperidine-1-carboxylate (508.1 mg), methanol (8 mL), water (2 mL) and lithium hydroxide (204 mg) was stirred at room temperature for 4 days, and the resultant mixture was then extracted with ethyl acetate. The organic layer was washed with saturated brine and then dried over anhydrous sodium sulfate, and the solvent was distilled off under reduced pressure to give (((S,E)-4-((S)-2-((R)-1-(tert-butoxycarbonyl)piperidine-2-carboxamido)-N,3,3-trimethylbutanamido)-2,5-dimethyl-hex-2-enoic acid. The compound thus obtained was used for the next reaction as is without purification.

LC-MS: 518 (M+Na)$^+$ (1.19 min, Measurement Condition F)

d) Production of di-tert-butyl ((S,E)-4-((S)-2-((R)-1-(tert-butoxycarbonyl)piperidine-2-carboxamido)-N,3,3-trimethylbutanamido)-2,5-dimethylhex-2-enoyl)-D-glutamate Reference Example 29

A mixed solution of (S,E)-4-((S)-2-((R)-1-(tert-butoxycarbonyl)piperidine-2-carboxamido)-N,3,3-trimethylbutanamido)-2,5-dimethylhex-2-enoic acid (481 mg), N-ethyl-N-isopropylpropan-2-amine (0.501 mL), 3-(((ethylamino)methylene)amino)-N,N-dimethylpropan-1-amine hydrochloride (372 mg), 1H-benzo[d][1,2,3]triazol-1-ol (262 mg), di-tert-butyl D-glutamate hydrochloride (287 mg) and N,N-dimethylformamide (10 mL) was stirred at room temperature for 20 hours, and then extracted with ethyl acetate. The organic layer was washed with a saturated aqueous sodium bicarbonate solution and saturated brine, and then dried over anhydrous sodium sulfate. The residue was purified by silica gel chromatography (eluting solvent; hexane:ethyl acetate) to give Reference Example 29 (673.0 mg).

LC-MS: 759 (M+Na)$^+$ (1.35 min, Measurement Condition H)

Reference Examples 30 to 52

The compounds shown in the following Table 2 were obtained through the same reaction and treatment as step p) of Reference Example 1, using intermediate A15 of Reference Example 1, Reference Example 2 and Reference Example 53 as raw material compounds.

TABLE 2

| Reference Example | Structural Formula | LC-MS/ Rt (min) | LC-MS Measurement Condition |
|---|---|---|---|
| 30 | | 745(M + H)$^+$/ 1.594 | G |
| 31 | | 745(M + H)$^+$/ 1.526 | G |
| 32 | | 759(M + H)$^+$/ 1.693 | G |

TABLE 2-continued

| Reference Example | Structural Formula | LC-MS/ Rt (min) | LC-MS Measurement Condition |
|---|---|---|---|
| 33 | | 759(M + H)+/ 1.732 | G |
| 34 | | 745(M + H)+/ 1.439 | G |
| 35 | | 745(M + H)+/ 1.400 | G |
| 36 | | 759(M + H)+/ 1.413 | G |

TABLE 2-continued

| Reference Example | Structural Formula | LC-MS/ Rt (min) | LC-MS Measurement Condition |
|---|---|---|---|
| 37 | | 759(M + H)+/ 1.475 | G |
| 38 | | 812(M + H)+/ 1.560 | G |
| 39 | | 798(M + H)+/ 1.415 | G |
| 40 | | 798(M + H)+/ 1.474 | G |

TABLE 2-continued

| Reference Example | Structural Formula | LC-MS/ Rt (min) | LC-MS Measurement Condition |
|---|---|---|---|
| 41 | | 798(M + H)+/ 1.470 | G |
| 42 | | 812(M + H)+/ 1.460 | G |
| 43 | | 812(M + H)+/ 1.450 | G |
| 44 | | 798(M + H)+/ 1.420 | G |

TABLE 2-continued

| Reference Example | Structural Formula | LC-MS/ Rt (min) | LC-MS Measurement Condition |
|---|---|---|---|
| 45 | | 812(M + H)+/ 1.457 | G |
| 46 | | 944(M + H)+/ 1.407 | G |
| 47 | | 1129(M + H)+/ 1.30 | F |
| 48 | | 911(M + H)+/ 1.709 | G |

TABLE 2-continued

| Reference Example | Structural Formula | LC-MS/ Rt (min) | LC-MS Measurement Condition |
|---|---|---|---|
| 49 | | 802(M + H)+/ 1.390 | G |
| 50 | | 855(M + H)+/ 1.588 | G |
| 51 | | 952(M − H)−/ 1.399 | G |
| 52 | | 802(M + H)+/ 1.452 | G |

Reference Example 53

The compound shown in the following Table 3 was obtained through the same reaction and treatment as Reference Example 1, using a corresponding raw material compound.

TABLE 3

| Reference Example | Structural Formula | LC-MS/ Rt (min) | LC-MS Measurement Condition |
|---|---|---|---|
| 53 | | 742 (M + H)+/ 1.488 | G |

Reference Examples 54 to 73

The compounds shown in the following Table 4 were obtained through the same reaction and treatment as step c) of Reference Example 3, using corresponding raw material compounds.

TABLE 4

| Reference Example | Structural Formula | LC-MS/ Rt (min) | LC-MS Measurement Condition |
|---|---|---|---|
| 54 | | 889 (M + Na)+/ 1.498 | G |
| 55 | | 867 (M + H)+/ 1.433 | G |
| 56 | | 881 (M + H)+/ 1.701 | G |

TABLE 4-continued

| Reference Example | Structural Formula | LC-MS/ Rt (min) | LC-MS Measurement Condition |
|---|---|---|---|
| 57 | | 881 (M + H)+/ 1.710 | G |
| 58 | | 867 (M + H)+/ 1.447 | G |
| 59 | | 867 (M + H)+/ 1.413 | G |
| 60 | | 881 (M + H)+/ 1.422 | G |
| 61 | | 895 (M + H)+/ 1.419 | G |

TABLE 4-continued

| Reference Example | Structural Formula | LC-MS/ Rt (min) | LC-MS Measurement Condition |
|---|---|---|---|
| 62 | | 909 (M + H)⁺/ 1.475 | G |
| 63 | | 934 (M + H)⁺/ 1.441 | G |
| 64 | | 920 (M + H)⁺/ 1.498 | G |
| 65 | | 920 (M + H)⁺/ 1.443 | G |
| 66 | | 942 (M + Na)⁺/ 1.440 | G |

TABLE 4-continued

| Reference Example | Structural Formula | LC-MS/ Rt (min) | LC-MS Measurement Condition |
|---|---|---|---|
| 67 | | 934 (M + H)+/ 1.475 | G |
| 68 | | 970 (M + Na)+/ 1.503 | G |
| 69 | | 920 (M + H)+/ 1.459 | G |
| 70 | | 934 (M + H)+/ 1.497 | G |
| 71 | | 881 (M + H)+/ 1.373 | G |

TABLE 4-continued

| Reference Example | Structural Formula | LC-MS/ Rt (min) | LC-MS Measurement Condition |
|---|---|---|---|
| 72 | | 1066 (M + H)+/ 1.415 | G |
| 73 | | 1273 (M + Na)+/ 1.624 | G |

Reference Examples 74 to 78

The compounds shown in the following Table 5 were obtained through the same reaction and treatment as Example M1, using corresponding raw material compounds.

TABLE 5

| Reference Example | Structural Formula | LC-MS/ Rt (min) | LC-MS Measurement Condition |
|---|---|---|---|
| 74 | | 800 (M − H)−/ 0.923 | G |
| 75 | | 653 (M − H)−/ 0.853 | G |
| 76 | | 653 (M − H)−/ 0.952 | G |

TABLE 5-continued

| Reference Example | Structural Formula | LC-MS/ Rt (min) | LC-MS Measurement Condition |
|---|---|---|---|
| 77 | | 600 (M − H)⁻/ 0.853 | G |
| 78 | | 525 (M + H)⁺/ 0.82 | G |

Reference Examples 79 to 88

The compounds shown in the following Table 6 were obtained through the same reaction and treatment as step m) of Reference Example 1, using corresponding raw material compounds and Reference Example 5.

TABLE 6

| Reference Example | Structural Formula | LC-MS/ Rt (min) | LC-MS Measurement Condition |
|---|---|---|---|
| 79 | | 849 (M + H)⁺/ 1.138 | G |
| 80 | | 799 (M + H)⁺/ 0.976 | F |
| 81 | | 787 (M + H)⁺/ 1.387 | G |
| 82 | | 795 (M − H)⁻/ 1.24 | G |

TABLE 6-continued

| Reference Example | Structural Formula | LC-MS/ Rt (min) | LC-MS Measurement Condition |
|---|---|---|---|
| 83 | | 806 (M + H)+/ 1.34 | G |
| 84 | | 981 (M + H)+/ 1.702 | G |
| 85 | | 811 (M + H)+/ 1.10 | G |
| 86 | | 809 (M + H)+/ 1.17 | G |
| 87 | | 787 (M + H)+/ 1.060 | G |
| 88 | | 831 (M + H)+/ 1.173 | G |

Reference Examples 89 to 95

The compounds shown in the following Table 7 were obtained through the same reaction and treatment as step o) of Reference Example 1, using corresponding raw material compounds.

TABLE 7

| Reference Example | Structural Formula | LC-MS/ Rt (min) | LC-MS Measurement Condition |
|---|---|---|---|
| 89 | | 647 (M + H)+/ 0.89 | G |
| 90 | | 585 (M + H)+/ 0.67 | G |
| 91 | | 535 (M + H)+/ 0.707 | F |
| 92 | | 649 (M + H)+/ 0.81 | G |
| 93 | | 649 (M + H)+/ 0.86 | G |
| 94 | | 671 (M + H)+/ 1.08 | G |

TABLE 7-continued

| Reference Example | Structural Formula | LC-MS/ Rt (min) | LC-MS Measurement Condition |
|---|---|---|---|
| 95 | 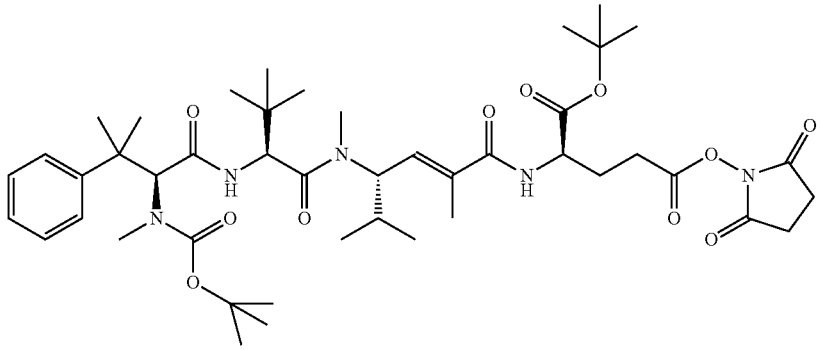 [SMILES: C/C(=C\[C@H](C(C)C)N(C)C(=O)[C@@H](NC(=O)[C@@H](N(C)C(=O)OC(C)(C)C)C(C)(C)c1ccccc1)C(C)(C)C)C(=O)N[C@H](CCC(=O)ON1C(=O)CCC1=O)C(=O)OC(C)(C)C] | 878 (M + Na)+/ 1.426 | G |

Reference Example 96

The compound shown in the following Table 8 was obtained through the same reaction and treatment as Example M1, using a corresponding raw material compound.

TABLE 8

| Reference Example | Structural Formula | LC-MS/ Rt (min) | LC-MS Measurement Condition |
|---|---|---|---|
| 96 | 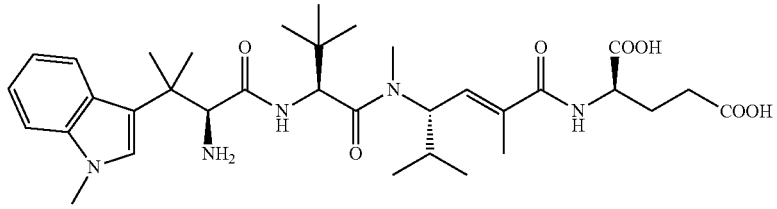 [SMILES: C/C(=C\[C@H](C(C)C)N(C)C(=O)[C@@H](NC(=O)[C@@H](N)C(C)(C)c1cn(C)c2ccccc12)C(C)(C)C)C(=O)N[C@H](CCC(=O)O)C(=O)O] | 642 (M + H)+/ 1.056 | D |

Reference Example 97

(R)-4-((R)-4-((R)-4-Amino-5-(tert-butoxy)-5-oxopentanamido)-5-(tert-butoxy)-5-oxopentanamido)-5-(tert-butoxy)-5-oxopentanoic Acid

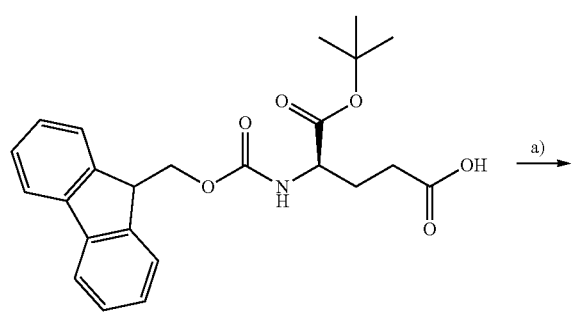

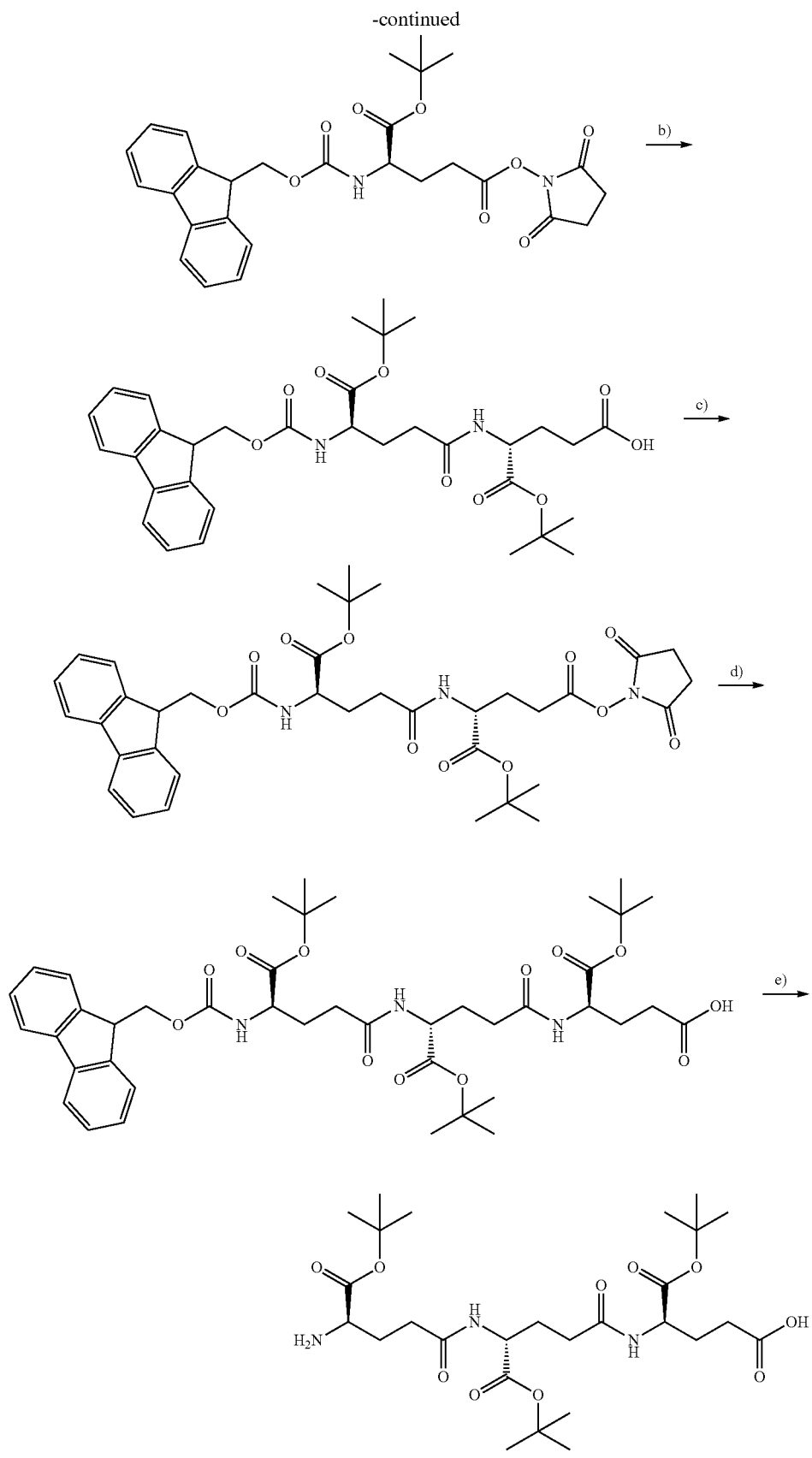
Reference Example 97 a) Production of 1-(tert-butyl) 5-(2,5-dioxopyrrolidin-1-yl) (((9H-fluoren-9-yl)methoxy)carbonyl)-D-glutamate By the same approach as Reference Example 2-c), from (R)-4-(((((9H-fluoren-9-yl)methoxy)carbonyl)amino)-5-(tert-butoxy)-5-oxopentanoic acid (500 mg), 1-(tert-butyl) 5-(2,5-dioxopyrrolidin-1-yl) (((9H-fluoren-9-yl)methoxy)carbonyl)-D-glutamate (520 mg) was obtained.

LC-MS: 523(M+H)$^+$ (1.324 min, Measurement Condition G)

b) Production of (R)-4-((R)-4-((((9H-fluoren-9-yl)methoxy)carbonyl)amino)-5-(tert-butoxy)-5-oxopentanamido)-5-(tert-butoxy)-5-oxopentanoic Acid By the same approach as Reference Example 3, from 1-(tert-butyl) 5-(2,5-dioxopyrrolidin-1-yl) (((9H-fluoren-9-yl)methoxy)carbonyl)-D-glutamate (520 mg), (R)-4-((R)-4-(((((9H-fluoren-9-yl)methoxy)carbonyl)amino)-5-(tert-butoxy)-5-oxopentanamido)-5-(tert-butoxy)-5-oxopentanoic acid (428.7 mg) was obtained.

LC-MS: 611(M+H)$^+$ (1.551 min, Measurement Condition G)

c) Production of 1-(tert-butyl) 5-(2,5-dioxopyrrolidin-1-yl) ((R)-4-((((9H-fluoren-9-yl)methoxy)carbonyl)amino)-5-(tert-butoxy)-5-oxopentanoyl)-D-glutamate By the same approach as Reference Example 2-c), from (R)-4-((R)-4-((((9H-fluoren-9-yl)methoxy)carbonyl)amino)-5-(tert-butoxy)-5-oxopentanamido)-5-(tert-butoxy)-5-oxopentanoic acid (100 mg), 1-(tert-butyl) 5-(2,5-dioxopyrrolidin-1-yl) ((R)-4-((((9H-fluoren-9-yl)methoxy)carbonyl)amino)-5-(tert-butoxy)-5-oxopentanoyl)-D-glutamate (33 mg) was obtained.

LC-MS: 708(M+H)$^+$ (1.598 min, Measurement Condition G)

d) Production of (5R,10R,15R)-5,10,15-tris(tert-butoxycarbonyl)-1-(9H-fluoren-9-yl)-3,8,13-trioxo-2-oxa-4,9,14-triazaoctadecan-18-oic Acid By the same approach as Reference Example 3, from 1-(tert-butyl) 5-(2,5-dioxopyrrolidin-1-yl) ((R)-4-((((9H-fluoren-9-yl)methoxy)carbonyl)amino)-5-(tert-butoxy)-5-oxopentanoyl)-D-glutamate (33 mg), (5R,10R,15R)-5,10,15-tris(tert-butoxycarbonyl)-1-(9H-fluoren-9-yl)-3,8,13-trioxo-2-oxa-4,9,14-triazaoctadecan-18-oic acid (16.6 mg) was obtained.

LC-MS: 796(M+H)$^+$ (1.119 min, Measurement Condition F)

e) Production of (R)-4-((R)-4-((R)-4-amino-5-(tert-butoxy)-5-oxopentanamido)-5-(tert-butoxy)-5-oxopentanamido)-5-(tert-butoxy)-5-oxopentanoic Acid Reference Example 97

By the same approach as Reference Example 103-b), from (5R,10R,15R)-5,10,15-tris(tert-butoxycarbonyl)-1-(9H-fluoren-9-yl)-3,8,13-trioxo-2-oxa-4,9,14-triazaoctadecan-18-oic acid (16.6 mg), Reference Example 97 (7.5 mg) was obtained.

LC-MS: 574(M+H)$^+$ (0.698 min, Measurement Condition F)

Reference Example 98

The compound shown in the following Table 9 was obtained through the same reaction and treatment as Reference Example 2, using a corresponding raw material compound.

TABLE 9

| Reference Example | Structural Formula | LC-MS/ Rt (min) | LC-MS Measurement Condition |
|---|---|---|---|
| 98 | 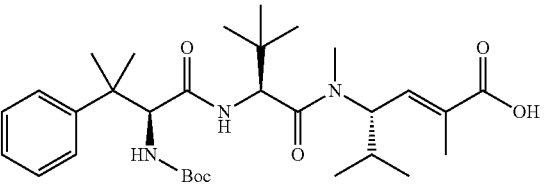 [SMILES: C/C(=C\[C@H](C(C)C)N(C)C(=O)[C@@H](NC(=O)[C@@H](NC(=O)OC(C)(C)C)C(C)(C)c1ccccc1)C(C)(C)C)C(=O)O] | 560 (M + H)$^+$/ 1.480 | G |

Reference Example 99

The compound shown in the following Table 10 was obtained through the same reaction and treatment as step m) of Reference Example 1, using Reference Example 98 and Reference Example 5.

TABLE 10

| Reference Example | Structural Formula | LC-MS/ Rt (min) | LC-MS Measurement Condition |
|---|---|---|---|
| 99 | 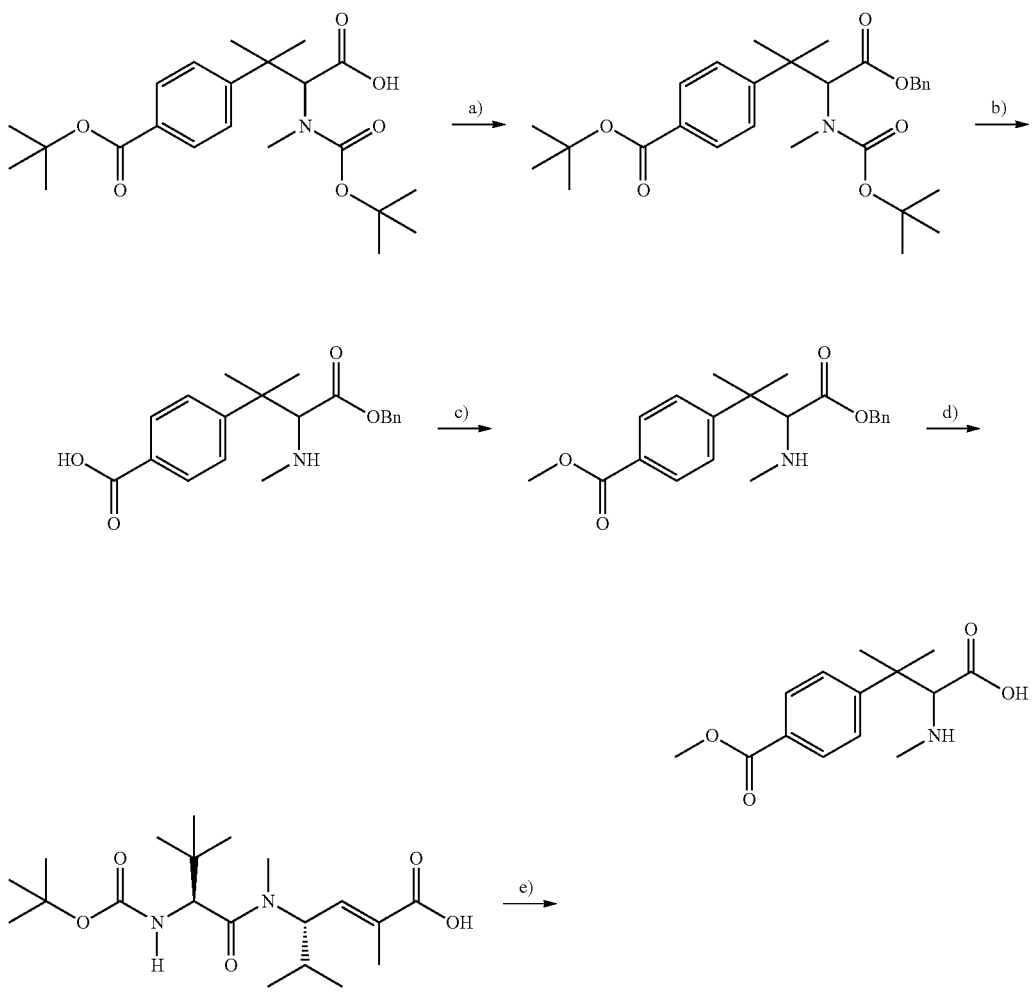 | 889 (M + Na)⁺/ 1.524 | G |

Reference Example 100 di-tert-butyl ((4S,E)-4-((2 S)-2-(3-(4-((2-(2,5-Di-oxo-2,5-dihydro-1H-pyrrol-1-yl)ethyl)carbamoyl)phenyl)-3-methyl-2-(methylamino)butanamido)-N,3,3-trimethylbutanamido)-2,5-dimethylhex-2-enoyl)-D-glutamate

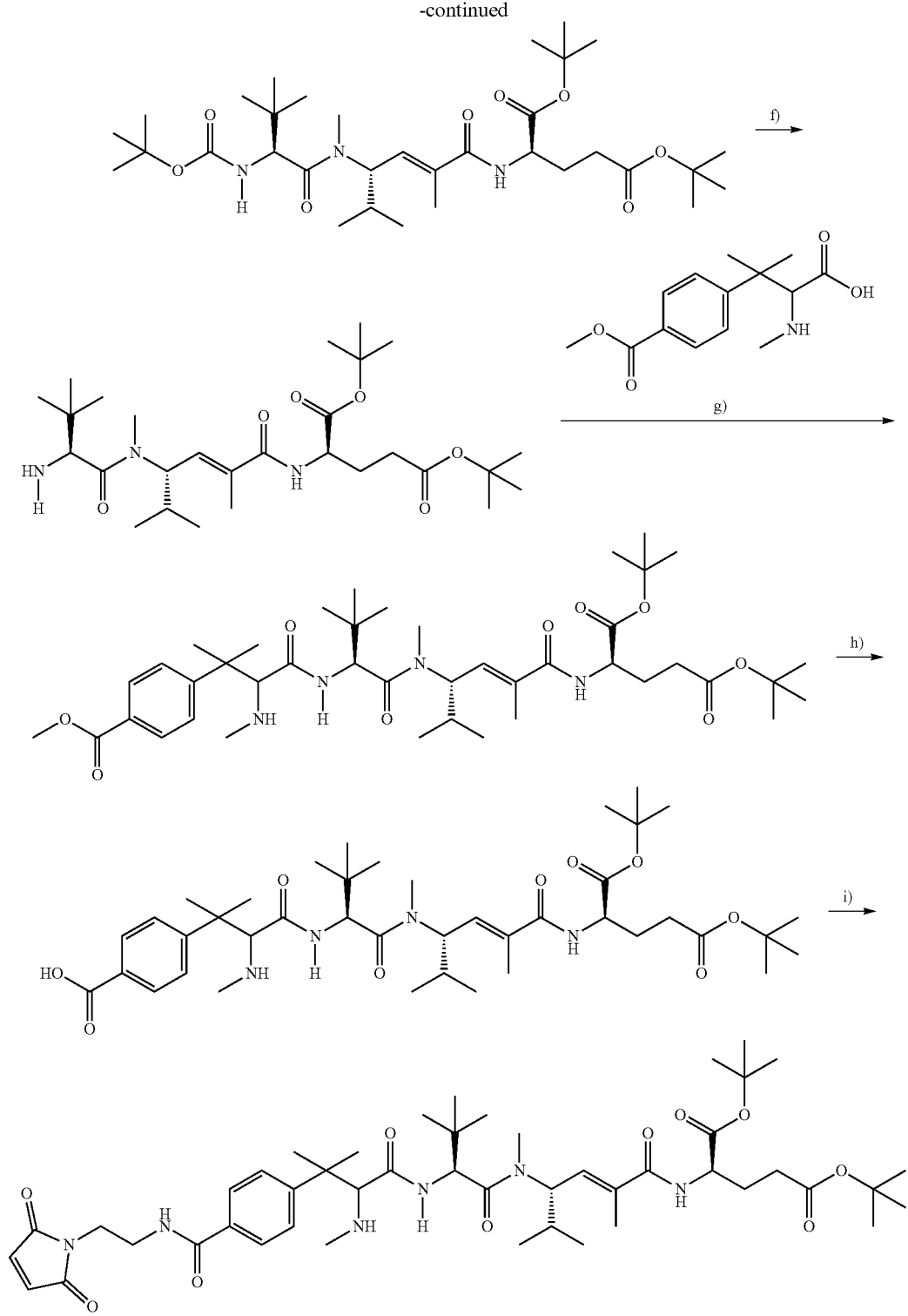

Reference Example 100 a) Production of tert-butyl 4-(4-(benzyloxy)-3-((tert-butoxycarbonyl)(methyl)amino)-2-methyl-4-oxobutan-2-yl)benzoate To a suspension of 2-((tert-butoxycarbonyl)(methyl)amino)-3-(4-(tert-butoxycarbonyl)phenyl)-3-methylbutanoic acid (1.48 g), sodium carbonate (0.77 g) and N,N-dimethylformamide (7 mL), benzyl bromide (0.647 mL) was added, and the resultant mixture was stirred at room temperature for 17 hours. Ethyl acetate was added to the reaction solution. The organic layer was washed with water and saturated brine and then dried over anhydrous sodium sulfate, and the solvent was distilled off under reduced pressure. The residue was purified by silica gel chromatography (eluting solvent; hexane:ethyl acetate) to give tert-butyl 4-(4-(benzyloxy)-3-((tert-butoxycarbonyl)(methyl)amino)-2-methyl-4-oxobutan-2-yl)benzoate (1.78 g).

LC-MS: 520 (M+Na)+ (1.778 min, Measurement Condition G)

b) Production of 4-(4-(benzyloxy)-2-methyl-3-(methylamino)-4-oxobutan-2-yl)benzoic Acid Trifluoroacetate To a mixed solution of tert-butyl 4-(4-(benzyloxy)-3-((tert-butoxycarbonyl)(methyl)amino)-2-methyl-4-oxobutan-2-yl)benzoate (1.78 g) and chloroform (40 mL), trifluoroacetic acid (10 mL) was added, and the resultant mixture was stirred at room temperature for 5 hours. The solvent was distilled off under reduced pressure to give 4-(4-(benzyloxy)-2-methyl-3-(methylamino)-4-oxobutan-2-yl)benzoic acid trifluoroacetate. The compound was used for the next reaction without purification.

LC-MS: 342(M+H)+ (1.05 min, Measurement Condition F)

c) Production of Methyl 4-(4-(benzyloxy)-2-methyl-3-(methylamino)-4-oxobutan-2-yl)benzoate To a suspension of 4-(4-(benzyloxy)-2-methyl-3-(methylamino)-4-oxobutan-2-yl)benzoic acid trifluoroacetate, sodium carbonate (379 mg) and N,N-dimethylformamide (9 mL), iodomethane (0.169 mL) was added, and the resultant mixture was stirred at room temperature. Ethyl acetate was added to the reaction solution. The organic layer was washed with water and saturated brine and then dried over anhydrous sodium sulfate, and the solvent was distilled off under reduced pressure. The residue was purified by silica gel chromatography (eluting solvent; hexane:ethyl acetate) to give methyl 4-(4-(benzyloxy)-2-methyl-3-(methylamino)-4-oxobutan-2-yl)benzoate (362.3 mg).

LC-MS: 356(M+H)+ (1.08 min, Measurement Condition F)

d) Production of 3-(4-(methoxycarbonyl)phenyl)-3-methyl-2-(methylamino)butanoic Acid A suspension of methyl 4-(4-(benzyloxy)-2-methyl-3-(methylamino)-4-oxobutan-2-yl)benzoate (362.3 mg), palladium-carbon (85.5 mg) and ethyl acetate (10 mL) was stirred at room temperature for 5 hours under hydrogen atmosphere. Furthermore, the resultant mixture was stirred for 5 hours. After filtering the reaction solution through a filter paper, the solvent was distilled off under reduced pressure to give 3-(4-(methoxycarbonyl)phenyl)-3-methyl-2-(methylamino)butanoic acid.

LC-MS: 266(M+H)+ (0.82 min, Measurement Condition F)

e) Production of di-tert-butyl ((S,E)-4-((S)-2-((tert-butoxycarbonyl)amino)-N,3,3-trimethylbutanamido)-2,5-dimethylhex-2-enoyl)-D-glutamate A mixed solution of (S,E)-4-((S)-2-((tert-butoxycarbonyl)amino)-N,3,3-trimethylbutanamido)-2,5-dimethylhex-2-enoic acid (220.2 mg), di-tert-butyl D-glutamate hydrochloride (254 mg), N-ethyl-N-isopropylpropan-2-amine (0.300 mL), 1-ethyl-3-(3-dimethylaminopropyl)carbodiimide hydrochloride (220 mg), 1-hydroxybenzotriazole (175 mg) and N,N-dimethylformamide was stirred at room temperature for 17 hours. Ethyl acetate was added to the reaction solution. The organic layer was washed with water and saturated brine and then dried over anhydrous sodium sulfate, and the solvent was distilled off under reduced pressure. di-tert-butyl ((S,E)-4-((S)-2-((tert-butoxycarbonyl)amino)-N,3,3-trimethylbutanamido)-2,5-dimethylhex-2-enoyl)-D-glutamate (232.4 mg) was obtained.

LC-MS: 626(M+H)+ (1.76 min, Measurement Condition F)

f) Production of di-tert-butyl ((S,E)-4-((S)-2-amino-N,3,3-trimethylbutanamido)-2,5-dimethylhex-2-enoyl)-D-glutamate To a mixed solution of di-tert-butyl ((S,E)-4-((S)-2-((tert-butoxycarbonyl)amino)-N,3,3-trimethylbutanamido)-2,5-dimethylhex-2-enoyl)-D-glutamate (232.4 mg) and ethyl acetate (3.7 mL), a solution of hydrochloric acid (13.54 mg) in ethyl acetate was added under ice cooling, and the resultant mixture was stirred at room temperature for 1 hour and 20 minutes. The reaction solution was ice-cooled, a 28% aqueous ammonia was added thereto, and the reaction solution was extracted with ethyl acetate. The organic layer was dried over anhydrous sodium sulfate, and the solvent was distilled off under reduced pressure to give di-tert-butyl ((S,E)-4-((S)-2-amino-N,3,3-trimethylbutanamido)-2,5-dimethylhex-2-enoyl)-D-glutamate (62.2 mg). The compound was used for the next reaction without purification.

LC-MS: 526(M+H)+ (1.14 min, Measurement Condition F)

g) Production of di-tert-butyl ((4S,E)-4-((2S)-2-(3-(4-(methoxycarbonyl)phenyl)-3-methyl-2-(methylamino)butanamido)-N,3,3-trimethylbutanamido)-2,5-dimethylhex-2-enoyl)-D-glutamate A suspension of di-tert-butyl ((S,E)-4-((S)-2-amino-N,3,3-trimethylbutanamido)-2,5-dimethylhex-2-enoyl)-D-glutamate (31.4 mg), di-tert-butyl ((S,E)-4-((S)-2-amino-N,3,3-trimethylbutanamido)-2,5-dimethylhex-2-enoyl)-D-glutamate (62.2 mg), 1-ethyl-3-(3-dimethylaminopropyl)carbodiimide hydrochloride (45.4 mg), 1-hydroxybenzotriazole (32.0 mg), N-ethyl-N-isopropylpropan-2-amine (0.062 mL) and N,N-dimethylformamide (2 mL) was stirred at room temperature for 17 hours. The solvent was distilled off under reduced pressure. To the residue, ethyl acetate was added, and after washing with water, a saturated aqueous sodium bicarbonate solution and saturated brine, the organic layer was dried over anhydrous sodium sulfate, and the solvent was distilled off under reduced pressure. The residue was purified by silica gel chromatography (eluting solvent; hexane:ethyl acetate) to give di-tert-butyl ((4S,E)-4-((2S)-2-(3-(4-(methoxycarbonyl)phenyl)-3-methyl-2-(methylamino)butanamido)-N,3,3-trimethylbutanamido)-2,5-dimethylhex-2-enoyl)-D-glutamate (60.1 mg).

LC-MS: 774(M+H)+ (1.341 min, Measurement Condition G)

h) Production of 4-((7R,12S,15 S,E)-7-(tert-butoxycarbonyl)-15-(tert-butyl)-12-isopropyl-2,2,10,13,19-pentamethyl-18-(methylamino)-4,9,14,17-tetraoxo-3-oxa-8,13,16-triazaicos-10-en-19-yl)benzoic Acid To a mixed solution of tert-butyl ((4S,E)-4-((2S)-2-(3-(4-(methoxycarbonyl)phenyl)-3-methyl-2-(methylamino)butanamido)-N,3,3-trimethylbutanamido)-2,5-dimethylhex-2- enoyl)-D-glutamate (56.3 mg), methanol (4 mL) and water (1 mL), lithium hydroxide (9.17 mg) was added under ice cooling, and the resultant mixture was stirred at room temperature for 17 hours. The solvent was distilled off under reduced pressure. The residue was purified by reversed phase HPLC (the mobile phase was water with 0.1% TFA/acetonitrile with 0.035% TFA solvent) to give 4-((7R,12S,15 S,E)-7-(tert-butoxycarbonyl)-15-(tert-butyl)-12-isopropyl-2,2,10,13,19-pentamethyl-18-(methylamino)-4,9,14,17-tetraoxo-3-oxa-8,13,16-triazaicos-10-en-19-yl)benzoic acid (14.8 mg).

LC-MS: 759(M+H)+ (1.334 min, Measurement Condition G)

i) Production of di-tert-butyl ((4S,E)-4-((2 S)-2-(3-(4-((2-(2,5-Dioxo-2,5-dihydro-1H-pyrrol-1-yl)ethyl)carbamoyl)phenyl)-3-methyl-2-(methylamino)butanamido)-N,3,3-trimethylbutanamido)-2,5-dimethylhex-2-enoyl)-D-glutamate (Reference Example 100)

A mixed solution of 4-((7R,12S,15 S,E)-7-(tert-butoxycarbonyl)-15-(tert-butyl)-12-isopropyl-2,2,10,13,19-pentamethyl-18-(methylamino)-4,9,14,17-tetraoxo-3-oxa-8,13,16-triazaicos-10-en-19-yl)benzoic acid (14.8 mg), 3-(((ethylimino)methylene)amino)-N,N-dimethylpropan-1-amine hydrochloride (7.48 mg), 1-hydroxybenzotriazole (5.97 mg), N-ethyl-N-isopropylpropan-2-amine (0.014 mL), 1-(2-aminoethyl)-pyrrole-2,5-dione hydrochloride (6.86 mg) and N,N-dimethylformamide (2 mL) was stirred at room temperature for 3 hours. Ethyl acetate was added, and after washing with a saturated aqueous sodium bicarbonate solution and saturated brine, the organic layer was dried over anhydrous sodium sulfate, and the solvent was distilled off under reduced pressure. The residue was purified by silica gel chromatography (eluting solvent; chloroform:methanol) to give Reference Example 100 (9.00 mg).

LC-MS: 881(M+H)+ (1.287 min, Measurement Condition G)

Example M1

(3S,6S,9S,10E,14R)-6-tert-Butyl-14-(3-{[2-(2,5-dioxo-2,5-dihydro-1H-pyrrol-1-yl)ethyl]amino}-3-oxopropyl)-8,11-dimethyl-3-[2-(1-methyl-1H-indol-3-yl)propan-2-yl]-4,7,12-trioxo-9-(propan-2-yl)-2,5,8,13-tetraazapentadec-10-en-15-oic Acid

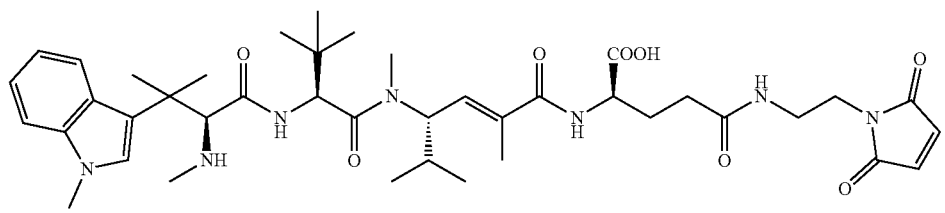 [SMILES: CN[C@H](C(=O)N[C@H](C(=O)N(C)[C@H](/C=C(\C)C(=O)N[C@H](CCC(=O)NCCN1C(=O)C=CC1=O)C(=O)O)C(C)C)C(C)(C)C)C(C)(C)c1cn(C)c2ccccc12]

To a solution of Reference Example 1 (14 mg) in chloroform (1.0 mL), trifluoroacetic acid (0.2 mL) was added, and the resultant mixture was stirred at 25° C. for 4 hours. Thereafter, trifluoroacetic acid (0.2 mL) was further added, and the mixture was further stirred at 25° C. for 2 hours. After the reaction ended, the solvent was distilled off under reduced pressure, and the residue was purified by reversed phase column chromatography (eluting solvent; acetonitrile with 0.1% TFA:water) to give Example M1 (2.8 mg).

LC-MS: 778(M+H)+, 776 (M−H)− (1.081 min, Measurement Condition D)

Example M2

N-{(2E,4S)-2,5-Dimethyl-4-[methyl(N,β,β,1-tetramethyl-L-tryptophyl-3-methyl-L-valyl)amino]hex-2-enoyl}-D-γ-glutamyl-N6-[6-(2,5-dioxo-2,5-dihydro-1H-pyrrol-1-yl)hexanoyl]-L-lysine

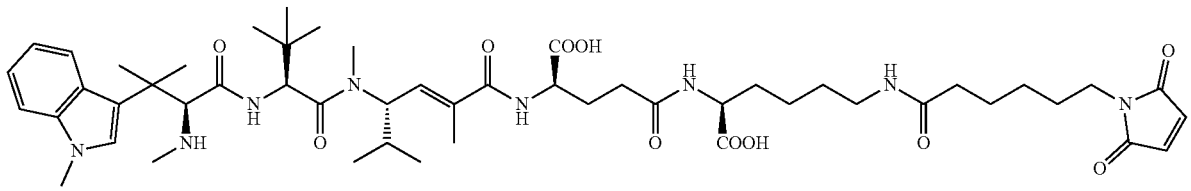 [SMILES: CN[C@H](C(=O)N[C@H](C(=O)N(C)[C@H](/C=C(\C)C(=O)N[C@H](CCC(=O)N[C@@H](CCCCNC(=O)CCCCCN1C(=O)C=CC1=O)C(=O)O)C(=O)O)C(C)C)C(C)(C)C)C(C)(C)c1cn(C)c2ccccc12]

A mixed solution of Reference Example 4 (7.2 mg), N-succinimidyl 6-maleimidohexanoate (2.8 mg), N,N-diisopropylethylamine (2.3 mg) and N,N-dimethylformamide (1 mL) was stirred at 25° C. for 18 hours. After the reaction ended, the reaction solution was purified by reversed phase column chromatography (eluting solvent; acetonitrile with 0.1% TFA:water) to give Example M2 (2.8 mg).

LC-MS: 977(M+H)$^+$, 975 (M–H)$^-$ (1.061 min, Measurement Condition D)

Examples M3 to M8

The compounds shown in the following Table 11 were obtained through the same reaction and treatment as Example M1 or M2, using corresponding raw material compounds. Note that, in the formulas shown in the column of "(AA)$_n$" in Table 11", "L" indicates a terminus that is bonded to L among the two termini of (AA)$_n$. In addition, in the formulas shown in the column of "L" in Table 11, "(AA)$_n$" indicates a terminus that is bonded to (AA)$_n$ among the two termini of L.

TABLE 11

| Example | Q | (AA)$_n$ | L | LC-MS/ Rt (min) | LC-MS Measurement Condition |
|---|---|---|---|---|---|
| M3 | 1-methylindol-3-yl | (see structure) | (see structure) | 907 (M + H)$^+$/ 1.045 | D |
| M4 | phenyl | (see structure) | (see structure) | 725 (M + H)$^+$/ 0.821 | D |
| M5 | phenyl | (see structure) | (see structure) | 854 (M + H)$^+$/ 0.902 | D |
| M6 | phenyl | (see structure) | (see structure) | 983 (M + H)$^+$/ 1.003 | D |
| M7 | phenyl | (see structure) | (see structure) | 854 (M + H)$^+$/ 1.005 | D |
| M8 | 1-methylindol-3-yl | (see structure) | (see structure) | 820 (M + H)$^+$/ 1.014 | D |

Examples M9 to 25

The compounds shown in the following Table 12 were obtained through the same reaction and treatment as Example M1, using corresponding raw material compounds.

TABLE 12

| Example | Structural Formula | LC-MS/ Rt (min) | LC-MS Measurement Condition |
| --- | --- | --- | --- |
| M9 | | 711 (M + H)$^+$/ 0.979 | G |
| M10 | | 711 (M + H)$^+$/ 0.924 | G |
| M11 | | 725 (M + H)$^+$/ 1.120 | G |
| M12 | | 725 (M + H)$^+$/ 0.896 | G |
| M13 | | 711 (M + H)$^+$/ 0.839 | G |
| M14 | | 711 (M + H)$^+$/ 0.838 | G |

TABLE 12-continued
| Example | Structural Formula | LC-MS/ Rt (min) | LC-MS Measurement Condition |
|---|---|---|---|
| M15 | 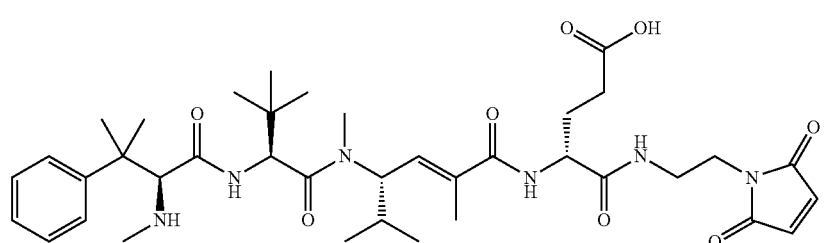 | 725 (M + H)+/ 0.847 | G |
| M16 | 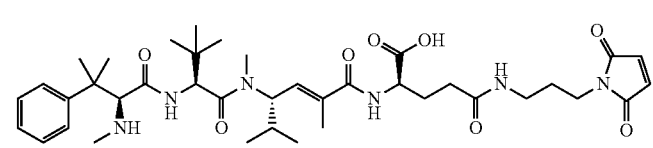 [SMILES: CN[C@H](C(=O)N[C@H](C(=O)N(C)[C@H](/C=C(\C)C(=O)N[C@H](CCC(=O)NCCCN1C(=O)C=CC1=O)C(=O)O)C(C)C)C(C)(C)C)C(C)(C)c1ccccc1] | 739 (M + H)+/ 0.852 | G |
| M17 | 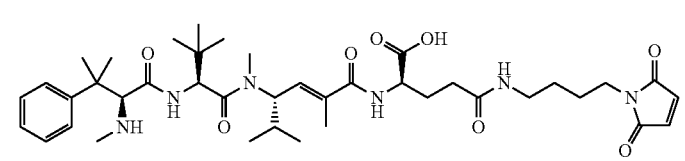 [SMILES: CN[C@H](C(=O)N[C@H](C(=O)N(C)[C@H](/C=C(\C)C(=O)N[C@H](CCC(=O)NCCCCN1C(=O)C=CC1=O)C(=O)O)C(C)C)C(C)(C)C)C(C)(C)c1ccccc1] | 753 (M + H)+/ 1.059 | G |
| M18 | 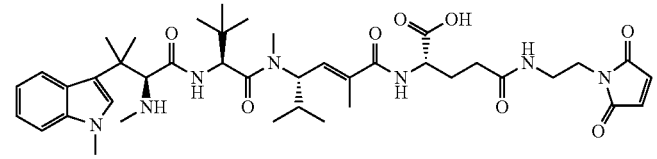 [SMILES: CN[C@H](C(=O)N[C@H](C(=O)N(C)[C@H](/C=C(\C)C(=O)N[C@@H](CCC(=O)NCCN1C(=O)C=CC1=O)C(=O)O)C(C)C)C(C)(C)C)C(C)(C)c1cn(C)c2ccccc12] | 778 (M + H)+/ 1.174 | G |
| M19 | 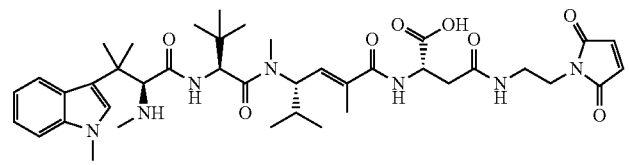 [SMILES: CN[C@H](C(=O)N[C@H](C(=O)N(C)[C@H](/C=C(\C)C(=O)N[C@@H](CC(=O)NCCN1C(=O)C=CC1=O)C(=O)O)C(C)C)C(C)(C)C)C(C)(C)c1cn(C)c2ccccc12] | 764 (M + H)+/ 1.108 | G |
| M20 | 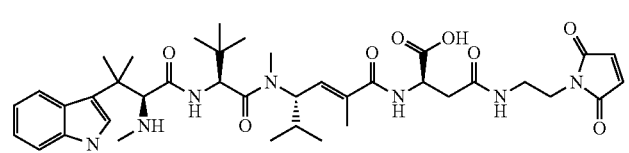 | 764 (M + H)+/ 1.077 | G |
| M21 | 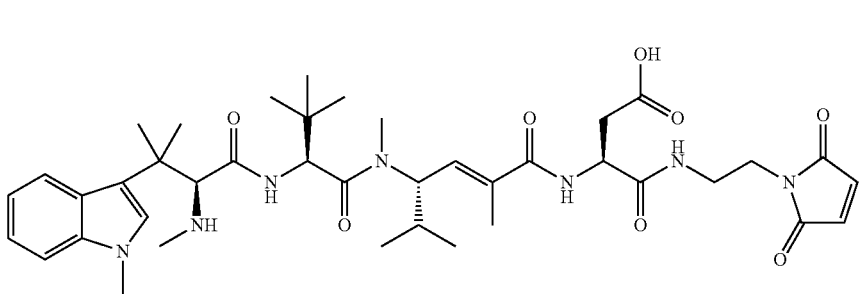 [SMILES: CN[C@H](C(=O)N[C@H](C(=O)N(C)[C@H](/C=C(\C)C(=O)N[C@@H](CC(=O)O)C(=O)NCCN1C(=O)C=CC1=O)C(C)C)C(C)(C)C)C(C)(C)c1cn(C)c2ccccc12] | 764 (M + H)+/ 1.023 | G |

TABLE 12-continued

| Example | Structural Formula | LC-MS/ Rt (min) | LC-MS Measurement Condition |
|---|---|---|---|
| M22 | | 778 (M + H)⁺/ 1.043 | G |
| M23 | | 792 (M + H)⁺/ 1.122 | G |
| M24 | | 764 (M + H)⁺/ 1.086 | G |
| M25 | | 778 (M + H)⁺/ 1.081 | G |

Examples M26 to 30

The compounds shown in the following Table 13 were obtained through the same reaction and treatment as Example M2, using corresponding raw material compounds.

TABLE 13

| Example | Structural Formula | LC-MS/ Rt (min) | LC-MS Measurement Condition |
|---|---|---|---|
| M26 | | 951 (M − H)⁻/ 1.011 | G |

TABLE 13-continued

| Example | Structural Formula | LC-MS/ Rt (min) | LC-MS Measurement Condition |
|---|---|---|---|
| M27 | 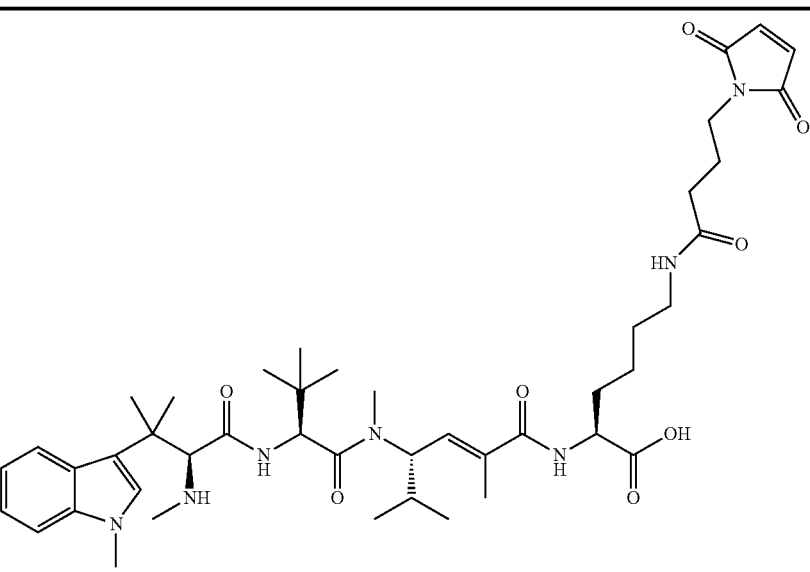 | 820 (M + H)+/ 1.027 | G |
| M28 | 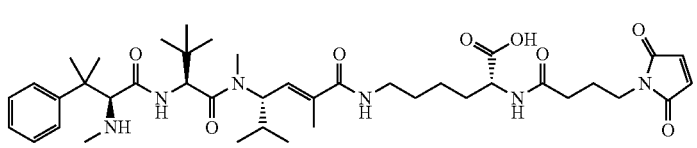 [SMILES: CN[C@H](C(=O)N[C@H](C(=O)N(C)[C@H](/C=C(\C)C(=O)NCCCC[C@@H](NC(=O)CCCN1C(=O)C=CC1=O)C(=O)O)C(C)C)C(C)(C)C)C(C)(C)c1ccccc1] | 767 (M + H)/ 0.969 | G |
| M29 | 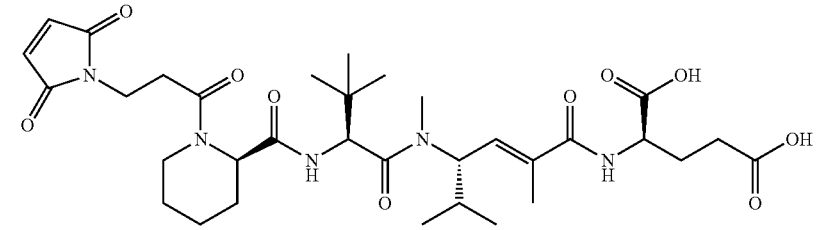 [SMILES: C/C(=C\[C@H](C(C)C)N(C)C(=O)[C@@H](NC(=O)[C@H]1CCCCN1C(=O)CCN1C(=O)C=CC1=O)C(C)(C)C)C(=O)N[C@H](CCC(=O)O)C(=O)O] | 674 (M − H)−/ 1.02 | G |
| M30 | 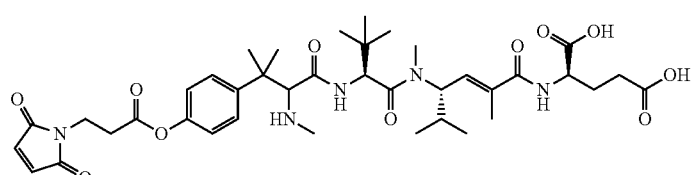 | 770 (M + H)+/ 0.997 | G |

Examples M31 to 40

The compounds shown in the following Table 14 were obtained through the same reaction and treatment as Example M1, using corresponding raw material compounds.

TABLE 14

| Example | Structural Formula | LC-MS/ Rt (min) | LC-MS Measurement Condition |
|---|---|---|---|
| M31 | 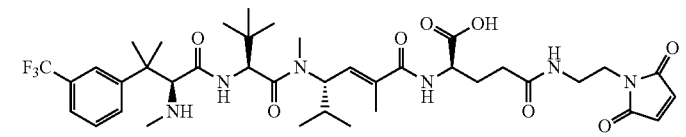 [SMILES: CN[C@H](C(=O)N[C@H](C(=O)N(C)[C@H](/C=C(\C)C(=O)N[C@H](CCC(=O)NCCN1C(=O)C=CC1=O)C(=O)O)C(C)C)C(C)(C)C)C(C)(C)c1cccc(C#N)c1] | 791 (M − H)−/ 1.07 | G |

TABLE 14-continued

| Example | Structural Formula | LC-MS/ Rt (min) | LC-MS Measurement Condition |
|---|---|---|---|
| M32 | | 741 (M − H)⁻/ 0.99 | G |
| M33 | | 729 (M − H)⁻/ 1.18 | G |
| M34 | | 739 (M − H)⁻/ 1.05 | G |
| M35 | | 748 (M − H)⁻/ 1.03 | G |
| M36 | | 767 (M − H)⁻/ 0.98 | G |
| M37 | | 755 (M + H)⁺/ 0.99 | G |
| M38 | | 753 (M + H)⁺/ 1.05 | G |
| M39 | | 731 (M + H)⁺/ 0.94 | G |
| M40 | | 775 (M + H)⁺/ 1.019 | G |

Examples M41 to 46

The compounds shown in the following Table 15 were obtained through the same reaction and treatment as step p) of Reference Example 1, using corresponding raw material compounds.

TABLE 15
| Example | Structural Formula | LC-MS/ Rt (min) | LC-MS Measurement Condition |
|---|---|---|---|
| M41 | | 799 (M − H)−/ 1.13 | G |
| M42 | | 737 (M − H)−/ 0.96 | G |
| M43 | | 687 (M − H)−/ 0.82 | G |
| M44 | | 801 (M − H)−/ 0.96 | F |
| M45 | | 801 (M − H)−/ 1.02 | G |
| M46 | | 823 (M − H)−/ 1.28 | G |
Example M47
((4S,E)-4-((2 S)-2-(3-(4-((2-(2,5-Dioxo-2,5-dihydro-1H-pyrrol-1-yl)ethyl)carbamoyl)phenyl)-3-methyl-2-(methylamino)butanamido)-N,3,3-trimethylbutanamido)-2,5-dimethylhex-2-enoyl)-D-glutamic Acid
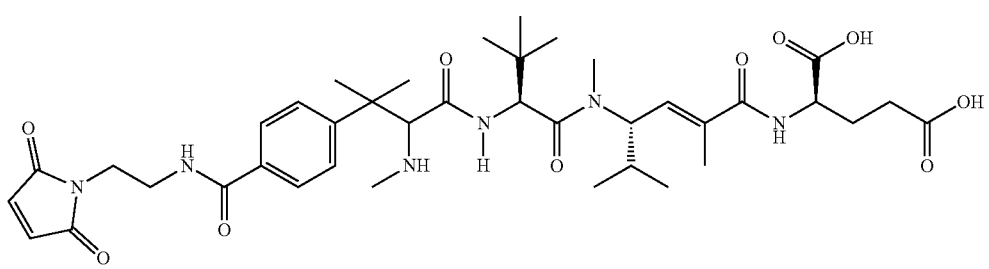
Example M47

To a mixed solution of Reference Example 100 (9.0 mg) and chloroform (4 mL), trifluoroacetic acid (1 mL) was added, and the resultant mixture was stirred at room temperature for 4 hours. The solvent was distilled off under reduced pressure. The residue was purified by reversed phase HPLC (the mobile phase was water with 0.1% TFA/acetonitrile with 0.035% TFA solvent) to give Example M47 (5.4 mg).

LC-MS: 769(M+H)$^+$ (0.919 min, Measurement Condition G)

Example M48

The compound shown in the following Table 16 was obtained through the same reaction and treatment as Example M2, using Reference Example 96 as a raw material compound.

TABLE 16

| Example | Structural Formula | LC-MS/ Rt (min) | LC-MS Measurement Condition |
|---|---|---|---|
| M48 | | 835 (M + H)$^+$/ 1.396 | D |

Example M49

N$^2$—((S,E)-4-((S)-2-((S)-2-(Dimethylamino)-3-methyl-3-phenylbutanamido)-N,3,3-trimethylbutanamido)-2,5-dimethylhex-2-enoyl)-N$^5$-(2-(2,5-dioxo-2,5-dihydro-1H-pyrrolo-1-yl)ethyl)-D-glutamine Example M49

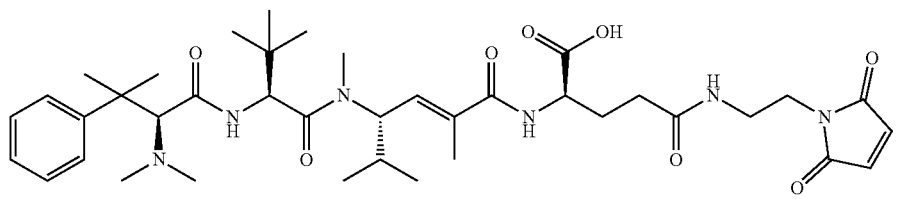

To a solution of monotrifluoroacetate salt of Example M4 (10 mg) in acetonitrile (1 mL), an aqueous formaldehyde solution (1 mL) was added and sodium triacetoxyborate (15 mg) was added, and the resultant mixture was stirred at room temperature for 3 hours. After concentrating the reaction solution, through purification by reversed phase HPLC (the mobile phase was water with 0.1% TFA/acetonitrile with 0.035% TFA solvent), Example M49 (5.4 mg) was obtained.

LC-MS: 739(M+H)$^+$ (1.007 min, Measurement Condition G)

Example M50

The compound shown in the following table was obtained through the same reaction and treatment as Example M1, using Reference Example 99 as a raw material compound.

TABLE 17

| Example | Structural Formula | LC-MS/ Rt (min) | LC-MS Measurement Condition |
|---|---|---|---|
| M50 | [structure] | 711 (M + H)$^+$/ 1.263 | G |

The NMR data of Examples M4, M29, M31, M32, M33, M35 and M41 to M45 are shown in the following tables.

TABLE 18-1

| Example No. | NMR Data |
|---|---|
| M4 | $^1$H-NMR (DMSO-D$_6$) δ: 0.75 (3H, d, J = 6.7 Hz), 0.84 (3H, d, J = 6.7 Hz), 0.96 (9H, s), 1.23 (3H, s), 1.35 (3H, s), 1.80 (3H, s), 1.87-1.96 (3H, br m), 2.09 (2H, t, J = 7.9 Hz), 2.05-2.20 (3H, br m), 2.98 (3H, s), 3.13-3.23 (2H, m), 3.43-3.48 (2H, m), 4.15 (1H, dd, J = 13.1, 8.2 Hz), 4.78 (1H, d, J = 9.1 Hz), 4.95 (1H, t, J = 9.8 Hz), 6.31 (1H, d, J = 9.1 Hz), 7.00 (2H, s), 7.24-7.26 (1H, br m), 7.34-7.37 (2H, br m), 7.46 (2H, d, J = 7.9 Hz), 8.00 (1H, t, J = 6.1 Hz), 8.15 (1H, d, J = 7.3 Hz). |
| M29 | $^1$H-NMR (CD$_3$OD) δ: 0.70 (3H, d, J = 6.7 Hz), 0.82 (3H, d, J = 6.7 Hz), 0.90 (9H, s),1.27-1.62 (5H, m), 1.82 (3H, s), 1.86-2.00 (2H, m), 2.14 (2H, m), 2.32 (2H, t, J = 7.9 Hz), 2.67-2.73 (2H, m), 2.98 (3H, s), 3.04 (1H, dd, J = 21.0, 10.7 Hz), 3.68 (3H, m), 4.38 (1H, dd, J = 9.1, 4.9 Hz), 4.89 (1H, dd, J = 18.9, 9.1 Hz), 5.06 (1H, d, J = 4.3 Hz), 6.27 (1H, d, J = 9.1 Hz), 6.73 (2H, s, J = 4.3 Hz), 7.20 (1H, d, J = 9.1 Hz). |
| M31 | $^1$H-NMR (CD$_3$OD) δ: 0.86-0.94 (6H, m), 1.07 (9H, s), 1.41 (3H, s), 1.53 (3H, s), 1.96 (3H, s), 2.02 (2H, m), 2.15 (1H, m), 2.26 (2H, t, J = 2.7 Hz), 2.51 (3H, s, 5.5 Hz), 3.14 (3H, s), 3.36 (2H, m), 3.61 (2H, m), 4.38 (2H, m), 4.93 (1H, d, J = 2.4 Hz), 5.07 (1H, m), 6.41 (1H, d, J = 8.5 Hz), 6.80 (2H, d, J = 6.1 Hz), 7.66 (2H, m), 7.79 (1H, m), 7.88 (1H, s), 8.54 (1H, s). |
| M32 | $^1$H-NMR (CD$_3$OD) δ: 0.87-0.93 (6H, m), 1.06 (9H, s), 1.37 (3H, s), 1.46 (3H, s), 1.95 (3H, d, J = 2.7 Hz), 1.95-2.08 (2H, m), 2.14 (1H, dd, J = 11.6, 4.9 Hz), 2.24-2.28 (2H, m), 2.51 (3H, d, J = 5.5 Hz), 3.14 (3H, s, J = 4.9 Hz), 3.32-3.38 (2H, m), 3.60-3.62 (2H, m), 4.32 (1H, d, J = 4.9 Hz), 4.37 (1H, t, J = 4.3 Hz), 4.93 (1H, t, J = 4.3 Hz), 5.05-5.10 (1H, m), 6.41 (1H, d, J = 9.1 Hz), 6.79 (2H, d, J = 4.2 Hz), 7.05-7.12 (1H, m), 7.27-7.36 (2H, m), 7.46 (1H, dd, J = 9.8, 4.3 Hz), 8.44 (1H, s). |

TABLE 18-1-continued

| Example No. | NMR Data |
|---|---|
| M33 | $^1$H-NMR (CD$_3$OD) δ: 0.74 (3H, d, J = 6.7 Hz), 0.81 (3H, t, J = 6.7 Hz), 0.94 (9H, s), 0.96-1.10 (3H, m), 1.19-1.30 (3H, m), 1.60-1.76 (5H, m), 1.85 (3H, s), 1.92 (2H, td, J = 14.8, 6.3 Hz), 2.06 (1H, dq, J = 27.1, 7.2 Hz), 2.17 (2H, dd, J = 9.4, 6.4 Hz), 2.54 (3H, s), 3.01 (3H, s), 3.25 (2H, dd, J = 11.3, 5.8 Hz), 3.51 (2H, t, J = 5.5 Hz), 3.89 (1H, s), 4.28 (1H, dd, J = 8.8, 4.6 Hz), 4.82 (1H, t, J = 3.7 Hz), 4.95 (1H, t, J = 9.8 Hz), 6.30 (1H, d, J = 9.8 Hz), 6.70 (2H, d, J = 1.2 Hz). |
| M35 | $^1$H-NMR (CD$_3$OD) δ: 0.79 (3H, d, J = 6.1 Hz), 0.83 (3H, d, J = 6.7 Hz), 0.97 (9H, s), 1.30 (3H, s), 1.42 (3H, s), 1.86 (3H, s), 1.90-1.97 (2H, m), 2.02-2.12 (1H, m), 2.15-2.21 (2H, m), 2.43 (3H, s), 3.05 (3H, s), 3.27 (2H, q, J = 5.3 Hz), 3.52 (2H, t, J = 5.5 Hz), 4.22 (1H, s), 4.28 (1H, dd, J = 8.5, 4.9 Hz), 4.82 (1H, s), 4.98 (1H, t, J = 10.1 Hz), 6.31 (1H, d, J = 9.8 Hz), 6.71 (2H, s), 7.54 (1H, t, J = 7.9 Hz), 7.64 (1H, d, J = 7.9 Hz), 7.75 (1H, d, J = 7.9 Hz), 7.81 (1H, s). |

TABLE 18-2

| Example No. | NMR Data |
|---|---|
| M41 | $^1$H-NMR (CD$_3$OD) δ: 0.77-0.83 (6H, m), 0.97 (9H, s), 1.34 (3H, s), 1.43 (3H, s), 1.87 (3H, s), 1.90-1.95 (2H, m), 2.15-2.19 (2H, m), 2.42 (3H, s), 3.04 (3H, s), 3.26 (2H, m), 3.53 (2H, m), 4.28 (1H, dd, J = 8.8, 4.6 Hz), 4.34 (1H, s), 4.86 (1H, t, J = 4.3 Hz), 4.98 (1H, t, J = 9.8 Hz), 6.32 (1H, d, J = 9.1 Hz), 6.71 (2H, s), 7.28 (1H, t, J = 7.0 Hz), 7.41 (4H, dt, J = 26.2, 7.6 Hz), 7.52 (1H, d, J = 6.7 Hz), 7.57 (2H, d, J = 7.3 Hz), 7.72 (1H, s), 8.38 (1H, d, J = 8.5 Hz). |
| M42 | $^1$H-NMR (CD$_3$OD) δ: 0.77-0.84 (6H, m), 0.97 (9H, s), 1.26 (3H, s), 1.35 (3H, s), 1.83 (3H, s), 1.84-1.94 (2H, m), 2.03-2.10 (1H, m), 2.17 (2H, dd, J = 9.8, 6.7 Hz), 2.30 (3H, s), 2.39 (3H, s), 3.05 (3H, s), 3.26 (2H, t, J = 5.8 Hz), 3.37 (1H, dd, J = 8.8, 1.5 Hz), 3.52 (2H, t, J = 5.5 Hz), 4.24 (1H, s), 4.28 (1H, dd, J = 8.5, 4.3 Hz), 4.83 (1H, d, J = 5.5 Hz), 4.98 (1H, t, J = 10.1 Hz), 6.31 (1H, d, J = 9.1 Hz), 6.71 (2H, s), 7.08 (1H, d, J = 6.1 Hz), 7.23 (2H, d, J = 5.5 Hz), 7.27 (1H, s). |
| M43 | $^1$H-NMR (CD$_3$OD) δ: 0.83 (3H, d, J = 6.1 Hz), 0.91 (3H, t, J = 7.0 Hz), 1.04 (9H, s), 1.28 (6H, td, J = 16.1, 7.5 Hz), 1.60 (1H, t, J = 13.4 Hz), 1.76-2.30 (15H, m), 2.95 (1H, t, J = 12.2 Hz), 3.11 (3H, s), 3.32-3.50 (5H, m), 3.60 (2H, t, J = 7.6 Hz), 4.09 (1H, d, J = 11.6 Hz), 4.37 (1H, dt, J = 17.1, 7.3 Hz), 4.72 (1H, d, J = 7.9 Hz), 5.04 (1H, dd, J = 17.7, 7.9 Hz), 6.39 (1H, d, J = 9.1 Hz), 6.80 (2H, s), 8.55 (1H, d, J = 7.9 Hz). |
| M44 | $^1$H-NMR (CD$_3$OD) δ: 0.79 (3H, d, J = 3.6 Hz), 0.83 (3H, d, J = 3.6 Hz), 0.98 (9H, s), 1.27 (3H, s), 1.37 (3H, s), 1.87 (3H, s), 1.90-1.98 (2H, m), 2.13-2.21 (1H, m), 2.02-2.10 (1H, m), 2.13-2.21 (2H, m), 2.42 (3H, d, J = 2.4 Hz), 3.05 (3H, d, J = 1.8 Hz), 3.23-3.29 (2H, m), 3.52 (2H, t, J = 4.9 Hz), 4.23 (1H, d, J = 1.2 Hz), 4.29 (1H, td, J = 4.4, 2.0 Hz), 4.82-4.85 (1H, m), 4.98 (1H, t, J = 9.2 Hz), 6.32 (1H, d, J = 8.5 Hz), 6.71 (2H, d, J = 2.1 Hz), 7.28 (1H, td, J = 7.9, 2.4 Hz), 7.42 (2H, t, J = 7.9 Hz), 7.66 (1H, s). |

TABLE 18-2-continued

| | |
|---|---|
| M45 | $^1$H-NMR (CD$_3$OD) δ: 0.73-0.81 (6H, m), 0.83 (9H, s), 1.37 (3H, s), 1.44 (3H, s), 1.83 (3H, s), 1.86-2.35 (5H, m), 2.39 (3H, s), 3.03 (3H, s), 3.23-3.39 (3H, m), 3.49-3.58 (2H, m), 4.18 (1H, s), 4.46 (1H, t, J = 3.4 Hz), 4.82-5.00 (2H, m), 6.71 (2H, d, J = 3.9 Hz), 7.26 (1H, t, J = 7.9 Hz), 7.39 (2H, t, J = 5.5 Hz), 7.59 (1H, s). |

Antibodies used for Example ADCs are commercially available, or may be produced in accordance with the literatures shown in the following table.

TABLE 19

| Antibody Name | Reference Literature |
|---|---|
| Brentuximab | Japanese Patent No. 4303964 |
| Labetuzumab | Cancer Res., 1995, 55, 5935s-5945s |
| Coltuximab | Proc. Natl. Acad. Sci. U.S.A. 1994, 91, 969-973 |
| Anetumab | Mol. Cancer Thar., 2014, 13, 1537-1548 |
| Polatuzumab | Blood, 2007, 110, 616-623 |
| Vadastuximab | Japanese Unexamined Patent Publication No. 2015-520758 |
| Glembatumumab | Japanese Patent No. 5716151 |
| Indatuximab | Japanese Unexamined Patent Publication No. 2016-053053 |
| Depatuxizumab | Mol. Cancer Thar., 2015, 14, 1141-1151 |
| Antibody of AMG 595 | Mol. Cancer Thar., 2015, 14, 1614-1624 |
| Inotuzumab | Japanese Patent No. 04486494 |

Example ADC1

Brentuximab-Example M3 Conjugate (Average Drug Antibody Ratio: 7.55)

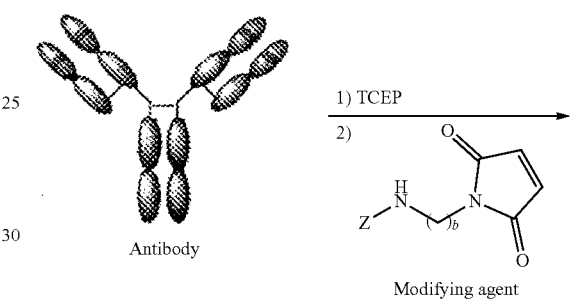

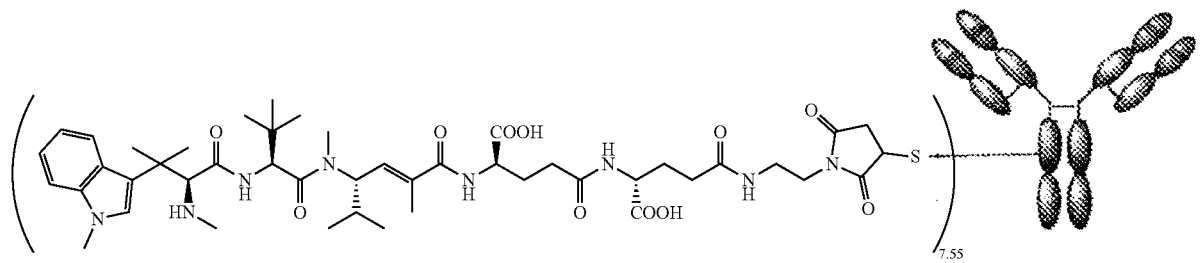

Example ADC1

To a phosphate buffered saline solution (0.039 mL) of brentuximab (1 mg), a trishydroxymethylaminomethane hydrochloride buffered solution (0.133 mL) of 1 mmol/L tris(2-carboxyethyl)phosphine (TCEP) was added, and the resultant solution was incubated at 37° C. for 45 minutes. After cooling the antibody solution to 0° C., through treatment with a PD-10 desalination column pre-equilibrated with a phosphate buffered saline solution, a phosphate buffered saline solution of the reduced brentuximab was obtained. After cooling this to 0° C., a 1 mmol/L DMSO solution of Example M3 10 times diluted with a phosphate buffered saline solution was added and completely mixed, and the resultant solution was incubated at 4° C. for 16 hours. Thereafter, through purification by a PD-10 desalination column pre-equilibrated with a phosphate buffered saline solution and subsequent centrifugal concentration, Example ADC1 (0.819 mg) was obtained.

The average DAR of the ADC thus obtained was measured by reducing or non-reducing SDS-PAGE, or HPLC-HIC. Alternatively, the average DAR may be measured qualitatively or quantitatively by ultraviolet-visible absorption spectroscopy (UV-Vis), reducing or non-reducing SDS-PAGE, HPLC-HIC, SEC, RP-HPLC, LC-MS or the like. These technologies are described in Antibody Drug Conjugates, Methods in Molecular Biology vol. 1045, 2013. pp 267-284. L. Ducry, Ed.

As a result of carrying out HPLC-HIC analysis (measurement condition E) of Example ADC1 obtained by the above protocol, the Rt of the peak of Example ADC1 with a DAR of 8 was 5.67 min.

Examples ADC2 to ADC9

The ADCs shown in the following Table 20 were obtained through the same reaction and treatment as Example ADC1, using corresponding antibodies and modifying agents (compounds of Examples).

-continued

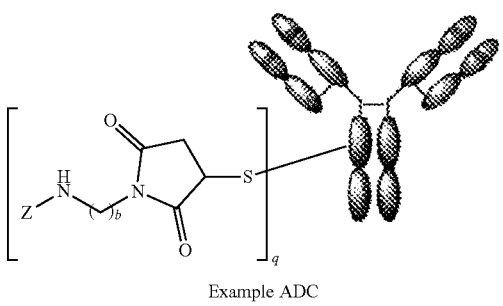

Example ADC

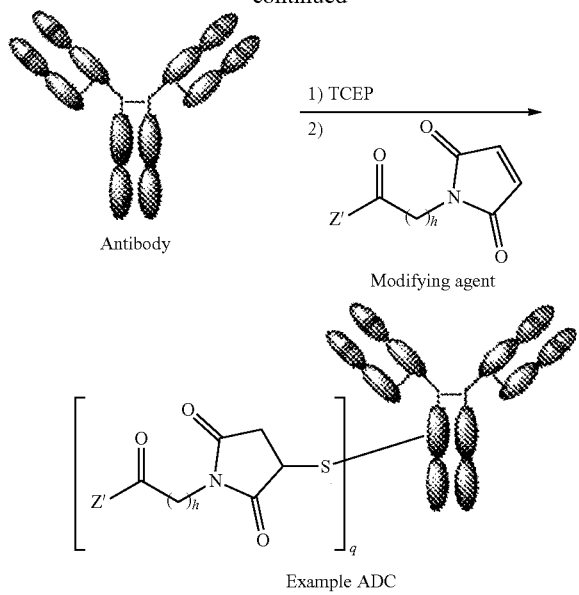

Example ADC

TABLE 20

| Example | Antibody (mAb) | Modifying agent | Average DAR | HPLC Rt(min) |
|---|---|---|---|---|
| Comparative Example 1 | Brentuximab | — | 0 | 3.72 |
| Comparative Example 2 | Trastuzumab | — | 0 | 3.41 |
| Comparative Example 3 | Brentuximab | Comparative Example compound | 7.65 | 7.30 |
| ADC2 | Brentuximab | Example M1 | 8.00 | 5.94 |
| ADC3 | Brentuximab | Example M2 | 7.31 | 5.45 |
| ADC4 | Brentuximab | Example M4 | 8.00 | 4.89 |
| ADC5 | Brentuximab | Example M5 | 8.00 | 4.75 |
| ADC6 | Brentuximab | Example M6 | 8.00 | 4.66 |
| ADC7 | Brentuximab | Example M7 | 8.00 | 4.42 |
| ADC8 | Brentuximab | Example M8 | 6.79 | 6.01 |
| ADC9 | Trastuzumab | Example M3 | 7.30 | 5.41 |

The Rt (min) of the Example ADCs in the above Table 20 is that of the peak of ADCs with a DAR of 8, observed by HPLC-HIC analysis (measurement condition E). In addition, the Rt (min) of the ADC of Comparative Example 3 is that of the peak of ADC with a DAR of 8.

The Comparative Example compound in the above Table 20 represents the following compound disclosed in International Publication No. WO 2014/057436 (Patent Literature 8).

Examples ADC10 to 44

The Example ADCs shown in the following Table 21 were obtained through the same reaction and treatment as Example ADC1, using brentuximab and modifying agents (compounds of Examples).

TABLE 21

| Example | Modifying agent | Average DAR | HIC retention time (min) | HIC condition |
|---|---|---|---|---|
| ADC10 | M4 | 4.6 | — | I |
| ADC11 | M9 | 8 | 5.72 | E |
| ADC12 | M27 | 8 | 7.08 | E |
| ADC13 | M10 | 8 | 5.77 | E |
| ADC14 | M11 | 8 | 6.02 | E |
| ADC15 | M12 | 8 | 5.45 | E |
| ADC16 | M13 | 8 | 5.88 | E |
| ADC17 | M14 | 8 | 5.69 | E |
| ADC18 | M15 | 7.03 | 5.89 | E |
| ADC19 | M16 | 8 | 6.03 | E |
| ADC20 | M17 | 7.76 | 6.08 | E |
| ADC21 | M18 | 7.70 | 6.80 | E |
| ADC22 | M19 | 7.82 | 6.56 | E |
| ADC23 | M20 | 7.73 | 6.6 | E |
| ADC24 | M21 | 7.75 | 6.54 | E |
| ADC25 | M22 | 7.74 | 6.57 | E |
| ADC26 | M23 | 7.8 | 6.86 | E |
| ADC27 | M24 | 7.64 | 6.67 | E |
| ADC28 | M25 | 7.7 | 6.73 | E |
| ADC29 | M28 | 7.5 | 6.79 | E |
| ADC30 | M42 | ADC production confirmed by SDS-PAGE | | |
| ADC31 | M26 | ADC production confirmed by SDS-PAGE | | |
| ADC32 | M41 | ADC production confirmed by SDS-PAGE | | |
| ADC33 | M36 | 8 | 4.02 | E |
| ADC34 | M35 | 7.72 | 5.38 | E |
| ADC35 | M34 | 8 | 4.62 | E |
| ADC36 | M33 | 7.79 | 4.95 | E |
| ADC37 | M45 | 7.7 | 6.98 | E |
| ADC38 | M43 | 8 | 3.80 | E |
| ADC39 | M31 | 7.7 | 7.38 | E |
| ADC40 | M32 | 7.76 | 5.32 | E |
| ADC41 | M47 | 8 | 3.83 | E |
| ADC42 | M29 | 8 | 3.94 | E |
| ADC43 | M46 | ADC production confirmed by SDS-PAGE | | |
| ADC44 | M30 | ADC production confirmed by SDS-PAGE | | |

The "ADC production confirmed by SDS-PAGE" means that bands are strongly detected in the vicinity of a molecular weight of 50 kDa and a molecular weight of 25 kDa as a result of SDS-PAGE analysis for Example ADC under disulfide non-reducing conditions, using SeeBlue® Plus2 (Thermo Fisher Scientific K.K.) as a marker. This indicates that the modifying agent conjugates to the cysteine residues involved in the disulfide bonds between the light chains and heave chains and of the hinge of the antibody, which means that an ADC is obtained.

Comparative Example compound

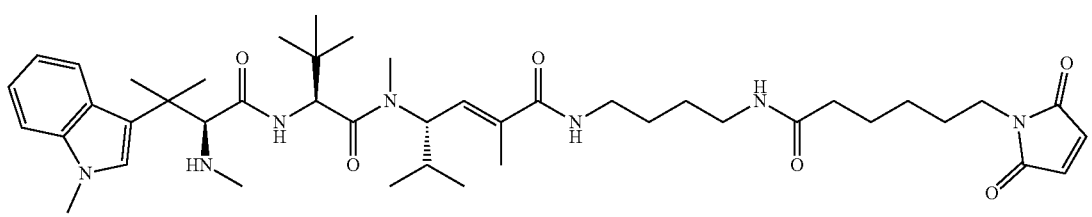

Examples ADC45 to 62

The Example ADCs shown in the following Table 22 were obtained through the same as Example ADC1, using antibodies and modifying agents (compounds of Examples).

TABLE 22

| Example | Antibody | Modifying agent | HIC retention time (min) | HIC condition. | Average DAR |
|---|---|---|---|---|---|
| ADC45 | Trastuzumab | M4 | 5.94 | E | 7.7 |
| ADC46 | Gemtuzumab | M4 | 6.08 | E | 8 |
| ADC47 | Labetuzumab | M4 | 6.61 | E | 8 |
| ADC48 | Rituximab | M4 | 5.16 | E | 7.7 |
| ADC49 | Coltuximab | M4 | 4.58 | E | 8 |
| ADC50 | Denintuzumab | M4 | 5.37 | E | 7.56 |
| ADC51 | Alemtuzumab | M4 | 4.41 | E | 7.7 |
| ADC52 | Anetumab | M4 | 5.26 | E | 6.9 |
| ADC53 | Polatuzumab | M4 | 4.47 | E | 7.3 |
| ADC54 | Vadastuximab | M4 | 4.55 | E | 5.3 |
| ADC55 | Glembatumumab | M4 | 6.83 | E | 8 |
| ADC56 | Indatuximab | M4 | 5.13 | E | 7.8 |
| ADC57 | Depatuxizumab | M4 | 4.76 | E | 7.3 |
| ADC58 | Depatuxizumab | M17 | 4.86 | E | 7.4 |
| ADC59 | Laprituximab | M4 | 4.66 | E | 7.0 |
| ADC60 | Cetuximab | M4 | 4.87 | E | 8 |
| ADC61 | Antibody of AMG 595 | M4 | 5.17 | E | 6.54 |
| ADC62 | Inotuzumab | M4 | 4.72 | E | 5.64 |

Examples ADC63 to ADC64

The Example ADCs shown in the following Table 23 were obtained through the same reaction and treatment as Example ADC1, using brentuximab and modifying agents (compounds of Examples).

TABLE 23

| Example | Modifying agent Example No. | Average DAR | HIC retention time (min) | HIC condition |
|---|---|---|---|---|
| ADC63 | M48 | 8.0 | 5.75 | E |
| ADC64 | M49 | ADC production confirmed by SDS-PAGE | | |

Test Examples

Hereinafter, results of pharmacological tests with respect to particular Examples of the antibody-drug conjugate according to the present invention will be shown and their pharmacological actions will be explained, but the present invention is not limited to these Test Examples.

Test Examples 1: Cellular Toxicity Test (1)

Karpas-299 cells (European Collection of Authenticated Cell Cultures, hereinafter, ECACC), which are human lymphoma cell lines, were cultured in RPMI 1640 (GIBCO) containing 10% fetal bovine serum (MP Biomedicals) (hereinafter, referred to as the "culture medium"). Cells were prepared to be $2 \times 10^6$ cells/mL in the culture medium, and were added to a 96 well microplate for cell culturing in an amount of 50 μL for each well. Compounds of Examples or Comparative Example compound 4 times diluted with the culture medium in 8 stages were added to the microplate in an amount of 50 μL for each well. These were cultured at 37 degree under 5% $CO_2$ for 4 days. After culturing, the microplate was taken out from the incubator, and was left at rest at room temperature for 10 minutes. To each well, 50 μL of CellTiter-Glo Luminescent Cell Viability Assay (Promega) was added, and the resultant mixture was stirred. This mixture was incubated at a dark place for 20 minutes. Using a microplate luminometer, luminescence at each well was measured, thereby calculating the cell viability. In addition, from the value of cell viability, the $IC_{50}$ value was calculated. The results are shown in Table 24.

The $IC_{50}$ value was calculated by the following formula:

$$IC_{50} (nM) = \text{antilog}(LOG_{10}(a/b) \times (e-d)/(c-d) + LOG_{10} b)$$

a: concentration a of test substance
b: concentration b of test substance
c: cell viability upon adding test substance with concentration a
d: cell viability upon adding test substance with concentration b
e: intermediate value between maximum and minimum among cell viabilities upon adding test substances with different concentrations (a and b are concentrations crossing the cell viability e, and a>b is indicated).

The cell viability at each concentration was calculated by the following formula:

$$\text{Cell Viability (\%)} = a'/b' \times 100$$

a': mean value of luminescence amount of wells to which test substance was added (n=6)
b': mean value of luminescence amount of wells to which test substance was not added (n=6)
(n represents the number of evaluations performed per test substance concentration).

TABLE 24

| Cell | Compound | $IC_{50}$(nM) |
|---|---|---|
| Karpas-299 | Comparative Example compound | 19.1 |
| | Example M1 | 726 |
| | Example M2 | 780 |
| | Example M3 | 443 |
| | Example M4 | >1000 |
| | Example M5 | 607 |
| | Example M6 | 952 |
| | Example M7 | 181 |
| | Example M8 | 27.7 |
| | Example M9 | 576 |
| | Example M10 | 544 |
| | Example M11 | >1000 |
| | Example M12 | 29.8 |
| | Example M13 | 999 |
| | Example M14 | >1000 |
| | Example M15 | >1000 |
| | Example M16 | 573 |
| | Example M17 | 35 |
| | Example M18 | 148 |
| | Example M19 | 169 |
| | Example M20 | 406 |
| | Example M21 | 226 |
| | Example M22 | 154 |
| | Example M23 | 49.7 |
| | Example M24 | 166 |
| | Example M25 | 140 |
| | Example M26 | 80.1 |
| | Example M27 | 192 |
| | Example M28 | 50.8 |
| | Example M29 | >1000 |
| | Example M31 | 197 |
| | Example M32 | 616 |
| | Example M33 | 228 |
| | Example M34 | 8.0 |
| | Example M35 | 8.6 |
| | Example M36 | >1000 |

TABLE 24-continued

| Cell | Compound | IC$_{50}$(nM) |
|---|---|---|
| | Example M37 | 403 |
| | Example M39 | 379 |
| | Example M40 | 176 |
| | Example M41 | 26.3 |
| | Example M42 | 91.1 |
| | Example M43 | 3.8 |
| | Example M44 | 9.2 |
| | Example M45 | 189 |
| | Example M47 | >1000 |
| | Example M48 | >1000 |
| | Example M49 | >1000 |

As shown in the above Table 24, the Comparative Example compound exhibited strong cellular toxicity to Karpas-299 cells. On the other hand, compounds of Examples exhibited weak cellular toxicities to Karpas-299 cells. It is inferred that this difference in the cytotoxic activity is due to the difference in the membrane permeability, which will be shown in Test Example 4.

Test Examples 2: Cellular Toxicity Test (2)

SK-BR-3 cells (ATCC), which are human breast cancer cell line, were cultured in McCoy's 5A (GIBCO) containing 10% fetal bovine serum (MP Biomedicals) (hereinafter, referred to as the "culture medium" in this test). SK-BR-3 cells were prepared to be 2×10$^6$ cells/mL in the culture medium, added to a 96 well microplate for cell culturing in an amount of 50 μL for each well, and cultured at 37 degree under 5% $CO_2$ overnight, and then, compounds of Examples or Comparative Example compound 4 times diluted with the culture medium in 8 stages were added to the microplate in an amount of 50 μL for each well. These were cultured at 37 degree under 5% $CO_2$ for 3 days. After culturing, the microplate was taken out from the incubator, and was left at rest at room temperature for 10 minutes. 50 μL of CellTiter-Glo Luminescent Cell Viability Assay (Promega) was added to each well, and the resultant mixture was stirred. This mixture was incubated at a dark place for 20 minutes. Using a microplate luminometer, luminescence at each well was measured, thereby calculating the cell viability. The IC$_{50}$ value was calculated in accordance with the method described in Test Example 1. The results are shown in Table 25.

TABLE 25

| Cell | Compound | IC$_{50}$(nM) |
|---|---|---|
| SK-BR-3 | Comparative Example compound | 162 |
| | Example M1 | >1000 |
| | Example M3 | >1000 |
| | Example M4 | >1000 |

As shown in the above Table 25, the Comparative Example compound exhibited strong cellular toxicity to SK-BR-3 cells. On the other hand, compounds of Examples exhibited weak cellular toxicities to SK-BR-3 cells. It is inferred that this difference in the cytotoxic activity is due to the difference in the membrane permeability, which will be shown in Test Example 4.

Test Examples 3: Cellular Toxicity Test (1) for ADCs

Karpas-299 cells (ECACC), which are CD30 antigen-positive and HER2 antigen-negative, were cultured in RPMI 1640 (GIBCO) containing 10% fetal bovine serum (MP Biomedicals) (hereinafter, referred to as "culture medium A" in this test). In addition, SK-BR-3 cells (ATCC), which are CD30 antigen-negative and HER2 antigen-positive, were cultured in McCoy's 5A (GIBCO) containing 10% fetal bovine serum (MP Biomedicals) (hereinafter, referred to as "culture medium B" in this test). Karpas-299 cells and SK-BR-3 cells were prepared to be 2×10$^6$ cells/mL in culture medium A or culture medium B, and were added to a 96 well microplate for cell culturing in an amount of 50 μL for each well. After the addition, SK-BR-3 cells were cultured at 37 degree under 5% $CO_2$ overnight. ADCs 4 times diluted with culture medium A or culture medium B in 8 stages were added to the microplate in an amount of 50 μL for each well, and Karpas-299 cells and SK-BR-3 cells were cultured at 37 degree under 5% $CO_2$ for 4 days or 3 days, respectively. After culturing, the microplate was taken out from the incubator, and was left at rest at room temperature for 10 minutes. To each well, 50 μL of CellTiter-Glo Luminescent Cell Viability Assay (Promega) was added, and the resultant mixture was stirred. This mixture was incubated at a dark place for 20 minutes. Using a microplate luminometer, luminescence was measured, thereby calculating the cell viability for each concentration of the ADC. The IC$_{50}$ value was calculated in accordance with the method described in Test Example 1. The results are shown in Table 26.

TABLE 26

| Cell | Example ADC | IC$_{50}$(nM) |
|---|---|---|
| Karpas-299 (CD30 antigen-positive cell line) (HER2 antigen-negative cell line) | Comparative Example 1 | >6.6 |
| | Comparative Example 3 | 0.056 |
| | Example ADC1 | 0.020 |
| | Example ADC2 | 0.020 |
| | Example ADC3 | 0.019 |
| | Example ADC4 | 0.019 |
| | Example ADC5 | 0.036 |
| | Example ADC6 | 0.034 |
| | Example ADC7 | 0.046 |
| | Example ADC8 | 0.034 |
| | Example ADC9 | 3.77 |
| SK-BR-3 (CD30 antigen-negative cell line) (HER2 antigen-positive cell line) | Comparative Example 2 | >6.6 |
| | Example ADC1 | >6.6 |
| | Example ADC4 | >6.6 |
| | Example ADC9 | 0.21 |
| Karpas-299 (CD30 antigen-positive cell line) (HER2 antigen-negative cell line) | Example ADC10 | 0.027 |
| | Example ADC11 | 0.114 |
| | Example ADC12 | 0.034 |
| | Example ADC13 | 0.588 |
| | Example ADC14 | 0.050 |
| | Example ADC15 | 0.495 |
| | Example ADC16 | 0.029 |
| | Example ADC19 | 0.004 |
| | Example ADC20 | 0.008 |
| | Example ADC21 | 0.022 |
| | Example ADC22 | 0.029 |
| | Example ADC23 | 0.029 |
| | Example ADC24 | 0.043 |
| | Example ADC25 | 0.046 |
| | Example ADC26 | 0.0098 |
| | Example ADC27 | 0.040 |
| | Example ADC28 | 0.036 |
| | Example ADC29 | 0.028 |
| | Example ADC30 | 0.015 |
| | Example ADC31 | 0.0072 |
| | Example ADC32 | 0.083 |
| | Example ADC33 | 0.011 |
| | Example ADC34 | 0.061 |
| | Example ADC35 | 0.018 |
| | Example ADC36 | 0.098 |

TABLE 26-continued

| Cell | Example ADC | IC$_{50}$(nM) |
|---|---|---|
| | Example ADC37 | 0.030 |
| | Example ADC38 | 0.021 |
| | Example ADC39 | 0.042 |
| | Example ADC40 | 0.022 |
| | Example ADC63 | 1.98 |
| | Example ADC64 | 0.050 |

As shown in the above Table 26, Example ADC1 (an antibody-drug conjugate between brentuximab, which is a CD30 antigen-specific antibody, and Example M3) exhibited strong cytotoxic activity to Karpas-299 cells, which are CD30 antigen-positive cells, but exhibited weak cytotoxic activity to SK-BR-3 cells, which are CD30 antigen-negative cells. Similarly, Example ADC4 (an antibody-drug conjugate between brentuximab, which is a CD30 antigen-specific antibody, and Example M4) also exhibited strong cytotoxic activity to Karpas-299 cells, which are CD30 antigen-positive cells, and exhibited weak cytotoxic activity to SK-BR-3 cells, which are CD30 antigen-negative cells. In addition, Example ADC9 (an antibody-drug conjugate between trastuzumab, which is a HER2 antigen-specific antibody, and Example M3) exhibited strong cytotoxic activity to SK-BR-3 cells, which are HER2 antigen-positive cells, and exhibited weak cytotoxic activity to Karpas-299 cells, which are HER2 antigen-negative cells.

That is, even compounds with weak cellular toxicities due to low membrane permeability (corresponding to the compounds of Examples), by forming conjugates with antibodies (corresponding to Example ADCs), exhibited strong cytotoxic activities selectively to antigen-positive cells that are specifically bonded to the antibodies.

Test Example 4: Membrane Permeability Test

By the parallel artificial membrane permeability assay (PAMPA), the membrane permeability of compounds of Examples was examined as follows: To the donor plate, System solution (pION inc.) and GIT Lipid-0 (pION inc.) were added in an amount of 200 μL and 4 μL for each well, respectively. To the acceptor plate, Acceptor Sink Buffer (pION inc.) was added in an amount of 200 μL. Both plates were superposed and incubated at 37° C. for 4 hours, and then, UVs in the solutions on the side of acceptor and on the side of donor were measured with an UV plate reader (190 to 500 nm). Compounds with poor UV absorption were measured by LC-MS. The permeability coefficient $P_e$ ($10^{-6}$ cm/sec) of the drug was calculated by the following formula. The results are shown in Table 27.

$$P_e = -\frac{2.303 V_D}{A(t - \tau_{SS})} \left(\frac{1}{1 + r_e}\right) \cdot \log_{10}\left[-r_e + \left(\frac{1 + r_e}{1 - R}\right) \cdot \frac{C_D(t)}{C_D(0)}\right]$$ [Expression 1]

$r_a = (V_D/V_A) P_a^{(A-D)}/P_a^{(D-A)} = r_V P_e^{(A-D)}/P_a^{(D-A)}$ $r_V = (V_D/V_A)$ $V_D$=volume of doner well $V_A$=volume of acceptor well t=permeation time $\tau^{SS}$=steady state time R=retention $C_D = C_A$=concentration in donor and acceptor well

TABLE 27

| Compound | $P_e$ ($10^{-6}$ cm/sec) (pH7.4) |
|---|---|
| Comparative Example compound | 16.9 |
| Example M1 | <0.1 |
| Example M2 | <0.1 |
| Example M3 | <0.1 |
| Example M8 | 0.4 |
| Example M4 | <0.1 |
| Example M9 | <0.1 |
| Example M10 | <0.1 |
| Example M11 | <0.1 |
| Example M12 | <0.1 |
| Example M17 | <0.1 |
| Example M18 | <0.1 |
| Example M19 | <0.1 |
| Example M20 | <0.1 |
| Example M21 | <0.1 |
| Example M22 | <0.1 |
| Example M23 | <0.1 |
| Example M24 | <0.1 |
| Example M25 | <0.1 |
| Example M26 | <0.1 |
| Example M27 | <0.1 |
| Example M28 | <0.1 |
| Example M29 | <0.1 |
| Example M30 | <0.1 |
| Example M31 | 1.0 |
| Example M32 | 0.6 |
| Example M33 | <0.1 |
| Example M34 | 2.7 |
| Example M35 | 0.8 |
| Example M36 | 0.6 |
| Example M37 | <0.1 |
| Example M39 | <0.1 |
| Example M40 | <0.1 |
| Example M41 | 0.8 |
| Example M42 | 4.9 |
| Example M43 | 2.0 |
| Example M44 | 6.8 |
| Example M45 | 4.0 |
| Example M47 | 1.2 |
| Example M48 | 0.3 |

From the results of Test Examples 1 to 4, it is inferred that the reason why the compounds of Examples consequently exhibited lower activities compared to that of the Comparative Example compounds in the cellular toxicity tests is based on the difference between cell membrane permeabilities of these compounds. That is, it is believed that the compounds of Examples have low cell membrane permeability and transfer of the Example compounds into cells was suppressed, and therefore, they exhibited weaker cellular toxicities compared to the Comparative Example compounds. As such, according to antibody-drug conjugates containing the compounds of Examples, it is suggested that, even if reversible dissociation of the antibody moiety and the drug moiety is brought about in the systemic blood, transfer of the compounds of Examples with low cell membrane permeability into normal cells can be suppressed, thereby reducing side effects.

Test Example 5: Efficacy Test for Antibody-Drug Conjugates in Karpas-299 Tumor Type Using CB-17SCID Mice This test is a representative test for evaluating antitumor actions of drugs. Karpas human anaplastic giant cell lymphoma models are made by subcutaneously transplanting 5×10$^6$ cells to CB-17SCID mice. In such tumor models, treatment was initiated after the tumor reached a mean volume of 90 to 110 mm$^3$. To mice, a solution formed by dissolving ADC in phosphate buffered saline is injected intravenously once. The tumor volume is calculated using the formula: 0.5 (longest dimension×vertical dimension$^2$). When the tumor reached about 2000 mm$^3$, the mouse is excluded from the test and the mean tumor size is no longer plotted. Note that the method of this test is described in Hamblett K. J. et al., Clin. Cancer Res., 2004, 10, 7063-7070 and the like.

Test Example 6: Toxicity (Safety) Test of Drug or Antibody-Drug Conjugate Using Mouses or Rats This test is a representative test for evaluating toxicity (safety) of antibody-drug conjugates. The toxicity may be confirmed by single or repetitive tail intravenous administration of an antibody-drug conjugate to mouses or rats and by performing general symptom observation, hematologic test, blood chemistry study, bone marrow examination, autopsy, organ weight, histopathologic examination and the like. Note that this test is described in New Edition Toxicology, edited by Board of Education in The Japanese Society of Toxicology, Asakura Publishing Co., Ltd., (2009); Summary Technical Documentation for Brentuximab Vedotin, Pharmaceuticals and Medical Devices Agency; and the like.

Test Examples 7: Cellular Toxicity Test (2) for ADCs

The cellular toxicity was measured using Example ADC17, Example ADC18, Example ADC41 and Example ADC42. Specifically, Karpas-299 cells (ECACC) were cultured in RPMI 1640 (GIBCO) containing 10% fetal bovine serum (MP Biomedicals) (hereinafter, referred to as "culture medium A" in this test). Karpas-299 cells were prepared to be 2×10$^6$ cells/mL in culture medium A, and were added to a 96 well microplate for cell culturing in an amount of 50 μL for each well. Brentuximab or Example ADCs, the concentration of which was prepared to be 2000 ng/mL with culture medium A, was added to the microplate in an amount of 50 μL for each well, and cultured at 37 degree under 5% CO$_2$ for 4 days. After culturing, the microplate was taken out from the incubator, and was left at rest at room temperature for 10 minutes. To each well, 50 μL of CellTiter-Glo Luminescent Cell Viability Assay (Promega) was added, and the resultant mixture was stirred. This mixture was incubated at a dark place for 20 minutes, and luminescence was measured using a microplate luminometer, thereby determining the percentage of the number of cells that survived upon the treatment with Example ADCs relative to the number of cells that survived upon the treatment with brentuximab. The results are shown in the following table.

TABLE 28

| ADC or antibody | Compound contained | Cell survival rate (%) |
|---|---|---|
| Brentuximab (Comparative Example) | — | 100 |
| Example ADC17 | Example M14 | 55 |
| Example ADC18 | Example M15 | 53 |
| Example ADC41 | Example M47 | 63 |
| Example ADC42 | Example M29 | 19 |

As shown in Test Example 7, when Example ADCs were used, more remarkable reduction in the number of cells was confirmed than when brentuximab, which is their antibody moiety, was used. From this, it was revealed that the ADCs according to the present invention exhibit stronger cellular toxicities, compared to the antibodies themselves.

Test Examples 8: Cellular Toxicity Test (3) for ADCs

In accordance with the method described in Test Example 3 or Test Example 7, cellular toxicities of Example ADCs were measured using the cell types shown in the following table. As an indicator for the cellular toxicity, IC$_{50}$ or the cell survival rate upon the treatment with 333 nM of ADC was measured. However, for ADC 51, the cell survival rate upon the treatment with 26.6 nM of ADC51 was measured. The results are shown in the following table.

TABLE 29

| Example | IC$_{50}$ (nM) | Cell survival rate (%) | Cell |
|---|---|---|---|
| ADC45 | 0.18 | 17 | SK-BR-3 |
| ADC46 | — | 78 | HL-60 |
| ADC47 | — | 62 | LS174T |
| ADC48 | — | 62 | Raji |
| ADC49 | 0.006 | — | Ramos |
| ADC50 | 0.01 | — | Ramos |
| ADC51 | — | 96 | Raji |
| ADC52 | 2.1 | 10 | OVCAR-3 |
| ADC53 | <0.005 | — | SUDHL-16 |
| ADC54 | — | 68 | HL-60 |
| ADC55 | 13 | 33 | SK-Mel-2 |
| ADC56 | 1.9 | — | SK-BR-3 |
| ADC57 | 40 | — | MDA-MB-468 |
| ADC58 | 43 | — | MDA-MB-468 |
| ADC59 | 0.022 | — | MDA-MB-468 |
| ADC60 | 0.027 | — | MDA-MB-468 |
| ADC62 | 0.33 | — | Raji |

As shown in the above table, Example ADCs exhibited cytotoxic activities to cells expressing antigens that are bonded to the antibody moieties of the ADCs.

From the results of Test Examples 1 to 8, it was found that the compounds of Examples exhibit lower activities in the cellular toxicity tests, compared to the Comparative Example compounds. On the other hand, the antibody-drug conjugates obtained by bonding the Example compounds to antibodies exhibited high activity in the cellular toxicity tests. From these results, it is inferred that the difference between cellular toxicities of the Comparative Example compounds and the Example compounds is based on the difference between cell membrane permeabilities. That is, it is believed that the compounds of Examples have low cell membrane permeability and transfer of the Example compounds into cells was suppressed, and therefore, they exhibited weaker cellular toxicities compared to the Comparative Example compounds. As such, according to antibody-drug conjugates containing the compounds of Examples, it is suggested that, even if reversible dissociation of the antibody moiety and the drug moiety is brought about in the systemic blood, transfer of the compounds of Examples with low cell membrane permeability into normal cells can be suppressed, thereby reducing side effects.

INDUSTRIAL APPLICABILITY

As explained above, the antibody-drug conjugates according to the present invention exhibits cytotoxic activity selectively in antigen-expressing cells and has low cytotoxicity in normal cells, and therefore, is expected to be an anticancer agent excellent in safety.

The invention claimed is:
1. A compound selected from the following compounds:
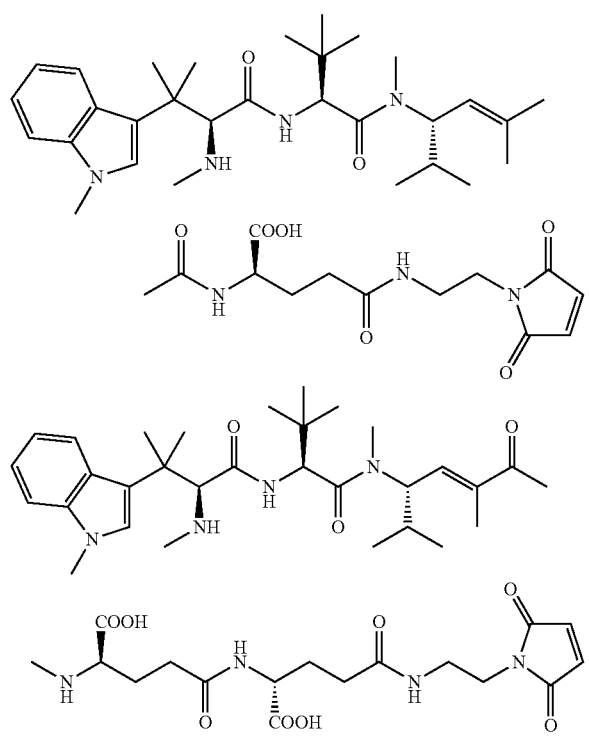
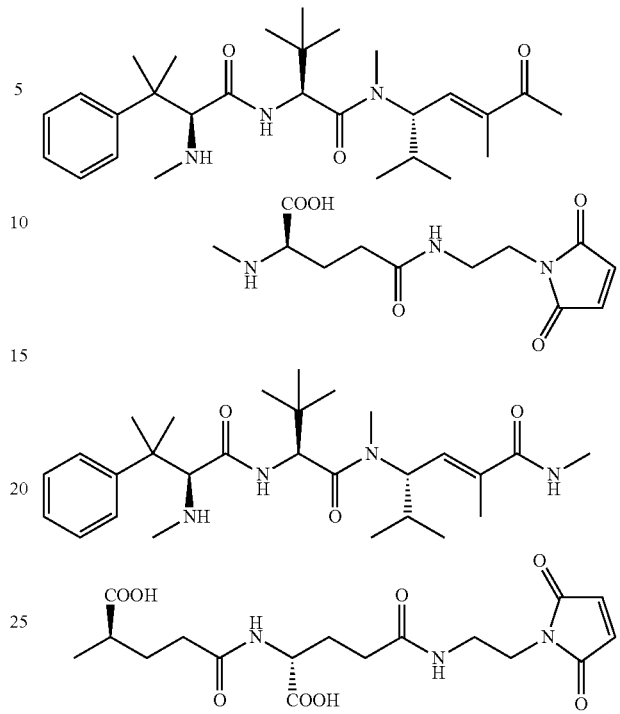
or a salt thereof.
2. A compound below:
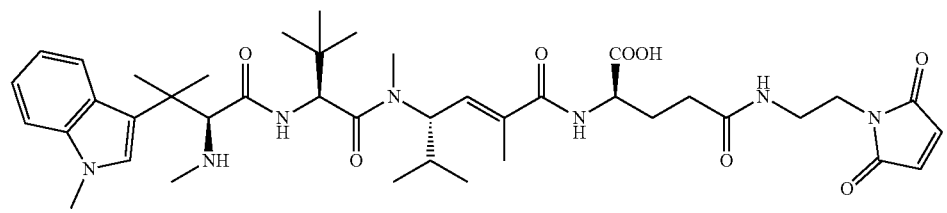 [SMILES: CN[C@H](C(=O)N[C@H](C(=O)N(C)[C@H](/C=C(\C)C(=O)N[C@H](CCC(=O)NCCN1C(=O)C=CC1=O)C(=O)O)C(C)C)C(C)(C)C)C(C)(C)c1cn(C)c2ccccc12]
or a salt thereof.
3. A compound below:
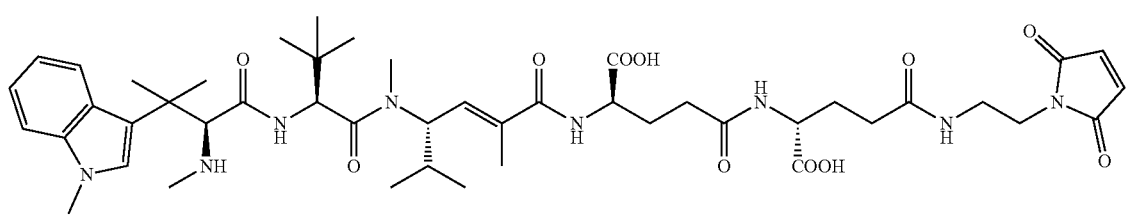 [SMILES: CN[C@H](C(=O)N[C@H](C(=O)N(C)[C@H](/C=C(\C)C(=O)N[C@H](CCC(=O)N[C@H](CCC(=O)NCCN1C(=O)C=CC1=O)C(=O)O)C(=O)O)C(C)C)C(C)(C)C)C(C)(C)c1cn(C)c2ccccc12]
or a salt thereof.

4. A compound below:
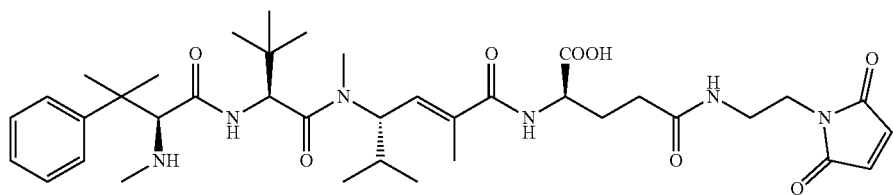 [SMILES: CN[C@H](C(=O)N[C@H](C(=O)N(C)[C@H](/C=C(\C)C(=O)N[C@H](CCC(=O)NCCN1C(=O)C=CC1=O)C(=O)O)C(C)C)C(C)(C)C)C(C)(C)c1ccccc1]
or a salt thereof.
5. A compound below:
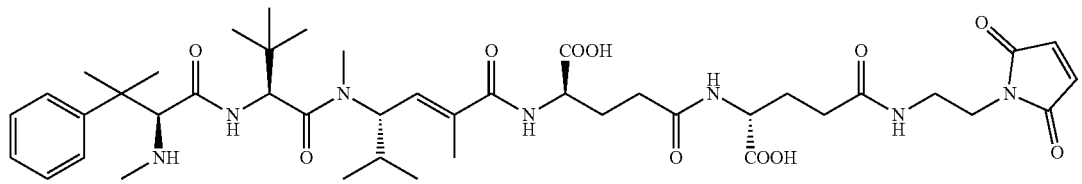 [SMILES: CN[C@H](C(=O)N[C@H](C(=O)N(C)[C@H](/C=C(\C)C(=O)N[C@H](CCC(=O)N[C@H](CCC(=O)NCCN1C(=O)C=CC1=O)C(=O)O)C(=O)O)C(C)C)C(C)(C)C)C(C)(C)c1ccccc1]
or a salt thereof.
6. A compound below:
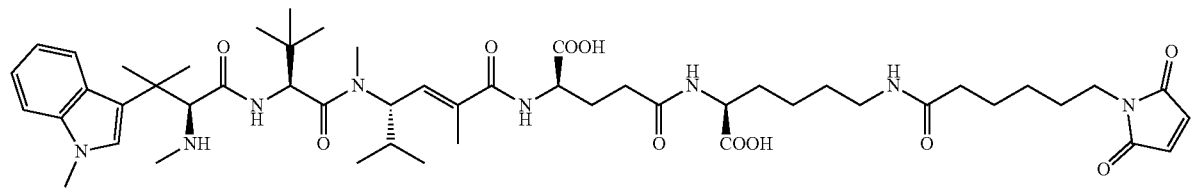 [SMILES: CN[C@H](C(=O)N[C@H](C(=O)N(C)[C@H](/C=C(\C)C(=O)N[C@H](CCC(=O)N[C@@H](CCCCNC(=O)CCCCCN1C(=O)C=CC1=O)C(=O)O)C(=O)O)C(C)C)C(C)(C)C)C(C)(C)c1cn(C)c2ccccc12]
or a salt thereof.
7. An antibody-drug conjugate selected from the following antibody-drug conjugates:
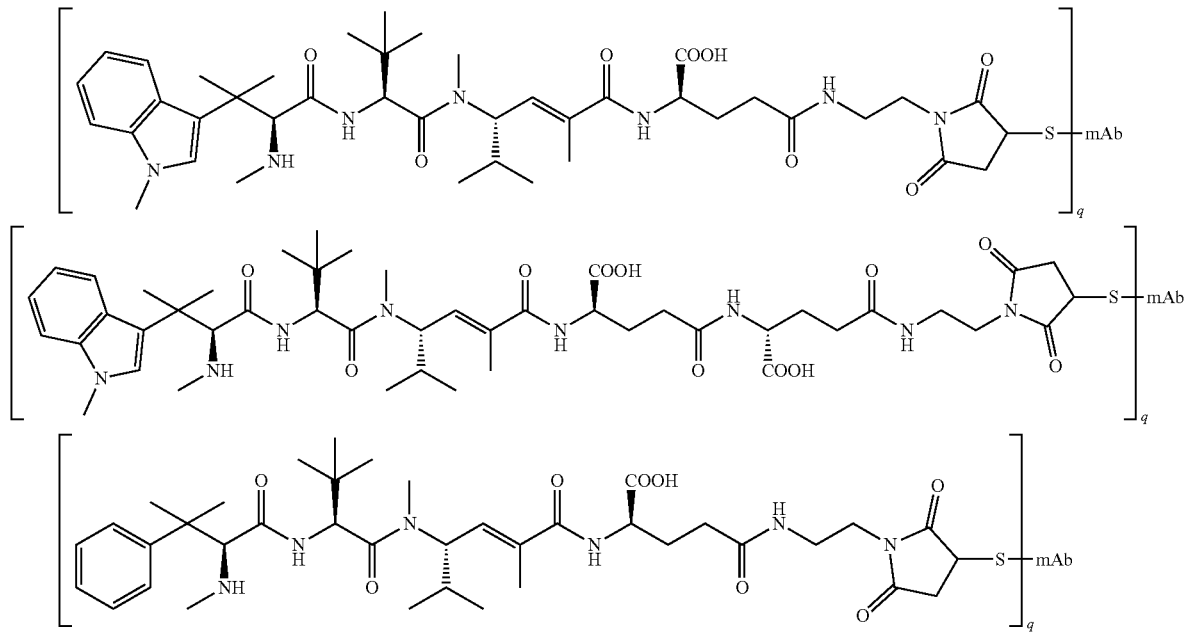

-continued

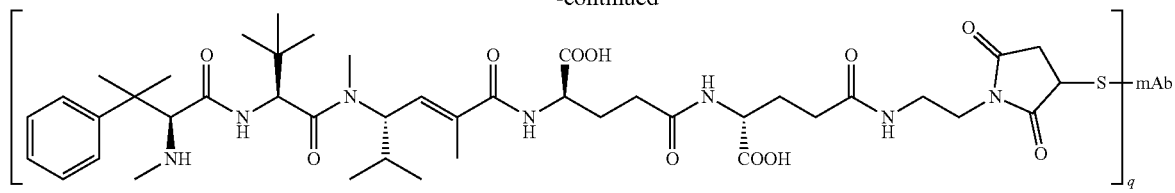

wherein mAb represents an antibody and q represents an integer of 1 to 8,
or a pharmaceutically acceptable salt thereof.

8. An antibody-drug conjugate below:

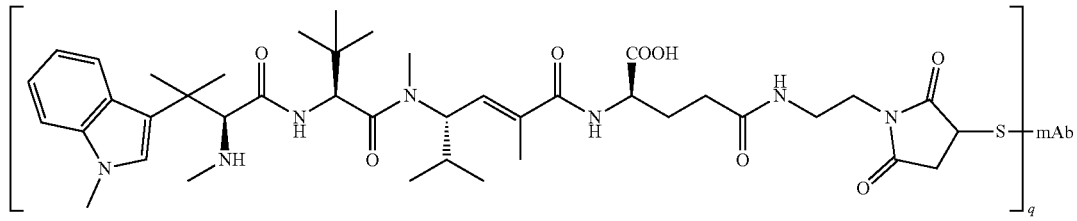

wherein mAb represents an antibody and q represents an integer of 1 to 8,
or a pharmaceutically acceptable salt thereof.

9. An antibody-drug conjugate below:

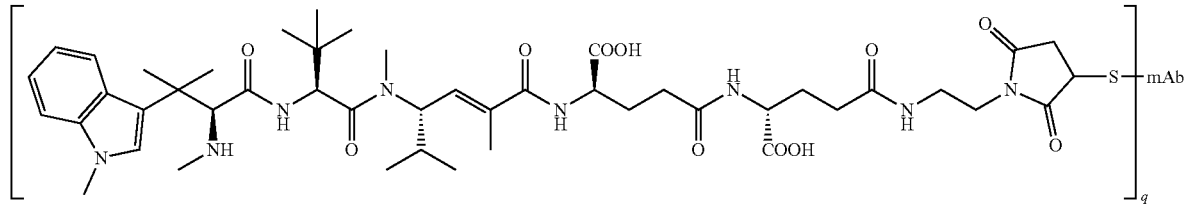

wherein mAb represents an antibody and q represents an integer of 1 to 8,
or a pharmaceutically acceptable salt thereof.

10. An antibody-drug conjugate below:

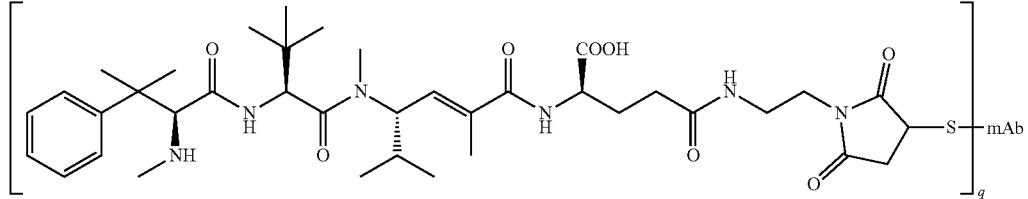

wherein mAb represents an antibody and q represents an integer of 1 to 8,
or a pharmaceutically acceptable salt thereof.

11. An antibody-drug conjugate below:

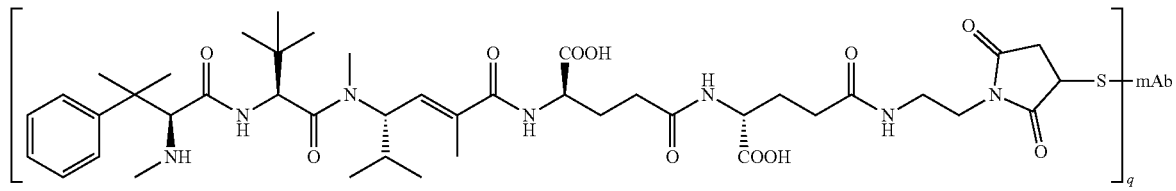

wherein mAb represents an antibody and q represents an integer of 1 to 8,
or a pharmaceutically acceptable salt thereof.

12. The antibody-drug conjugate or the pharmaceutically acceptable salt thereof according to claim 7, wherein the mAb comprises brentuximab, trastuzumab, inotuzumab, gemtuzumab, glembatumumab, labetuzumab, sacituzumab, lifastuzumab, indusatumab, polatuzumab, pinatuzumab, coltuximab, indatuximab, milatuzumab, rovalpituzumab, anetumab, tisotumab, mirvetuximab, lorvotuzumab, rituximab, depatuxizumab, denintuzumab, enfortumab, telisotumab, vandortuzumab, sofituzumab, vorsetuzumab, mirvetuximab, naratuximab, cantuzumab, laprituximab, bivatuzumab, vadastuximab, lupartumab, aprutumab, abagovomab, abciximab, abituzumab, abrilumab, actoxumab, adalimumab, adecatumumab, aducanumab, afasevikumab, afelimomab, alacizumab, alemtuzumab, alirocumab, altumomab, amatuximab, anatumomab, anifrolumab, anrukinzumab, apolizumab, arcitumomab, ascrinvacumab, aselizumab, atezolizumab, atinumab, atorolimumab, avelumab, azintuxizumab, bapineuzumab, basiliximab, bavituximab, bectumomab, begelomab, belimumab, benralizumab, bertilimumab, besilesomab, bevacizumab, bezlotoxumab, biciromab, bimagrumab, bimekizumab, bleselumab, blinatumomab, blontuvetmab, blosozumab, bococizumab, brazikumab, briakinumab, brodalumab, brolucizumab, brontictuzumab, burosumab, cabiralizumab, camrelizumab, caplacizumab, capromab, carlumab, carotuximab, catumaxomab, cedelizumab, certolizumab, cetuximab, citatuzumab, cixutumumab, clenoliximab, clivatuzumab, codrituzumab, conatumumab, concizumab, cosfroviximab, crenezumab, crizanlizumab, crotedumab, dacetuzumab, daclizumab, dalotuzumab, dapirolizumab, daratumumab, dectrekumab, demcizumab, denosumab, detumomab, dezamizumab, dinutuximab, diridavumab, domagrozumab, dorlimomab, drozitumab, duligotuzumab, dupilumab, durvalumab, dusigitumab, duvortuxizumab, ecromeximab, eculizumab, edobacomab, edrecolomab, efalizumab, efungumab, eldelumab, elezanumab, elotuzumab, elsilimomab, emactuzumab, emapalumab, emibetuzumab, emicizumab, enavatuzumab, enlimomab, enoblituzumab, enokizumab, enoticumab, ensituximab, epitumomab, epratuzumab, eptinezumab, erenumab, erlizumab, ertumaxomab, etaracizumab, etrolizumab, evinacumab, evolocumab, exbivirumab, faralimomab, farletuzumab, fasinumab, felvizumab, fezakinumab, ficlatuzumab, figitumumab, firivumab, flanvotumab, fletikumab, fontolizumab, foralumab, foravirumab, fremanezumab, fresolimumab, frunevetmab, fulranumab, futuximab, galcanezumab, galiximab, ganitumab, gantenerumab, gatipotuzumab, gavilimomab, gedivumab, gevokizumab, gilvetmab, girentuximab, golimumab, guselkumab, ibalizumab, ibritumomab, icrucumab, idarucizumab, ifabotuzumab, igovomab, imalumab, imciromab, imgatuzumab, inclacumab, inebilizumab, infliximab, inolimomab, intetumumab, ipilimumab, iratumumab, isatuximab, itolizumab, ixekizumab, keliximab, lacnotuzumab, lampalizumab, lanadelumab, landogrozumab, larcaviximab, lebrikizumab, lemalesomab, lenzilumab, lerdelimumab, lesofavumab, letolizumab, lexatumumab, libivirumab, lifatuzumab, ligelizumab, lilotomab, lintuzumab, lirilumab, lodelcizumab, lokivetmab, lorvotuzumab, losatuximab, lucatumumab, lulizumab, lumretuzumab, lutikizumab, mapatumumab, margetuximab, maslimomab, matuzumab, mavrilimumab, mepolizumab, metelimumab, minretumomab, mitumomab, modotuximab, mogamulizumab, monalizumab, morolimumab, motavizumab, moxetumomab, muromonab, nacolomab, namilumab, naptumomab, narnatumab, natalizumab, navicixizumab, navivumab, nebacumab, necitumumab, nemolizumab, nerelimomab, nesvacumab, nimotuzumab, nivolumab, obiltoxaximab, obinutuzumab, ocaratuzumab, ocrelizumab, odulimomab, ofatumumab, olaratumab, oleclumab, olendalizumab, olokizumab, omalizumab, onartuzumab, ontuxizumab, opicinumab, oportuzumab, oregovomab, oreticumab, orticumab, otelixizumab, otlertuzumab, oxelumab, ozanezumab, ozoralizumab, pagibaximab, palivizumab, pamrevlumab, panitumumab, panobacumab, parsatuzumab, pascolizumab, pasotuxizumab, pateclizumab, patritumab, pembrolizumab, perakizumab, pertuzumab, pexelizumab, pidilizumab, placulumab, plozalizumab, ponezumab, porgaviximab, prezalumab, priliximab, pritoxaximab, pritumumab, quilizumab, racotumomab, radretumab, rafivirumab, ralpancizumab, ramucirumab, ranevetmab, ranibizumab, raxibacumab, refanezumab, regavirumab, remtolumab, reslizumab, rilotumumab, rinucumab, risankizumab, rivabazumab, robatumumab, roledumab, romosozumab, rontalizumab, rosmantuzumab, rovelizumab, rozanolixizumab, ruplizumab, samalizumab, sarilumab, satralizumab, satumomab, secukinumab, selicrelumab, seribantumab, setoxaximab, sevirumab, sibrotuzumab, sifalimumab, siltuximab, simtuzumab, siplizumab, sirukumab, solanezumab, solitomab, sontuzumab, stamulumab, sulesomab, suptavumab, suvizumab, suvratoxumab, tabalumab, tadocizumab, talizumab, tamtuvetmab, tanezumab, taplitumomab, tarextumab, tavolixizumab, fanolesomab, nofetumomab, pintumomab, tefibazumab, telimomab, telisotuzumab, tenatumomab, teneliximab, teplizumab, teprotumumab, tesidolumab, tezepelumab, tigatuzumab, tildrakizumab, timigutuzumab, timolumab, tocilizumab, tomuzotuximab, toralizumab, tosatoxumab, tositumomab, tovetumab, tralokinumab, tregalizumab, tremelimumab, trevogrumab, tucotuzumab, tuvirumab, ublituximab, ulocuplumab, urelumab, urtoxazumab, ustekinumab, utomilumab, vantictumab, vanucizumab, vapaliximab, varisakumab, varlilumab, vatelizumab, vedolizumab, veltuzumab, vepalimomab, vesencumab, visilizumab, vobarilizumab, volociximab, vonlerolizumab, votumumab, vunakizumab, tacatuzumab, zalutumumab, zanolimumab, ziralimumab, zolimomab, camidanlumab, cofetuzumab, ladiratuzumab, loncastuximab, telisotuzumab, enapotamab, an antibody of AMG 595 or anti-embigin antibody, or a pharmaceutically acceptable salt thereof.

13. The antibody-drug conjugate or the pharmaceutically acceptable salt thereof according to claim 12, wherein the mAb comprises brentuximab, trastuzumab, inotuzumab, gemtuzumab, labetuzumab, polatuzumab, coltuximab, indatuximab, anetumab, rituximab, denintuzumab, laprituximab, vadastuximab, glembatumumab, cetuximab, alemtuzumab or depatuxizumab.

14. The antibody-drug conjugate or the pharmaceutically acceptable salt thereof according to claim 13, wherein the mAb comprises brentuximab or trastuzumab.

15. A pharmaceutical composition comprising the antibody-drug conjugate or the pharmaceutically acceptable salt thereof according to claim 7.

16. The antibody-drug conjugate or the pharmaceutically acceptable salt thereof according to claim 15 in combination with one or more anticancer compounds selected from the group consisting of an anticancer alkylating agent, an anticancer antimetabolite, an anticancer antibiotic, an anticancer platinum coordination compound, an anticancer camptothecin derivative, an anticancer tyrosine kinase inhibitor, an anticancer serine-threonine kinase inhibitor, an anticancer phospholipid kinase inhibitor, an anticancer monoclonal antibody, an interferon, a biological response modifier, a hormonal agent, an immune checkpoint inhibitor, an epigenetics-related molecule inhibitor and a post-translational protein modification inhibitor.

17. A pharmaceutical composition comprising:
the antibody-drug conjugate or the pharmaceutically acceptable salt thereof according to claim 7; and
one or more anticancer compounds selected from the group consisting of an anticancer alkylating agent, an anticancer antimetabolite, an anticancer antibiotic, an anticancer platinum coordination compound, an anticancer camptothecin derivative, an anticancer tyrosine kinase inhibitor, an anticancer serine-threonine kinase inhibitor, an anticancer phospholipid kinase inhibitor, an anticancer monoclonal antibody, an interferon, a biological response modifier, a hormonal agent, an immune checkpoint inhibitor, an epigenetics-related molecule inhibitor and a post-translational protein modification inhibitor, or pharmaceutically acceptable salts thereof.

18. The antibody-drug conjugate or the pharmaceutically acceptable salt thereof according to claim 15 for treating cancer selected from the group consisting of breast cancer, gastric cancer, lung cancer, liver cancer, cervical cancer, large bowel cancer, rectal cancer, colon cancer, glioma, lymphoma, ovarian cancer, pancreatic cancer, prostate cancer, renal cancer, urothelial cancer, skin cancer, thyroid cancer, bladder cancer, head and neck cancer, endometrial cancer, mesothelioma, melanoma, multiple myeloma and leukemia.

19. A medical product comprising:
the antibody-drug conjugate or the pharmaceutically acceptable salt thereof according to claim 7; and
one or more anticancer compounds selected from the group consisting of an anticancer alkylating agent, an anticancer antimetabolite, an anticancer antibiotic, an anticancer platinum coordination compound, an anticancer camptothecin derivative, an anticancer tyrosine kinase inhibitor, an anticancer serine-threonine kinase inhibitor, an anticancer phospholipid kinase inhibitor, an anticancer monoclonal antibody, an interferon, a biological response modifier, a hormonal agent, an immune checkpoint inhibitor, an epigenetics-related molecule inhibitor and a post-translational protein modification inhibitor.

20. The medical product according to claim 19 for treating cancer.

21. An anticancer agent comprising the antibody-drug conjugate or the pharmaceutically acceptable salt thereof according to claim 7.

22. The anticancer agent according to claim 21, wherein cancer comprises breast cancer, gastric cancer, lung cancer, liver cancer, cervical cancer, large bowel cancer, rectal cancer, colon cancer, glioma, lymphoma, ovarian cancer, pancreatic cancer, prostate cancer, renal cancer, urothelial cancer, skin cancer, thyroid cancer, bladder cancer, head and neck cancer, endometrial cancer, mesothelioma, melanoma, multiple myeloma or leukemia.

23. The pharmaceutical composition according to claim 15 for treating at least one cancer selected from the group consisting of breast cancer, gastric cancer, lung cancer, liver cancer, cervical cancer, large bowel cancer, rectal cancer, colon cancer, glioma, lymphoma, ovarian cancer, pancreatic cancer, prostate cancer, renal cancer, urothelial cancer, skin cancer, thyroid cancer, bladder cancer, head and neck cancer, endometrial cancer, mesothelioma, melanoma, multiple myeloma and leukemia.

24. The pharmaceutical composition according to claim 16 for treating at least one cancer selected from the group consisting of breast cancer, gastric cancer, lung cancer, liver cancer, cervical cancer, large bowel cancer, rectal cancer, colon cancer, glioma, lymphoma, ovarian cancer, pancreatic cancer, prostate cancer, renal cancer, urothelial cancer, skin cancer, thyroid cancer, bladder cancer, head and neck cancer, endometrial cancer, mesothelioma, melanoma, multiple myeloma and leukemia.

\* \* \* \* \*